(12) United States Patent
Zempleni

(10) Patent No.: US 11,883,434 B2
(45) Date of Patent: Jan. 30, 2024

(54) EXTRACELLULAR VESICLES AND METHODS OF USING

(71) Applicant: NUtech Ventures, Lincoln, NE (US)

(72) Inventor: Janos Zempleni, Lincoln, NE (US)

(73) Assignee: NUtech Ventures, Lincoln, NE (US)

(*) Notice: Subject to any disclaimer, the term of this patent is extended or adjusted under 35 U.S.C. 154(b) by 987 days.

(21) Appl. No.: 16/493,945

(22) PCT Filed: Mar. 15, 2018

(86) PCT No.: PCT/US2018/022750
§ 371 (c)(1),
(2) Date: Sep. 13, 2019

(87) PCT Pub. No.: WO2018/170332
PCT Pub. Date: Sep. 20, 2018

(65) Prior Publication Data
US 2021/0113622 A1 Apr. 22, 2021

Related U.S. Application Data

(60) Provisional application No. 62/471,572, filed on Mar. 15, 2017.

(51) Int. Cl.
*A61K 35/20* (2006.01)
*C07K 14/705* (2006.01)
*A61K 9/127* (2006.01)
*A61K 35/12* (2015.01)

(52) U.S. Cl.
CPC ............ *A61K 35/20* (2013.01); *A61K 9/1276* (2013.01); *C07K 14/705* (2013.01); *A61K 2035/128* (2013.01)

(58) Field of Classification Search
CPC .................................................. A61K 9/1276
See application file for complete search history.

(56) References Cited

U.S. PATENT DOCUMENTS

| | | |
|---|---|---|
| 9,085,778 B2 | 7/2015 | Lotvall et al. |
| 2016/0000710 A1 | 1/2016 | Gupta et al. |
| 2016/0068880 A1 | 3/2016 | Gerngross |
| 2016/0243171 A1 | 8/2016 | Shiels et al. |
| 2017/0087087 A1 | 3/2017 | Leonard et al. |
| 2021/0228634 A1 | 7/2021 | Zempleni |

FOREIGN PATENT DOCUMENTS

| | | |
|---|---|---|
| WO | WO 2015/161184 | 10/2015 |
| WO | WO 2017/173367 | 10/2017 |
| WO | WO 2018/170332 | 9/2018 |

OTHER PUBLICATIONS

Tovah et al, The Intestinal Transport of Bovine Milk Exosomes Is Mediated by Endocytosis in Human Colon Carcinoma Caco-2 Cells and Rat Small Intestinal IEC-6 Cells. The Journal of nutrition, (Oct. 2015) vol. 145, No. 10, pp. 2201-2206 (Year: 2015).*
Wolf et al, The Intestinal Transport of Bovine Milk Exosomes Is Mediated by Endocytosis in Human Colon Carcinoma Caco-2 Cells and Rat Small Intestinal IEC-6 Cells. The Journal of nutrition, (Oct. 2015) vol. 145, No. 10, pp. 2201-2206 (Year: 2015).*
Liang et al, Complex N-Linked Glycans Serve as a Determinant for Exosome/Microvesicle Cargo Recruitment. Journal of Biological Chemistry, (Nov. 21, 2014) vol. 289, No. 47. 32526-32537 (Year: 2014).*
Adams, L. A et al., "The Microbiome in Obesity, Diabetes, and NAFLD: What is Your Gut Telling Us?" Curr. Hepatol. Rep., 2016, 15(2):96-102.
Aguilar-Lozano et al., "Depletion of Dietary microRNAs from Cow's Milk Causes an Increase of Purine Metabolites in Human Body Fluids and Mouse Livers," Experimental Biology, 2016, 2 pages.
Alvarez-Erviti L. et al., "Delivery of siRNA to the mouse brain by systemic injection of targeted exosomes," Nat Biotechnol 2011, 29(4):341-5.
An et al., "Exosomes neutralize synaptic-plasticity-disrupting activity of Abeta assemblies in vivo," Mol. Brain 2013;6:47.
Baier et al., "MicroRNAs are absorbed in biologically meaningful amounts from nutritionally relevant doses of cow milk and affect gene expression in peripheral blood mononuclear cells, HEK-293 kidney cell cultures, and mouse livers," J Nutr., 2014, 144(10):1495-500.
Berge et al., "Pharmaceutical salts," J. Pharm. Sci., 1977, 66:1-19.
Caco-2, Dec. 2016, Wikipedia, pp. 1-3.
Cui et al., "Nutrition, microRNAs, and Human Health." American Society for Nutrition, 2017, 8:105-12.
Cummings et al. "Antibodies and Lectins in Glycan Analysis", 2009, Essentials of Glycobiology, 2nd ed., pp. 1-22.
Daulatzai M. A., "Obesity and gut's dysbiosis promote neuroinflammation, cognitive impairment, and vulnerability to Alzheimer's disease: new directions and therapeutic implications," Mol. Genet. Med, 2014, S1(01).
Dongen et al. "Extracellular Vesicles Exploit Viral Entry Routes for Cargo Delivery," Microbiology and Molecular Biology Reviews, 2016, 80(2):369-386.
Dr. Michael Roberts, "Bovine milk exosomes and their cargos may regulate metabolism through non-canonical pathways in non-bovine species," Exo-Glow Kit, PowerPoint Presentation, 7 pages.
Forbes et al., "The Gut Microbiota in Immune-Mediated Inflammatory Diseases," Front Microbiol., 2016, 7:1081.
Hayashi et al., "Efficient Recombination in Diverse Tissues by a Tamoxifen-Inducible Form of Cre: A Tool for Temporally Regulated Gene Activation/Inactivation in the Mouse," Developmental Biology, 2002, 244(2):305-318.

(Continued)

*Primary Examiner* — Qiuwen Mi
(74) *Attorney, Agent, or Firm* — Fish & Richardson P.C.

(57) ABSTRACT

The present disclosure relates to materials and methods for extracellular vesicle (e.g., exosome)-mediated delivery of cargo (e.g., endogenous and/or exogenous) to non-bovine mammalian (e.g., human) cells. For example, exosomes isolated from bovine milk for delivering cargo to non-bovine mammalian (e.g., human) cells are provided.

29 Claims, 58 Drawing Sheets
Specification includes a Sequence Listing.

(56) References Cited

OTHER PUBLICATIONS

Hood, J.L., "Post isolation modification of exosomes for nanomedicine applications," Nanomedicine (Lond), 2016, 11:1745-56.
Hung et al. "Stabilization of Exosome-targeting Peptides via Engineered Glycosylation," The Journal of Biological Chemistry, 2015, 290(13):8166-8172.
Imai et al., "Macrophage-dependent clearance of systemically administered B16BL6-derived exosomes from the blood circulation in mice," J Extracell Vesicles., 2015, 4:26238.
International Preliminary Report on Patentability in International Appln. No. PCT/US2018/022750, dated Sep. 17, 2019, 11 pages.
International Search Report and Written Opinion in International Appln. No. PCT/US2018/022750, dated Jun. 4, 2018, 14 pages.
International Search Report and Written Opinion in International Appln. No. PCT/US2019/035826, dated Sep. 24, 2019, 12 pages.
Kalra et al. "Focus on Extracellular Vesicles: Introducing the Next Small Big Thing", 2016, Int. J. Mol. Sci., vol. 17 (170): 1-30.
Kang et al., "Dysbiosis of fecal microbiota in Crohn's disease patients as revealed by a custom phylogenetic microarray," Inflamm Bowel Dis., 2010, 16(12):2034-42.
Kolho et al., "Fecal Microbiota in Pediatric Inflammatory Bowel Disease and Its Relation to Inflammation," Am J Gastroenterol. 2015, 110(6):921-30.
Kostova et al. "Importance of carbohydrate positioning in the recognition of mutated CPY for ER-associated degradation", 2005, Journal of Cell Science, 118:1485-1492.
Kusuma et al., "Human vascular endothelial cells transport foreign exosomes from cow's milk by endocytosis," Am. J. Physiol., 2016, 310:C800-C807.
Liang et al. "Complex N-linked Glycans Serve as a Determinant for Exosome/Microvesicle Cargo Recruitment", Jan. 26, 2014, JBC Papers, pp. 1-27.
Lotvall et al., "Minimal experimental requirements for definition of extracellular vesicles and their functions: a position statement from the International Society for Extracellular Vesicles," Journal of Extracellular Vesicles, 2014 3:26913.
Luan et al., "Engineering exosomes as refined biological nanoplatforms for drug delivery," Acta Pharmacol Sin., 2017, 38(6): 754-763.
Manca et al., "Milk exosomes are bioavailable and distinct microRNA cargos have unique tissue distribution patterns," Scientific Reports, 2018, 8(11321):1-11.
Manichanh et al., "Reduced diversity of faecal microbiota in Crohn's disease revealed by a metagenomic approach," Gut., 2006, 55(2):205-11.
Munagala et al., "Bovine milk-derived exosomes for drug delivery," Cancer Lett., 2016, 371(1):48-61.
Nagao-Kitamoto et al., "Functional Characterization of Inflammatory Bowel Disease-Associated Gut Dysbiosis in Gnotobiotic Mice,"CMGH Cell. Mol. Gastroenterol. Hepatol., 2016, 2(4):468-481.
Nagy A at al., "Cre recombinase: the universal reagent for genome tailoring." Genesis, 2000, 26(2):99-109.
Ohno et al., "Systematically injected exosomes targeted to EGFR deliver antitumor microRNA to breast cancer cells," Mol. Ther. 2013, 21:185-91.
Raposo and Stoorvogel "Delivery of functional RNA cargos by dietary exosomes from cow's milk in mice," Poster, 2013, 10 pages.
Raposo and Stoorvogel, "Delivery of functional RNA cargos by dietary exosomes from cow's milk in C57CL/6J mice," 2013, PowerPoint Presentation.
Shu et al., "Computational Characterization of Exogenous MicroRNAs that Can Be Transferred into Human Circulation," PLoS One. 2015, 3;10(11):e0140587.
Sukreet et al. "Identification of Glycoproteins on the Surface of Cow's Milk Exosomes that Mediate the Uptake of Exosomes into Human Colon Carcinoma Caco-2 Cells," Experimental Biology, 2016, 1 page.
Sukreet et al. "Milk Exosomes that Mediate the Uptake of Exosomes into Human Colon Carcinoma Caco-2 Cells", Apr. 1, 2016, Faseb Journal: pp. 1-4.
Sukreet, S., et al., "Identification of Glycoproteins on the Surface of Bovine Milk Exosomes and Intestinal Cells that Facilitate Exosome Uptake in Human Colon Carcinoma Caco-2 Cells," The FASEB Journal 2017, 31, 646.25.
Williams et al., "Glycosylation of extracellular vesicles: current knowledge, tools and clinical perspectives," Journal Extracellular Vesicles, 2018, 7(1442985):1-14.
Wolf et al., "The Intestinal Transport of Bovine Milk Exosomes Is Mediated by Endocytosis in Human Colon Carcinoma Caco-2 Cells and Rat Small Intestinal IEC-6 Cells," Journal of Nutrition, 2015, 145:2201-2216.
Zempleni et al., "Bioavailability, distribution and bioactivity of cow's milk exosomes and their RNA cargos in mice and humans," Gordon Conference, Aug. 2016, Abstract, 1 page.
Zempleni et al., "Bioavailability, distribution and bioactivity of cow's milk exosomes and their RNA cargos in mice and humans," Gordon Conference, Aug. 2016, Poster Presentation, 1 page.
Zempleni et al., "Biological activities of extracellular vesicles and their cargos from bovine and human milk in humans and implications for infants," Journal of Nutrition, 2017, 3-10.
Zempleni et al., "Bovine milk exosomes and their cargos may regulate through non-canonical pathways in non-bovine species," ISEV, 2017, Abstract, 1 page.
Zempleni et al., "Delivery of functional RNA cargos by dietary exosomes from cow's milk in C57BL/6J mice," Genomics and Pharmacogenomics, 2016, 30 slides.
Zempleni et al., "Delivery of functional RNA cargos by dietary exosomes from cow's milk in mice," Keystone, 2016, 1 page.
Zempleni et al., "Delivery of functional RNA cargos by dietary exosomes from cow's milk in mice," Keystone, 2016, Poster Presentation, 1 page.
Zempleni et al., "Extracellular vesicles: biology and emerging therapeutic opportunities," Nature Reviews Drug Discovery, 2013, 12:347-357.
Zempleni et al., "Non-canonical pathways of signaling and metabolic regulation by extracellular vesicles from cow's milk," ASEMV, 2016, Poster Presentation, 1 page.
Zempleni et al., "Non-canonical pathways of signaling and metabolic regulation by extracellular vesicles from cow's milk," ASEMV, 2016, PowerPoint Presentation, 31 slides.
Zempleni et al., "Non-canonical pathways of signaling and metabolic regulation by extracellular vesicles from cow's milk," ISEV, 2017 PowerPoint Presentation.
Zempleni, "Delivery of Functional RNA Cargos by Dietary Exosomes from Cow's Milk in C57BL/6J Mice," Genomics, 2016, 1 page.
Zitomersky et al., "Characterization of adherent bacteroidales from intestinal biopsies of children and young adults with inflammatory bowel disease," PLoS One, 2013, 8(6):e63686.
Chong et al., "The RNAseIII enzyme Drosha is critical in T cells for preventing lethal inflammatory disease," J Exp. Med., 2008, 205:2005-2017.
Desaulniers et al., "Production of a gonadotropin-releasing hormone 2 receptor knockdown (GNRHR2KD) swine line," Transgenic Res., 2017, 26(4):567-575.
International Preliminary Report on Patentability in International Appln. No. PCT/US2019/035826, dated Dec. 17, 2020, 9 pages.
Izumi et al., "Bovine milk exosomes contain microRNA and mRNA and are taken up by human macrophages," J Dairy Sci., 2015, 98(5):2920-2933.
Wiklander et al., "Extracellular vesicle in vivo biodistribution is determined by cell source, route of administration and targeting," J Extracell. Vesicles, 2015, 4:26316, 13 pages.

* cited by examiner

GAPDH

ALIX

CD 63

CD 9

Averaged FTLA Concentration / Size for Experiment:
Capture 2017-10-11 14-45-50
Error bars indicate + / -1 standard error of the mean

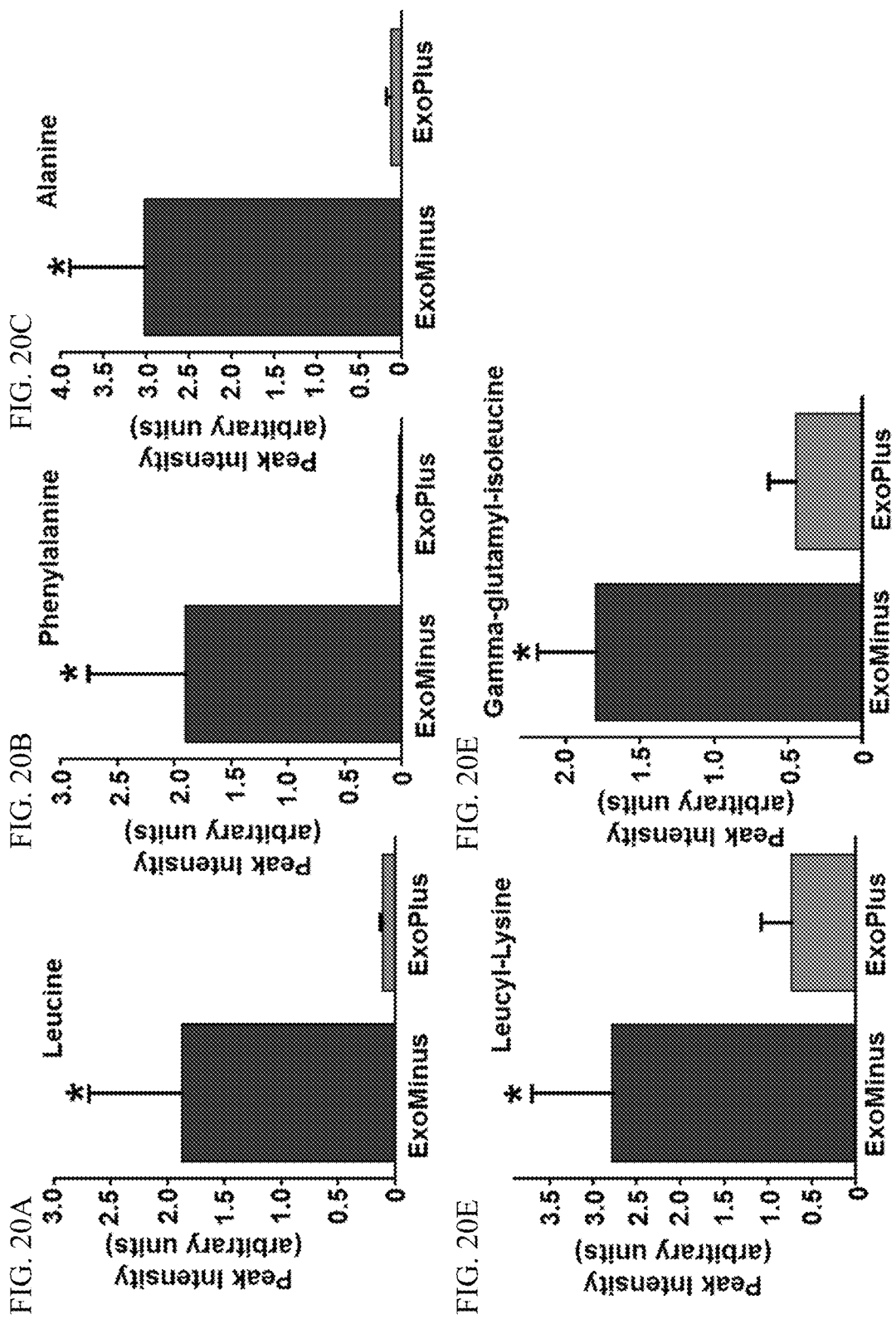

Milk exosomes
(μg exosomal protein/200 μL media)

Dose Curve

Protease Treatment of exosomes
(Caco2 Cells)

Protease Treatment of Cells
(Caco2 Cells)

Protease Treatment of Exosomes
(FHs Cells)

Protease Treatment of Cells
(FHs Cells)

FIG. 44

| Enzyme Treatment to remove surface protein of exosome | Number of Predicted TMHs | Predicted Glycan Binding sites on Identified Proteins | | |
|---|---|---|---|---|
| | | Gly N | Gly C | Gly O |
| Trypsin | 23 | 2 | 1 | - |
| Glc C | 22 | 1 | - | - |
| Asp N | 28 | 1 | 1 | - |
| Arg C | 10 | 2 | - | - |
| T.D + Trypsin | 59 | 13 | 7 | 4 |
| T.D + Glc C | 39 | 11 | 3 | 6 |
| T.D + Asp N | 79 | 17 | 5 | 7 |
| T.D + Arg C | 70 | 14 | 1 | 2 |

SBA

PNA

SNA

Con A

Tamoxifen-inducible Conditional glycan transferrase KO mouse;
(Homozygous)

FIG. 54A
| Knockout | Strain | Glycan/Enzyme/Loss |
|---|---|---|
| B6.129-Gcnt3$^{tm1Jxm}$/J | JL[1] | Core 2 and 4 O-glycans |
| OGT$^{tm}$ | JH[2] | O-GlcNac-transferase |
| Pofut1$^{tm}$ | PS[3] | Protein-O-fucosyl transferase |
| B6.129S2-Mgat1$^{tm}$ | PS[3] | Mannoside acetyl glucosaminyltransferase |
FIG. 54B
Genotyping Result
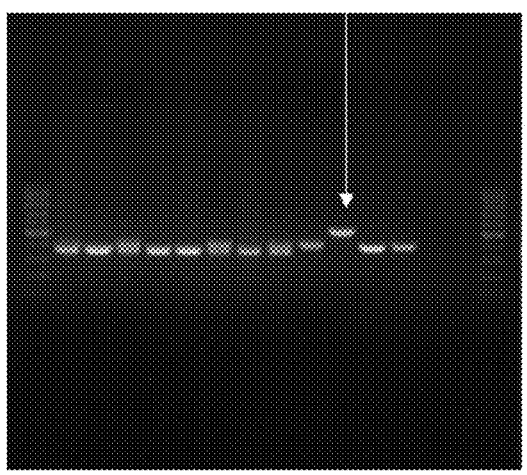
MGAT Gene
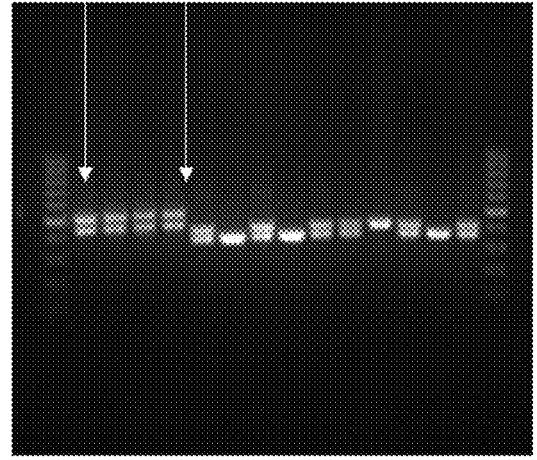
PoFUT 1 Gene FIG. 55A
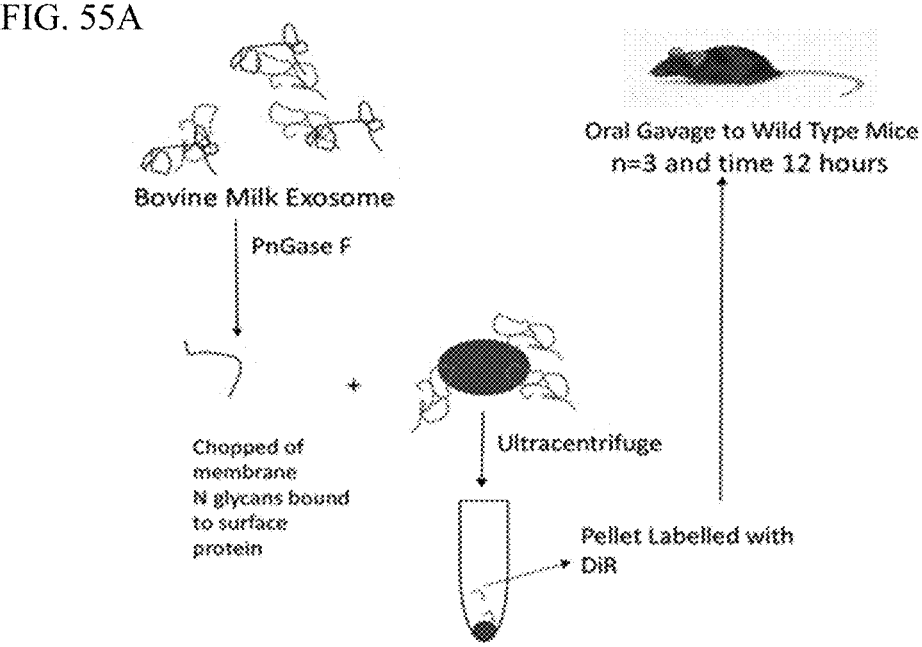
FIG. 55B
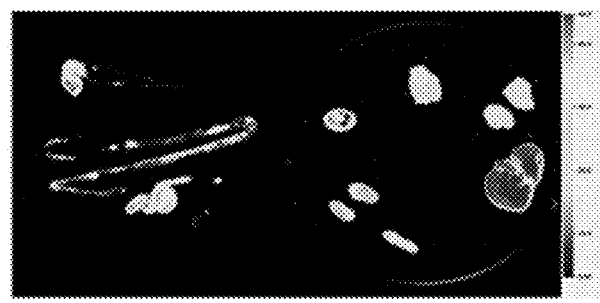
Control –DiR Labelled Exosome
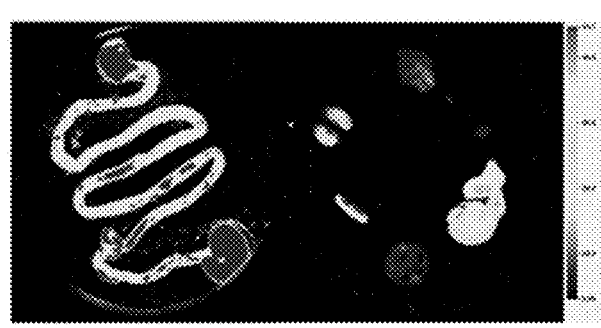
Treatment –DiR Labelled PNGase Treated Exosome

SEQUENCE LISTING

<160> NUMBER OF SEQ ID NOS: 3

<210> SEQ ID NO 1
<211> LENGTH: 66
<212> TYPE: PRT
<213> ORGANISM: Artificial
<220> FEATURE:
<223> OTHER INFORMATION: Synthetic peptide

<400> SEQUENCE: 1

Gly Arg Gly Glu Leu Val Ile Ser Ile Ser Ala Leu Ile Val Glu Tyr
1               5                   10                  15

Gln Arg Pro Trp Gln Met Lys Ala Gly Gly Phe Asp Ala Asn Asp Ile
            20                  25                  30

Leu Lys Ser Ile Ser His Glu Arg Glu Thr Glu Asp Phe Val Ser Lys
        35                  40                  45

Cys His Arg Ile Ser His Glu Ile Asp His Glu Leu Pro Glu Asp Arg
    50                  55                  60

Trp Ala
65

<210> SEQ ID NO 2
<211> LENGTH: 34
<212> TYPE: DNA
<213> ORGANISM: Artificial
<220> FEATURE:
<223> OTHER INFORMATION: Synthetic oligonucleotide

<400> SEQUENCE: 2
ataacttcgt atagcataca ttatacgaag ttat                           34

<210> SEQ ID NO 3
<211> LENGTH: 34
<212> TYPE: DNA
<213> ORGANISM: Artificial
<220> FEATURE:
<223> OTHER INFORMATION: Synthetic oligonucleotide

<400> SEQUENCE: 3
gaagttccta ttctctagaa agtataggaa cttc                           34

EXTRACELLULAR VESICLES AND METHODS OF USING

CROSS-REFERENCE TO RELATED APPLICATIONS

This application is a national stage application of International Application No.: PCT/US2018/022750, filed Mar. 15, 2018, which claims the benefit of priority to U.S. Provisional Patent Application Ser. No. 62/471,572, filed Mar. 15, 2017, the entirety of which is hereby incorporated by reference.

STATEMENT REGARDING FEDERAL FUNDING

This invention was made with government support under 2015-67017-23181 and 2016-67001-25301 awarded by the United States Department of Agriculture, National Institute of Food and Agriculture. The government has certain rights in the invention.

INCORPORATION BY REFERENCE

This application contains a Sequence Listing that has been submitted electronically as an ASCII text file named 24742-0106US1_SL_ST25.txt. The ASCII text file, created on Sep. 1, 2023, is 1,371 bytes in size. The material in the ASCII text file is hereby incorporated by reference in its entirety.

TECHNICAL FIELD

This document relates to materials and methods for extracellular vesicle-mediated delivery of cargo to mammalian cells. For example, this document provides exosomes isolated from milk for delivering cargo to mammalian cells.

BACKGROUND OF THE INVENTION

Exosomes, microvesicles, and apoptotic bodies are extracellular vesicles distinguished by size, biogenesis, and cargos. Exosomes contain diverse cargos, and are involved in cell-to-cell communication.

SUMMARY

Encapsulation of cargos in exosomes protects the cargo against harsh physiological conditions such as low pH in the stomach, and against exposure to enzymes such as RNases and proteases in the small intestine and during manufacturing, thereby conferring protection against degradation and providing a pathway for transport through the gastrointestinal tract.

The present disclosure relates to materials and methods for extracellular vesicle (e.g., exosome)-mediated delivery of cargo (e.g., endogenous and/or exogenous) to mammalian (e.g., human) cells. In some embodiments, this disclosure provides exosomes isolated from milk, i.e. milk exosomes, for delivering cargo to non-bovine mammalian (e.g., human) cells. In some embodiments, the exosomes are isolated from sheep, goat, camel, horse, donkey, reindeer, yak, buffalo, or bovine (cow) milk or colostrum.

As provided herein, exosome-rich preparations of extracellular vesicles from milk are bioavailable in mammals, including humans. For example, milk exosomes administered to human intestinal cells and venous endothelial cells are taken up, and cargos present in such exosomes are secreted or delivered into a receptor cell. The cellular uptake of the milk exosomes depends on surface glycoproteins on both the exosome and the receptor cell. mRNAs (endogenous and exogenous) present in milk exosomes can be translated into peptides by cells to which they are delivered. In some embodiments, the present disclosure provides a method of altering the metabolism (e.g., the metabolism of purines and/or amino acids) of a receptor cell; of increasing muscle strength; altering the gut microbiome (e.g., increasing or decreasing populations of particular gut flora); enhancing neurological processes (e.g., enhancing spatial learning and memory, and/or sensorimotor gating); or increasing fertility, comprising the step of administering an effective amount of milk exosomes loaded with a cargo to a mammal in need thereof. In some embodiments, the exosomes are isolated from bovine milk or colostrum.

Having the ability to deliver exosomal cargo to recipient cells provides a unique and unrealized opportunity to deliver exosomal (e.g., endogenous and/or exogenous) cargo.

In some embodiments, the disclosure provides a milk exosome comprising a biological membrane surrounding a lumen, wherein the biological membrane comprises one or more glycoprotein(s), wherein the biological membrane is modified as compared with the natural biological membrane of the milk exosome. In some embodiments, the biological membrane is modified such that it has an increased number of one or more of its native glycoprotein(s). In some embodiments, the biological membrane is modified such that it has a decreased number of one or more of its native glycoprotein(s). In some embodiments, the exosome is produced using an enzyme selected from a serine protease, cysteine protease or metalloprotease. In some embodiments, the enzyme is selected from trypsin, AspN, GluC, ArgC, chymotrypsin, proteinase K, and Lys-C. In some embodiments, the biological membrane is modified such that one or more of its native glycoprotein(s) is not present. In some embodiments, the biological membrane is modified such that it includes one or more glycoprotein(s) that is not naturally present in the natural biological membrane.

In some embodiments of the present disclosure, the biological membrane of the exosome is modified such that one or more of its native glycoprotein(s) is altered. In some embodiments, the one or more native glycoprotein(s) is altered such that the number of glycan residues present on the glycoprotein(s) is increased. In some embodiments, the exosome is produced using glycosylation that adds one or more glycans to the glycoprotein. In some embodiments, the one or more native glycoprotein(s) is altered such that the number of glycan residues present on the glycoprotein(s) is decreased. In some embodiments, the number of glycan residues is decreased by cleavage of one or more glycan residues present on the glycoprotein(s). In some embodiments, the exosome is produced using an enzyme selected from a glycosidase, exoglycosidase, endoglycosidase, glycoamidase, neuraminidase, galactosidase, peptide:N-glycosidase (PNGase), glycohydrolase, and any combination thereof. In some embodiments, the enzyme is selected from a β-N-acetylglucosaminidase, PNGase F, β (1-4) Galactosidase, O-Glycosidase, N-Glycosidase, N-glycohydrolase, Endo H, Endo D, Endo $F_2$, EndoF$_3$, and any combination thereof. In some embodiments, two or more native glycoprotein(s) are altered such that at least one glycoprotein has an increased number of glycan residues and at least one other glycoprotein has a decreased number of glycan residues or is missing its glycan residue(s), wherein the glycoprotein(s) having an increased number of glycan residues is different from the glycoprotein(s) having a decreased number of glycan residues or missing glycan residues. In some embodiments, the one or more native glycoprotein(s) is altered such that it comprises a modified glycan. In some embodiments, the modified glycan comprises at least one carbohydrate moiety that differs from that of the glycan in the native glycoprotein(s). In some embodiments, the modified glycan comprises one or more galactose, mannose, O-glycans, N-acetyl-glucosamines, and/or N-glycan chains or any combination thereof. In some embodiments, the glycan is selected from comprises one or more D- or L-glucose, erythrose, fucose, galactose, mannose, lyxose, gulose, xylose, arabinose, ribose, 2'-deoxyribose, glucosamine, lactosamine, polylactosamine, glucuronic acid, sialic acid, sialyl-Lewis X (SLex), N-acetyl-glucosamine, N-acetyl-galactosamine, neuraminic acid, N-glycolyl-neuraminic acid (Neu5Gc), N-acetylneuraminic acid (Neu5Ac), an N-glycan chain, an O-glycan chain, a Core 1, Core 2, Core 3, or Core 4 structure, or a phosphate- or acetate-modified analog thereof or a combination thereof. In some embodiments, the modified glycan lacks a portion of one or more of its carbohydrate chain(s). In some embodiments, the modified glycan is missing one or more of its carbohydrate chain(s). In some embodiments, the modified glycan comprises one or more altered carbohydrate chain(s). In some embodiments, the one or more native glycoprotein(s) is altered such that at least one glycan present on the glycoprotein(s) is substituted with a glycan that is not naturally present in the native glycoprotein(s). In some embodiments, the one or more native glycoprotein(s) is altered by blocking one or more glycan residue(s) present on the glycoprotein(s). In some embodiments, the one or more glycan residue(s) is blocked by lectin binding to the glycan residue. In some embodiments, the lectin is selected from Concanavalin A, Lentil lectin, Snowdrop lectin, Ricin (*Ricinus communis* Agglutinin, RCA120), Peanut agglutinin, Jacalin, Hairy vetch lectin, *Dolichos biflorus* agglutinin, Soybean agglutinin, N-acetylglucosamine binding lectins, Wheat Germ Agglutinin (WGA), *Phaseolus vulgaris* agglutinin, Elderberry lectin, *Maackia amurensis* leukoagglutinin, *Maackia amurensis* hemoagglutinin, *Ulex europaeus* agglutinin, or *Aleuria aurantia* lectin.

In some embodiments of the present disclosure, the uptake of the milk exosome into a mammalian cell is altered as compared with the uptake of a corresponding milk exosome having its natural biological membrane. In some embodiments, the uptake of the milk exosome into a mammalian cell is increased. In some embodiments, the uptake of the milk exosome into a mammalian cell is decreased. In some embodiments, the mammalian cell is selected from an intestinal cell, venous endothelial cell or other endothelial cell, immune cell, macrophage, intestinal mucosa, peripheral cell of the liver, spleen, lung, brain, kidneys, or pancreas, cancer cell, or fetal cell. In some embodiments, the cell is a human cell.

In some embodiments of the present disclosure, the milk exosome is targeted to a specific mammalian cell or tissue. In some embodiments, the mammalian cell is selected from an intestinal cell, venous endothelial cell or other endothelial cell, immune cell, macrophage, intestinal mucosa, peripheral cell of the liver, spleen, lung, brain, kidneys, or pancreas, cancer cell, or fetal cell. In some embodiments, the mammalian tissue is selected from liver, spleen, lung, brain, kidneys, pancreas, gastrointestinal tract, small intestine, colon, stomach, heart.

In some embodiments of the present disclosure, degradation of the exosome by macrophages is reduced as compared with an exosome having its natural biological membrane. In some embodiments, the stability of the exosome in the gastrointestinal tract, systemic circulation, lymphatic circulation, intracellular conditions, or other tissues or organs of a human is increased as compared with an exosome having its natural biological membrane. In some embodiments, the stability of the exosome under physiological conditions in a human is increased as compared with an exosome having its natural biological membrane. In some embodiments of the present disclosure, the exosome further comprises an exogenous cargo encapsulated in said lumen. In some embodiments, the exosome further comprises a miRNA or mRNA that is biologically active in a mammal. In some embodiments, the exosome is isolated from sheep, goat, camel, horse, donkey, reindeer, yak, buffalo, or bovine (cow) milk or colostrum. In some embodiments, the exogenous cargo is selected from one or more nucleic acid molecules, polypeptides, lipids, vitamins, minerals, small molecules, pharmaceuticals, hormones, or enzymes. In some embodiments, the exogenous cargo comprises a therapeutic agent. In some embodiments, the therapeutic agent is selected from mRNAs, polypeptides, miRNAs, miRNA antagonists, nutrients, antibiotics, cancer drugs, activators of Toll-like receptors, or molecules capable of delivery to macrophages. In some embodiments, the therapeutic agent is a cancer drug selected from a chemotherapeutic, an immunotherapeutic, a hormone therapeutic, or a targeted therapeutic. In some embodiments, the exogenous cargo comprises a nutritional agent. In some embodiments, the nutritional agent is selected from vitamins, minerals, lipids, fatty acids, mRNAs, or polypeptides. In some embodiments, the nutritional agent is a fatty acid selected from omega-3 fatty acids or omega-6 fatty acids.

In some embodiments the disclosure provides a composition formulated for oral administration to a human, said composition comprising any of the exosome described herein. In some embodiments, the exosome comprises an endogenous cargo. In some embodiments, the exosome comprises an exogenous cargo.

In some embodiments the present disclosure provides an infant formula or nutritional supplement, said infant formula or nutritional supplement comprising any of the exosomes described herein. In some embodiments, the exosome in the infant formula or nutritional supplement comprises an endogenous cargo. In some embodiments, the exosome in the infant formula or nutritional supplement comprises an exogenous cargo. In some embodiments, the exosome in the infant formula or nutritional supplement comprises one or more nutritional agents selected from vitamins, minerals, lipids, fatty acids, mRNAs, or polypeptides.

In some embodiments the present disclosure provides a method of altering the uptake of a milk exosome into a mammalian cell or tissue, said exosome having a biological membrane comprising one or more glycoprotein(s), comprising modifying the biological membrane of the exosome. In some embodiments, the uptake of the milk exosome into a mammalian cell or tissue is increased. In some embodiments, the uptake of the milk exosome into a mammalian cell or tissue is decreased. In some embodiments, the uptake of the milk exosome into a mammalian cell or tissue is selectively increased in a targeted mammalian cell or tissue. In some embodiments, the uptake of the milk exosome into a mammalian cell or tissue is selectively decreased in a targeted mammalian cell or tissue. In some embodiments the present disclosure provides a method of targeting a milk exosome to a selected mammalian cell or tissue, said exosome having a biological membrane comprising one or more glycoprotein(s), comprising modifying the biological membrane of the exosome.

In some embodiments of these methods, the biological membrane is modified such that it has an increased number of one or more of its native glycoprotein(s). In some embodiments of these methods, the biological membrane is modified such that it has a decreased number of one or more of its native glycoprotein(s). In some embodiments of these methods, the exosome is produced using an enzyme selected from a serine protease, cysteine protease or metalloprotease. In some embodiments of these methods, the enzyme is selected from trypsin, AspN, GluC, ArgC, chymotrypsin, proteinase K, and Lys-C. In some embodiments of these methods, the biological membrane is modified such that one or more of its native glycoprotein(s) is not present. In some embodiments of these methods, the biological membrane is modified such that it includes one or more glycoprotein(s) that is not naturally present in the natural biological membrane. In some embodiments of these methods, the biological membrane is modified such that one or more of its native glycoprotein(s) is altered. In some embodiments of these methods, the one or more native glycoprotein(s) is altered such that the number of glycan residues present on the glycoprotein(s) is increased. In some embodiments of these methods, the one or more native glycoprotein(s) is altered such that the number of glycan residues present on the glycoprotein(s) is decreased. In some embodiments of these methods, the number of glycan residues is decreased by cleavage of one or more glycan residues present on the glycoprotein(s) using an enzyme selected from a glycosidase, exoglycosidase, endoglycosidase, glycoamidase, neuraminidase, galactosidase, peptide:N-glycosidase (PNGase), glycohydrolase, and any combination thereof. In some embodiments of these methods, the enzyme is selected from a β-N-acetylglucosaminidase, PNGase F, β (1-4) Galactosidase, O-Glycosidase, N-Glycosidase, N-glycohydrolase, Endo H, Endo D, Endo $F_2$, EndoF$_3$, and any combination thereof. In some embodiments of these methods, two or more native glycoprotein(s) are altered such that at least one glycoprotein has an increased number of glycan residues and at least one other glycoprotein has a decreased number of glycan residues or is missing its glycan residue(s), wherein the glycoprotein(s) having an increased number of glycan residues is different from the glycoprotein(s) having a decreased number of glycan residues or missing glycan residues. In some embodiments of these methods, the one or more native glycoprotein(s) is altered such that it comprises a modified glycan. In some embodiments of these methods, the modified glycan comprises one or more D- or L-glucose, erythrose, fucose, galactose, mannose, lyxose, gulose, xylose, arabinose, ribose, 2'-deoxyribose, glucosamine, lactosamine, polylactosamine, glucuronic acid, sialic acid, sialyl-Lewis X (SLex), N-acetyl-glucosamine, N-acetyl-galactosamine, neuraminic acid, N-glycolylneuraminic acid (Neu5Gc), N-acetylneuraminic acid (Neu5Ac), an N-glycan chain, an O-glycan chain, a Core 1, Core 2, Core 3, or Core 4 structure, or a phosphate- or acetate-modified analog thereof or a combination thereof and wherein the modified glycan lacks a portion of one or more of its carbohydrate chain(s), is missing one or more of its carbohydrate chain(s), or comprises one or more altered carbohydrate chain(s). In some embodiments of these methods, the one or more native glycoprotein(s) is altered such that at least one glycan present on the glycoprotein(s) is substituted with a glycan that is not naturally present in the native glycoprotein(s). In some embodiments of these methods, the one or more native glycoprotein(s) is altered by blocking one or more glycan residue(s) present on the glycoprotein(s). In some embodiments of these methods, the one or more glycan residue(s) is blocked by lectin binding to the glycan residue. In some embodiments of these methods, the lectin is selected from Concanavalin A, Lentil lectin, Snowdrop lectin, Ricin (*Ricinus communis* Agglutinin, RCA120), Peanut agglutinin, Jacalin, Hairy vetch lectin, *Dolichos biflorus* agglutinin, Soybean agglutinin, N-acetylglucosamine binding lectins, Wheat Germ Agglutinin (WGA), *Phaseolus vulgaris* agglutinin, Elderberry lectin, *Maackia amurensis* leukoagglutinin, *Maackia amurensis* hemoagglutinin, *Ulex europaeus* agglutinin, or *Aleuria aurantia* lectin. In some embodiments of these methods, the mammalian cell is selected from an intestinal cell, venous endothelial cell or other endothelial cell, immune cell, macrophage, intestinal mucosa, peripheral cell of the liver, spleen, lung, brain, kidneys, or pancreas, cancer cell, or fetal cell. In some embodiments of these methods, the cell is a human cell. In some embodiments of these methods, the mammalian tissue is selected from liver, spleen, lung, brain, kidneys, pancreas, gastrointestinal tract, small intestine, colon, stomach, or heart.

In some embodiment, the present disclosure provides a method of correcting dysbiosis or improving the gut microbiome or gut health of a subject, comprising administering to said subject an effective amount of any of the exosomes described herein. In some embodiments, the correcting dysbiosis or improving the gut microbiome or gut health of a subject comprises a decrease in Ruminococcaceae and/or Verrucomicrobiae. In some embodiments, the correcting dysbiosis or improving the gut microbiome or gut health of a subject comprises an increase in Clostridiales or Erysipelotrichaceae.

In some embodiments, the present disclosure provides a method of treating inflammatory bowel disease in a subject, comprising administering to a subject in need thereof an effective amount of any of the exosome provided herein. In some embodiments, the treating inflammatory bowel disease in a subject comprises an increase in Lachnospiraceae and Ruminococcaceae. In some embodiments, the treating inflammatory bowel disease in a subject comprises a decrease in Enterobacteriaceae.

In some embodiments, the present disclosure provides a method of treating obesity in a subject, comprising administering to a subject in need thereof an effective amount of any of the exosomes described herein. In some embodiments, the treating obesity in a subject comprises a decrease in the ratio of Firmicutes and Bacteroidetes. In some embodiments, the treating obesity in a subject comprises a decrease in the ratio of Firmicutes and Bacteroidetes.

In some embodiments, the present disclosure provides a method of treating non-alcoholic fatty liver in a subject, comprising administering to a subject in need thereof an effective amount of any of the exosomes described herein. In some embodiments, the treating non-alcoholic fatty liver in a subject comprises an increase in Ruminococcaceae and *Escherichia*.

In some embodiments, the present disclosure provides a method of increasing muscle strength, enhancing sensorimotor gating or cognitive performance, or increasing fertility or fecundity in a subject, comprising administering to said subject an effective amount of any of the exosomes described herein or any of the nutritional supplements described herein. In some embodiments, the present disclosure provides a method of treating sarcopenia, muscle loss after injury, atherosclerosis, cancer, an immune disease, impaired fecundity, or cognitive impairment, comprising administering to a subject in need thereof any of the exosomes provided herein or any of the nutritional supplements described herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety.

The details of one or more embodiments of the invention are set forth in the accompanying drawings, description, and the claims. Other features, objects, and advantages of the invention will be apparent from the description and drawings, and from the claims.

BRIEF DESCRIPTIONS OF THE DRAWINGS

FIG. 1 is a schematic depicting an exosome that includes various exemplary cargos, surface proteins, and other associated biological molecules.

FIGS. 2A and 2B show milk exosome preparations from cow's milk. FIG. 2A shows exosome extracts probed using anti-CD63, anti-CD9, anti-Alix, anti-α-s1 casein, and anti-histone H3. Protein extracts were run on the same gel, membranes were cut for probing with the three antibodies, and images were reassembled after probing. FIG. 2B shows transmission electron microscope images of exosome preparations. The large field image was obtained with a 15,000-fold magnification; the insert depicts a single particle selected from the same image. M, molecular weight markers; E, exosome extract.

FIGS. 3A-D show exosome cytoplasmic extract vs. exosome membrane protein characterization of membrane proteins isolated from milk exosomes. FIG. 3A shows GADPH expression in the cytoplasmic extract. FIG. 3B shows ALIX expression in the exosome membrane protein extract (ALIX is a marker for exosomes). FIG. 3C shows CD63 expression in the membrane protein extract (CD63 is a marker for exosomes). FIG. 3D shows CD9 expression in the exosome membrane protein extract (CD9 is a marker for exosomes).

FIG. 4 shows characterization assay results for bovine milk exosomes. Rabbit anti-bovine α-s1 casein and gel electrophoresis were used to probe membrane blots of 1) cow's milk exosomes, 2) cow's milk, 3) human breast milk, 4) platelet glycoprotein 1 synthetic peptide, 5) α-s1 casein peptide, and 6) chicken egg yolk exosomes. Ten micrograms of milk and exosome protein were loaded per lane, whereas only 1 μg of synthetic peptides were loaded. M, molecular weight markers.

Figure 7A:
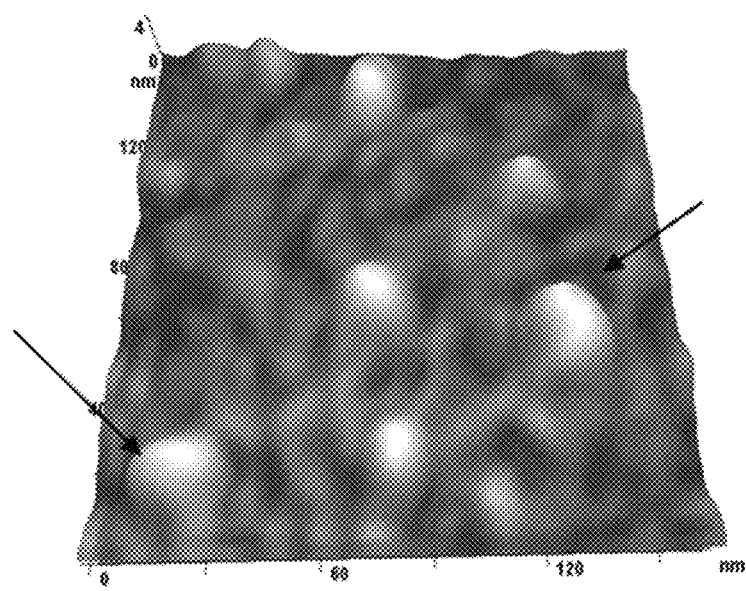
Figure 7B:
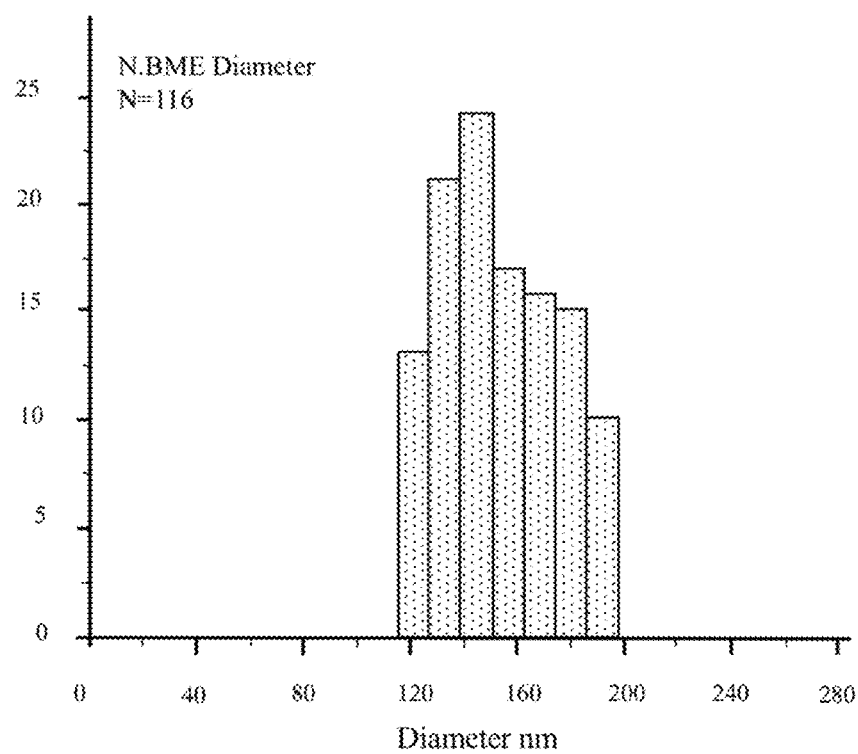

FIGS. 7A and 7B show control/normal (non-sonicated) bovine milk exosome atomic force microscopy results. FIG. 7A shows that exosomes have individual, smooth and well-formed surfaces. FIG. 7B is a graphical representation of the range of diameters for non-sonicated exosomes.

Figure 8A:
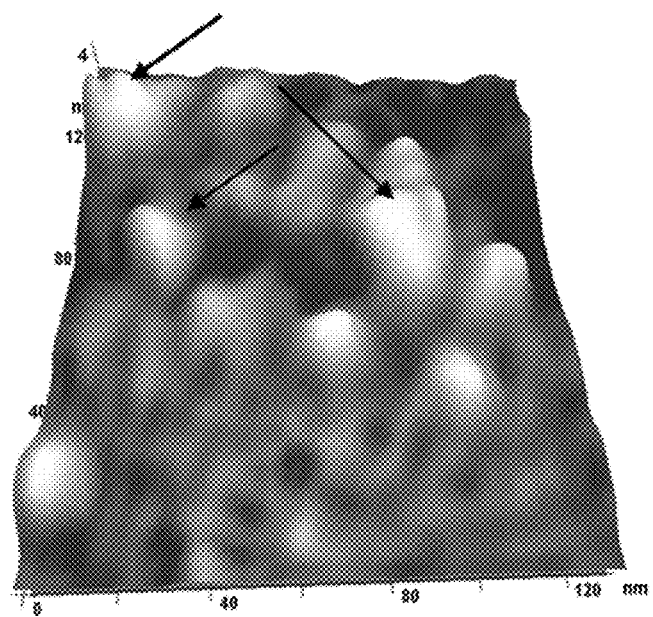
Figure 8B:
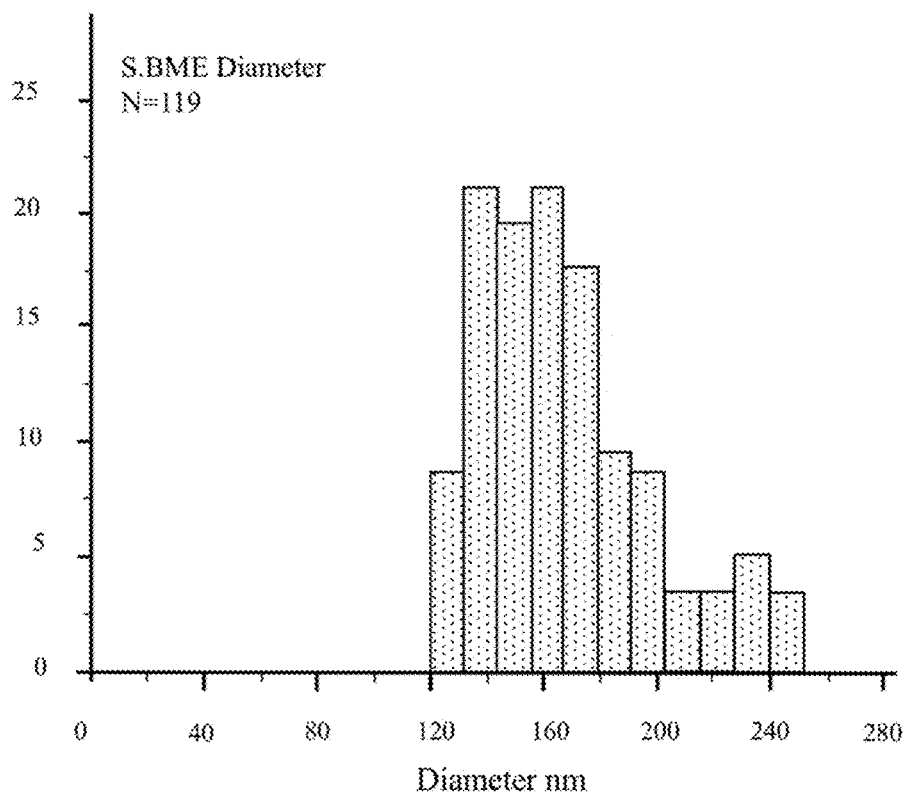

FIGS. 8A and 8B show atomic force microscopy results for sonicated bovine milk exosomes. FIG. 8A shows that in comparison to the normal exosomes, sonicated exosomes have rough edges and some clustering or aggregation (black arrow points on the 3D images of exosomes). FIG. 8B is a graphical representation of the range of diameters for sonicated exosomes.

Figure 9A:
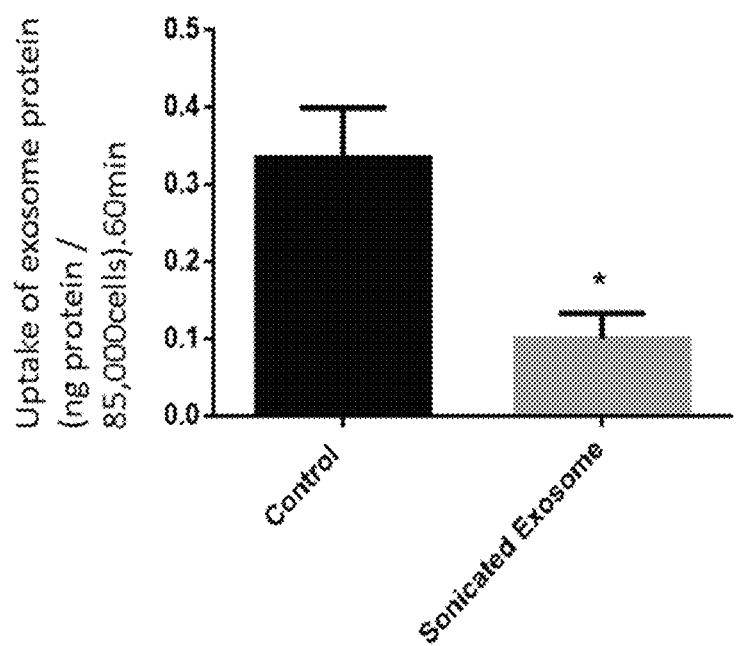
Figure 9B:
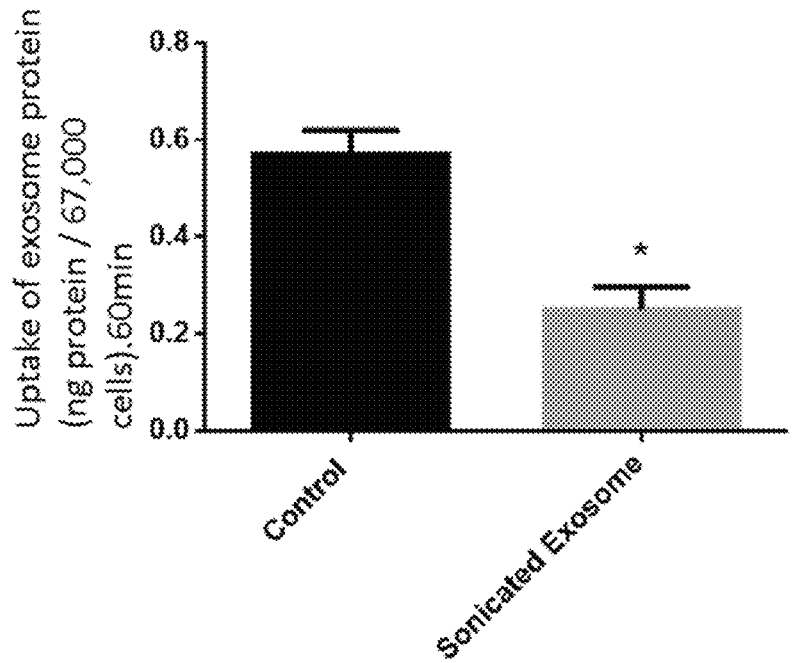

FIGS. 9A and 9B show the effect of sonication treatment on the uptake of exosomes in cells. FIG. 9A shows the uptake of non-sonicated and sonicated exosomes into Caco-2 cells. FIG. 9B shows the uptake of non-sonicated and sonicated exosomes into FH cells (n=3; *Different from control, $P<0.05$. Values are means±S.D).

Figure 10:
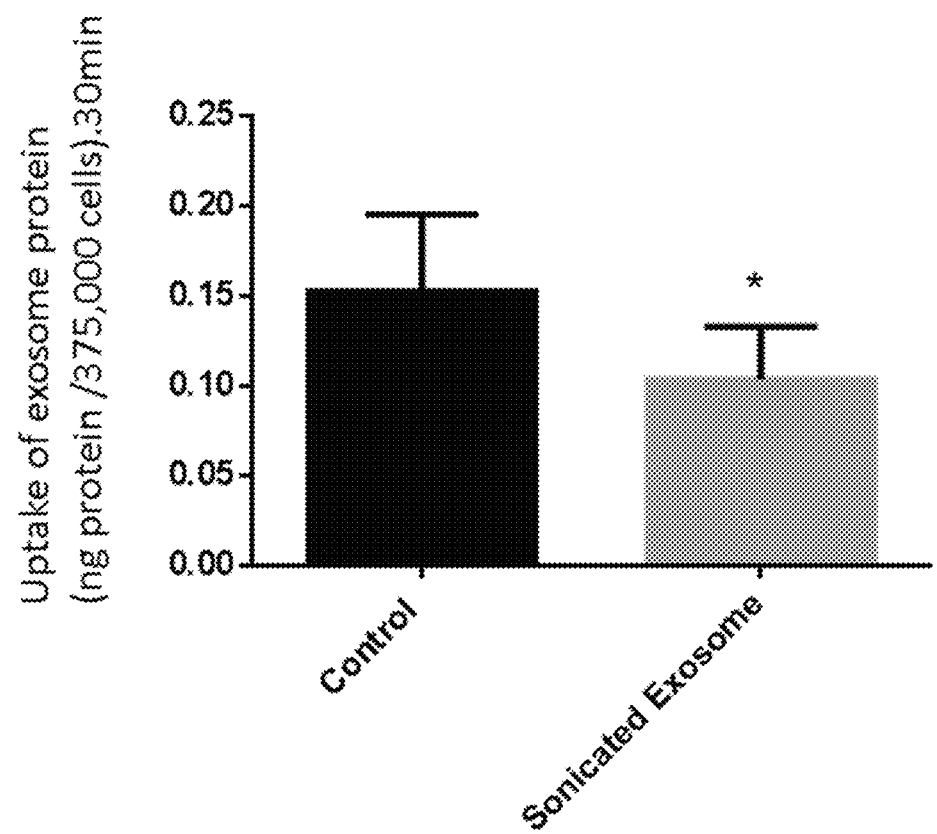

FIG. 10 shows the effect of sonication treatment on the uptake of exosomes in U937 cells (n=3). *Different from control, $P<0.05$. Values are means±S.D.

Figure 11A:
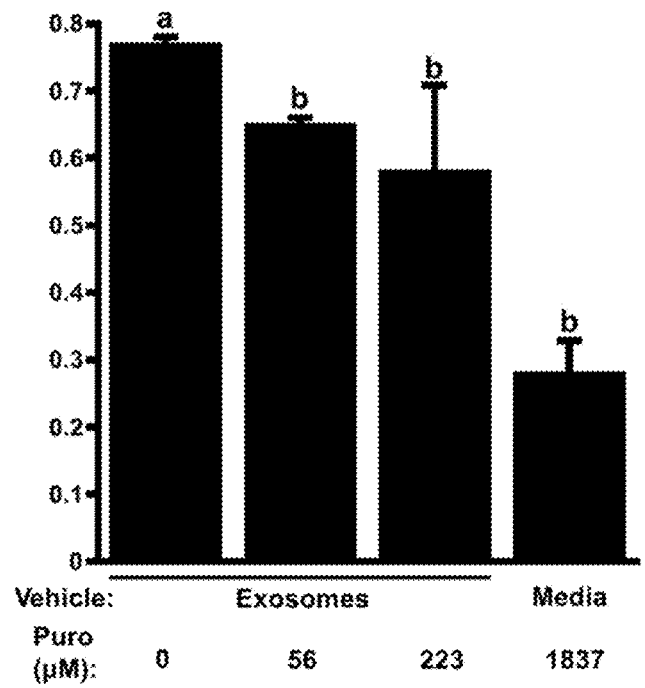
Figure 11B:
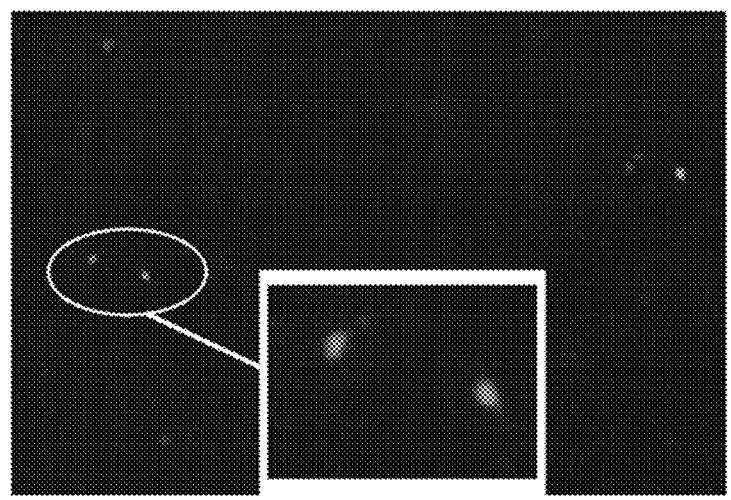

FIGS. 11A and 11B show the uptake of milk exosomes loaded with puromycin (Puro) or enhanced green fluorescent protein (eGFP) plasmid, respectively, into HUVEC cells. FIG. 11A shows the effects of puromycin-loaded milk exosomes on HUVEC survival. Cells were treated with puromycin-free exosomes (left bar), puromycin-loaded exosomes (middle bar), and free puromycin (right bar) ($^{a,b}$ $P<0.05$ for bars not sharing a common letter). FIG. 11B shows the expression of eGFP after 3 days of HUVEC culture with eGFP plasmid-loaded exosomes.

Figure 12A:
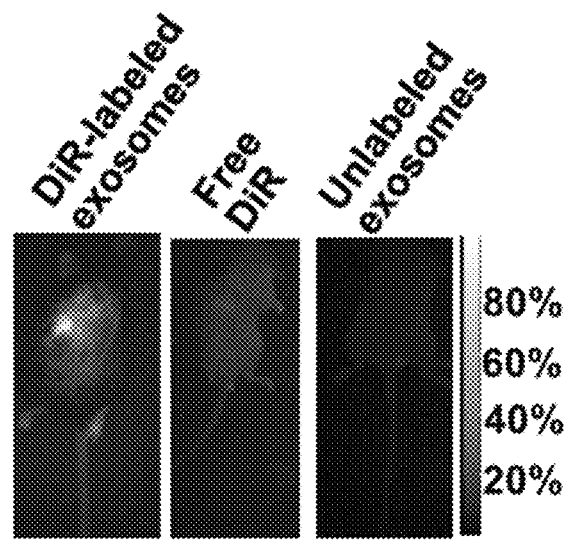
Figure 12B:
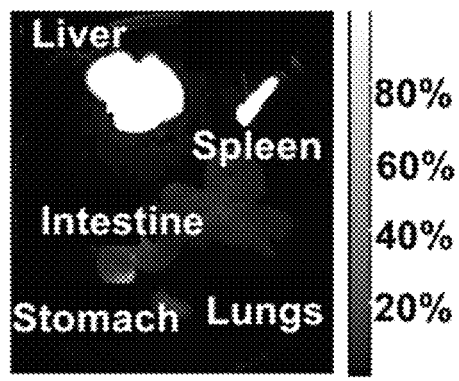

FIGS. 12A and B show uptake of milk exosomes loaded with puromycin (Puro) or enhanced green fluorescent protein (eGFP) plasmid, respectively. FIG. 12A shows the effects of puromycin-loaded milk exosomes on HUVEC survival. Cells were treated with puromycin-free exosomes (left bar), puromycin-loaded exosomes (middle bar), and free puromycin (right bar) (ab $P<0.05$ for bars not sharing a common letter). FIG. 12B shows expression of eGFP after 3 days of HUVEC culture with eGFP plasmid-loaded exosomes.

Figure 13A:
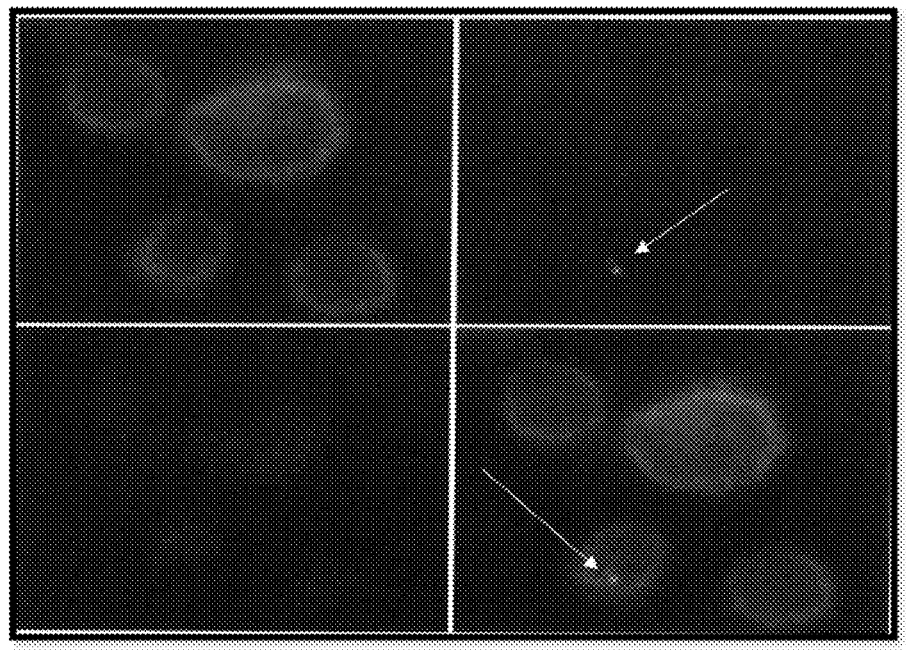
Figure 13B:
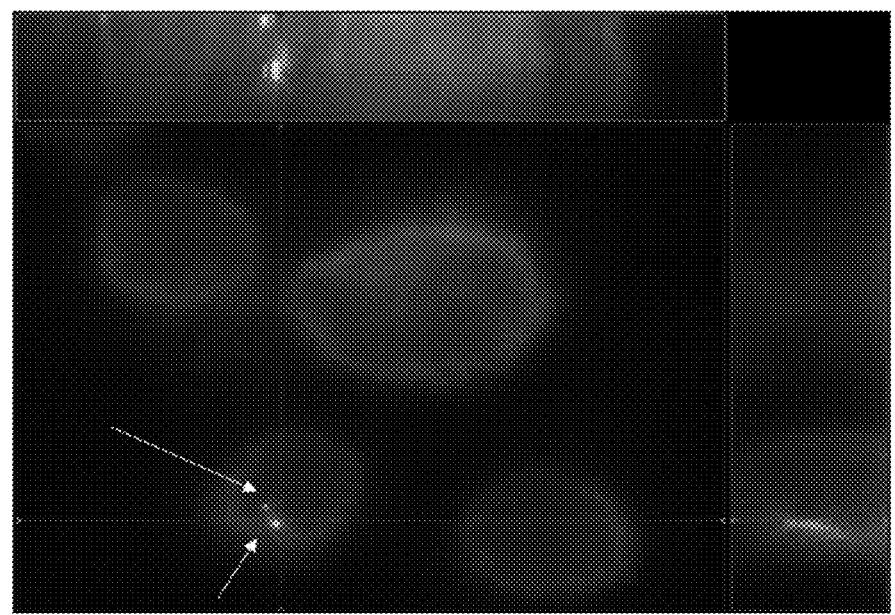

FIGS. 13A and B show super resolution microscopy results. The nuclei of the cell stained with Hoechst-blue, cytosol (f-Actin) with CF-594-red and milk exosomes with PKH-67-green. FIG. 13A shows a split image for only cells, only exosomes (top left and right panels, respectively), only nucleus and both exosomes and cells (bottom left and right panels, respectively). FIG. 13B is a orthogonal cross sectional image showing the presence of exosome in the cytosol after its uptake by the cells.

Figures 14A, 14B:
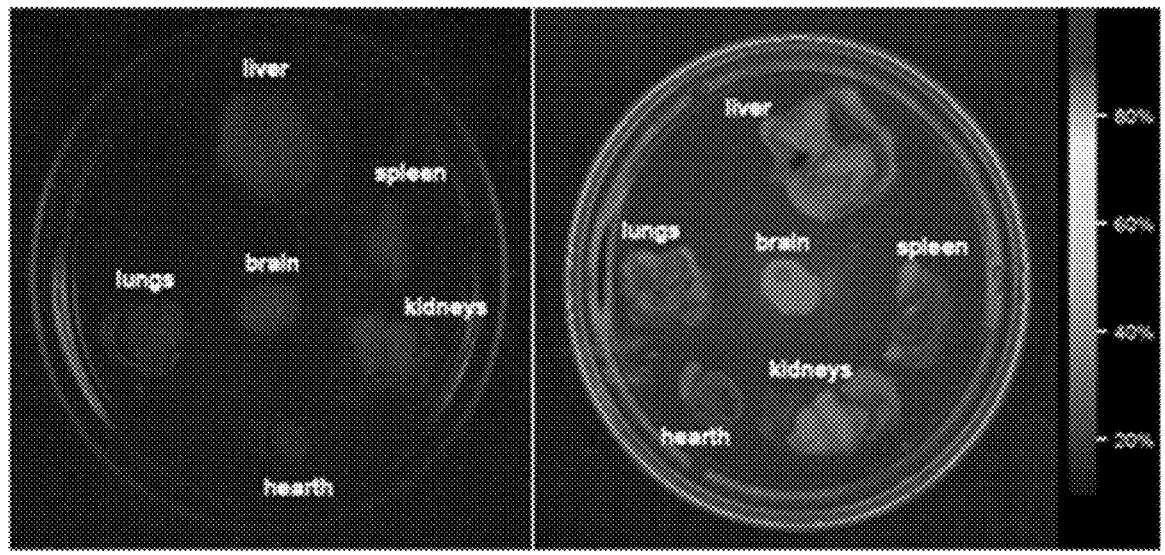
Figure 14C:
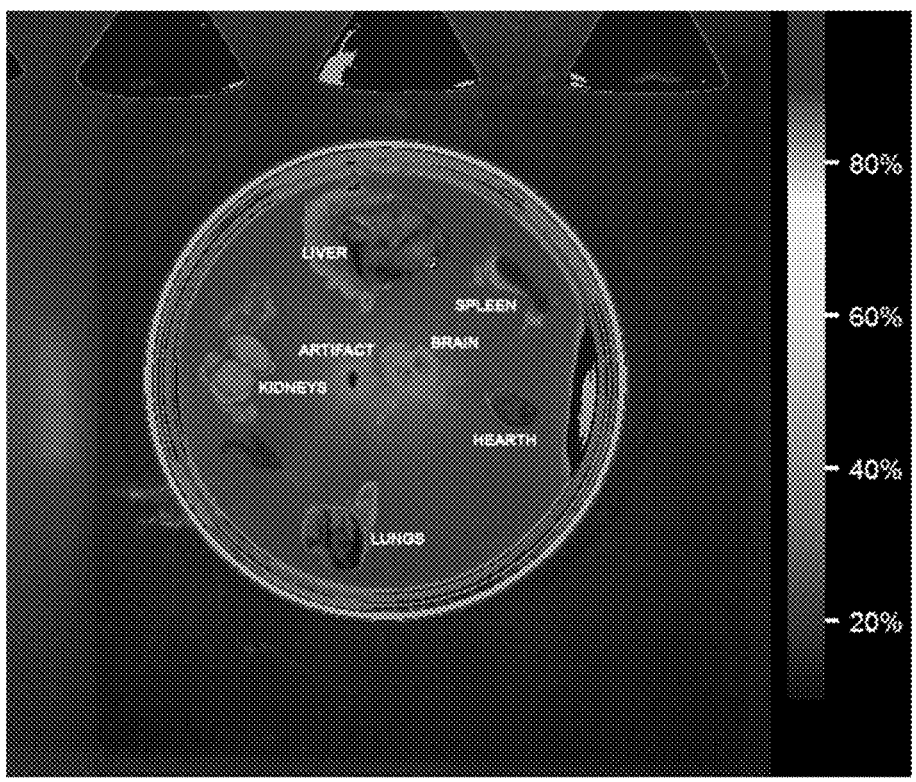

FIGS. 14A-C show DiR-labeled exosomes (FIG. 14A) and exo-GLOW red labeled RNA in exosomes (FIG. 14B) in excised tissues 12 hours after oral gavage. Also shown (FIG. 14C) are Exo– GLOW Red labeled RNA in exosomes in excised tissues 24 hours after oral gavage.

Figure 15:
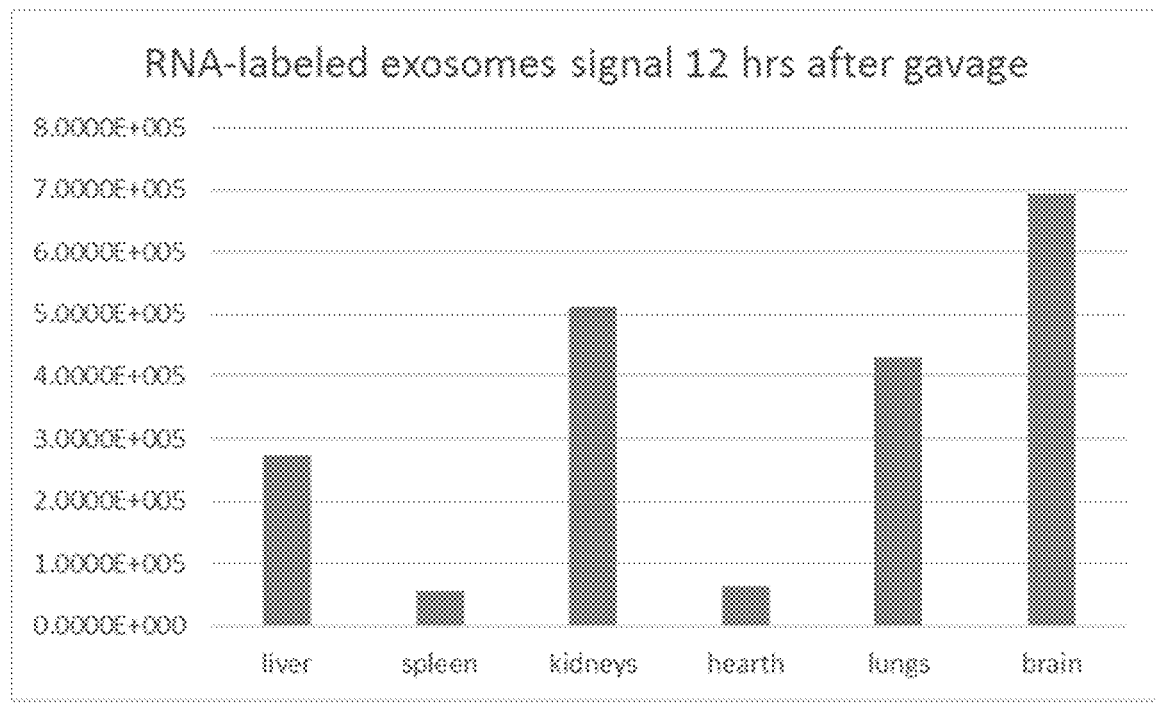

FIG. 15 is a graphical representation showing the signal density of Exo– GLOW Red labeled RNA in exosomes in excised tissues (liver, spleen, kidneys, heart, lungs, and brain) 12 hours after oral gavage.

Figure 16A:
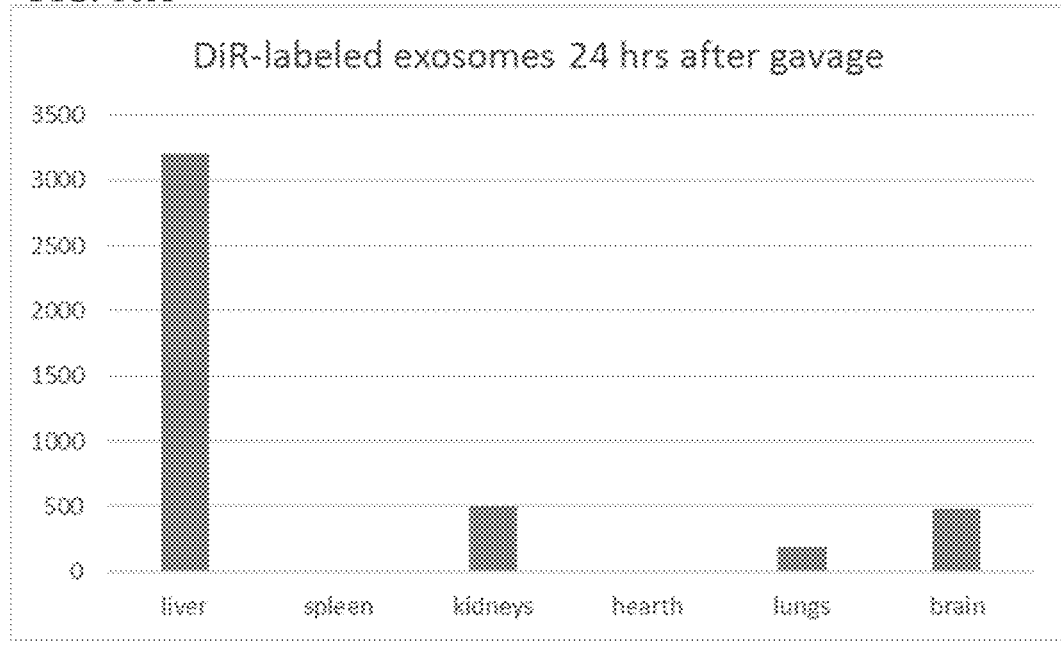

FIGS. 16A and B show DiR-labeled exosomes in excised tissues 24 hours after oral gavage (FIG. 16A) and Exo– GLOW Red labeled RNA in exosomes (FIG. 16B) in excised tissues 24 hours after gavage.

Figure 17:
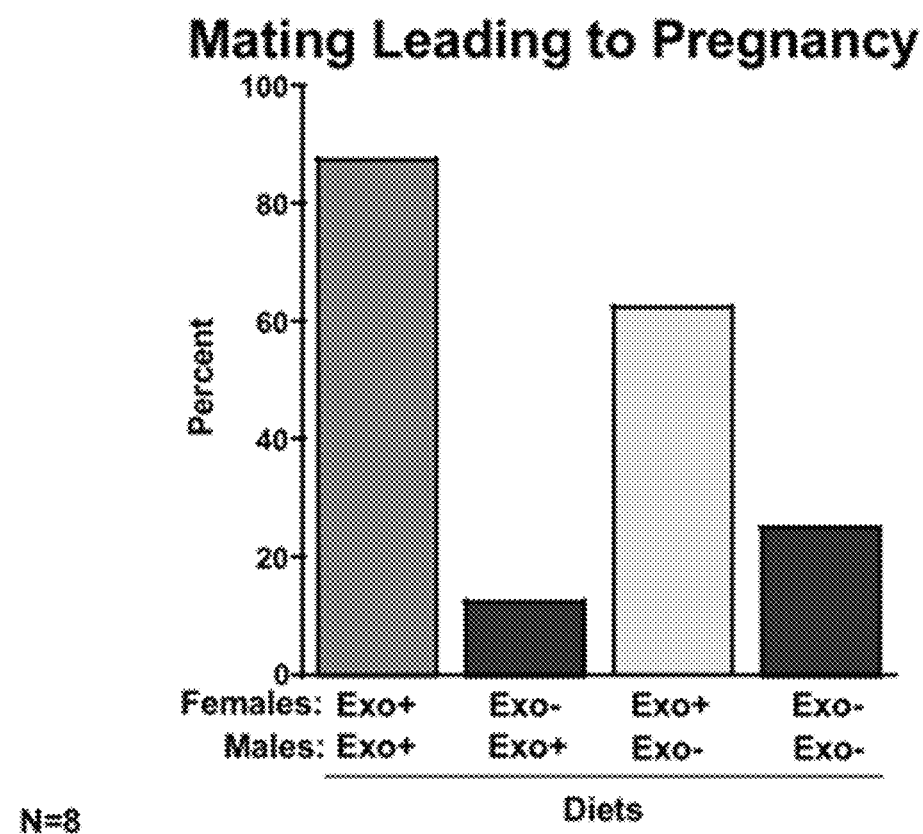

FIG. 17 shows the effects of exosome-defined diets on fertility in mice. Exosome-depleted (Exo–) diet mice had lower fertility than exosome-sufficient (Exo+) mice, particularly when both males and females were fed the Exo+ diet.

Figure 18:
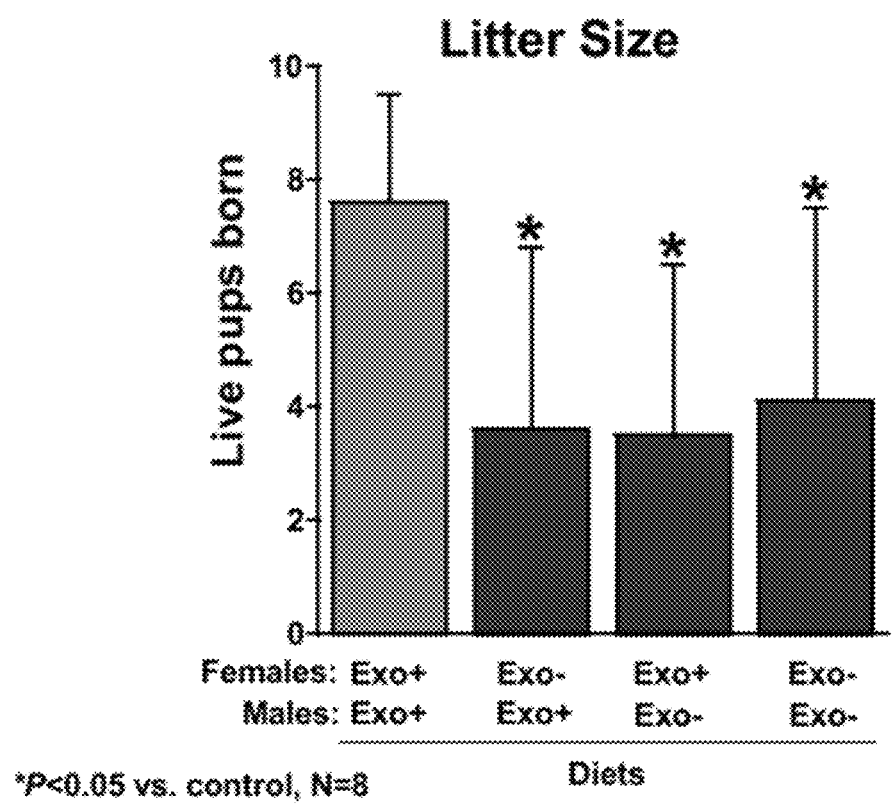

FIG. 18 shows the effects of Exo– and Exo+ diets on litter size in mice.

Figure 19:
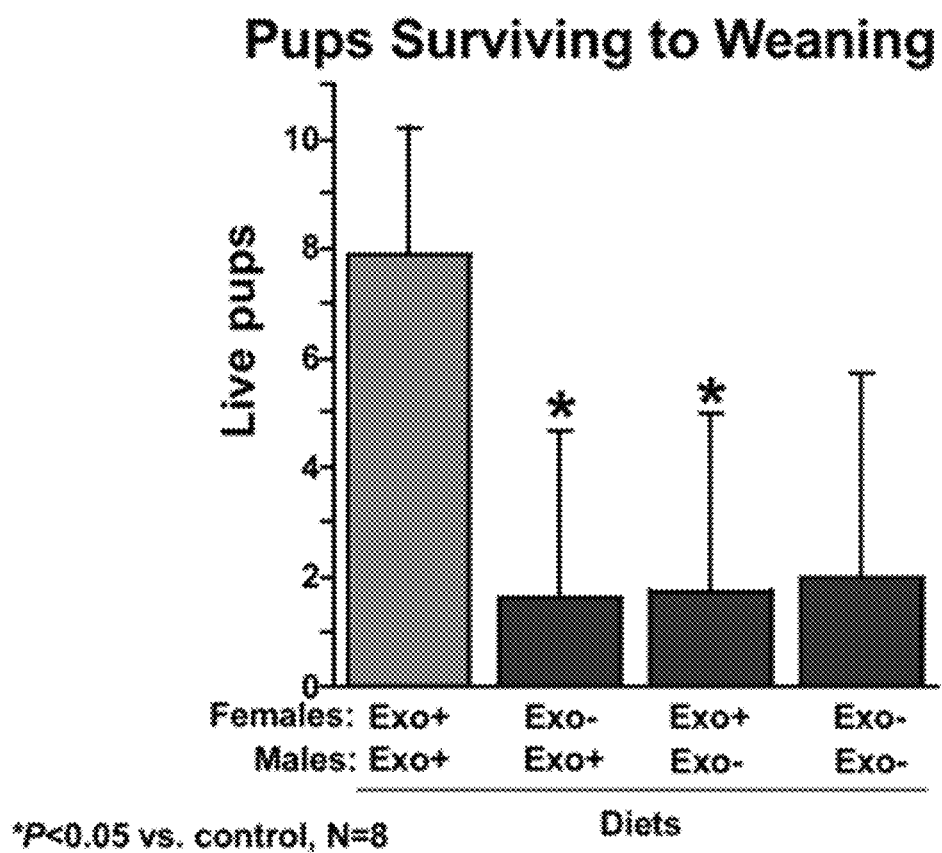

FIG. 19 shows the effects of Exo– and Exo+ diets on the survival of pups whose parents were fed exosome-defined diets.

FIGS. 20A-E show that hepatic concentrations of amino acids were up to 1800% higher in mice fed an exosome-depleted (Exo–) diet compared with mice fed an exosome-sufficient (Exo+) diet (control) for 4 weeks. N=8, *p<0.05 vs. Exo+. FIG. 20A shows the abundance of leucine in mice fed the Exo– versus Exo+ diet. FIG. 20B shows the abundance of phenylalanine in mice fed the Exo– versus Exo+ diet. FIG. 20C shows the abundance of alanine in mice fed the Exo– versus Exo+ diet. FIG. 20D shows the abundance of leucine-lysine dipeptide metabolite in mice fed the Exo– versus Exo+ diet. FIG. 20E shows the abundance of glutamyl-isoleucine dipeptide metabolite in mice fed the Exo– versus Exo+ diet.

Figure 21A:
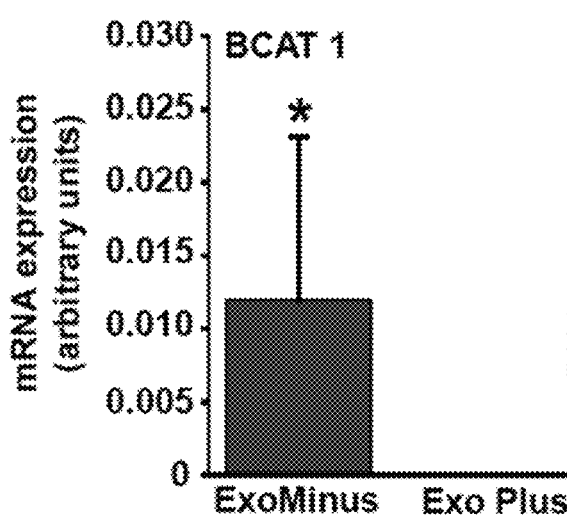
Figure 21B:
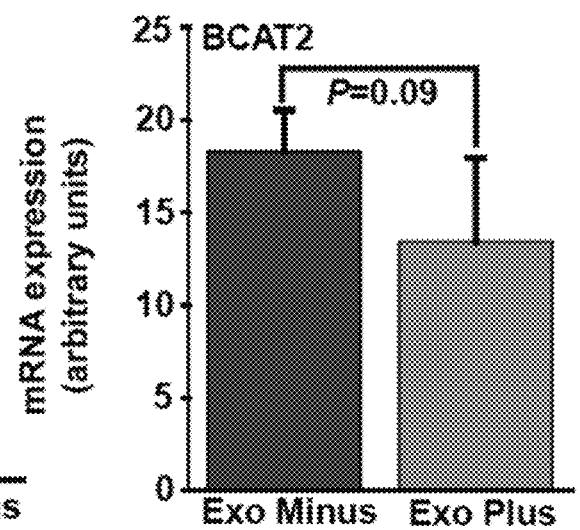

FIGS. 21A and 21B show that the mRNA expression of branched chain amino acid (BCAA) transporter 1 (cytoplasm, BCAT1, FIG. 21A) and BCAA transporter 2 (mitochondria, BCAT2, FIG. 21B) was greater in mice fed an Exo– diet compared to mice fed an Exo+ (n.s. for BCAT2). Expression of BCAA transporter mRNAs is shown in livers of C57BL/6 mice fed an Exo– or Exo+ (control) diet for 4 weeks. N=8, *p<0.05 vs. Exo+.

Figure 22:
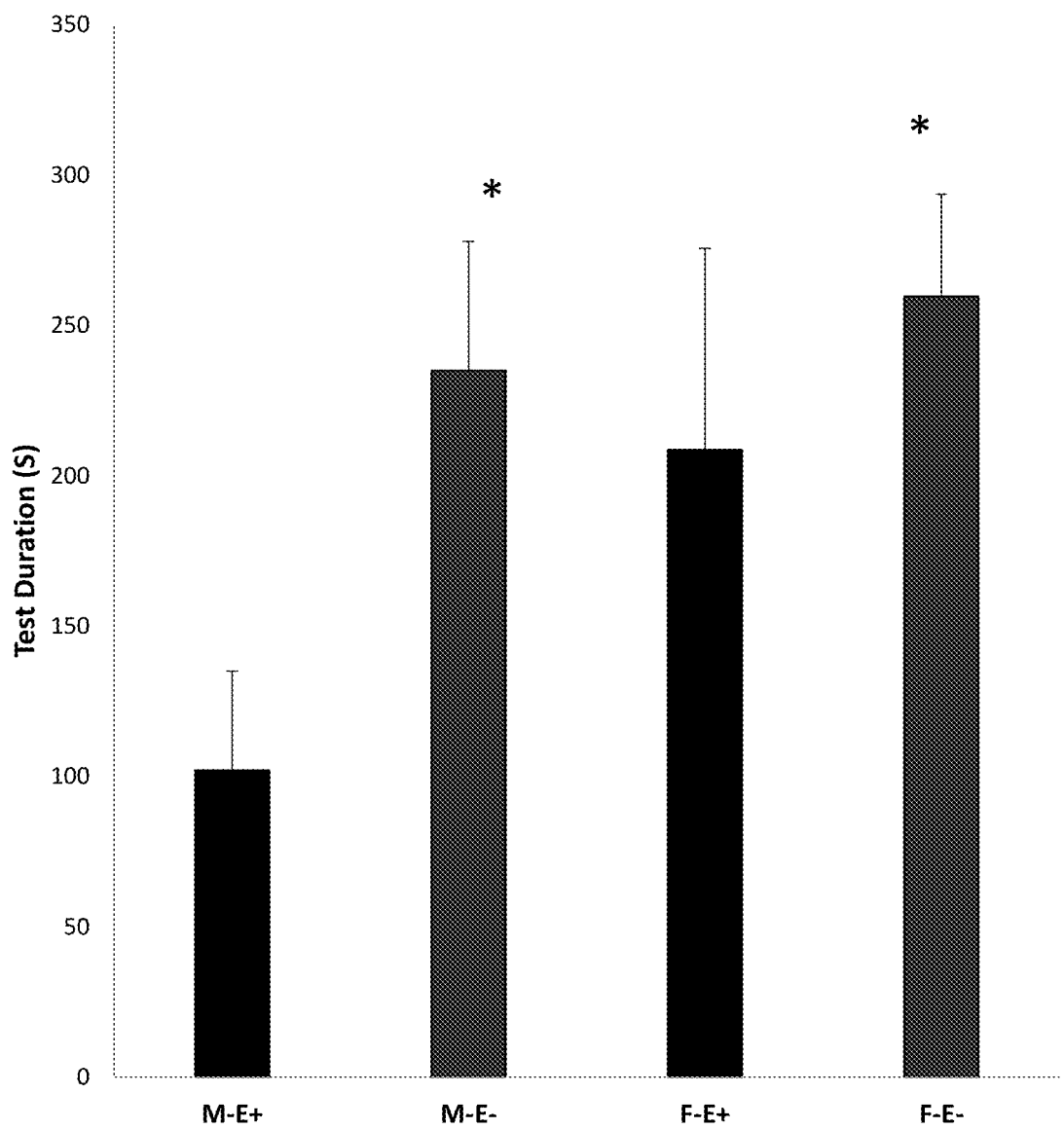

FIG. 22 shows latency to enter the escape hole in a Barnes maze by C57BL/6 mice fed bovine milk exosome-defined diet. Shown are Mean±SEM. N=5 per group. *p<0.05 vs. E+. Abbreviations: F, female; M, male; E+, Exo+ fed mice; Exo–, Exo– fed mice.

Figure 23:
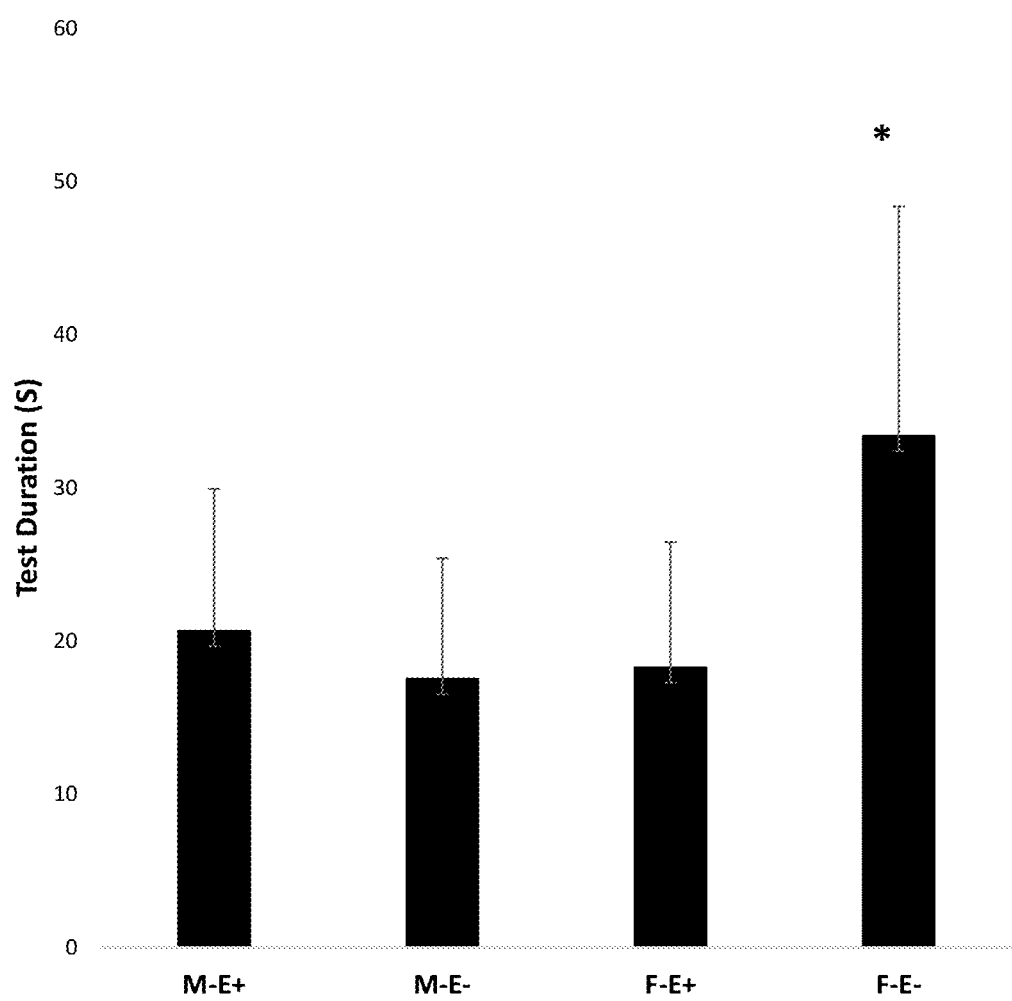

FIG. 23 shows latency to locate the escape platform in a Morris water maze by C57BL/6 mice fed bovine milk exosome-defined diet. Shown are Mean±SEM. N=5 per group. *p<0.05 vs. E+. Abbreviations: F, female; M, male; E; Exo+ fed mice; Exo–, Exo– fed mice.

Figure 24:
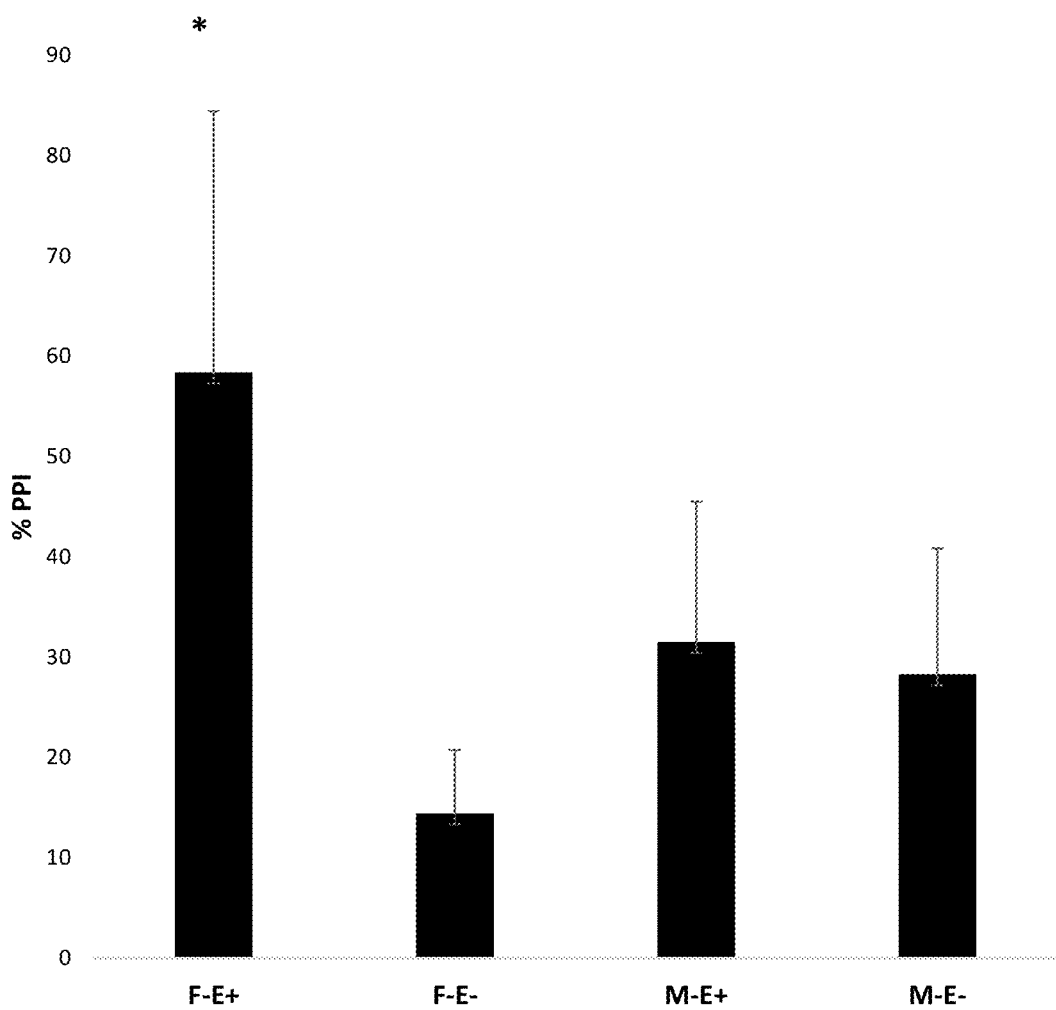

FIG. 24 shows effects of bovine milk exosome-defined diet on Prepulse inhibition (PPI) in C57BL/6 mice (68 dB prepulse intensity, 105 dB startle intensity). Shown are Mean±SEM. N=5 per group. *p<0.05 vs. E+. Abbreviations: F, female; M, male; E; Exo+ fed mice; Exo–, Exo– fed mice.

Figure 25:
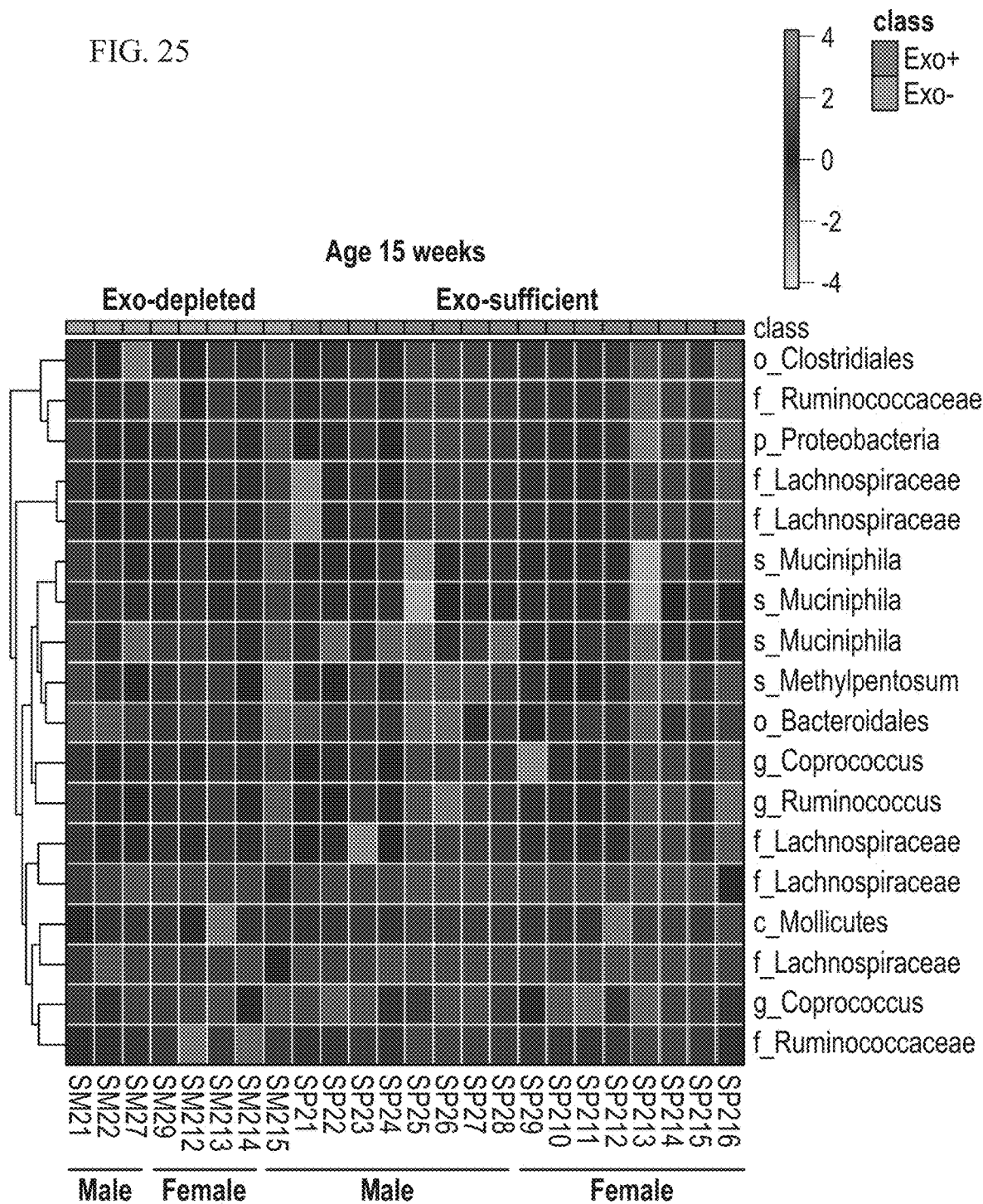

FIG. 25 shows different abundance of Operational Taxonomic Units (OTUs) in mice fed exosome-defined diets at age 15 weeks. For example, the relative abundance of Firmicute classes Clostridia (Ruminococcaceae) and Verrucomicrobia classes Verrucomicrobiae (Muciniphila) were greater in mice fed Exo– compared with Exo+ at age 15 weeks, whereas the relative abundance of Firmicute classes Clostridia (Clostridiales) was smaller in mice fed Exo– compared with Exo+ at age 45 weeks (see FIG. 26).

Figure 26:
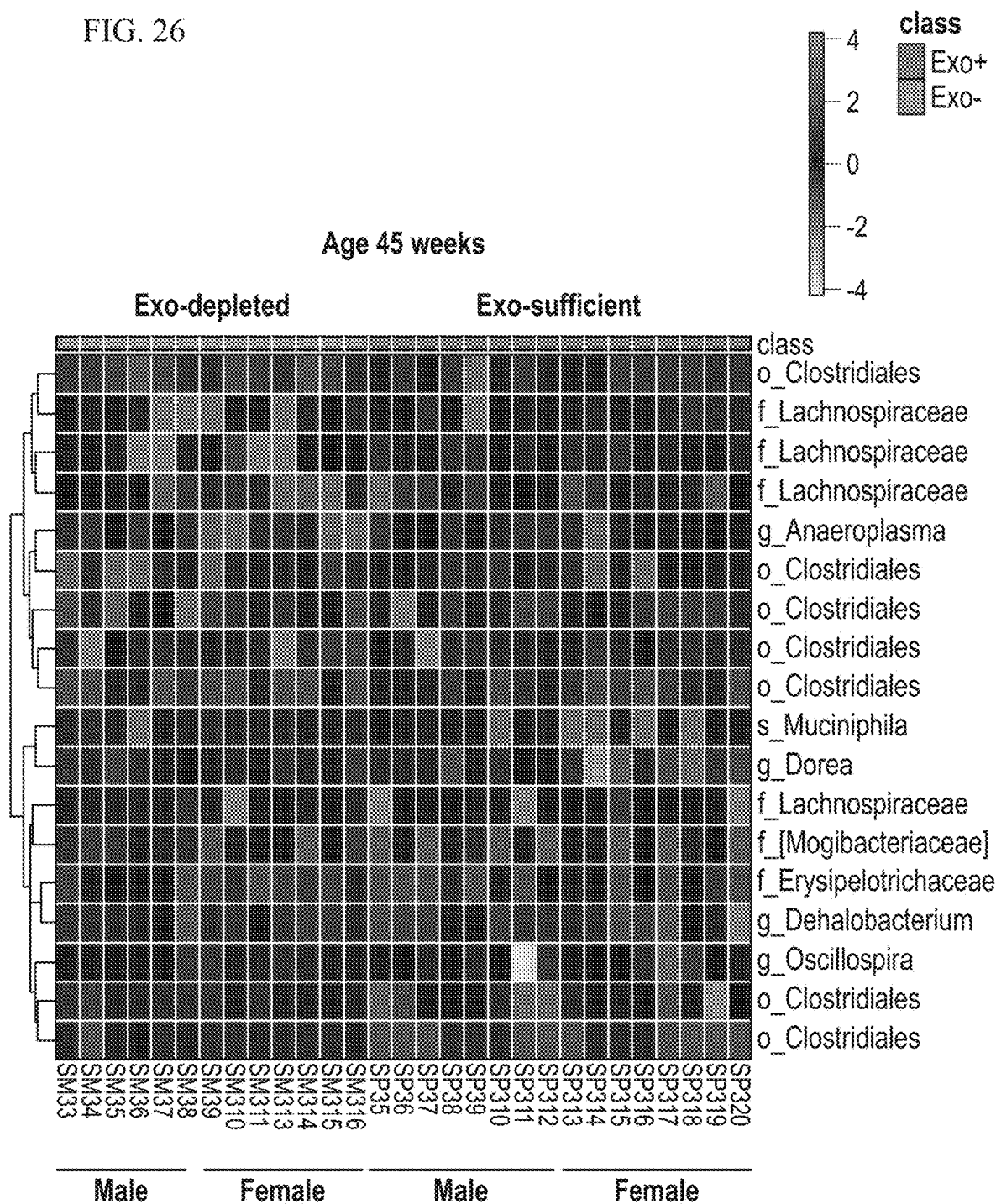

FIG. 26 shows different abundance of OTUs in mice fed exosome-defined diets at age 45 weeks.

Figure 27:
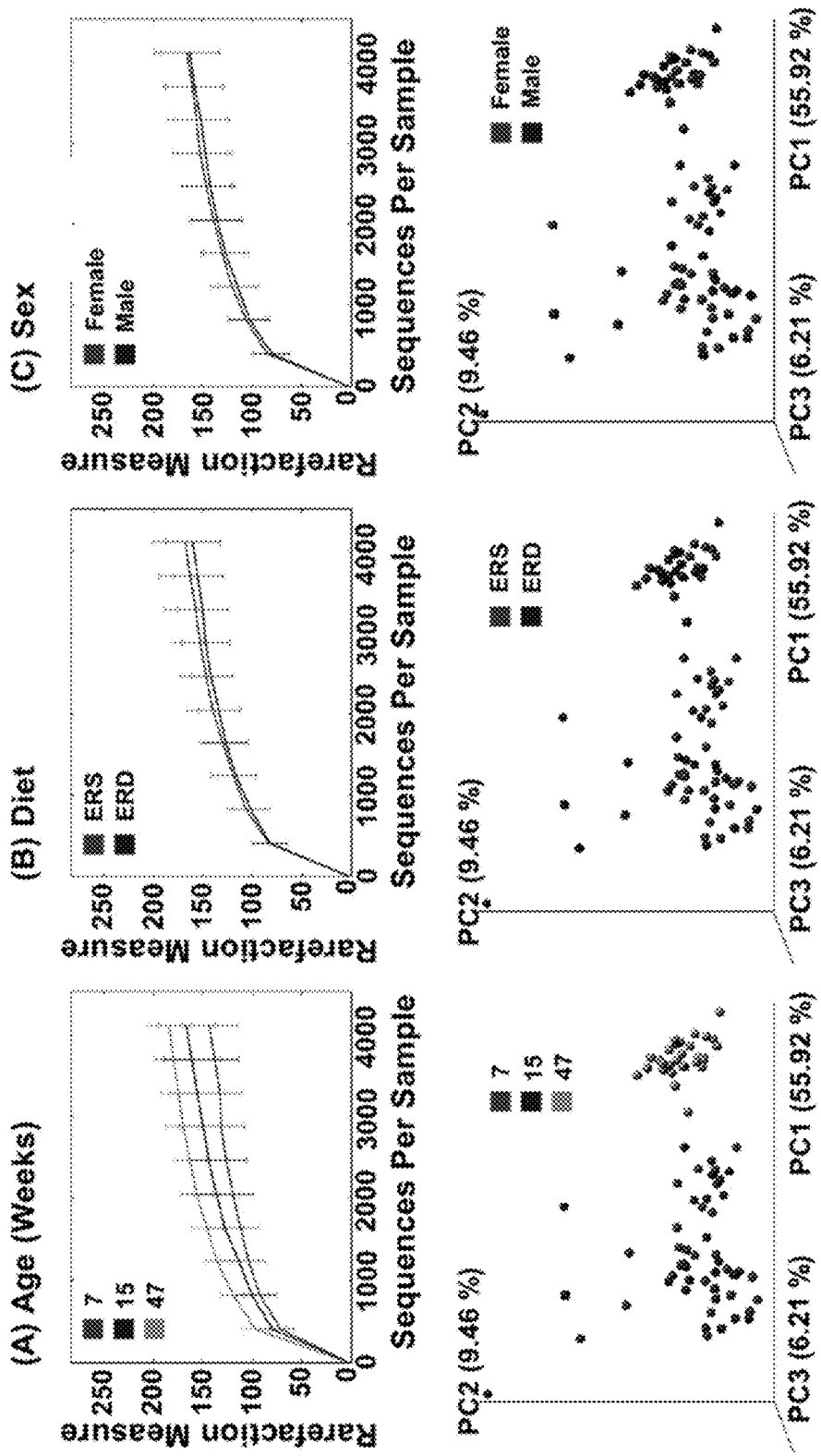

FIG. 27 shows alpha diversity (Chao1) and Beta diversity (Principal Coordinates Analysis) in the cecum of mice fed exosome RNA-sufficient (ERS) or exosome RNA-depleted (ERD) diets at ages 7, 15 and 47 weeks.

Figure 28:
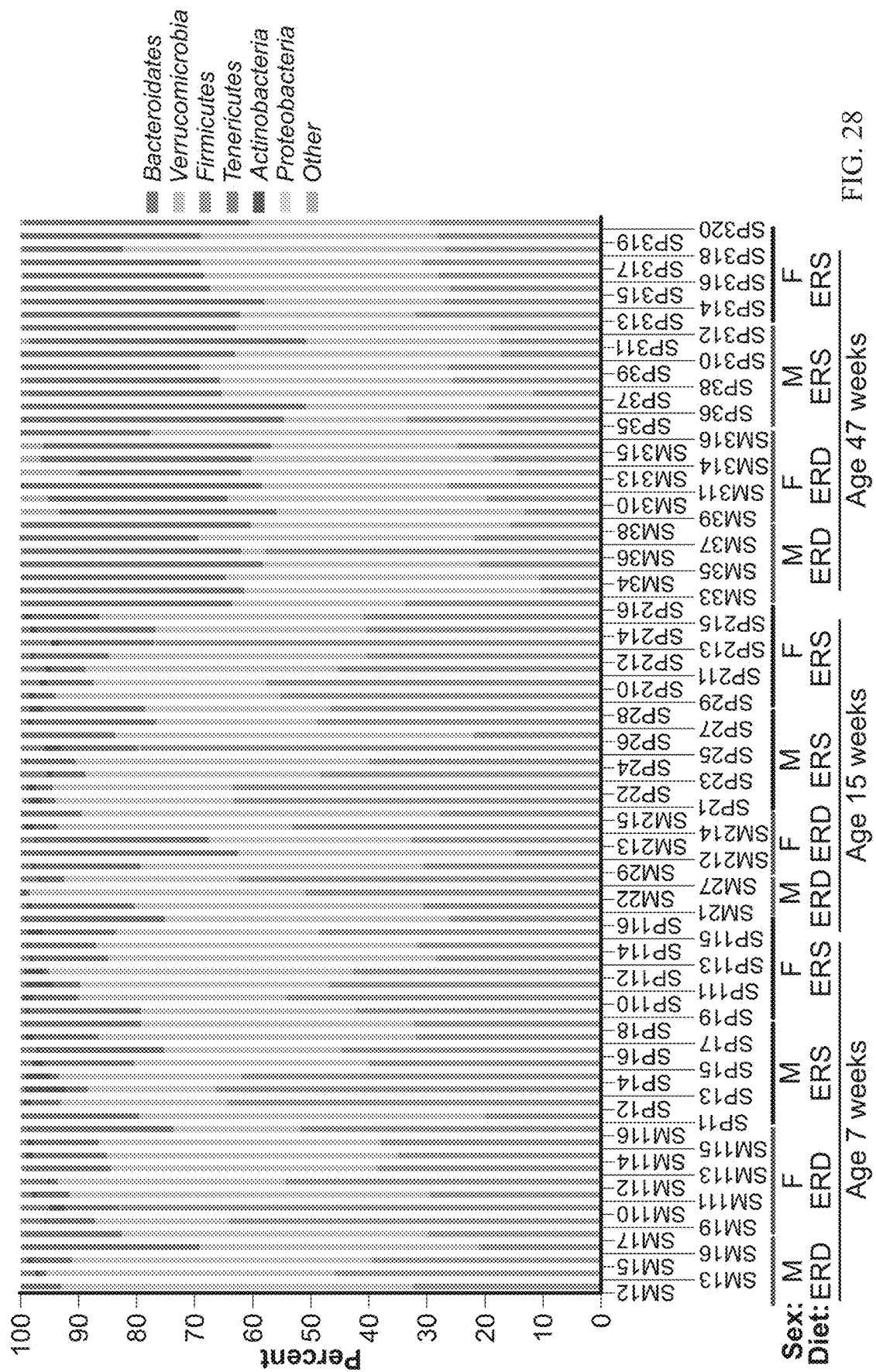

FIG. 28 shows microbial phyla in the cecum of mice fed exosome RNA-sufficient (ERS) or exosome RNA-depleted (ERD) diets at ages 7, 15 and 47 weeks. Values represent average percent relative abundance across all samples. F, female; M, male.

Figure 29:
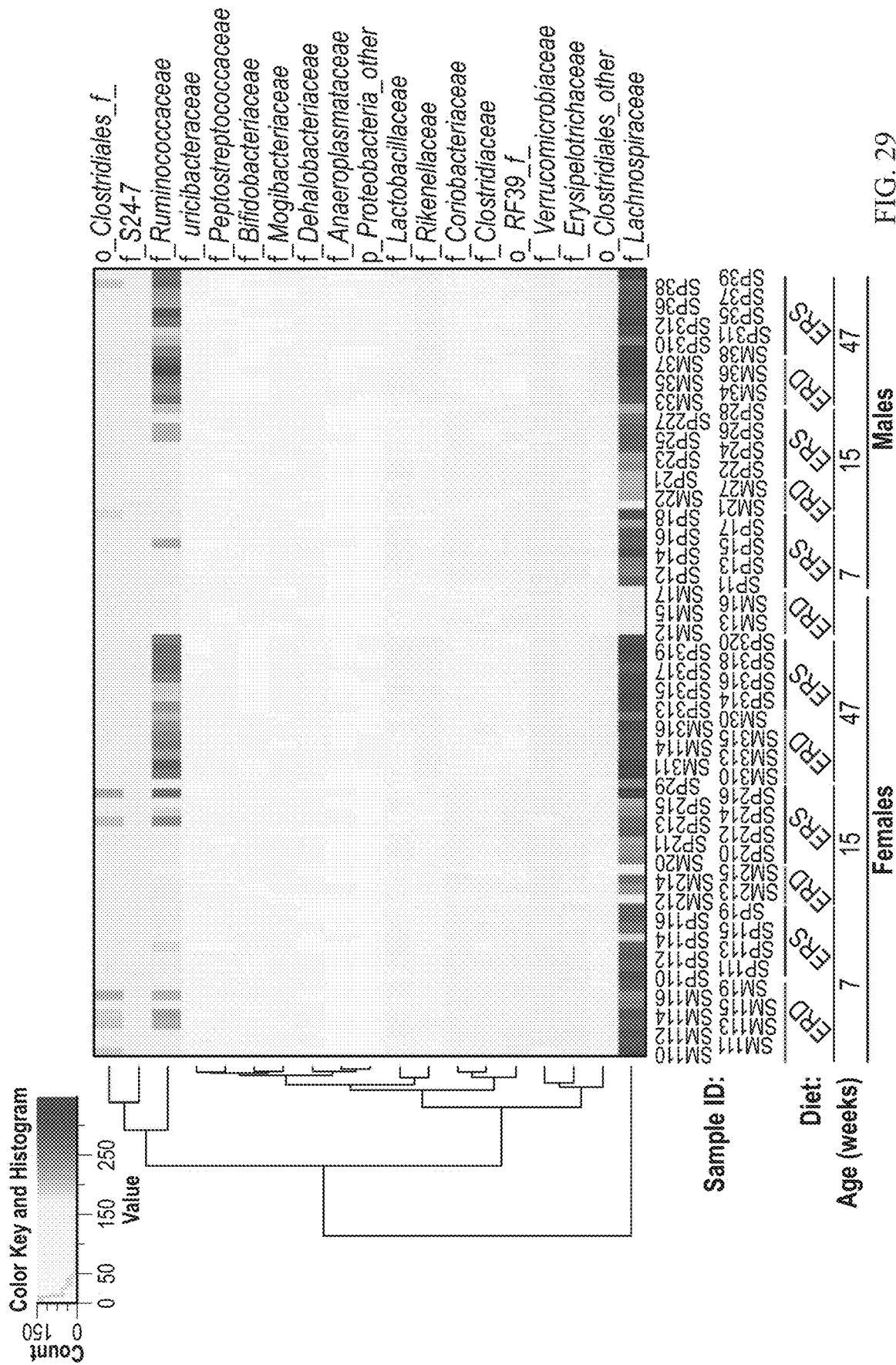

FIG. 29 shows microbial families in the cecum of mice fed exosome RNA-sufficient (ERS) or exosome RNA-depleted (ERD) diets at ages 7, 15 and 47 weeks. o, order; f, family; p, phylum.

Figure 30:
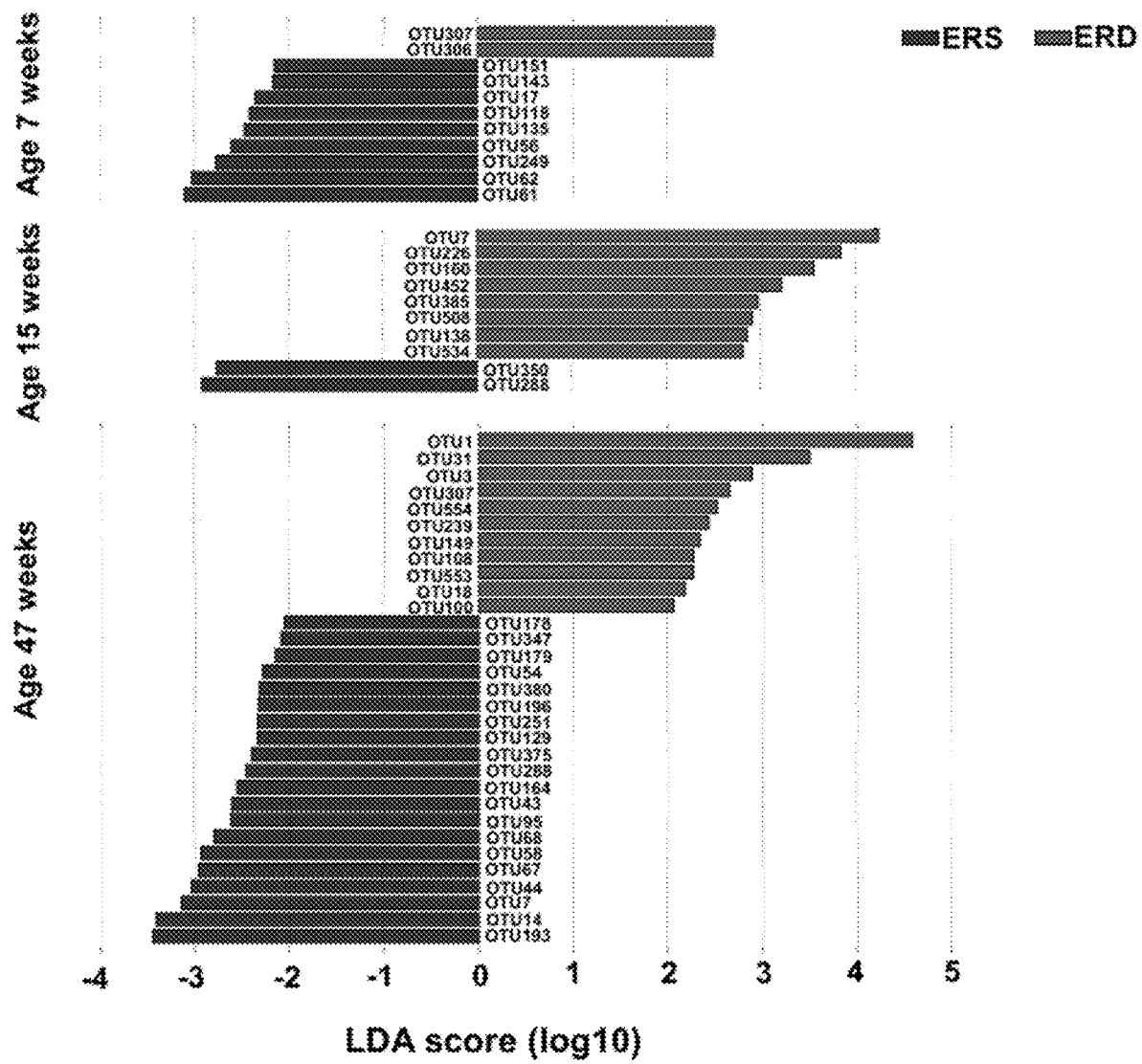

FIG. 30 shows microbial operational taxonomic units (OTUs) in the cecum of mice fed exosome RNA-sufficient (ERS) or exosome RNA-depleted (ERD) diets at ages 7, 15 and 47 weeks. Effects of diet were statistically significant (P<0.05), if the log score in the linear discriminant analysis (LDA) was greater than 2.

Figure 31:
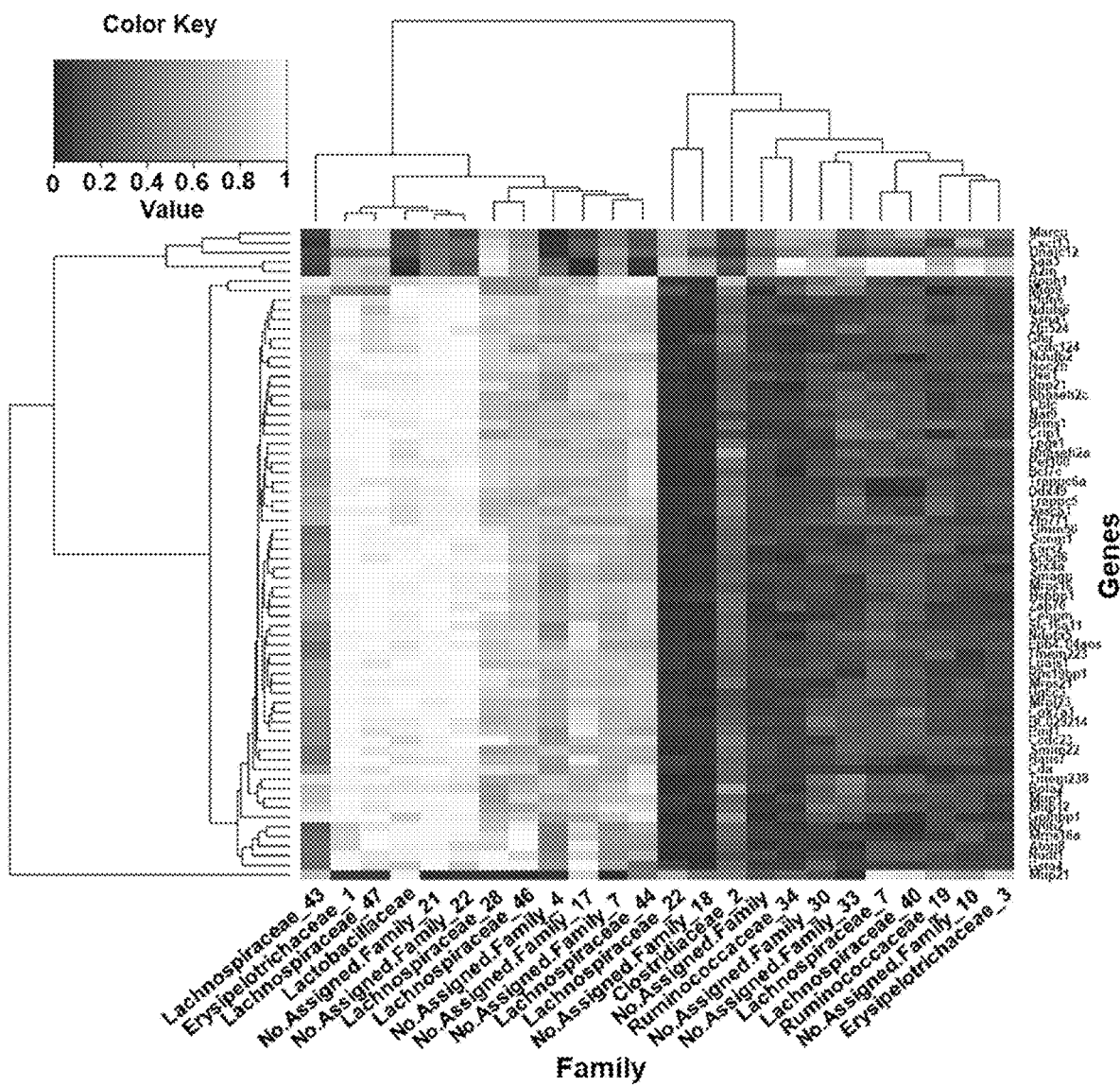

FIG. 31 shows the correlation between changes in OTUs with changes in the hepatic transcriptome in female mice, age 15 weeks fed exosome RNA-sufficient (ERS) or exosome RNA-depleted (ERD).

Figure 32:
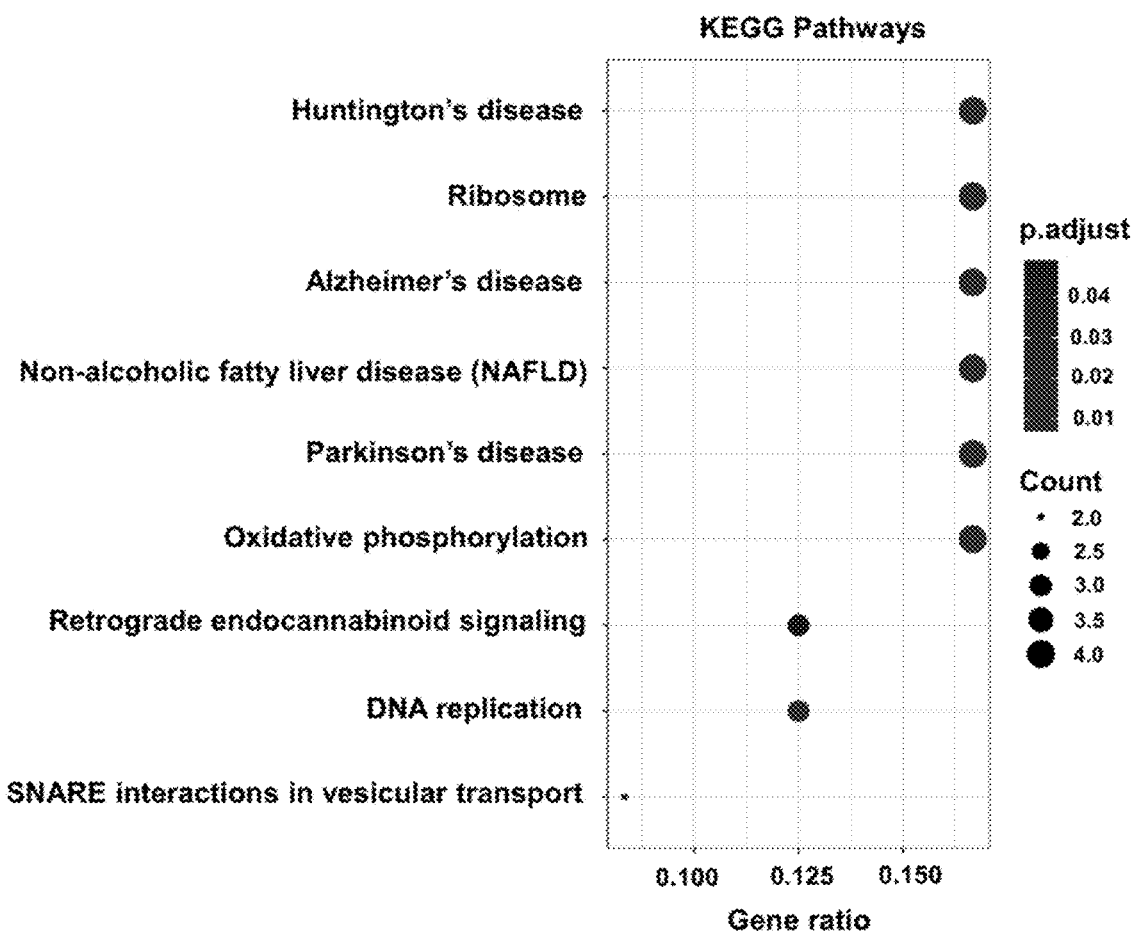

FIG. 32 shows KEGG pathway analysis for metabolic functions that are enriched in the hepatic transcriptome in female mice, age 15 weeks fed exosome RNA-sufficient (ERS) or exosome RNA-depleted (ERD).

Figure 33A:
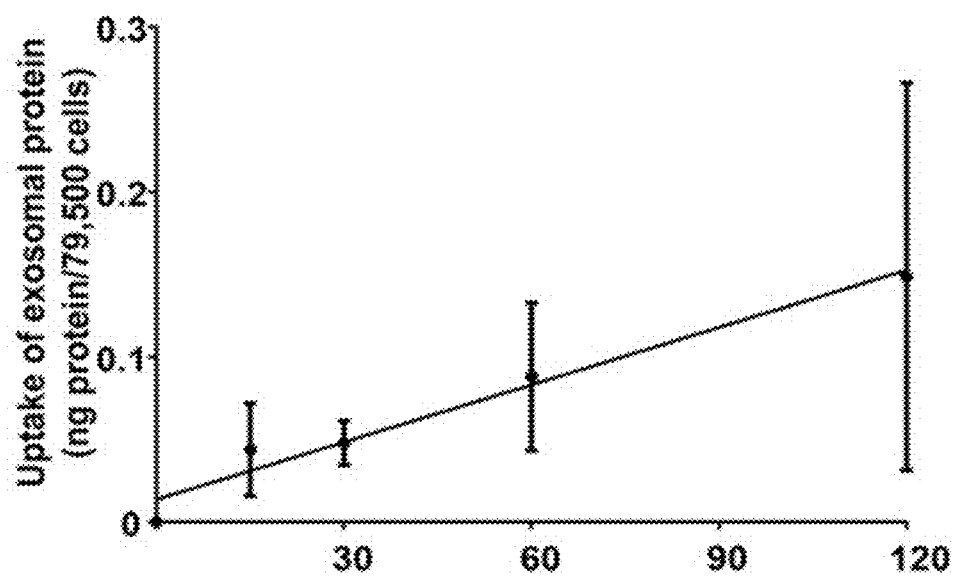
Figure 33B:
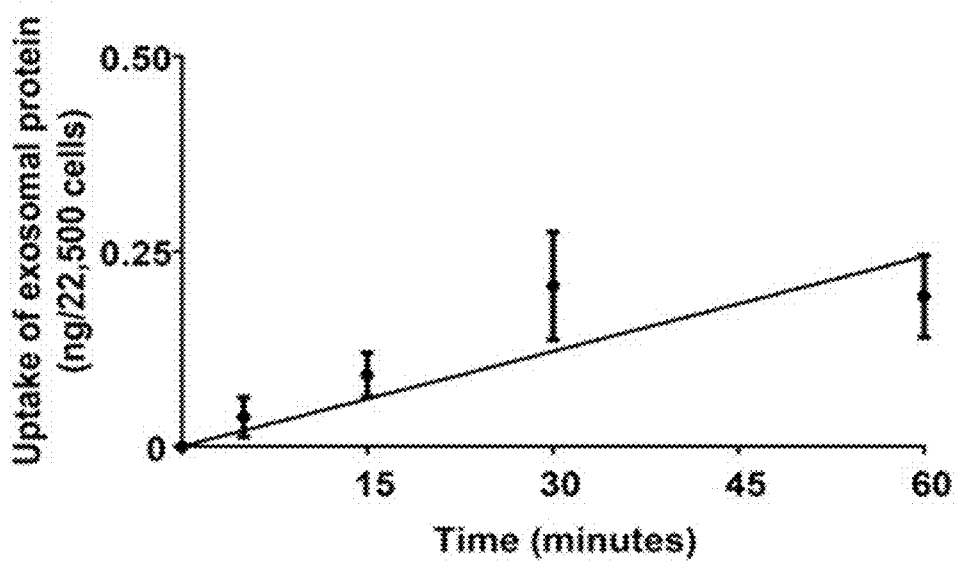

FIGS. 33 and 33B show time courses of bovine exosome uptake in Caco-2 cells and IEC-6 cells. FIG. 33A shows exosome uptake into human colon carcinoma Caco-2 cells as a function of time at a concentration of 110 mg exosome protein/200 mL media and a temperature of 37° C. (n=6). FIG. 33B shows exosome uptake into rat primary intestinal IEC-6 cells as a function of time at a concentration of 55 mg exosome protein/200 mL media and a temperature of 37° C. (n=3). Values are means 6 SDs.

Figure 34A:
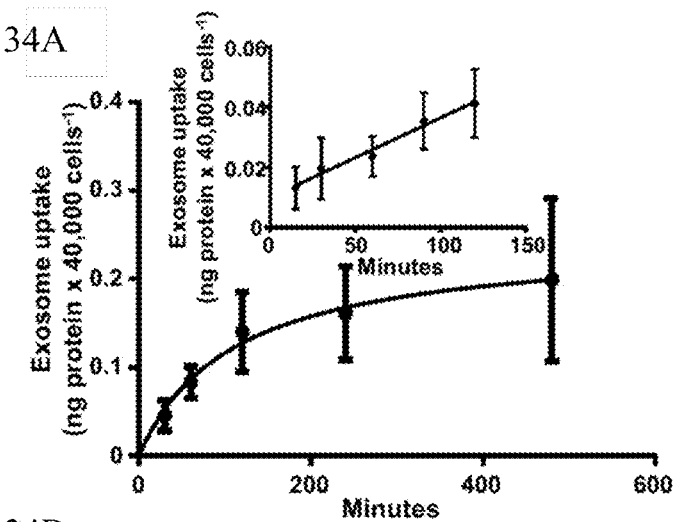
Figure 34B:
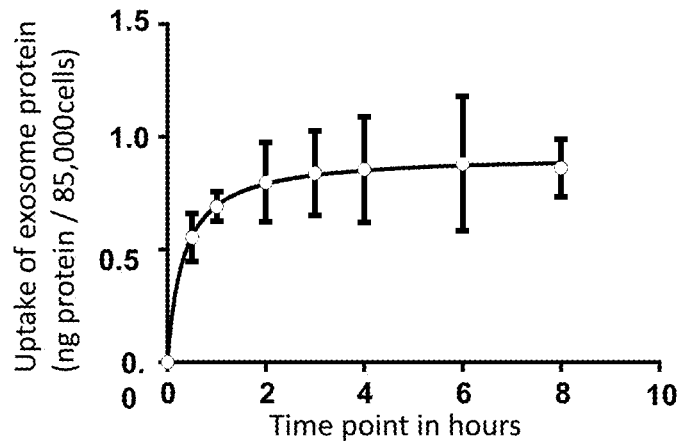
Figure 34C:
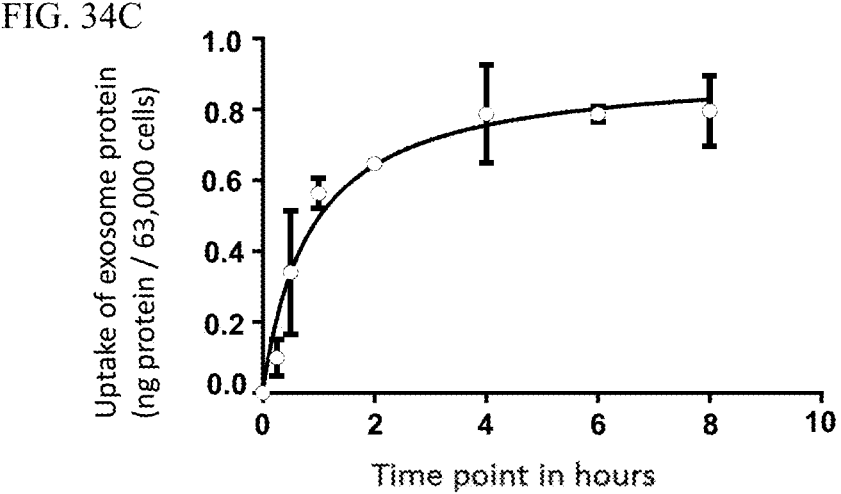

FIGS. 34A-34C show temporal kinetics of milk exosome uptake in mammalian cells. FIG. 34A shows the uptake of exosomes into human umbilical vein endothelial cells (HUVECs) over 480 minutes (4 hours) using 20 µg exosome protein/200 µl of media. The insert in FIG. 34A illustrates the temporal pattern for 120 min (2 hours): y=0.0003x+0.009, R 2=0.98. FIG. 34B shows a milk exosome uptake study in Caco-2 cells over the course of 8 hours in which N=3; p<0.05. FIG. 34C shows an exosome uptake study in human small intestinal cells (FHs cells) over the course of 8 hours.

Figure 35A:
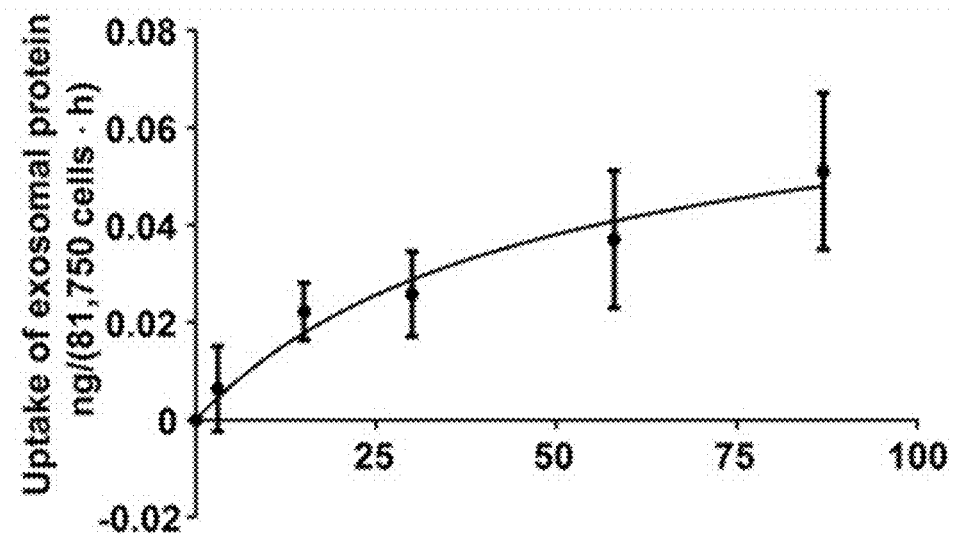
Figure 35B:
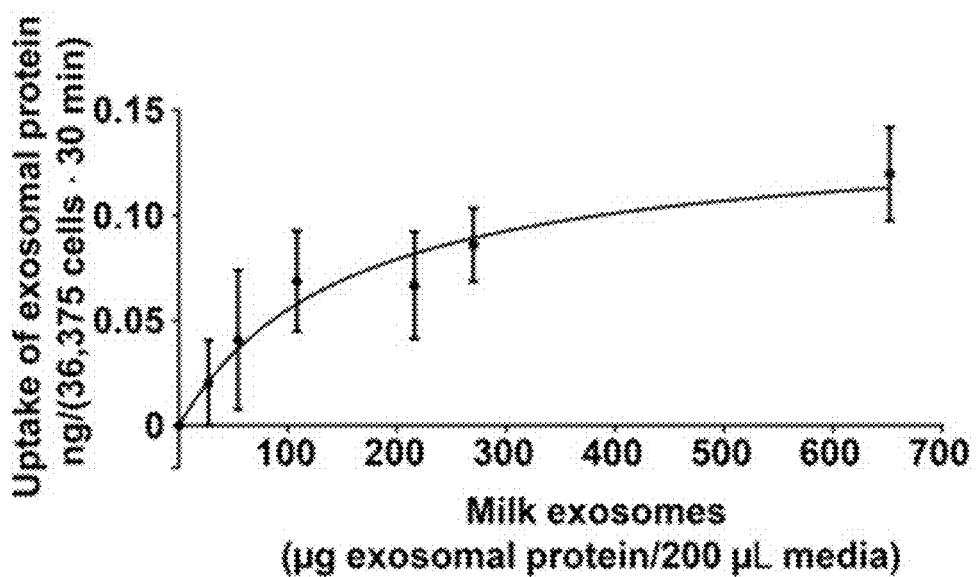

FIGS. 35A and 35B show saturation kinetics of bovine exosome transport in intestinal cells. FIG. 5A shows exosome uptake into human colon carcinoma Caco-2 cells as a function of substrate concentration at 37° C. (n=5). FIG. 5B shows exosome uptake into rat primary small intestinal IEC-6 cells as a function substrate concentration at 37° C. (n=3). Values are means 6 SDs.

Figure 36A:
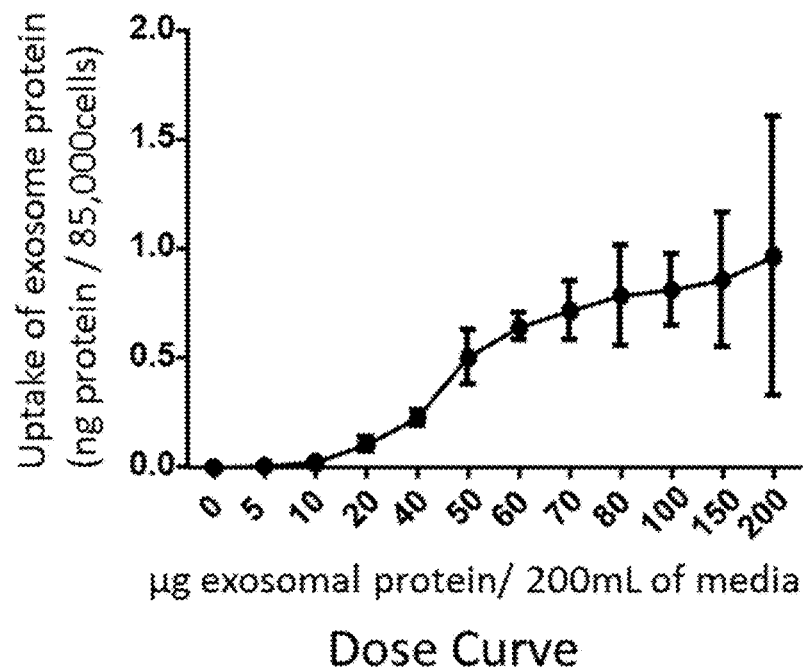
Figure 36B:
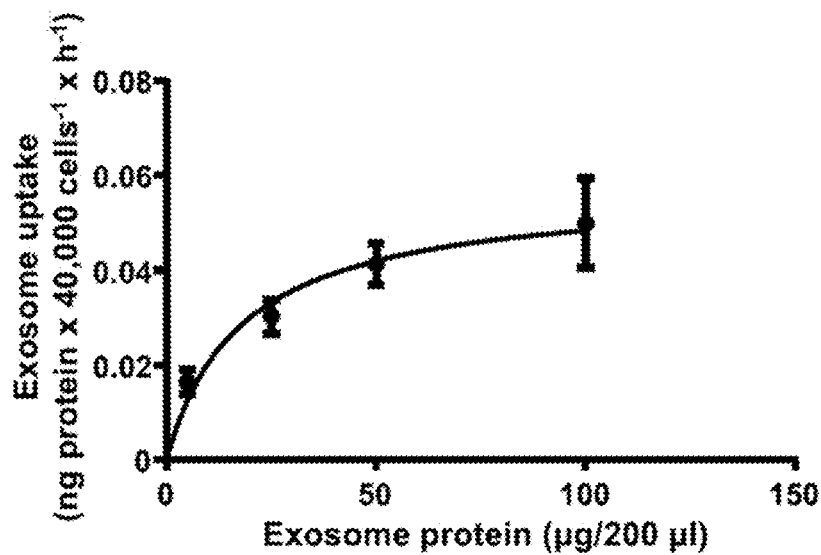

FIGS. 36A and 36B show saturation kinetics of milk exosome uptake in CaCo2 and HUVEC cells, respectively. FIG. 36A shows exosome uptake into human colon carcinoma Caco-2 cells as a function of substrate concentration at 37° C. (N=3; p<0.05). FIG. 36B shows exosome uptake into human umbilical vein endothelial cells as a function of substrate concentration at 37° C.

Figure 37A:
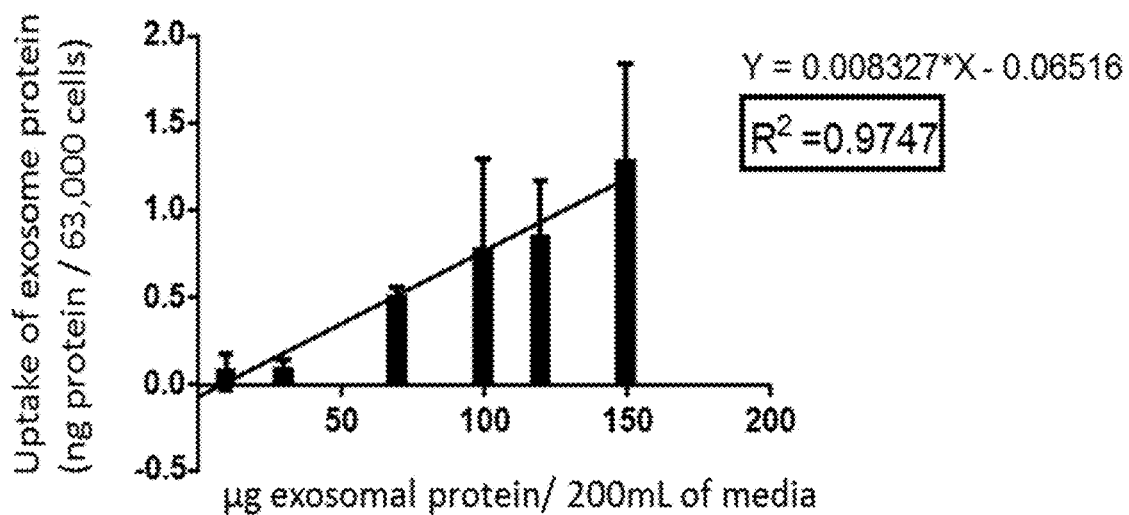
Figure 37B:
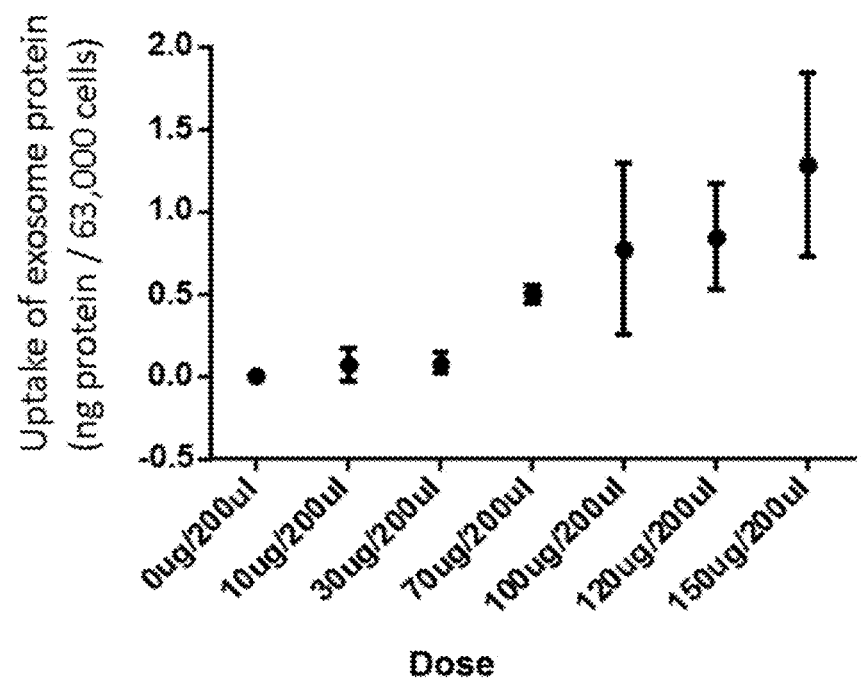

FIGS. 37A and 37B show saturation kinetics of milk exosome uptake in human small intestinal cells (FHs cells). FIG. 37A shows exosome uptake into FH cells as a function of substrate concentration at 37° C. (Y=0.008327*X−0.06516; $R^2$=0.9747). FIG. 37B shows another graphical representation of the experiment shown in FIG. 37A.

Figure 38:
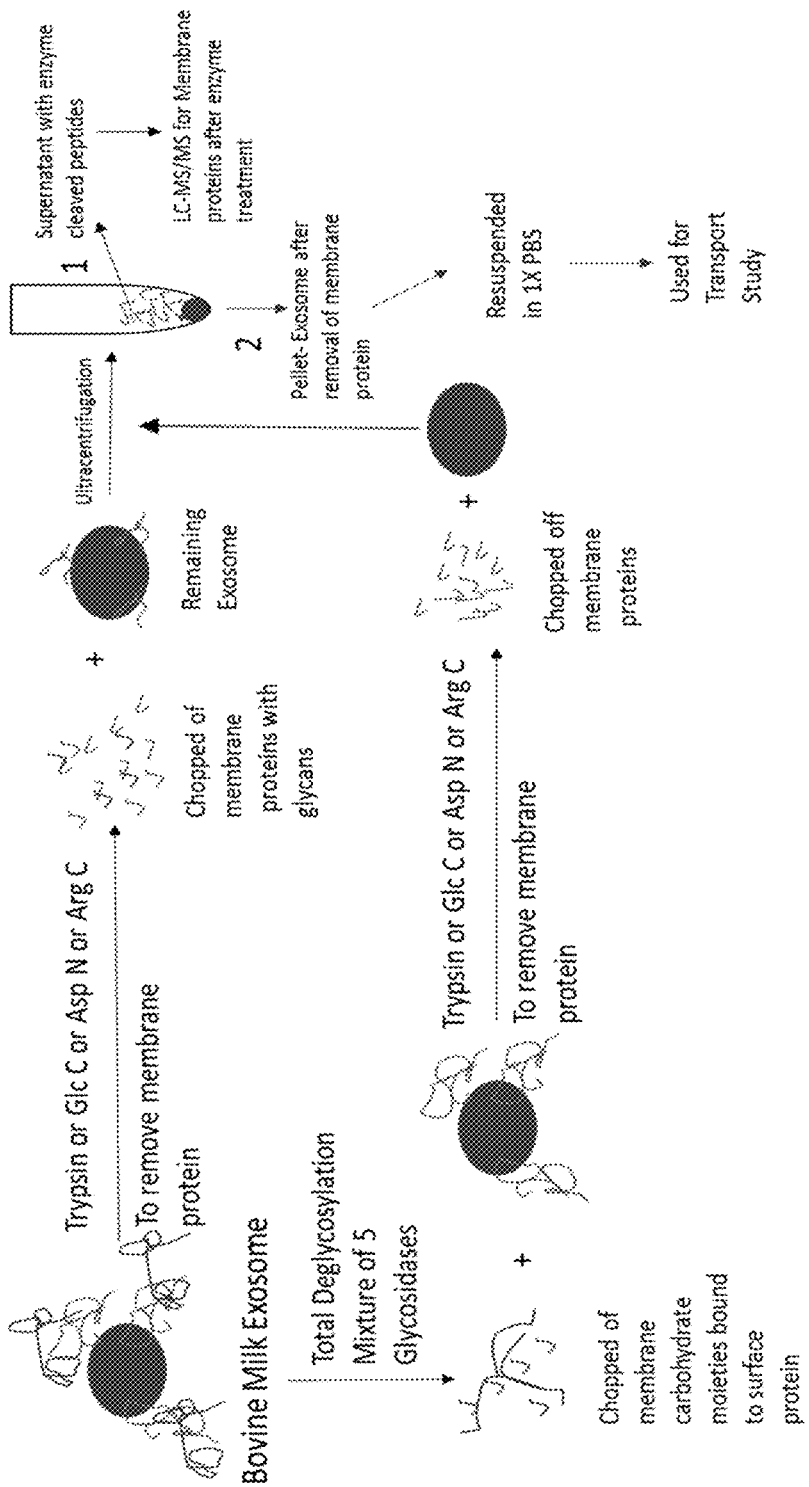

FIG. 38 shows a scheme for exosome processing to remove glycoproteins on the surface of milk exosomes and also to remove glycans from the surface glycoproteins. These methods were used to generate the data shown in FIGS. 4-43, 46-49, 51, 52.

Figure 39:
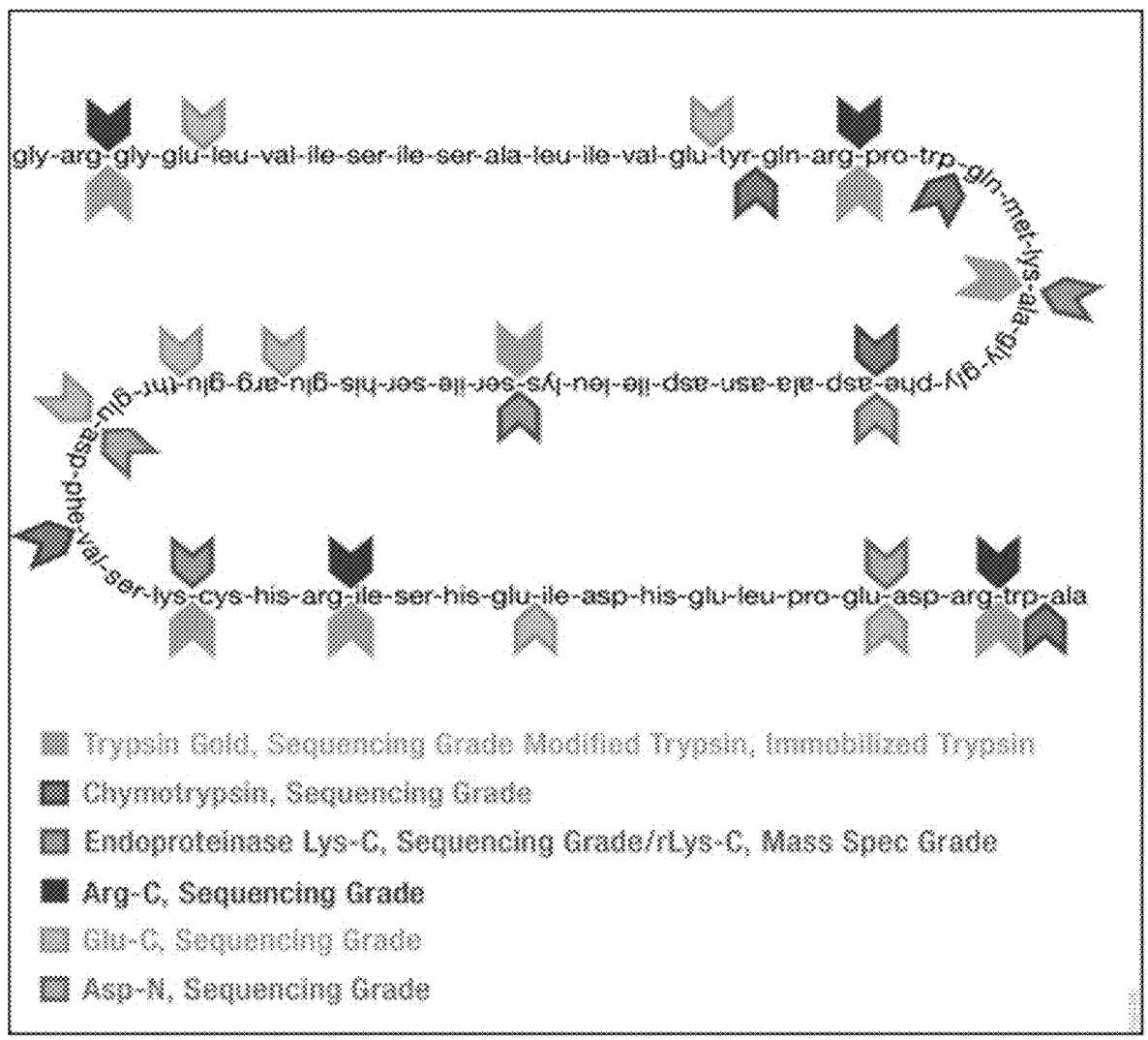

FIG. 39 is a graphical representation showing the cleavage sites of various proteases on a hypothetical sequence (SEQ ID NO:1). Trypsin cleaves at lysine or arginine residues; chymotrypsin cleaves at aromatic amino acids (phenylalanine, tryptophan, and tyrosine); lys-C cleaves at lysine; Arg-C cleaves at arginine and lysine residues; Glu-C cleaves at glutamic acid and aspartic acid residues; and Asp-N cleaves at aspartic acid residues.

Figure 40A:
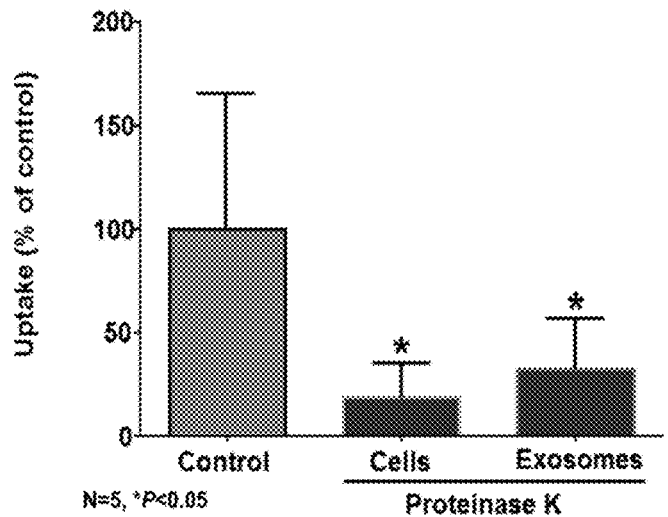
Figure 40B:
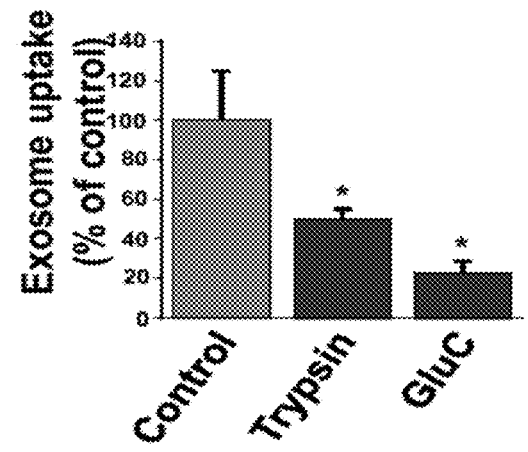
Figure 40C:
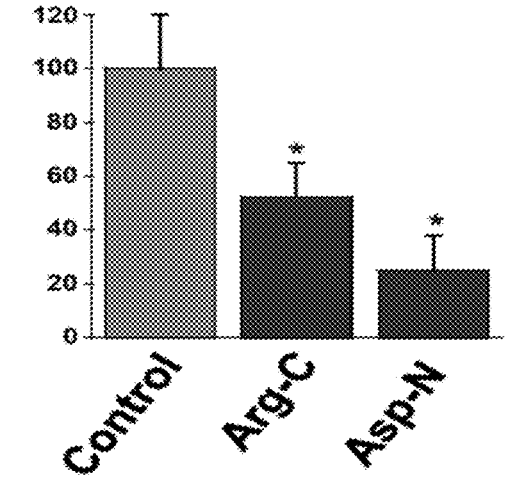

FIGS. 40A-C show the effect on exosome uptake by different cells after removal of surface proteins from the exosomes or the cells. FIG. 40A shows the effect on exosome uptake after treatment of milk exosomes or HUVEC cells with proteinase K (FIG. 40A). FIG. 40B shows the effect on exosome uptake after treatment of milk exosomes with trypsin or Glu-C (FIG. 40B) or Arg-C or Asp-N FIG. 40C). N=3, *P<0.05.

Figure 41A:
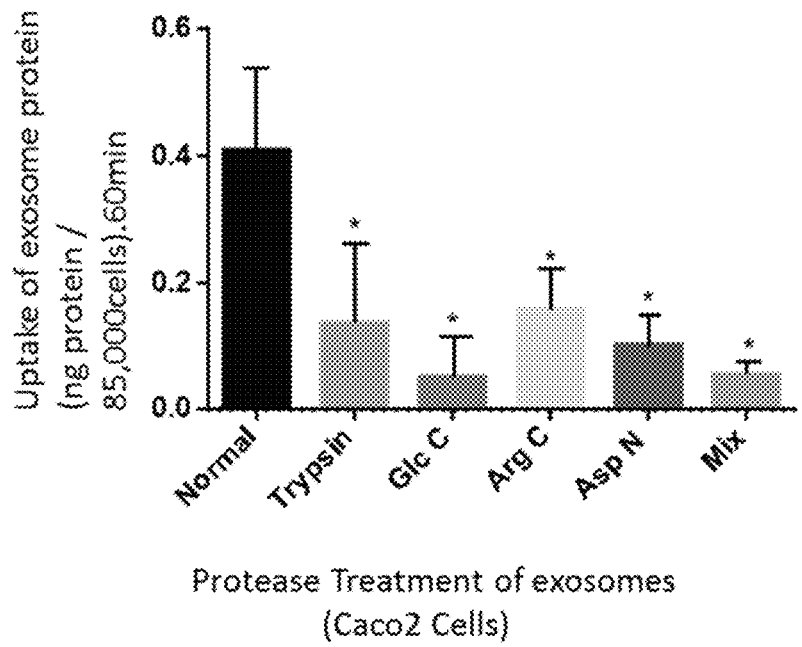
Figure 41B:
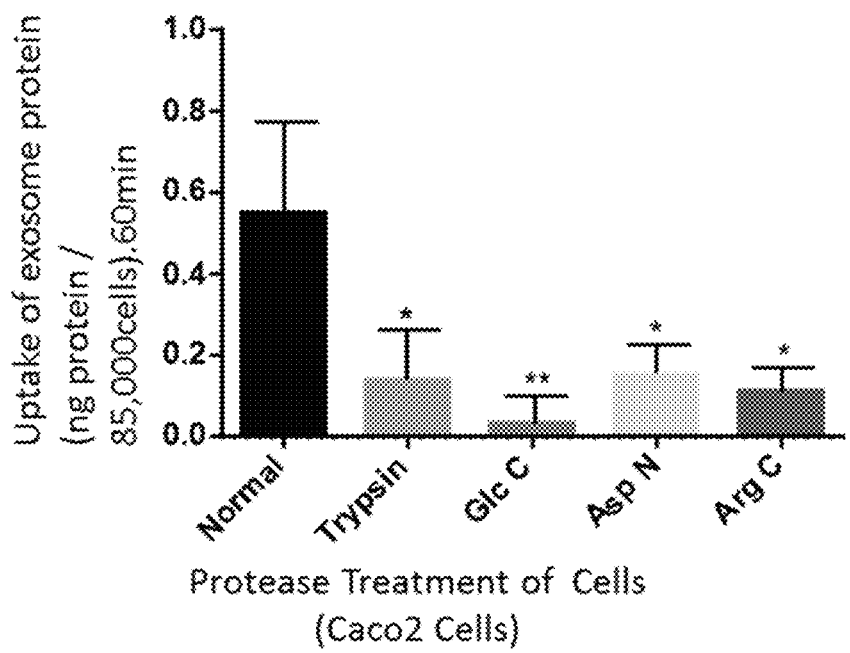

FIGS. 41A and 41B show exosome uptake by Caco-2 cells after treatments with the indicated protease(s) (n=3;

p<0.05). Treatment of exosomes (FIG. 41A) with protease decreases the uptake of cow's milk exosomes in cells. Treatment of Caco-2 cells (FIG. 41B) with protease decreases the uptake of cow's milk exosomes in cells. *P<0.05 vs. control. (N=3, means±S.D.).

Figure 42A:
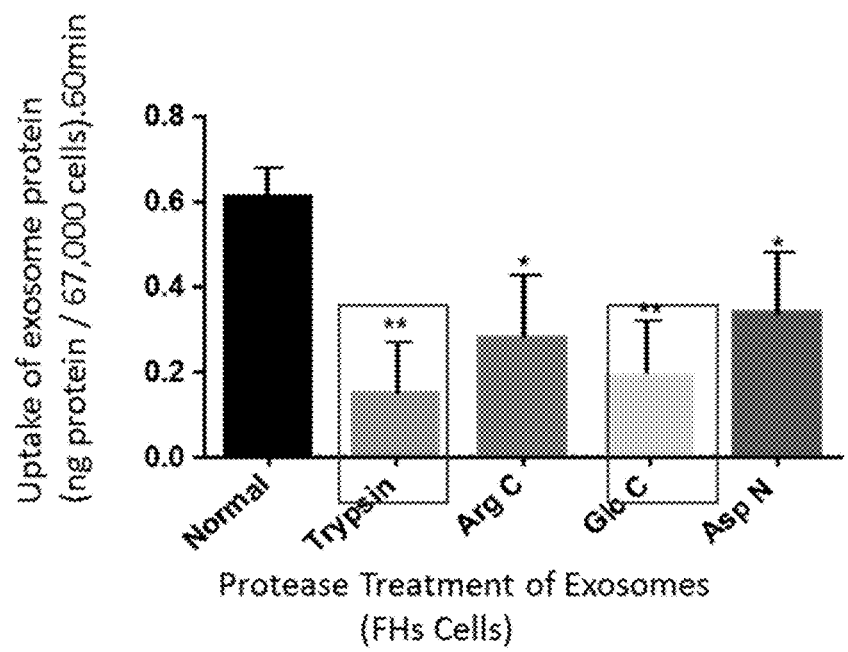
Figure 42B:
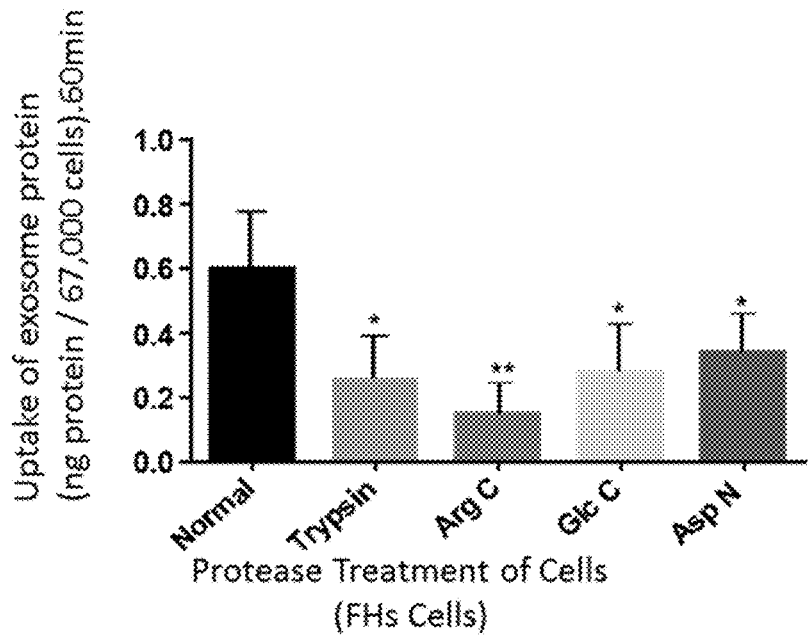

FIGS. 42A and 42B show an exosome uptake study in human small intestinal cells (FHs cells) after treatment with the indicated proteases (n=3; p<0.05). Treatment of exosomes (FIG. 42A) with proteases decreases the uptake of cow's milk exosomes in FH cells. Treatment of FH cells with proteases (FIG. 42B) decreases the uptake of cow's milk exosomes in FH cells. *P<vs. control. (N=3, means±S.D.).

Figure 43A:
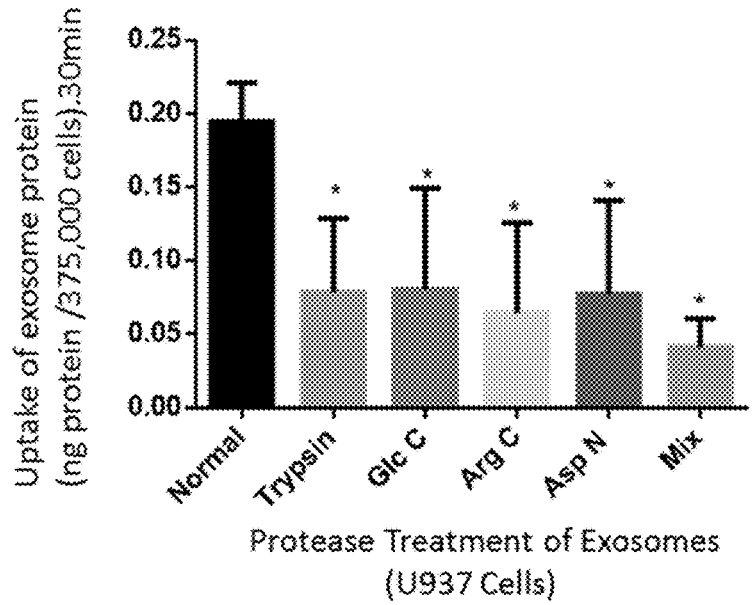
Figure 43B:
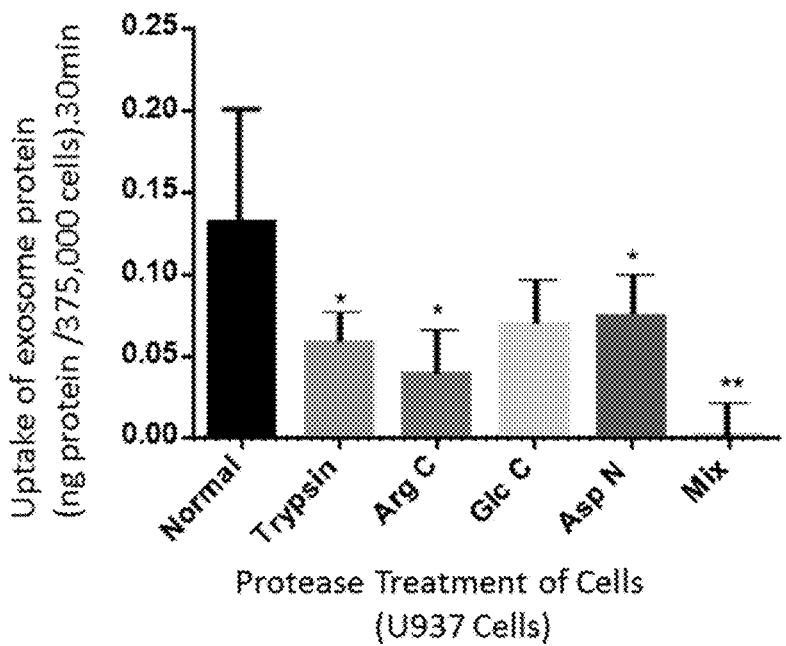

FIGS. 43A and 43B show an exosome uptake study in human macrophage U937 cells after treatment with the indicated proteases (n=3; p<0.05). Treatment of exosomes (FIG. 43A) with proteases decreases the uptake of cow's milk exosomes in U937 cells. Treatment of U937 cells with proteases (FIG. 43B) decreases the uptake of cow's milk exosomes in U937 cells. *P<vs. control. (N=3, means±S.D.).

FIG. 44 shows a table of exemplary enzyme treatments, expected number of TMHs, and predicted number of binding sites on exosome surface proteins. T.D.=Total Deglycosylation. TMHs=Transmembrane Helix.

Figure 45:
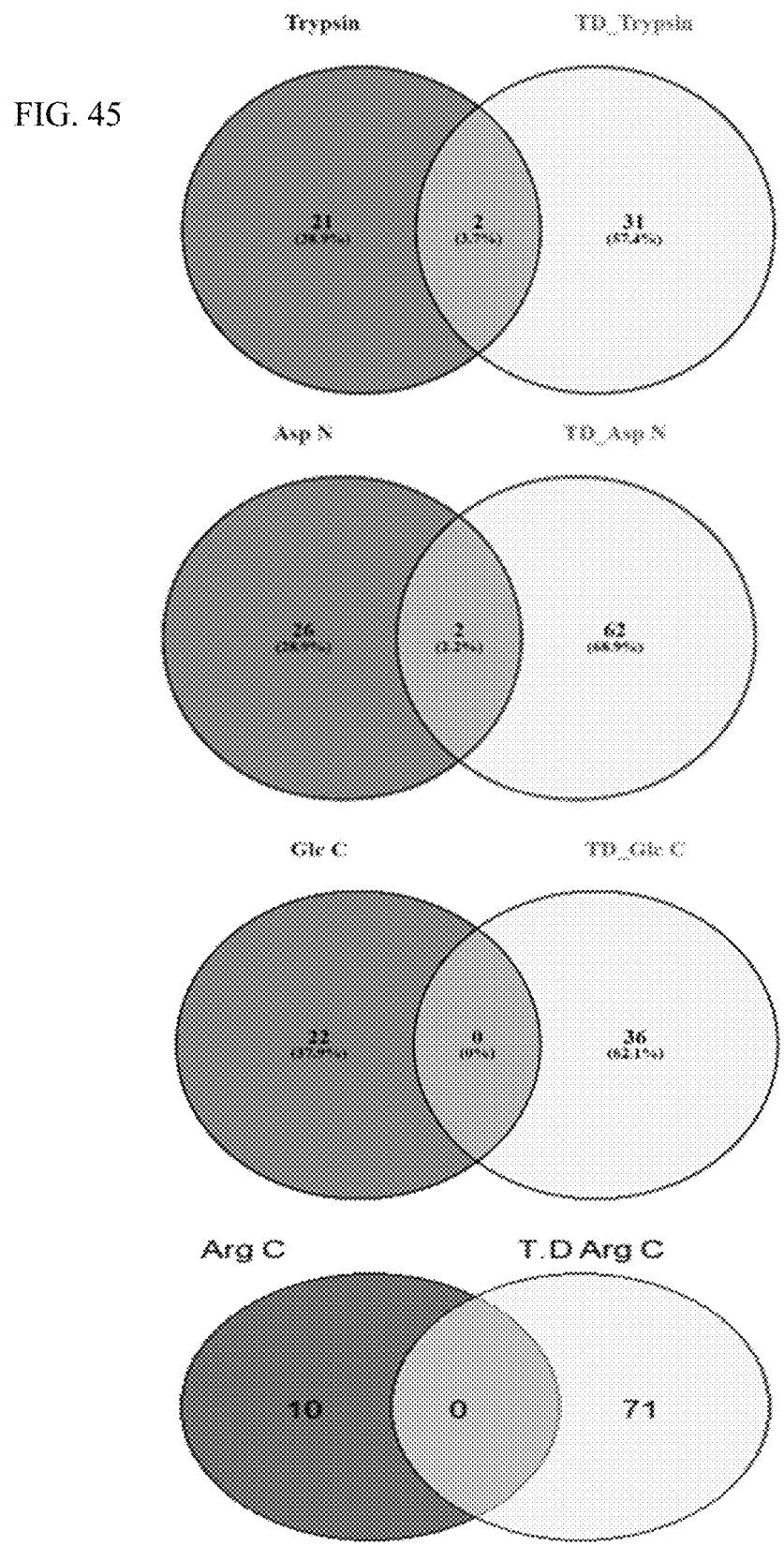

FIG. 45 shows a Venn diagram comparison for identified membrane proteins after specific protease treatment versus total glycan removal and specific protease treatment.

Figure 46:
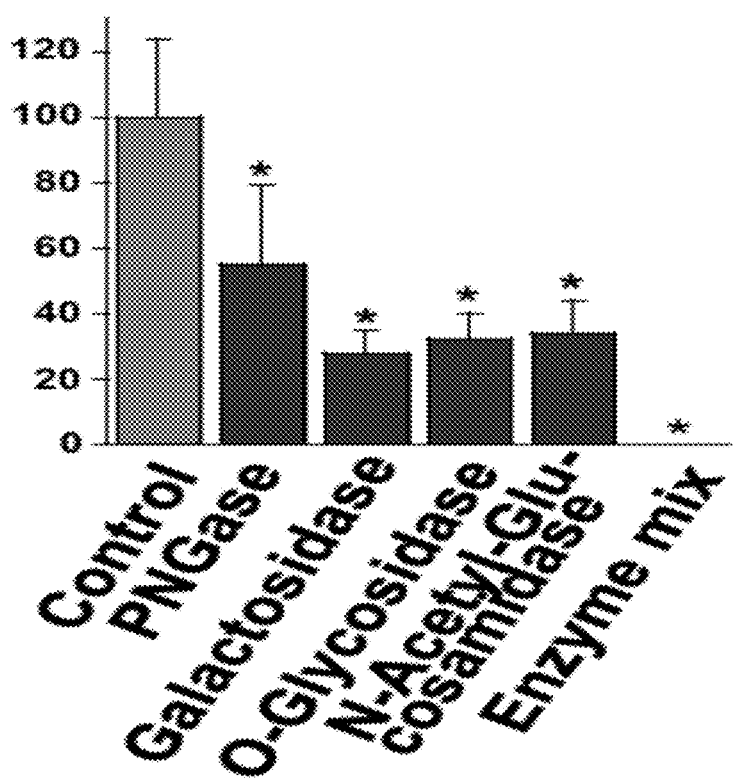

FIG. 46 shows exosome uptake in Caco2 cells following enzymatic removal of glycan from exosome cell surface proteins using PNGase, β-galactosidase, O-glycosidase, N-acetyl-glucosamidase, or a mixture thereof. Removal of glycan results in a decrease in exosome uptake in Caco-2 cells. LC/MS-MS: 4 N-, 2 O-, and 2 C-glycosylated proteins were identified on the milk exosome surface.

Figure 47A:
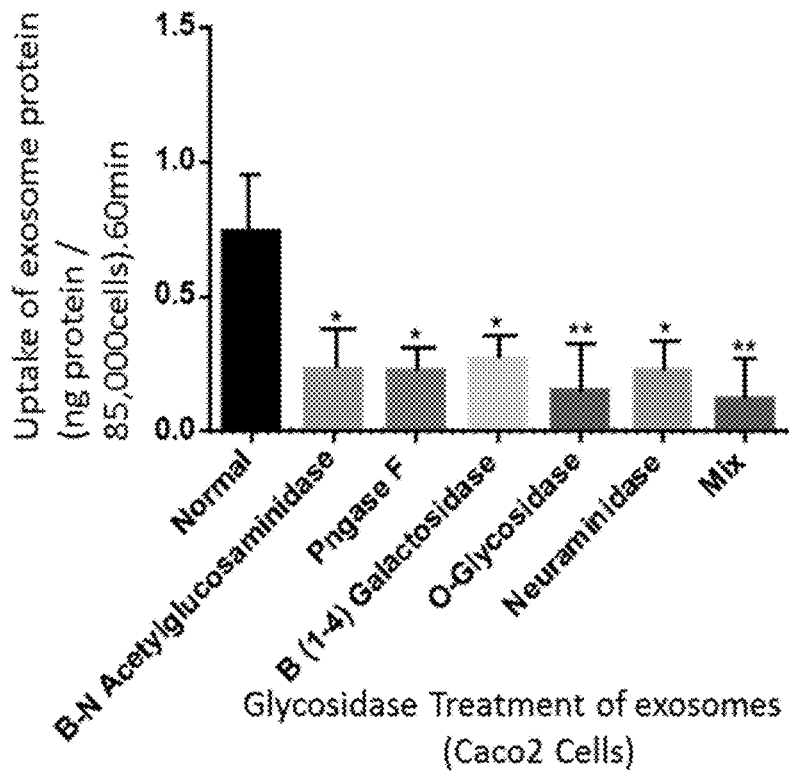
Figure 47B:
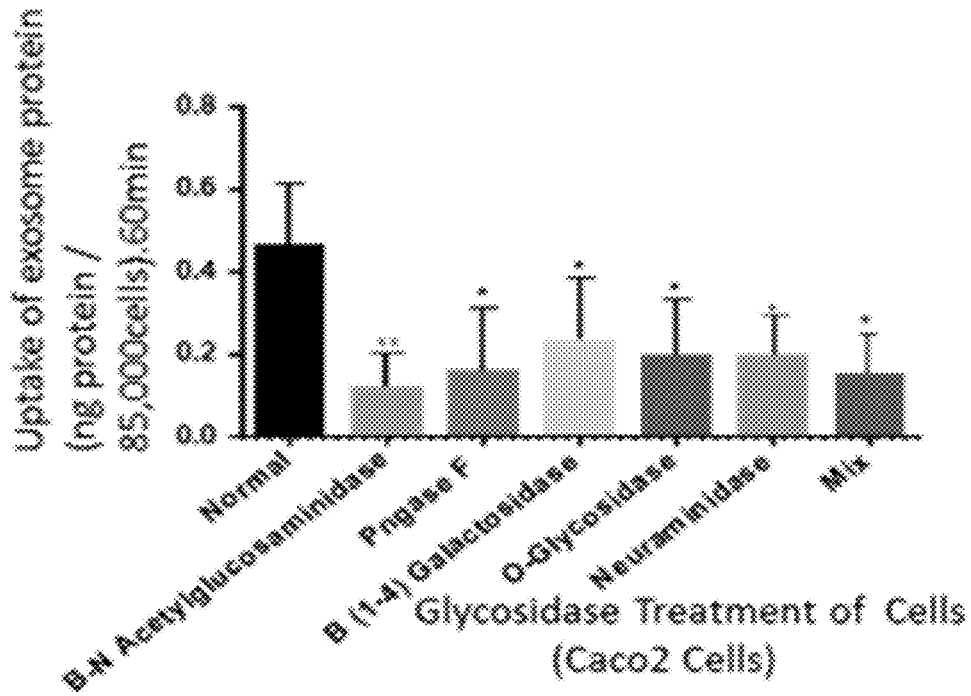

FIGS. 47A and 47B show exosome uptake by Caco-2 cells after treatments with various glycosidase(s) (β-N Acetylglucosaminidase, PngaseF, β(1→4 Galactosidase, O-Glycosidase, Neuraminidase, and mixed glycosidases) (n=3; p<0.05). Treatment of exosomes (FIG. 47A) with glycosidase decreases the uptake of cow's milk exosomes in Caco-2 cells. Treatment of Caco-2 cells (FIG. 47B) with glycosidase decreases the uptake of cow's milk exosomes in cells. *P<0.05 vs. control. (N=3, means±S.D.).

Figure 48:
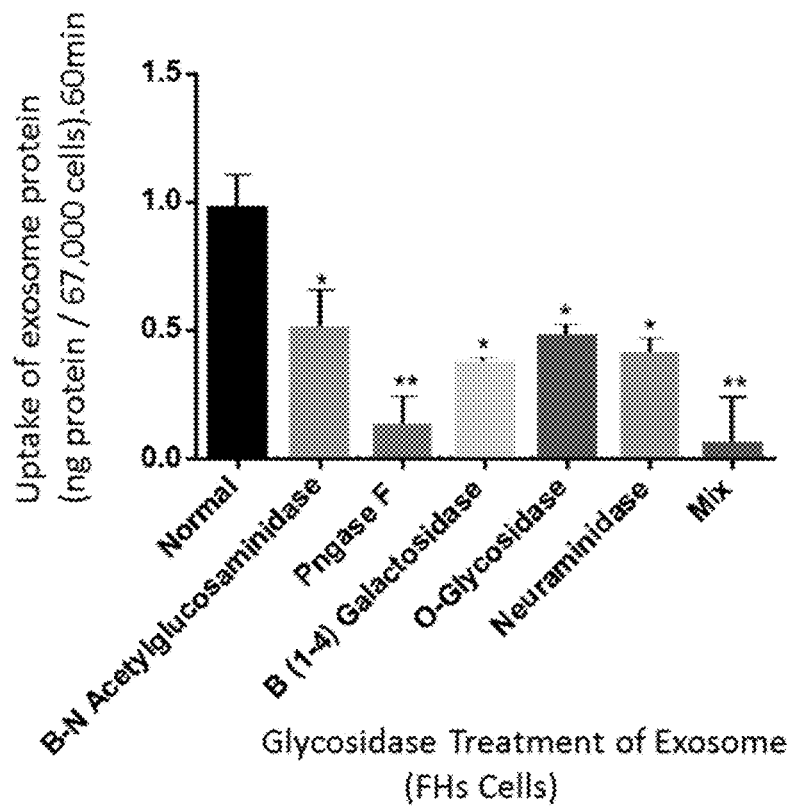

FIG. 48 shows exosome uptake by human small intestinal cells (FHs cells) after treatments with various glycosidases (β-N Acetylglucosaminidase, PngaseF, β (1→4 Galactosidase, O-Glycosidase, Neuraminidase, and mixed glycosidases). (n=3; p<0.05). Treatment of exosomes with glycosidase decreases the uptake of cow's milk exosomes in FH cells. *P<0.05 vs. control. (N=3, means±S.D.).

Figure 49A:
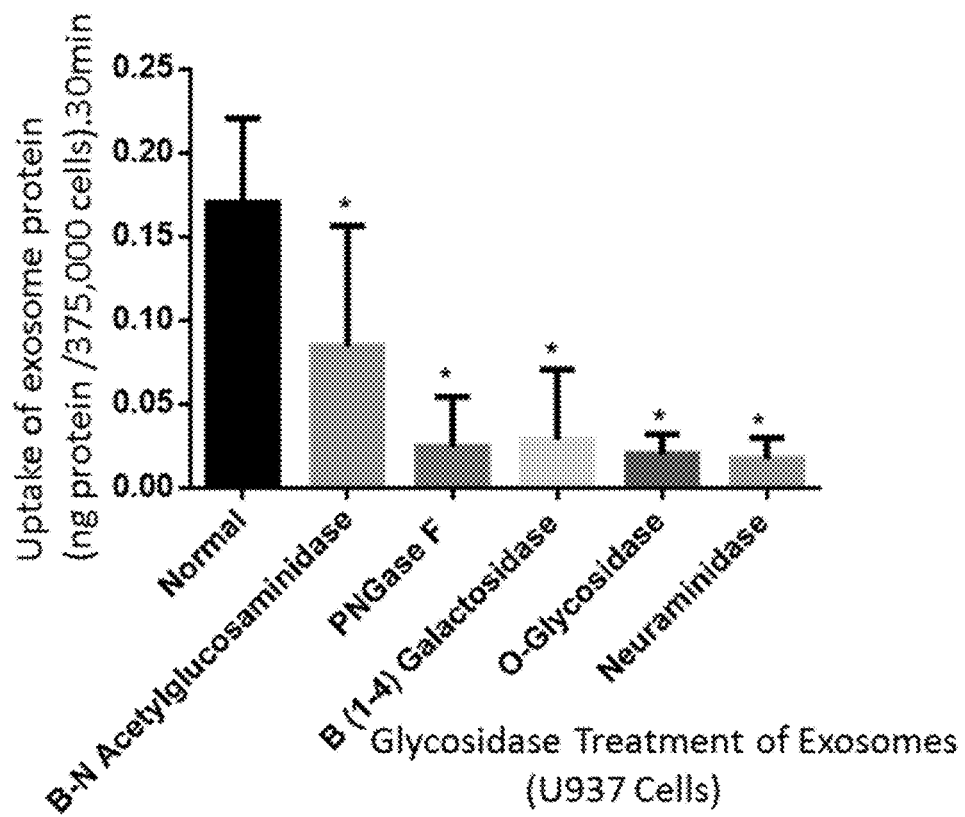
Figure 49B:
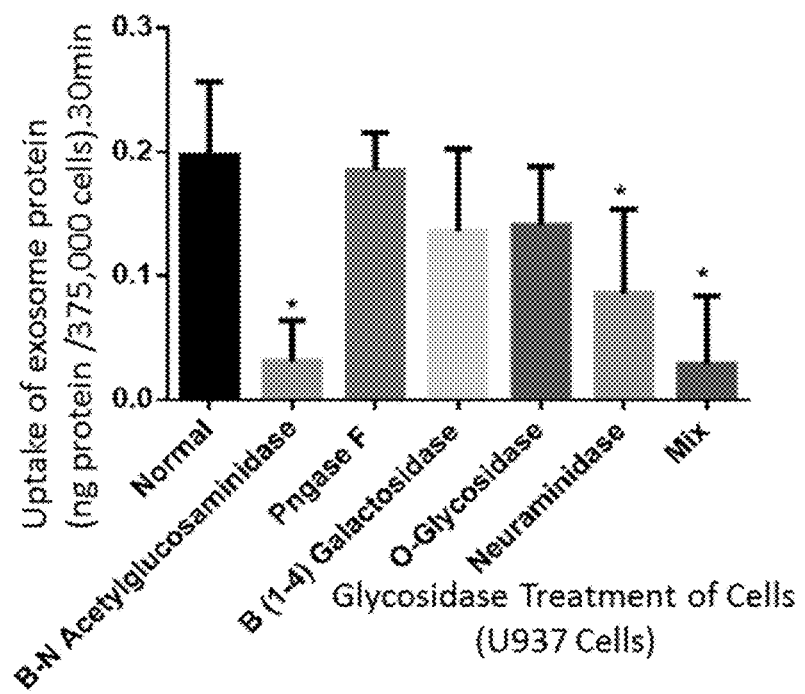

FIGS. 49A and 49B show exosome uptake by U937 cells after treatments with various glycosidases (β-N Acetylglucosaminidase, PngaseF, β(1→4 Galactosidase, O-Glycosidase, Neuraminidase, and mixed glycosidases). Treatment of exosomes (FIG. 49A) with glycosidase decreases the uptake of cow's milk exosomes in U937 cells. Treatment of U937 cells (FIG. 49B) with glycosidase decreases the uptake of cow's milk exosomes in the U937 cells. *P<0.05 vs. control. (N=3, means±S.D.).

Figure 50C:
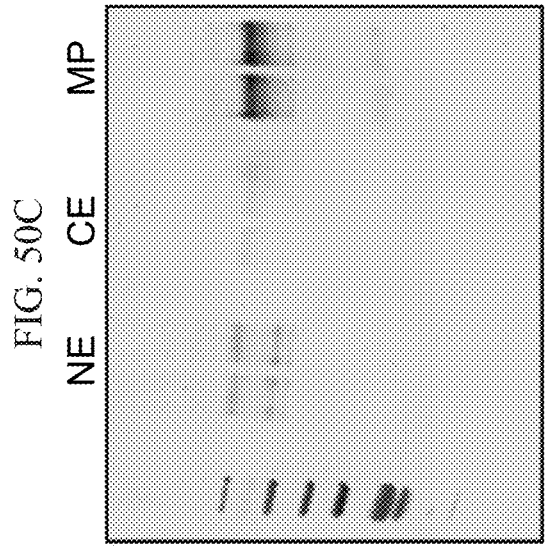
Figure 50B:
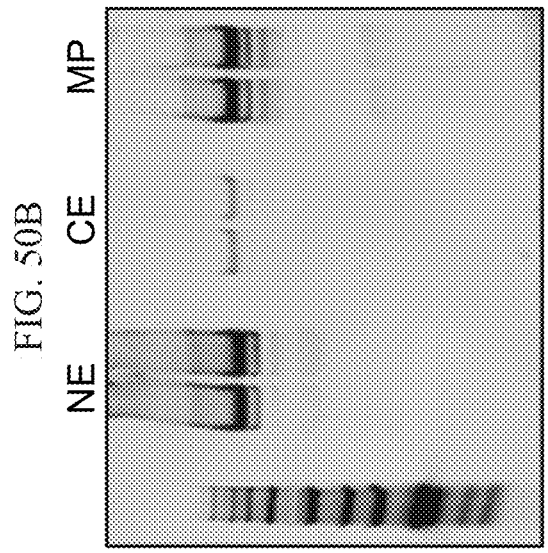
Figure 50E:
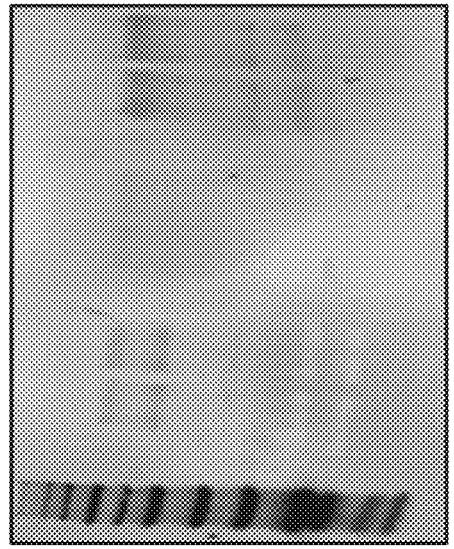

FIGS. 50A-D shows Eastern/Lectin Blots that identify glycans present on membranes of milk exosomes. NE—Normal Exosome; CE—Cytoplasmic Extract; MP—Membrane Protein; FIG. shows a blot using lectin Con A (Concanavalin A) as a probe which is specific for alpha linked mannose; FIG. 50B shows a blot using lectin PNA (Peanut agglutinina) as a probe, which is specific for Gal β1-3 GalNAc 1 Ser/Thr; FIG. 50C shows a blot using lectin SBA (Soybean agglutinin) as a probe which is specific for GalNAc; FIG. 50D shows a blot using lectin SNA (Elderberry lectin) as a probe which is specific for sialic acid. These results demonstrate the presence of alpha linked mannose, Gal β 1-3 GalNAc 1 Ser/Thr, GalNAc, and sialic acid glycosylation on exosome membrane proteins.

Figure 51A:
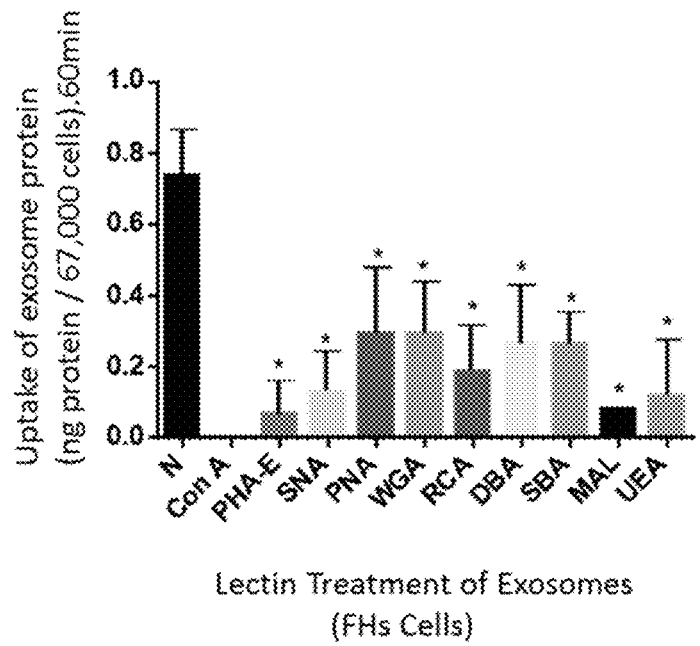
Figure 51B:
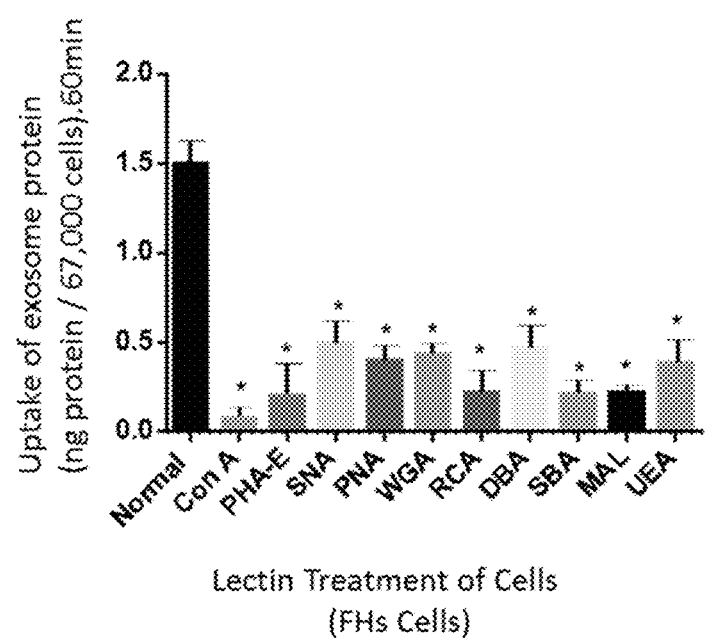

FIGS. 51A and 51B show results of a lectin blocking study. Blocking of glycans present on exosomes (FIG. 51A) and FHs cells (FIG. 51 B) with lectin decreases the uptake of cow's milk exosomes in cells. (*P<0.05 vs. control; N=3, means±S.D.)

Figure 52:
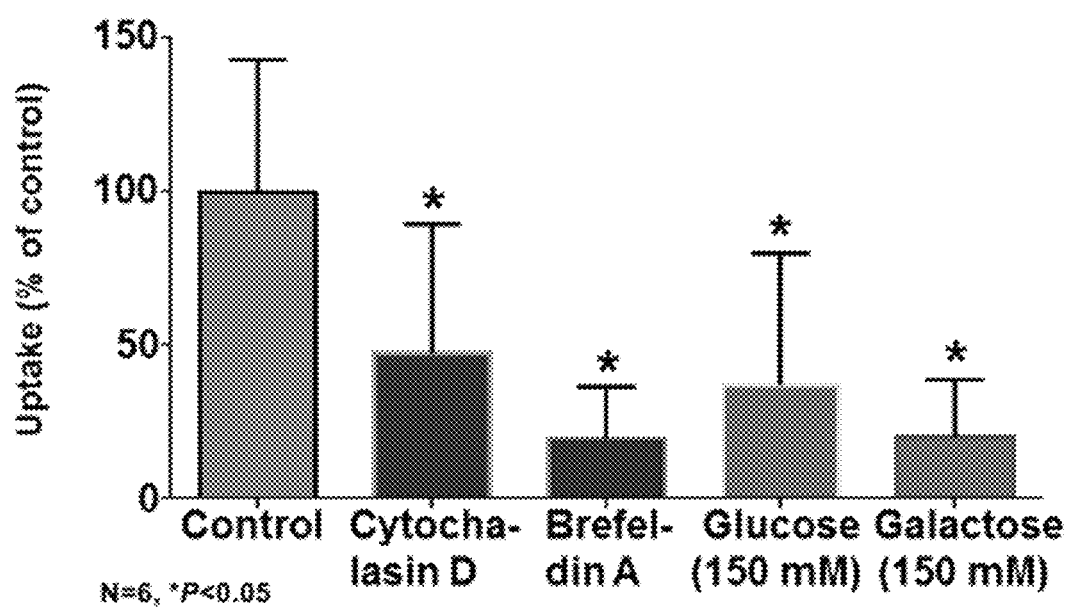

FIG. 52 shows the results of an exosome transport study in which inhibitors of endocytosis (cytochalasin D=Cyt D), vesicle trafficking (brefeldin A=BFA), and carbohydrate blockage (glucose, galactose) were shown to cause a decrease in exosome uptake in HUVEC cells.

Figure 53A:
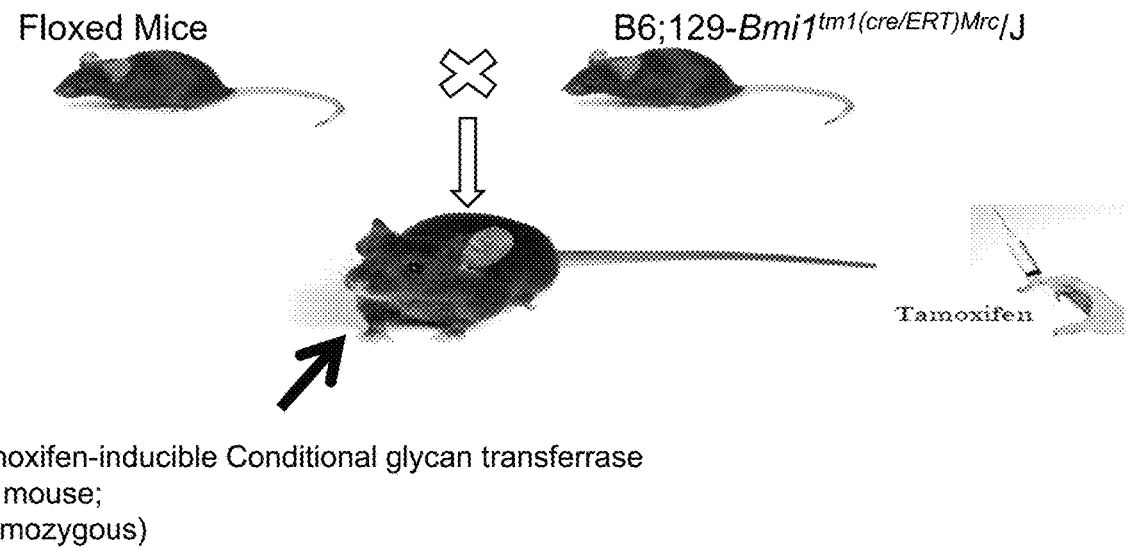
Figure 53B:
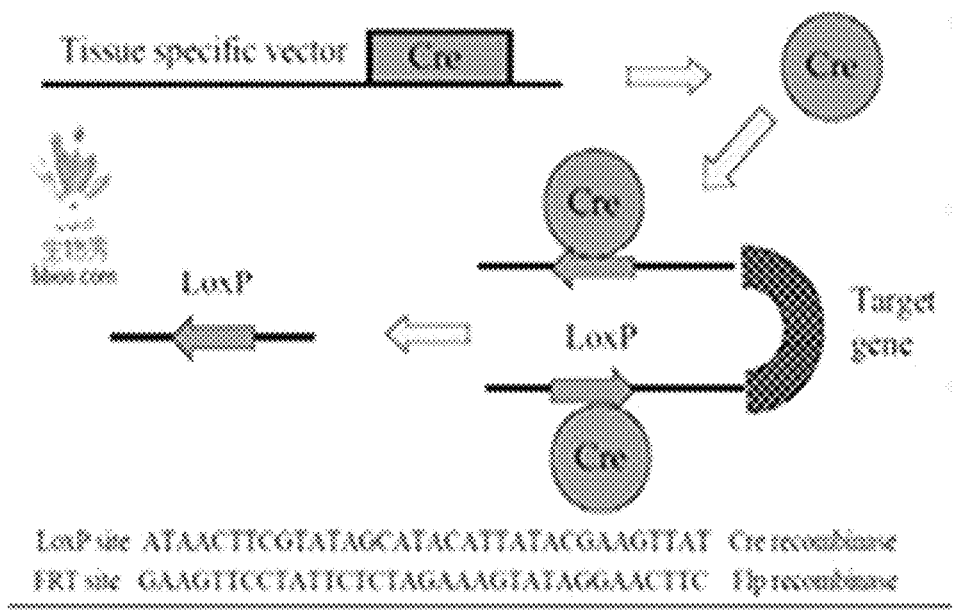

FIGS. 53A and 53B show the design of a transgenic mouse that is a tamoxifen-inducible conditional glycan transferase knockout mouse (homozygous). FIG. 53A shows that floxed B6 mice were crossed with B6; 129-Bmi1$^{tm1(cre/ERT)Mrc}$/J mice to generate a homozygous tamoxifen-inducible conditional glycan transferase knock-out mouse. FIG. 53B shows the Cre-LoxP mediated gene deletion method used to knock-out the glycan transferase gene; SEQ ID NO:2 (top); SEQ ID NO:3 (bottom).

FIGS. 54A and 54B show various gene knockouts which result in alteration of glycosylation and corresponding genotyping results. FIG. 54A provides a table showing glycosylation enzyme and corresponding glycan loss in various knockout mouse strains. FIG. 54B shows genotyping results showing knockout of the MGAT gene and knockout of the PoFUT1 gene.

FIGS. 55A and 55B depict the experimental process for administering fluorescence-labelled exosomes to mice and the corresponding fluorescence results between unmodified and PNGase F-treated milk exosomes. FIG. 55A shows a scheme for exosome processing to remove certain glycans from membrane proteins on the surface of exosomes, e.g., asparagine-linked complex, hybrid, or high mannose oligosaccharides (via the use of PnGase F). These methods were used to generate the data shown in FIG. 55B. FIG. 55B shows the results of a fluorescence study in which fluorescent-labelled exosomes having native glycosylation (control) versus altered glycosylation (removal of asparagine-linked complex, hybrid, or high mannose oligosaccharides via the use of PnGase F) were compared.

Figure 56:
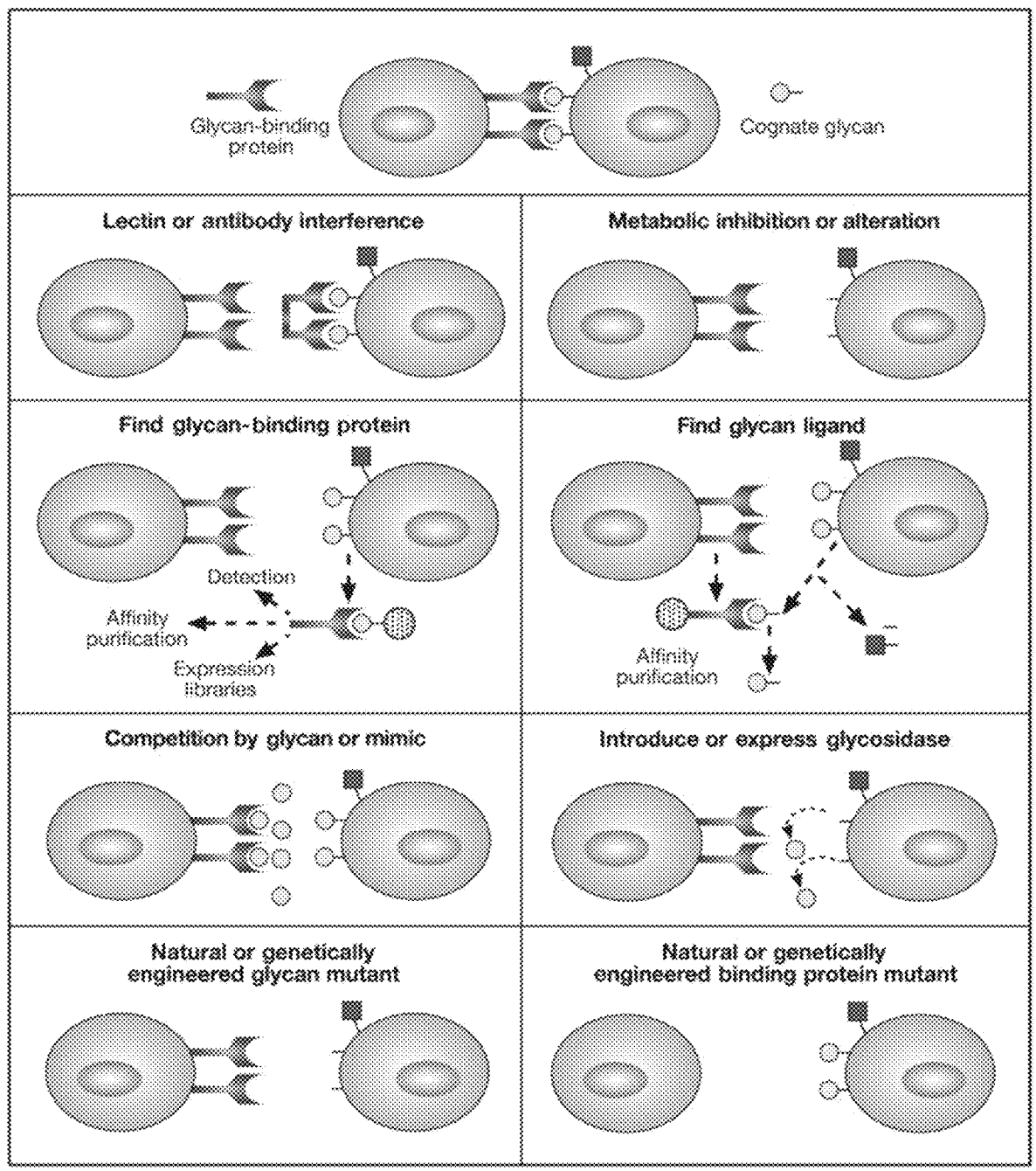

FIG. 56 shows approaches for elucidating the biological roles of glycans. The figure assumes that a specific biological role is being mediated by recognition of a certain glycan structure by a specific glycan-binding protein. Clues to this biological role could be obtained by a variety of different approaches.

Figure 57A:
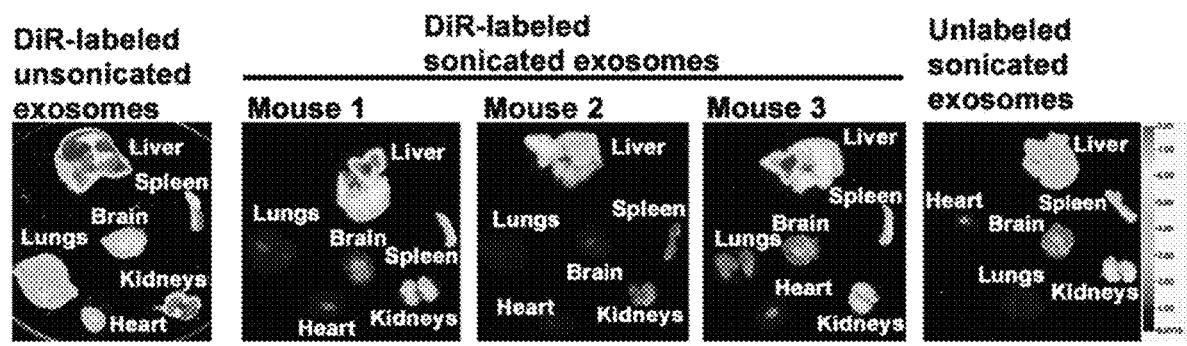
Figure 57B:
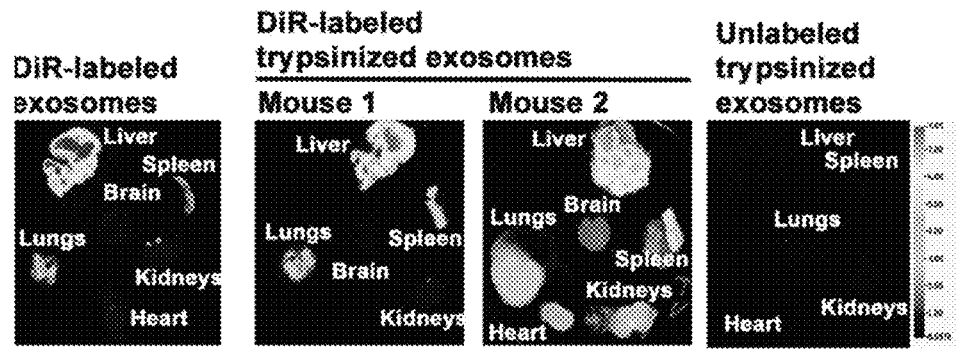

FIGS. 57A and 57B show images demonstrating that sonication of exosomes caused a loss of bioavailability to non-detectable levels after oral administration (FIG. 57A). Removal of exosomal surface proteins by treatment with trypsin caused a reduced accumulation of exosomes in the liver and lungs after intravenous injection (FIG. 57B). The images show distribution of sonicated and trypsinized exosomes in Balb/c mice. FIG. 57A shows fluorescence signal in excised tissues from Balb/c mice 24 hours after oral gavage of sonicated and DiR-labeled, unsonicated and DiR-labeled, or unlabeled and sonicated ($1\times10^{12}$/g body weight, n=3). FIG. 57B shows distribution of trypsinized DiR-labeled exosomes ($1\times10^{12}$/g body weight) in Balb/c mice in excised tissues 24 hours after oral gavage (n=2).

Figure 58:
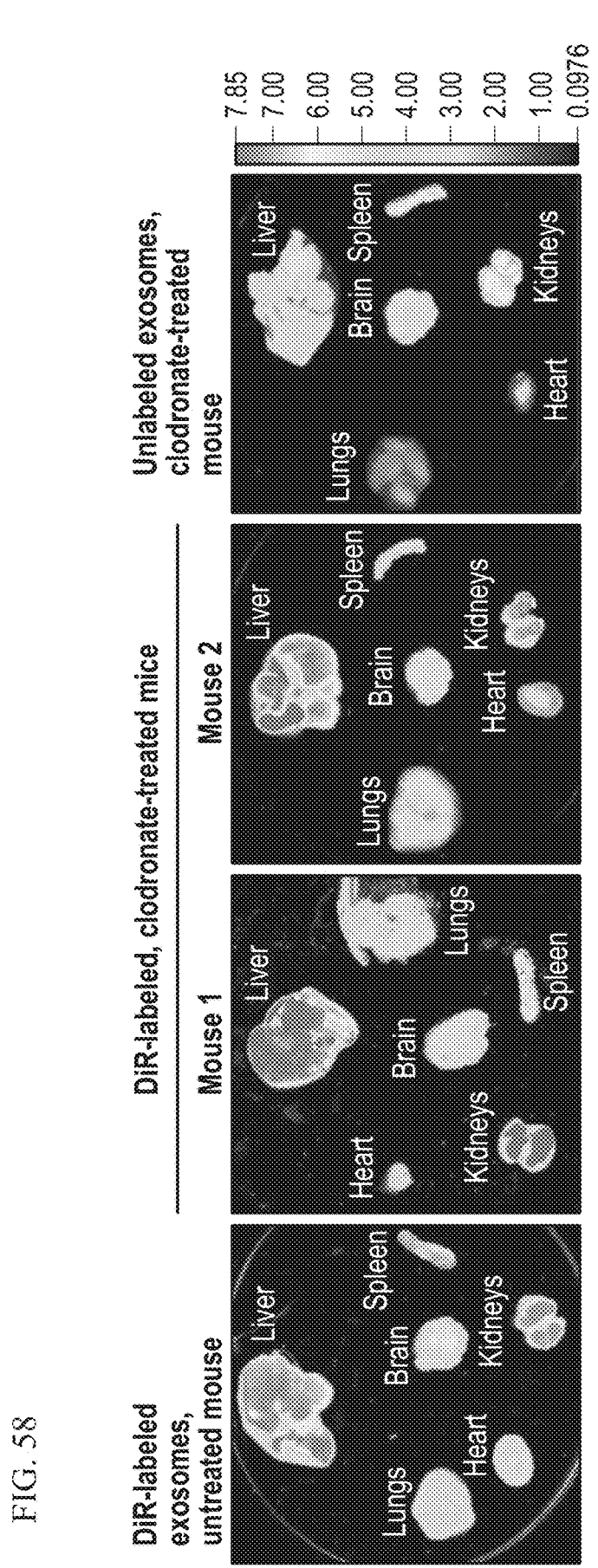

FIG. 58 shows distribution of exosomes in macrophage-depleted mice. Balb/c mice were treated with clodronate (150 ul) by intraperitoneal injection to ablate endogenous macrophage populations. Unlabeled or DiR-labeled exosomes were administered by oral gavage 24 hours after clodronate treatment, and tissues were harvested 24 hours after exosome administration for fluorescence analysis.

DETAILED DESCRIPTION

The present disclosure relates to materials and methods for extracellular vesicle-mediated delivery of cargo to mammalian cells. In some embodiments, the present disclosure provides milk exosomes for delivering cargo to a mammal (e.g., human). This disclosure also provides methods of using an extracellular vesicle (e.g., exosome), such as any of the vesicles described herein, to deliver one or more exosomal cargos to a recipient cell. For example, an exosome can be administered to a mammal (e.g., a human) to alter the gut microbiome of a mammal, to regulate (e.g., increase or decrease) the immune response of a mammal, to enhance the fertility of a mammal, to alter (e.g., increase or decrease) the metabolism of a mammalian cell, to alter (e.g., increase or decrease) the gene expression of a mammalian cell, to increase the muscle strength of a mammalian cell, to enhance neurological processes of a mammal, and/or to treat a mammal having a disease. In some embodiments, an exosome can be loaded with an exogenous cargo (e.g., a therapeutic agent) and used to deliver the exogenous cargo to a mammalian receptor cell.

In one aspect, the present invention provides a milk exosome comprising:
  a biological membrane surrounding a lumen;
  a glycoprotein embedded within said biological membrane, wherein said glycoprotein comprises a glycan present on the outer surface of said biological membrane; and
  an exogenous cargo present in said lumen.
In another aspect, the present disclosure provides a milk exosome comprising:
  a biological membrane surrounding a lumen, wherein the biological membrane comprises one or more glycoprotein(s),
  wherein the biological membrane is modified as compared with the natural biological membrane of the milk exosome.
In some embodiments, said exosome is isolated from sheep, goat, camel, horse, donkey, reindeer, yak, buffalo, or bovine (cow) milk or colostrum.

In some embodiments, said exosome further comprises an miRNA or mRNA that is biologically active in a mammal. In some embodiments, the miRNA or mRNA is present in the lumen of the exosome. In some embodiments, the miRNA or mRNA is endogenous miRNA or mRNA.

In some embodiments, said exogenous cargo is selected from one or more nucleic acid molecules, polypeptides, lipids, vitamins, minerals, small molecules, pharmaceuticals, hormones, or enzymes.

In some embodiments, said exogenous cargo comprises a therapeutic agent. In some embodiments, said therapeutic agent is selected from mRNAs, polypeptides, miRNAs, miRNA antagonists, nutrients, antibiotics, cancer drugs, activators of Toll-like receptors, or molecules capable of delivery to macrophages. In some embodiments, said therapeutic agent is a cancer drug selected from a chemotherapeutic, an immunotherapeutic, a hormone therapeutic, or a targeted therapeutic.

In some embodiments, said exogenous cargo comprises a nutritional agent. In some embodiments, said nutritional agent is selected from vitamins, minerals, lipids, fatty acids, mRNAs, or polypeptides.

In some embodiments, said nutritional agent is a fatty acid selected from omega-3 fatty acids or omega-6 fatty acids.

In another aspect, the present disclosure provides a milk exosome comprising:
  a biological membrane surrounding a lumen;
  a glycoprotein embedded within said biological membrane, wherein said glycoprotein comprises a modified glycan present on the outer surface of said biological membrane; and
  a cargo present in said lumen.
In some embodiments, said modified glycan modulates uptake of the exosome into a mammalian cell as compared with a corresponding glycan that is naturally-occurring on said outer surface of said biological membrane.

In some embodiments, said exosome is isolated from sheep, goat, camel, horse, donkey, reindeer, yak, buffalo, or bovine (cow) milk or colostrum.

In some embodiments, the modified glycan modulates uptake into a human receptor cell.

In some embodiments, the receptor cell is selected from intestinal cells, venous endothelial cells or other endothelial cells, immune cells, macrophages, intestinal mucosa, peripheral cells of the liver, spleen, lung, brain, kidneys, or pancreas, cancer cells, or fetal cells.

In some embodiments, said modified glycan comprises one or more D- or L-glucose, erythrose, fucose, galactose, mannose, lyxose, gulose, xylose, arabinose, ribose, 2'-deoxyribose, glucosamine, lactosamine, polylactosamine, glucuronic acid, sialic acid, sialyl-Lewis X (SLex), N-acetyl-glucosamine, N-acetyl-galactosamine, neuraminic acid, N-glycolylneuraminic acid (Neu5Gc), N-acetylneuraminic acid (Neu5Ac), an N-glycan chain, an O-glycan chain, a Core 1, Core 2, Core 3, or Core 4 structure, or a phosphate- or acetate-modified analog thereof or a combination thereof.

In some embodiments, said modified glycan reduces or eliminates degradation of the exosome by macrophages.

In some embodiments, the modified glycan is produced by removing one or more glycans from the surface glycoproteins of a naturally-occurring milk exosome and/or by removing the extrasomal surface portion of one or more surface glycoproteins.

In some embodiments, the modified exosome is produced by contacting a naturally-occurring milk exosome with a chemical agent capable of cleaving or covalently modifying glycans or proteins (e.g., hydrazine or an acylating or alkylating agent), or a protease or glycosidase or combination thereof. In some embodiments, the exosome is produced by contacting the naturally-occurring milk exosome with a lectin. In some embodiments, the exosome is produced by contacting the naturally-occurring milk exosome with β-N-acetylglucosaminidase, PNGase A, PNGase F, Endoglycosidase H, Endoglycosidase F, β (1-4) Galactosidase, O-Glycosidase, a neuraminidase, Glu-C, Glc C, Asp-N, trypsin, and/or Arg-C; or any combination thereof. In some embodiments, the naturally-occurring milk exosome is contacted with PNGase, a galactosidase, O-glycosidase, O-glycosidase-N-acetyl-glucosamidase, or a mixture thereof.

In some embodiments, the exosome is produced by introducing one or more glycans to the surface glycoprotein.

In some embodiments, the exosome is produced using glycosylation that adds one or more glycans to the surface glycoprotein.

In some embodiments, the exosome is produced by stabilizing one or more glycans already present on the surface glycoprotein.

In some embodiments, the modified glycan improves stability of the exosome in the gastrointestinal tract, systemic circulation, lymphatic circulation, intracellular conditions, or other tissues or organs of a human, for example, including without limitation liver, spleen, lung, brain, kidneys, or pancreas, cancer cells, or fetal cells.

In some embodiments, the modified glycan alters the stability of the exosome under physiological conditions in a human as compared with an exosome comprising the corresponding unmodified glycan.

In some embodiments, the modified glycan alters the stability of the exosome in the gastrointestinal tract, systemic circulation, lymphatic circulation, or intracellular conditions of a human as compared with an exosome comprising the corresponding unmodified glycan.

In some embodiments, said cargo is selected from one or more nucleic acid molecules, polypeptides, lipids, vitamins, minerals, small molecules, pharmaceuticals, hormones, or enzymes.

In some embodiments, said cargo comprises a therapeutic agent. In some embodiments, said therapeutic agent is selected from mRNAs, polypeptides, miRNAs, miRNA antagonists, nutrients, antibiotics, cancer drugs, activators of Toll-like receptors, or molecules capable of delivery to macrophages. In some embodiments, said therapeutic agent is a cancer drug selected from a chemotherapeutic, an immunotherapeutic, a hormone therapeutic, or a targeted therapeutic.

In some embodiments, said cargo comprises a nutritional agent. In some embodiments, said nutritional agent is selected from vitamins, minerals, lipids, fatty acids, mRNAs, or polypeptides. In some embodiments, said nutritional agent is a fatty acid selected from omega-3 fatty acids or omega-6 fatty acids.

In another aspect, the present disclosure provides a nutritional supplement formulated for oral administration to a human, said nutritional supplement comprising a disclosed exosome.

In some embodiments, the exosome comprises an endogenous cargo.

In some embodiments, the exosome comprises an exogenous cargo.

In another aspect, the present disclosure provides an infant formula comprising a disclosed exosome or nutritional supplement. In some embodiments, the exosome comprises one or more nutritional agents selected from vitamins, minerals, lipids, fatty acids, mRNAs, or polypeptides.

In another aspect, the present disclosure provides a method of treating a disease, disorder, or condition in a subject, comprising:
administering to said subject an effective amount of a disclosed exosome comprising a cargo capable of treating said disease, disorder, or condition.

In some embodiments, the disease, disorder, or condition is selected from a hyperproliferative disorder, viral or microbial infection, autoimmune disease, allergic condition, inflammatory disease, cardiovascular disease, metabolic disease, or neurodegenerative disease.

In some embodiments, the disease, disorder, or condition is selected from a proliferative disease. Exemplary proliferative diseases include a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins lymphoma, a mammary carcinoma, follicular carcinoma, undifferentiated carcinoma, papillary carcinoma, seminoma, melanoma, multiple myeloma, or a hematological malignancy (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, plasmacytoma, intravascular large B-cell lymphoma).

In some embodiments, the disease, disorder, or condition is selected from inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants," an established patient category of major medical concern and now often identified as incipient or early-phase asthmatics.

In some embodiments, the disease, disorder, or condition is selected from heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In some embodiments, the disease, disorder, or condition is selected from eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

In some embodiments, the disease, disorder, or condition is selected from inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

In some embodiments, the disease, disorder, or condition is selected from diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, aging, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

In another aspect, the present disclosure provides a method of correcting dysbiosis or improving the gut microbiome or gut health of a subject, comprising:
  administering to said subject an effective amount of a disclosed exosome comprising a cargo;
  wherein the cargo of said exosome is effective to correct dysbiosis or improve the gut microbiome or gut health of said subject.

In some embodiments, said correcting dysbiosis or improving the gut microbiome or gut health comprises a decrease in Ruminococcaceae and/or Verrucomicrobiae.

In some embodiments, said correcting dysbiosis or improving the gut microbiome or gut health comprises an increase in Clostridiales or Erysipelotrichaceae.

In another aspect, the present disclosure provides a method of treating inflammatory bowel disease, obesity, or non-alcoholic fatty liver disease, comprising:
  administering to a subject in need thereof an effective amount of a disclosed exosome, wherein the exosome comprises a cargo capable of treating inflammatory bowel disease, obesity, or non-alcoholic fatty liver disease.

In another aspect, the present disclosure provides a method of increasing muscle strength, enhancing sensorimotor gating or cognitive performance, or increasing fertility or fecundity in a subject, comprising administering to said subject an effective amount of a disclosed exosome or a disclosed nutritional supplement.

In another aspect, the present disclosure provides a method of treating sarcopenia, muscle loss after injury, atherosclerosis, cancer, an immune disease, impaired fecundity, or cognitive impairment, comprising administering to a subject in need thereof a disclosed exosome or a disclosed nutritional supplement.

In another aspect, the present disclosure provides a method of improving stability or uptake selectivity of a milk exosome in the gastrointestinal tract, systemic circulation, lymphatic circulation, intracellular conditions, or other tissue or organ of a human, comprising:
  i) providing a disclosed milk exosome; and
  ii) altering the exosome of step i) by: removing one or more glycans from a surface glycoprotein of the exosome; removing an extrasomal surface portion of the surface glycoprotein; introducing one or more glycans to a surface glycoprotein; stabilizing one or more glycans already present on a surface glycoprotein; or a combination thereof.

In some embodiments, step ii) comprises contacting the exosome of step i) with β-N-acetylglucosaminidase, PNGase A, PNGase F, Endoglycosidase H, Endoglycosidase F, β(1-4) Galactosidase, O-Glycosidase, a neuraminidase, Glu-C, Glc C, Asp-N, trypsin, and/or Arg-C; or any combination thereof.

In some embodiments, the method promotes selective delivery of the milk exosome or its cargo to cells in the gastrointestinal tract as compared with a milk exosome comprising the corresponding unmodified glycan. In some embodiments, the method promotes selective delivery of the milk exosome or its cargo to cells in the systemic circulation as compared with a milk exosome comprising the corresponding unmodified glycan. In some embodiments, the method promotes selective delivery of the milk exosome or its cargo to cells in the lymphatic circulation as compared with a milk exosome comprising the corresponding unmodified glycan. In some embodiments, the method promotes selective delivery of the milk exosome or its cargo to cells in the liver, spleen, lung, brain, kidneys, pancreas, cancer cell, or fetal cell as compared with a milk exosome comprising the corresponding unmodified glycan.

In some embodiments, said subject is a human.

Extracellular Vesicles

Extracellular vesicles that can be used to encapsulate or carry one or more cargos as described herein include a biological membrane (e.g., a lipid bilayer) that surrounds a lumen. Any appropriate extracellular vesicle can be used as described herein. Examples of extracellular vesicles include, without limitation, exosomes, microvesicles, oncosomes, ectosomes, prostasomes, matrix/calcifying vesicles, tolerosomes, cardiosomes, and vexosomes. Extracellular vesicles and their respective properties are discussed elsewhere (see, e.g., Lotvall et al. 2014 *Journal of Extracellular Vesicles* 3:26913; and Zempleni et al., 2013 *Nature Reviews Drug Discovery* 12:347-357). In some embodiments, an exosome can be used to carry or encapsulate one or more cargos as described herein. In some embodiments, an exosome comprises a biological membrane surrounding a lumen, glycoprotein(s) embedded within the biological membrane such that one or more glycans on the glycoprotein(s) are presented on the outer surface of the biological membrane, and cargo encapsulated in the lumen.

An extracellular vesicle described herein can be obtained by any appropriate method. In embodiments where an extracellular vesicle is an exosome, the exosome can be a milk exosome. As used herein a "milk exosome" is any exosome found in the milk or colostrum of a mammal (e.g., a lactating mammal), such as sheep, goat, camel, horse, donkey, reindeer, yak, buffalo, or bovine (cow) milk or colostrum. In some embodiments, an exosome is isolated from milk. A milk exosome can be isolated from milk by, for example, centrifugation (e.g., ultracentrifugation), size exclusion chromatography, affinity chromatography, and density gradient centrifugation. In some embodiments, milk exosomes isolated from milk can be concentrated, purified, and/or modified (e.g., loaded with one or more cargos). A milk exosome can be obtained from any appropriate mammal, including humans. Examples of non-human mammals include, without limitation, non-human primates (such as monkeys), cows, pigs, goats, horses, and donkeys. In some embodiments, an extracellular vesicle that can be used as described herein is a bovine milk exosome. In other embodiments, an extracellular vesicle that can be used as described herein is a goat milk exosome. In other embodiments, an extracellular vesicle that can be used as described herein is a pig milk exosome.

Methods for isolating a milk exosome as well as methods for determining purity thereof are provided in the Examples section.

Biological Membranes of the Extracellular Vesicles

Glycoproteins belong to a class of proteins having one or more carbohydrate groups attached to the polypeptide chain. Glycoproteins contain oligosaccharide chains (glycans) covalently attached to polypeptide side-chains. The carbohydrate is attached to the protein in a cotranslational or posttranslational modification process known as glycosylation. Glycoproteins are found on the outside biological membranes, with the sugar facing out. Thus, glycoproteins are often an important integral membrane proteins, where they play a role in cell-cell interactions. There are several types of glycosylation: N-glycosylation in which sugars are attached to nitrogen, typically on the amide side-chain of asparagine through N-glycosidic bonds; O-glycosylation in which sugars are attached to oxygen, typically on serine or threonine but also on non-canonical amino acids such as hydroxylysine & hydroxyproline through O-glycosidic bonds; P-glycosylationin which sugars are attached to phosphorus on a phosphoserine; C-glycosylation in which sugars are attached directly to carbon, such as in the addition of mannose to tryptophan. The different structure of N- and O-linked sugars give them different functions.

The eight sugars typically found in eukaryotic glycoproteins include β-D-Glucose (Glc) which is a hexose sugar, β-D-Galactose (Gal) which is a hexose sugar, β-D-Mannose (Man) which is a hexose sugar, N-Acetylneuraminic acid (NeuNAc) which is a Sialic acid, α-L-Fucose (Fuc) which is a deoxyhexose sugar, N-Acetylgalactosamine (GalNAc) which is an amino hexose, N-Acetylglucosamine (GlcNAc) which is an amino hexose Xylose (Xyl) which is a pentose. The sugar group(s) can assist in protein folding or improve a protein's stability. Examples of glycoproteins include lectins, mucins, and several polypeptide hormones. Glycoproteins are found on the outside biological membranes, with the sugar facing out. Thus, glycoproteins are often an important integral membrane proteins, where they play a role in cell-cell interactions.

An extracellular vesicle, e.g., exosome, that can be used to encapsulate one or more cargos as described herein can include a biological membrane containing one or more glycoproteins. An extracellular vesicle, e.g., exosome, that can be used to carry one or more cargos as described herein can include a biological membrane containing one or more glycoproteins. In some embodiments, an extracellular vesicle described herein can include a biological membrane comprising one or more surface glycoproteins. For example, one or more glycoproteins can be embedded within or otherwise present in or present on the surface of the biological membrane of an extracellular vesicle such that a glycan on the glycoprotein is presented on the outer surface of the biological membrane and thus the outer surface of the extracellular vesicle.

Glycoproteins that can be present in the biological membrane of an extracellular vesicle as described herein can include any appropriate glycan. Examples of glycans include, without limitation, N-glycans (e.g., N-acetyl-glucosamines and N-glycan chains), O-glycans, C-glycans, sialic acid, galactose or mannose residues, and combinations thereof. In some embodiments, the glycan is selected from an alpha-linked mannose, Gal β1-3 GalNAc 1 Ser/Thr, GalNAc, or sialic acid. In any of these embodiments, the extracellular vesicle is an exosome, e.g., a milk exosome.

In some embodiments, an extracellular vesicle that can be used to carry or encapsulate one or more cargos as described herein can include one or more modified glycoproteins. In some embodiments, the extracellular vesicle comprising one or more modified glycoproteins is an exosome, e.g., a milk exosome. Cellular uptake of milk exosomes (e.g., bovine milk exosome) is mediated by endocytosis and depends on both cell and exosome surface glycoproteins (see, e.g., Wolf et al., 2015 *Journal of Nutrition* 145:2201-2216). Modification the glycan(s) presented on the outer surface of the exosome can be used to control or alter cellular uptake of extracellular vesicles and/or delivery of cargo present in the exosome.

In some embodiments, the extracellular vesicle, e.g., exosome, can have a modified biological membrane such that one or more of its native glycoproteins is increased, decreased or altered. Thus in some embodiments, the present disclosure provides an extracellular vesicle, e.g., an exosome (e.g., milk exosome) comprising a biological membrane surrounding a lumen, wherein the biological membrane comprises one or more glycoprotein(s), wherein the biological membrane is modified as compared with the natural biological membrane of the milk exosome. In some embodiments, the extracellular vesicle (EV) or exosome contains a biological membrane which is modified such that it has an increased number of one or more of its native glycoprotein(s). In some embodiments, the EV or exosome contains a biological membrane is modified such that it has a decreased number of one or more of its native glycoprotein(s). In some embodiments, the EV or exosome contains a biological membrane which is modified such that one or more of its native glycoprotein(s) is not present. In some embodiments, the EV or exosome contains a biological membrane that is modified such that it includes one or more glycoprotein(s) that is not naturally present in the natural biological membrane. In some embodiments, the EV or exosome contains a biological membrane that is modified such that one or more of its native glycoprotein(s) is altered.

The biological membrane of the EV or exosome can be modified to increase one or more native glycoproteins or can be modified to include glycoproteins that are not naturally present in the native biological membrane using various methods known in the art to deliver or embed glycoproteins into the membranes of EV or exosomes, including for example, electroporation or transfection with cationic lipid reagents. Other methods include delivering the glycoprotein(s) by ultracentrifugation including using methods described in U.S. Pat. No. 9,085,778, US 2016/0000710, and WO 2015/161184, each of which is hereby incorporated by reference, as well as methods described in Luan, X. et al., Acta Pharmacol Sin. 2017 June; 38(6): 754-763 and Munagala R, et al., *Cancer Lett*. 2016 Feb. 1; 371(1):48-61, each of which is hereby incorporated by reference. Those procedures include i) suspending the glycoprotein(s) in PEG-400, mixing with milk-derived exosomes, followed by low-speed centrifugation; ii) mixing with milk- or colostrum-derived exosomes, low-speed centrifugation (10,000×g) to remove any glycoprotein that did not get incorporated into the biological membrane, and finally high-speed centrifugation; and iii) mixing the glycoprotein(s) in ethanol with 100,000 whey (obtained after the 100,000×g centrifugation), low-speed centrifugation and finally 120,000×g centrifugation. There are many methods, such as the methods described in the Examples section that can be used to confirm that the added glycoprotein(s) are present in the biological membrane of the EV or exosome.

The biological membrane of the EV or exosome can be modified to decrease or remove one or more native glycoproteins by contacting the EV or exosome with one or more proteases, which cleave amino acids. Thus, in some embodiments, the EV or exosome is produced by contacting it with an enzyme selected from a serine protease, cysteine protease or metalloprotease. In some embodiments, the EV or exosome is produced by contacting it with an enzyme is selected from trypsin, AspN, GluC, ArgC, chymotrypsin, proteinase K, and Lys-C. The specificities of these different proteases are provided herein in Table A. Methods for treating EV or exosomes with such proteases to decrease or remove glycoprotein(s) from the biological membrane of EV or exosomes are provided in detail in the Examples section.

Glycoproteins and Glycans

As with other major classes of macromolecules, the biological roles of glycans span the spectrum from those that appear to be relatively subtle, to those that are crucial for the development, growth, functioning, or survival of the organism that synthesizes them. See, e.g., *Essentials of Glycobi-*

*ology*, 2nd edition, Varki, A, Cummings, R. D., Esko, J. D., et al., eds. Cold Spring Harbor (NY): Cold Spring Harbor Laboratory Press; 2009.

The biological roles of glycans can be divided into two broad categories: (1) the structural and modulatory properties of glycans and (2) the specific recognition of glycans by other molecules—most commonly, glycan-binding proteins (GBPs). The GBPs can be subdivided into two major groups: (1) intrinsic GBPs, which recognize glycans from the same organism and (2) extrinsic GBPs, which recognize glycans from a different organism. Intrinsic GBPs typically mediate cell-cell interactions or recognize extracellular molecules, but they can also recognize glycans on the same cell. Extrinsic GBPs consist mostly of pathogenic microbial adhesins, agglutinins, or toxins, but some also mediate symbiotic relationships. These two types of glycan recognition likely act as opposing selective forces driving evolutionary change, at least partly accounting for the enormous diversity of glycan structure found in nature. Further complexity arises from the fact that some microbial pathogens engage in "molecular mimicry," evading immune reactions by decorating themselves with glycans typical of their hosts. Finally, some microbes are themselves targets of their own pathogens (e.g., bacteriophages that invade bacteria), and glycan recognition is a common feature of these interactions as well.

Approaches taken to understand the biological roles of glycans include the prevention of initial glycosylation, prevention of glycan chain elongation, alteration of glycan processing, enzymatic or chemical deglycosylation of completed chains, genetic elimination of glycosylation sites, and the study of naturally occurring genetic variants and mutants in glycosylation.

The first intrinsic glycan receptors to be identified were those that mediate clearance, turnover, and intracellular trafficking of soluble blood-plasma glycoproteins. Most of these receptors specifically recognize certain terminal or subterminal glycans on the soluble glycoprotein. There are also endocytic receptors, whose functions have yet to be assigned, that recognize specific glycan sequences. Several instances exist wherein free glycans can have hormonal actions that induce specific responses in a highly structure-specific manner. Examples include the interaction of small glycans from bacterial symbionts with plant roots and the bioactive properties of fragments of hyaluronan in mammalian systems, both of which can induce biological responses in a size- and structure-dependent manner. Likewise, free heparan or dermatan sulfate fragments released by certain cell types can have major biological effects in complex situations such as wound healing.

It is now clear that glycans have many specific biological roles in cell-cell recognition and cell-matrix interactions. One of the best characterized examples concerns the selectin family of adhesion molecules, which recognize glycan structures on their ligands and thereby mediate critical interactions between blood cells and vascular cells in a wide variety of normal and pathological situations. As indicated above, GBPs and glycans present on cell surfaces can interact specifically with molecules in the matrix or even with glycans on the same cell surface. In some such instances, the specific biological significance of recognition has yet to be conclusively demonstrated in the intact animal. Also, it is becoming clear that some critical recognition sites are actually combinations of glycans and protein. For example, P-selectin recognizes the generic selectin ligand sialyl Lewisx with high affinity only in the context of the amino-terminal 13 amino acids of P-selectin glycoprotein ligand-1 (PSGL-1), which include certain required sulfated tyrosine residues. More recently, a different form of intrinsic recognition has been described, in which glycan-binding sites of cell-surface receptors are masked by cognate glycans on the same cell surface, making them unavailable for recognition by external ligands. Generally speaking, terminal sugar sequences, unusual structures, or modifications of the glycans are more likely to be involved in recognizing highly specific cell types or other particular, unique recognition events.

Carbohydrate-carbohydrate interactions may also have a specific role in cell-cell interactions and adhesion. A dramatic example is the species-specific interaction between marine sponges, which is mediated via homotypic binding of the glycans on a large cell-surface glycoprotein. Certain glycans act as specific binding sites for a variety of viruses, bacteria, and parasites, and as recognition targets for many plant and bacterial toxins. In such situations, there is typically excellent recognition specificity for the sequence of the glycan involved. For example, the hemagglutinins of many viruses specifically recognize the type of host sialic acid, its modifications, and its linkage to the underlying sugar chain. Likewise, various toxins bind with high specificity to certain gangliosides but not to related structures. There is little doubt about the importance of structural specificity with respect to these functions of glycans. Indeed, many of the microbial binding proteins involved have been harnessed as specific tools for studying the expression of the cognate sugar chains.

Glycans can mediate uptake by and interactions with specific cell types, for example immune cells. Antigenic proteins must first be taken up by antigen presenting cells (macrophages and especially dendritic cells), which process them into peptides, to be presented by MHC Class II molecules, for recognition by T lymphocytes. This process can be facilitated by glycans on the target protein. For example, the presence of high densities of terminal Man or GlcNAc residues on foreign proteins or microbes can trigger phagocytosis via C-type lectins on antigen presenting cells, with resulting delivery of the antigenic proteins to processing compartments.

A variety of cell surface receptors that recognize terminal glycans can trigger uptake of molecules (endocytosis), particles (phagocytosis) or even intact cells. The classic examples are the asialoglycoprotein receptor of hepatocytes and the mannose receptor of macrophages, which bind to mannose glycans and mannose 6-phosphate glycans. The mannose receptor (Cluster of Differentiation 206, CD206) is a C-type lectin primarily present on the surface of macrophages and immature dendritic cells, but is also expressed on the surface of skin cells such as human dermal fibroblasts and keratinocytes, A C-type lectin (CLEC) is a type of carbohydrate-binding protein domain known as a lectin. The C-type designation is from their requirement for calcium for binding. Proteins that contain C-type lectin domains have a diverse range of functions including cell-cell adhesion, immune response to pathogens and apoptosis. Another glycan receptor is the sialic acid receptor Sialoadhesin which is expressed by macrophage subsets. A large variety of lectins are known to carry out endocytosis in macrophages and dendritic cells. Such recognition processes may be critical not only for providing antigens to process and present to T cells, but also for clearing away damaged cells or glycoproteins, such as occurs when microbial sialidases enter the circulation during sepsis and cause desialylation of platelets, or when cancers secrete incompletely glycosylated mucins.

Lectins

Antiglycan antibodies and lectins are widely used in glycan analysis because their specificities enable them to discriminate among a variety of glycan structures and their multivalency ensures high-affinity binding to the glycans and cell surfaces containing those glycans.

Many of the lectins currently used as tools in glycobiology come from plants and are commercially available. Most of these lectins were characterized initially by inhibition assays, in which monosaccharides, monosaccharide derivatives, or small oligosaccharides are used to block lectin binding to cells or some other glycan-coated target. Small molecules that compete with binding of a lectin or antibody to a larger-sized ligand are termed haptens. These lectins are grouped by specificity depending on the monosaccharide(s) for which they show the highest affinity and their distinct preference for α- or β-anomers of the sugar. However, lectins within a particular specificity group also may differ in their affinities for different glycans. The common method for grouping lectins according to monosaccharide specificity should thus be used with caution because it does not reflect the complex specific determinants a given lectin may recognize with high affinity. The binding affinity ($K_d$) of lectins for complex glycans is often in the range of 1 to 10 μM. For complex glycoconjugates with multiple determinants or multivalency, the binding affinity of lectins may approach nanomolar values. In contrast, the affinity of most lectins for monosaccharides is in the millimolar range. The specificity of concanavalin A (ConA), perhaps the most widely used lectin, demonstrates this point. This lectin (which is an α-mannose/α-glucose-binding lectin) binds to N-glycans and is not known to bind O-glycans on animal cell glycoproteins. However, it binds oligomannose-type N-glycans with much higher affinity than it binds complex-type biantennary N-glycans, and it fails to bind more highly branched complex-type N-glycans.

Lectins and antibodies are useful reagents for aiding in glycan identification. See, e.g., *Essentials of Glycobiology*, [internet] 3rd edition, Varki, A, Cummings, R. D., Esko, J. D., et al., eds. Cold Spring Harbor (NY): Cold Spring Harbor Laboratory Press; 2015-2017. They include agglutination of cells and blood typing, cell separation and analysis, bacterial typing, identification and selection of mutated cells with altered glycosylation, toxic conjugates for tumor cell killing, cytochemical characterization/staining of cells and tissues, inducing mitogenesis of cells, acting as growth inhibitors, mapping neuronal pathways, purification and characterization of glyco-conjugates, assays of glycosyltransferases and glycosidases, and defining glycosylation status of target glycoconjugates and cells. Thus, using a variety of lectins and antibodies, it is possible to deduce many aspects of glycan structures. Microarrays in which a variety of lectins and antibodies are printed on a slide can also give valuable information about the glycosylation status of cells and glycoconjugates. This approach is especially sensitive in regard to defining whether biological samples differ in glycosylation. For example, such approaches have been adapted to study differential glycosylation of prion glycoproteins using a panel of biotinylated lectins in ELISA-type formats.

Exosome Glycoproteins and Effects on Uptake and Delivery

Exosomes secreted from cells intrinsically express some lipids and cell adhesion molecules and ligands that naturally target certain types of recipient cells. Several studies have shown that cell-secreted exosomes have natural targeting ability based on their donor cells of origin (Luan, X. et al., "Engineering exosomes as refined biological nanoplatforms for drug delivery," *Acta Pharmacologica Sinica* 2017, 38: 754-763, hereby incorporated by reference). For instance, exosomes isolated from neuroblastoma intrinsically express glycosphingolipid glycan groups that can bind to the aggregates of amyloid-β in the brain, and therefore may provide an effective treatment for Alzheimer's disease (see, e.g., Hood, J. L., "Post isolation modification of exosomes for nanomedicine applications," *Nanomedicine (Loud)* 2016, 11, 1745-56, hereby incorporated by reference). As demonstrated by the present disclosure, it has now been found that modulation of the targeting and uptake of milk exosomes is possible.

Methods of characterizing and altering surface glycoproteins and glycans are known in the art. For example, after cleavage of surface peptides with one or more proteases, the peptides may be identified using LC/MS-MS, Mascot and Sequest databases. Glycoproteins may be identified using a series of tools based on neuronal networks including NetNglyc, NetOglyc, NetCglyc 1.0 and GlycoEP, and the like.

Targeting ligands on the surfaces of some cell-secreted exosomes can be engineered. The most commonly used technique is to insert the gene encoding the targeting proteins into the donor cells that produce the exosomes of interest. The donor cells then secrete this protein in the exosomes. For example, plasmids encoding Lamp2b have been constructed and transfected into dendritic cells. The exosomes harvested after the donor cells have been transfected and found to fuse strongly to the neuron-specific rabies viral glycoprotein (RVG) peptide through Lamp2b on the exosomal membrane. The expression of Lamp2b on the exosomes has been confirmed by western blotting. These targeted exosomes can effectively deliver siRNA to the brain in a mouse model (see, e.g., Alvarez-Erviti L. et al., "Delivery of siRNA to the mouse brain by systemic injection of targeted exosomes," *Nat Biotechnol* 2011, 29, 341-5, hereby incorporated by reference). Another study has used exosomes to deliver let-7a miRNA in a targeted manner to EGFR-overexpressing breast cancer cells in mice. GE11 or EGF was cloned into a pDisplay vector and transfected into HEK299 cells. The data suggest that intravenous injection of the let-7a-loaded GE11-targeting exosomes can deliver the gene to the EGFR-expressing tumor in a mouse xenograft model (Ohno, S. et al., "Systemically injected exosomes targeted to EGFR deliver antitumor microRNA to breast cancer cells," *Mol Ther* 2013, 21, 185-91, hereby incorporated by reference).

As disclosed herein, surface glycoproteins and their specific surface glycans affect the uptake and delivery of microvesicles such as milk exosomes (Sukreet, S., et al., "Identification of Glycoproteins on the Surface of Bovine Milk Exosomes and Intestinal Cells that Facilitate Exosome Uptake in Human Colon Carcinoma Caco-2 Cells," *The FASEB Journal* 2017, 31, 646.25, hereby incorporated by reference). Exosomes were isolated from bovine milk by differential centrifugation and authenticated as recommended by International Society for Extracellular Vesicles. Surface proteins or glycan modifications in exosomes or Caco-2 cells were removed using proteases (Glu-C, trypsin, Arg-C, Asp-N, or proteinase K) or glycosidases [N-glycosidase F (PNGase F), galactosidase, O-glycosidase, neuraminidase, N-acetyl glucosaminidase, or a combination of all]. Controls were incubated with solvent. Exosomes were labeled with FM4-64, and unlabeled fluorophore was removed. Surface peptides released after the treatment were identified using LC/MS-MS, Mascot and Sequest databases.

Glycoproteins on the external surface were identified using a series of tools based on neuronal networks including NetNglyc, NetOglyc, NetCglyc 1.0 and GlycoEP. Transport kinetics were modelled using the Michaelis-Menten equation. One-way ANOVA and Bonferroni's multiple comparison were used for statistical analyses. Treatment with galactosidase, PNGase F and O-glycosidase had a stronger effect than other glycosidases. When exosomes or cells were treated with the glycosidase mixture, no uptake was detected or uptake was decreased by 80%, respectively, in comparison to controls. 149 total proteins were identified in bovine exosome, including 4 (N), 2 (O) and 2 (C) glycan binding sites; 298 proteins were identified in Caco-2 cells, including 46 membrane proteins that included 29 (N), 33 (O) and 6 (C) glycan binding sites. Thus, glycoproteins on the surface of bovine milk exosomes and intestinal cells facilitate the uptake of exosomes in human intestinal cells. The β-galactoside, Core 1 & Core 3-O-linked disaccharide and N-acetylglucosamine modifications appear to be of greater importance than other glycan features present on complex glycoproteins.

In some embodiments, one or more glycan(s) present on the outer surface of the extracellular vesicle is modified by alteration, substitution, addition, and/or deletion of one or more amino acid residues. In some embodiments, the biological membrane of the EV or exosome is modified such that one or more of its native glycoprotein(s) is altered. In some embodiments, the one or more native glycoprotein(s) is altered such that the number of glycan residues present on the glycoprotein(s) is increased. In some embodiments, the exosome is produced using glycosylation that adds one or more glycans to the glycoprotein. In some embodiments, the one or more native glycoprotein(s) is altered such that the number of glycan residues present on the glycoprotein(s) is decreased. In some embodiments, the number of glycan residues is decreased by cleavage of one or more glycan residues present on the glycoprotein(s). In some embodiments, the exosome is produced using an enzyme selected from a glycosidase, exoglycosidase, endoglycosidase, glycoamidase, neuraminidase, galactosidase, peptide:N-glycosidase (PNGase), glycohydrolase, and any combination thereof wherein the EV or exosome is contacted with the enzyme to remove one or more glycans. In some embodiments, the enzyme is selected from a β-N-acetylglucosaminidase, PNGase F, β(1-4) Galactosidase, O-Glycosidase, N-Glycosidase, N-glycohydrolase, Endo H, Endo D, Endo $F_2$, $EndoF_3$, and any combination thereof.

In some embodiments, two or more native glycoprotein(s) are altered such that at least one glycoprotein has an increased number of glycan residues and at least one other glycoprotein has a decreased number of glycan residues or is missing its glycan residue(s), wherein the glycoprotein(s) having an increased number of glycan residues is different from the glycoprotein(s) having a decreased number of glycan residues or missing glycan residues. In some embodiments, the one or more native glycoprotein(s) is altered such that it comprises a modified glycan. In some embodiments, the modified glycan comprises at least one carbohydrate moiety that differs from that of the glycan in the native glycoprotein(s). In some embodiments, the modified glycan comprises one or more galactose, mannose, glucose, O-glycans, N-acetyl-glucosamine, sialic acid, xylose, fucose, and/or N-glycan chains or any combination thereof. In some embodiments, the modified glycan lacks a portion of one or more of its carbohydrate chain(s). In some embodiments, the modified glycan is missing one or more of its carbohydrate chain(s). In some embodiments, the modified glycan comprises one or more altered carbohydrate chain(s). In some embodiments, the one or more native glycoprotein(s) is altered such that at least one glycan present on the glycoprotein(s) is substituted with a glycan that is not naturally present in the native glycoprotein(s). In some embodiments, the one or more native glycoprotein(s) is altered by blocking one or more glycan residue(s) present on the glycoprotein(s). In some embodiments, the one or more glycan residue(s) is blocked by lectin binding to the glycan residue. In some embodiments the glycan is blocked by an antibody that binds to that glycan.

In some embodiments, modification of the glycan(s) present on the outer surface of the exosome is used to target the exosome to specific cell types. For example, polypeptide sequences adjacent to arginine and lysine residues in glycans are essential for exosome uptake by macrophages. In some embodiments, modification the glycan(s) presented on the outer surface of the exosome can be used to reduce and/or eliminate degradation of the exosome. In some embodiments, modification, e.g., alteration, substitution, addition, and/or deletion, of polypeptide sequences adjacent to arginine and lysine residues in a glycan(s) present on the outer surface of an exosome is used to reduce and/or eliminate degradation of an exosome (e.g., by macrophages). In some embodiments, removal of galactose residues in a glycan(s) present on the outer surface of an exosome is used to decrease the uptake of the exosome into intestinal cells.

In some embodiments, alteration or substitution of the glycan comprises adding a glucose, fucose, neuraminic acid, allose, xylose, ribose, arabinose, threose, galactose, mannose, or sialic acid moiety. In some embodiments, alteration or substitution of the glycan comprises adding an alpha-linked mannose, Gal β 1-3 GalNAc 1 Ser/Thr, GalNAc, or sialic acid.

An extracellular vesicle having one or more modified glycoproteins described herein can be made using any appropriate method. In some embodiments, an extracellular vesicle having one or more modified glycoproteins described herein can be made by removing certain glycans from the one or more surface glycoproteins and/or by removing the extrasomal surface portion of a surface glycoprotein. For example, an exosome can be treated with a protease (e.g., Glu-C (targeting glu), trypsin (targeting arg and lys), and/or Arg-C (targeting arg and lys)) to remove the extrasomal surface portion of a surface glycoprotein. In some embodiments, an EV or exosome can be contacted with a glycosidase to remove one or more glycan residues, for example, an enzyme selected from a glycosidase, exoglycosidase, endoglycosidase, glycoamidase, neuraminidase, galactosidase, peptide:N-glycosidase (PNGase), glycohydrolase, and any combination thereof. Specific exemplary enzymes include β-N-acetylglucosaminidase, PNGase F, β (1-4) Galactosidase, O-Glycosidase, N-Glycosidase, N-glycohydrolase, Endo H, Endo D, Endo $F_2$, $EndoF_3$, and any combination thereof which can be used to remove one or more glycans from the EV or exosomes. Methods for contacting exosomes with such enzymes are provided in the Examples section. In another embodiment, EVs or exosomes have glycoproteins with one or more modified glycans can be produced using a transgenic animal that has one or more glycan transferase enzyme(s) knocked out. Exemplary methods are provide in Example 9. In other embodiments, one or more native glycoprotein(s) is altered by blocking one or more glycan residue(s) present on the glycoprotein(s). In some embodiments, one or more glycan residue(s) is blocked by lectin binding to the glycan residue. In some embodiments, the lectin is selected from Concanavalin A, Lentil lectin, Snowdrop lectin, Ricin (*Ricinus communis* Agglutinin, RCA120), Peanut agglutinin, Jacalin, Hairy vetch lectin, *Dolichos biflorus* agglutinin, Soybean agglutinin, N-acetylglucosamine binding lectins, Wheat Germ Agglutinin (WGA), *Phaseolus vulgaris* agglutinin, Elderberry lectin, *Maackia amurensis* leukoagglutinin, *Maackia amurensis* hemoagglutinin, *Ulex europaeus* agglutinin, or *Aleuria aurantia* lectin.

In some embodiments, an extracellular vesicle having one or more modified glycoproteins described herein can be made by introducing one or more glycans to the surface glycoproteins. For example, glycosylation (e.g., chemical and/or enzymatic glycosylation) can be used to add one or more glycans to the surface glycoproteins. In some embodiments, an extracellular vesicle having one or more modified glycoproteins described herein can be made by stabilizing one or more glycans already present on the surface glycoproteins.

An extracellular vesicle having one or more modified glycoproteins described herein can be made using any appropriate method. In some embodiments, an extracellular vesicle having one or more modified glycoproteins described herein can be made by removing certain glycans from the one or more surface glycoproteins and/or by removing the extrasomal surface portion of a surface glycoprotein as taught herein.

An extracellular vesicle described herein can be used for extracellular vesicle-mediated delivery of one or more cargos to a mammal (e.g., a human). In some embodiments, the extracellular vesicle used for delivery of cargo comprises modification of one or more glycan(s) present on the outer surface of the extracellular vesicle. In some embodiments, one or more glycan(s) present on the outer surface of the extracellular vesicle is modified by alteration, substitution, addition, and/or deletion of one or more amino acid residues. In some embodiments, the modification of the one or more glycan(s) is used to target the extracellular vesicle to a specific cell type. In some embodiments, the modification of the one or more glycan(s) is used to reduce and/or eliminate degradation of the extracellular vesicle. In some embodiments, the modification of the one or more glycan(s) is used to reduce and/or eliminate degradation of the extracellular vesicle via macrophages. In some embodiments, the one or more glycan(s) is modified by alteration, substitution, and/or deletion of one or more polypeptide sequences adjacent to arginine and/or lysine residues in a glycan(s) present on the outer surface of the extracellular vesicle. In some embodiments, the modification of the one or more glycan(s) is used to decrease the uptake of the exosome into intestinal cells. In some embodiments, the one or more glycan(s) is modified by removal of galactosidase residues in a glycan(s) present on the outer surface of an extracellular vesicle.

In some embodiments, the extracellular vesicle used for delivery of cargo having one or more modified glycoproteins described herein can be made by removing certain glycans from the one or more surface glycoproteins and/or by removing the extrasomal surface portion of a surface glycoprotein. In some embodiments, the extracellular vesicle having one or more modified glycoproteins is treated with a protease (e.g., Glu-C (targeting glu), trypsin (targeting arg and lys), and/or Arg-C (targeting arg and lys)) to remove the extrasomal surface portion of a surface glycoprotein. In some embodiments, an extracellular vesicle having one or more modified glycoproteins described herein is made by introducing one or more glycans to the surface glycoproteins. For example, glycosylation (e.g., chemical and/or enzymatic glycosylation) can be used to add one or more glycans to the surface glycoproteins. In some embodiments, an extracellular vesicle having one or more modified glycoproteins described herein can be made by stabilizing one or more glycans already present on the surface glycoproteins. In any of these embodiments for delivery of one or more cargos to a mammal (e.g., a human), the extracellular vesicle can be an exosome, e.g., a milk exosome. In some embodiments, the extracellular vesicle is a bovine milk exosome. In some embodiments, the extracellular vesicle is a goat milk exosome. In some embodiments, the extracellular vesicle is a pig milk exosome.

In any of the embodiments described herein where the biological membrane of an EV or exosome has been modified to alter one or more glycoproteins (e.g., increase, decrease, or modify) or to alter one or more glycans (e.g., increase, decrease, or modify) on a glycoprotein in the biological membrane of an EV or exosome, the EV or exosome having the modified biological membrane can be used to alter the delivery of the modified EV or exosome, and its corresponding cargo, to a mammalian cell or tissue. For example, the EV or exosome having modified biological membrane can be used to increase or decrease the delivery, increase or decrease the transport, increase or decrease the uptake of the EV or exosome and/or its corresponding cargo to mammalian cells and tissues. Also, the EV or exosome having modified biological membrane can be used to selectively target a specific mammalian cell or tissue by altering the glycoprotein and/or glycan in its biological membrane, thus providing targeted delivery, transport, and/or uptake of the UV or exosome and/or its cargo. Using the compositions and methods described herein, the biological membrane of the EV or exosome can be customized by altering the amount and content of the glycoprotein or glycan in the biological membrane to effect any of the above-mentioned functions.

Extracellular vesicles vary in size and a given sample of vesicles will have an average diameter with individual vesicles varying within a range. Extracellular vesicles, e.g. milk exosomes, of a particular diameter or average diameter may be selected for use in accordance with the present disclosure. In some embodiments, an exosome is about 20 nm to about 200 nm in diameter. In some embodiments, an exosome is about 30 nm to about 190 nm or about 25 nm to about 180 nm in diameter. In some embodiments, an exosome is about 30 nm to about 170 nm in diameter. In some embodiments, an exosome is about 40 nm to about 160 nm in diameter. In some embodiments, an exosome is about 50 nm to about 150 or about 60 to about 140 nm, about 100 to about 200, about 80 to about 250, about 70 to about 130, about 80 to about 120, or about to about 110 nm in diameter. In some embodiments, an exosome is about 20, 25, 30, 35, 50, 100, 110, 125, or 150 nm in diameter. In some embodiments, an average exosome diameter in an exosomal composition or plurality of exosomes isolated or derived from milk is about 20, about 25, about 30, about 35, about 50, about 75, about 100, about 110, about 125, or about 150 nm; or about 20 to about 200, about 25 to about 250, about 100 to about 200, about 80 to about 250, about 30 to about 180, about 40 to about 170, about 50 to about 160, about 50 nm to about 150, about 60 to about 140 nm, about 70 to about 130, about 80 to about 120, or about 90 to about 110 nm in average diameter.

Cargos

An extracellular vesicle (e.g., an exosome) described herein can carry any appropriate cargo for delivery to a mammal (e.g., a human). The cargo can be conjugated to an extracellular vesicle, embedded within an extracellular vesicle, encapsulated within an extracellular vesicle, or otherwise carried by an extracellular vesicle, or any combination thereof. Thus, as used herein, a reference to a cargo being "present" in an extracellular vesicle or its lumen is understood to include any of the foregoing means of carrying the cargo.

In some embodiments, an exosome is loaded with 2-5 molecules or copies of a single cargo or two (or more) different cargos. In some embodiments, an exosome or pharmaceutical composition thereof is loaded with 1-4,000, 10-4,000, 50-3,500, 100-3,000, 200-2,500, 300-1,500, 500-1,200, 750-1,000, 1-2,000, 1-1,000, 1-500, 10-400, 50-300, 1-250, 1-100, 2-50, 2-25, 2-15, 2-10, 3-50, 3-25, 3-25, 3-10, 4-50, 4-25, 4-15, 4-10, 5-50, 5-25, 5-15, or 5-10 molecules or copies of a single cargo or two (or more) different cargos. The cargo is endogenous or exogenous, and where two or more cargos are present each cargo is independently endogenous or exogenous.

Examples of endogenous (naturally-occurring) cargos include proteins and other agents found naturally in microvesicles such as milk exosomes include CD63, Transferrin receptor, sialic acid, mucins, Tsg101 (Tumor susceptibility gene 101), Alix, annexin II, EF1a (Translation elongation factor 1a), CD82 (Cluster of Differentiation 82), ceramide, sphingomyelin, lipid raft markers, and PRNP (PRioN Protein), and other cargos shown in FIG. 50.

A cargo can be an endogenous cargo, an exogenous cargo, or a combination thereof. Examples of cargos that can be conjugated, embedded, encapsulated within or otherwise carried by an extracellular vesicle described herein include, without limitation, nucleic acid molecules (e.g., DNA, cDNA, antisense oligonucleotides, mRNA, inhibitory RNAs (e.g., antisense RNAs, miRNAs, small interfering RNAs (siRNAs), short hairpin RNAs (shRNAs), and agomiRs), antagomiRs, primary miRNAs (pri-miRNAs), long non-coding RNAs (lncRNAs), small nuclear RNA (snRNA), small nucleolar RNA (snoRNA), and microbial RNAs), polypeptides (e.g., enzymes, antibodies), lipids, hormones, vitamins, minerals, small molecules, and pharmaceuticals, or any combination thereof. In some embodiments, the miRNA is an endogenous miRNA such as miR-29b or miR-200c. In some embodiments, the miRNA is selected from those in Table 1 below:

TABLE 1

Comparison table for top miRs

| Column 1<br>Types | Column 2<br>Minimum RPKM<br>of Normal | Column 3<br>Minimum RPKM<br>of Sonicated |
|---|---|---|
| db_annotation | | |
| bta-miR-320a\|MI0012211 | 2363558.33 | 419367.6169 |
| bta-miR-3596\|MI0005453 | 400272.8183 | 4673 |
| bta-miR-423-5p\|MI0005046 | 449665.5261 | 2461 |
| bta-miR-3600\|MI0015943 | 65667.42731 | 305 |
| bta-miR-186\|MIMAT0003818 | 56127.64614 | 0 |
| bta-miR-181a\|MIMAT0003543 | 63842.85994 | 0 |
| bta-miR-148a\|MIMAT0003522 | 37266.265 | 0 |
| bta-miR-30a-5p\|MIMAT0003841 | 22698.08901 | 160 |
| bta-miR-378\|MIMAT0009305 | 27048.72601 | 412 |
| bta-miR-200a\|MIMAT0003822 | 18954.00743 | 0 |
| bta-miR-378\|MIMAT0009305_1 | 22045.49346 | 397 |
| bta-miR-26c\|MI0009784\|MI0015949 | 11491.79978 | 0 |
| bta-miR-26c\|MI0004731 | 11491.79978 | 0 |
| bta-miR-2285t\|MI0022348 | 22215.96884 | 0 |
| bta-miR-21-5p\|MI0004742 | 3432.615519 | 0 |
| bta-let-7c\|MI0005454 | 12387.2647 | 55 |
| bta-miR-26b\|MI0004745 | 2345.26561 | 0 |

TABLE 1-continued

Comparison table for top miRs

| Column 1<br>Types | Column 2<br>Minimum RPKM<br>of Normal | Column 3<br>Minimum RPKM<br>of Sonicated |
|---|---|---|
| bta-miR-24-3p\|MI0009761 | 13282.72962 | 0 |
| bta-miR-181b\|MIMAT0003793 | 8656.160873 | 0 |

An extracellular vesicle (e.g., an exosome) described herein can include one or more cargos, wherein the cargo(s) is a therapeutic molecule. Exemplary therapeutic molecules include small molecules of molecular weight of less than about 1000, 800, 500, or 300 amu and other therapeutic molecules described herein. Exemplary small molecules include, without limitation, antibiotics, steroids, sterols, peptides, natural products, alkaloids, terpenes, and synthetic molecules.

A therapeutic molecule can be conjugated to an extracellular vesicle, embedded within an extracellular vesicle, encapsulated within an extracellular vesicle, or otherwise carried by an extracellular vesicle or any combination thereof. Examples of therapeutic agents include, without limitation, mRNAs and/or polypeptides encoded by the mRNAs (e.g., Cre recombinase, insulin, peptide hormones, and enzymes), miRNAs, siRNAs, or miRNA antagonists of therapeutic value, nutrients that may be unstable or have low bioavailability (e.g., vitamins B1 and B12, polyunsaturated fatty acids), pharmaceuticals (e.g., antibiotics (such as puromycin, gentamycin, and neomycin), cancer drugs (such as chemotherapeutics, immunotherapies, hormone therapies, and targeted therapies), activators of Toll-like receptors), and molecules to be delivered to macrophages (e.g., to remove or prevent atherosclerotic plaques, or treat macrophage-related cancers), as well as any of the other therapeutic cargo molecules provided herein.

In some embodiments, the biologic therapeutic agent is a biologic. In some embodiments, the biologic is selected from a hormone, allergen, adjuvant, antigen, immunogen, vaccine, interferon, interleukin, growth factor, monoclonal antibody (mAb). In some embodiments, the biologic is a polypeptide, or a peptide, such as one containing ten or more amino acids but less than 50; a protein, such as a protein containing 50 or more amino acids but less than 300; or a protein having a mass from about 10 kD to about 30 kD, or about 30 kD to about 150 or to about 300 kD.

In some embodiments, the biologic is insulin or another peptide hormone.

In some embodiments, the cargo is selected from treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex ° and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In some embodiments, the cargo is a steroid or anti-inflammatory agent such as glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BILL, 284, ONO 4057, SB 209247; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (*Asta Medica*), CDC-801 (Celgene), SelCID™ CC-10004 (Celgene), VM554/UM565 (*Vernalis*), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

In some embodiments, the cargo is selected from small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In some embodiments, the cargo is selected from corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®); beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), rituximab (Rituxan®), cyclophosphamide (Cytoxan®), doxorubicin (Hydrodaunorubicin®), vincristine (Oncovin®), prednisone, a hedgehog signaling inhibitor, a Bcl-2 inhibitor, a BTK inhibitor, a JAK/pan-JAK inhibitor, a TYK2 inhibitor, a PI3K inhibitor, a SYK inhibitor, bortezomib (Velcade®), and dexamethasone (Decadron®), a hedgehog signaling inhibitor, a Bcl-2 inhibitor, a BTK inhibitor, a JAK/pan-JAK inhibitor, a TYK2 inhibitor, a PI3K inhibitor, a SYK inhibitor, or lenalidomide (Revlimid®).

An extracellular vesicle (e.g., an exosome) described herein can include one or more nutritional agents. A nutritional agent can be conjugated to an extracellular vesicle, embedded within an extracellular vesicle, encapsulated within an extracellular vesicle, or otherwise carried by an extracellular vesicle, or any combination thereof. Examples of nutritional agents include, without limitation, vitamins, minerals, lipids, fatty acids (e.g., omega-3 fatty acids such as docosahexaenoic acid (DHA), and omega-6 fatty acids), and mRNAs and/or polypeptides encoded by the mRNAs (e.g., insulin and enzymes).

An extracellular vesicle (e.g., an exosome) described herein also can include one or more detectable labels. A detectable label can be conjugated to an extracellular vesicle, embedded within an extracellular vesicle, encapsulated within an extracellular vesicle, or otherwise carried by an extracellular vesicle or any combination thereof. Examples of detectable molecules include, without limitation, bioluminescent label (e.g., luciferase), fluorescent molecules (e.g., GFP and mCherry), radionuclide molecules, biotin, and surface antigens. In some embodiments, an mRNA expressing a detectable label is encapsulated within an extracellular vesicle such that delivery (e.g., temporal and/or spatial delivery) of the encapsulated RNA can be monitored in a mammal.

In embodiments where an extracellular vesicle described herein contains an exogenous cargo, the exogenous cargo can be loaded (e.g., conjugated to an extracellular vesicle, embedded within an extracellular vesicle, encapsulated within an extracellular vesicle, or otherwise carried by an extracellular vesicles, or any combination thereof) with the exogenous cargo using any appropriate method. In some embodiments, an extracellular vesicle described herein can be loaded with an exogenous cargo by, for example, mixing cargos and exosomes, electroporation, calcium precipitation, amphipathic molecules, or alcohol-based solvents.

In some embodiments, an extracellular vesicle (e.g., an exosome) conjugated to, embedding, encapsulating, or otherwise carrying one or more cargos described herein can be administered to a mammal (e.g., a human). Methods of administration include, for example, subcutaneous, intraperitoneal, intravenous, and oral administration.

Methods of Using

This disclosure also provides methods of using an extracellular vesicle (e.g., an exosome) comprising one or more cargos described herein. In some embodiments, an exosome described herein can be administered to a mammal, e.g., human, to deliver one or more cargoes to a receptor cell in the mammal. The cargo of the exosome can be delivered over short distances (e.g., a receptor cell near the site of administration) or over long distances (e.g., a receptor cell in a distant tissue). In some embodiments, the cargo of the exosome can be delivered to a mammalian cell (e.g., a human cell) by endocytosis.

An extracellular vesicle (e.g., an exosome) comprising one or more cargos described herein can be administered to any type of mammal. In some embodiments, an extracellular vesicle comprising one or more cargos described herein can be administered to humans and other primates such as monkeys as described herein. In some embodiments, an extracellular vesicle comprising one or more cargos described herein can be administered to dogs, cats, horses, cows, pigs, sheep, rabbits, mice, and rats as described herein. In some embodiments wherein the extracellular vesicle is a bovine milk exosome, it can be administered to a non-bovine mammalian species. For example, a bovine milk exosome described herein can be administered to a human.

In some embodiments, an extracellular vesicle, e.g., exosome, described herein can be administered to a mammal, e.g., human, to deliver one or more cargoes to a receptor cell in the mammal. A receptor cell can be any appropriate receptor cell. Examples of receptor cells to which cargo of an exosome can be delivered include, without limitation, intestinal cells, endothelial cells (e.g., venous endothelial cells), immune cells (e.g., circulating immune cells), macrophages, intestinal mucosa (e.g., small intestinal mucosa), peripheral tissue (e.g., liver, spleen, lung, brain, kidneys, pancreas) cells, diseased cells (e.g., cancer cells), and fetal cells (e.g., fetal cells in the womb).

In some embodiments, extracellular vesicle-mediated delivery of one or more cargos to a mammal as described herein can be used to alter the gut microbiome of a mammal. Examples of cargos that can be used for altering the gut microbiome of a mammal include, without limitation, nucleic acids (e.g., RNAs), carbohydrates, lipids, and proteins. In some embodiments, administration of exosomes to a mammal can decrease the relative abundance of a bacterial species present in the gut microbiome. For example, the relative abundance of Firmicute classes Clostridia (e.g., Ruminococcaceae), and/or Verrucomicrobia classes (e.g., Verrucomicrobiae (such as Muciniphila species)) can be decreased by the exosome-mediated delivery of one or more cargos to a mammalian cell. In some embodiments, administration of exosomes to a mammal can increase the relative abundance of a bacterial species present in the gut microbiome. For example, the relative abundance of Firmicute classes (e.g., Clostridia (such as Clostridiales species)) or erysipelotrichaceae can be increased by the exosome-mediated delivery of one or more cargos to a mammalian cell, such as an endogenous or exogenous miRNA or mRNA. In some embodiments, the cargo is a vitamin or nutritional supplement.

In some embodiments, extracellular vesicle-mediated delivery of one or more cargos to a mammal as described herein can be used to regulate (e.g., increase or decrease) the immune response of a mammal. Examples of cargos that can be used to regulate the immune response of a mammal include, without limitation, proteins, glycoproteins, lectins, and nucleic acid molecules. In some embodiments, nucleic acid molecule (e.g., RNA) cargoes in exosomes can bind to Toll-like receptors to regulate the immune response of a mammal. Toll-like receptors (TLRs) are a class of proteins that plays a key role in the innate immune system. They are single, membrane-spanning, non-catalytic receptors expressed on macrophages and dendritic cells that recognize structurally conserved molecules derived from microbes. Microbes that have breached physical barriers such as the skin or intestinal tract mucosa are recognized by TLRs, which activate immune cell responses. The TLRs include TLR1, TLR2, TLR3, TLR4, TLR5, TLR6, TLR7, TLR8, TLR9, TLR10, TLR11, TLR12, and TLR13. This, in some embodiments, the exosome comprises cargo that binds to a TRL selected from: TRL1, TRL2, TRL3, TRL4, TRL5, TRL6, TLR7, TLR8, TLR9, TLR10, TLR11, TLR12, TLR13, and combinations thereof. In some embodiments, administration of bovine milk exosomes comprising cargo to a mammal can increase an immune response in a mammal. For example, the mammal's anti-viral and/or pro-inflammatory response can be increased by the exosome-mediated delivery of one or more cargos to a mammalian cell.

In some embodiments, extracellular vesicle-mediated delivery of one or more cargos to a mammal as described herein can be used to enhance the fertility or fecundity of a mammal. Examples of cargos that can be used for enhancing the fertility of a mammal include, without limitation, endogenous or exogenous miRNAs or mRNAs.

In some embodiments, extracellular vesicle-mediated delivery of one or more cargos to a mammal as described herein can be used to alter (e.g., increase or decrease) the metabolism of a mammalian cell. Examples of cargos that can be used for altering the metabolism of a mammalian cell include, without limitation, nucleic acid molecules, lipids, and polypeptides. In some embodiments, administration of an exosome, e.g., bovine milk exosome to a mammal can decrease purine metabolism in a mammalian cell. In some embodiments, administration of an exosome, e.g. bovine milk exosome to a mammal can decrease amino acid metabolism in a mammalian cell. For example, the metabolism of leucine, phenylalanine, alanine, lysine (e.g., leucyl-lysine), and/or isoleucine (e.g., gamma-glutamyl-isoleucine) can be altered by the exosome-mediated delivery of one or more cargos to a mammalian cell. In some embodiments, the cargo is an endogenous or exogenous miRNA or mRNA.

In some embodiments, extracellular vesicle-mediated delivery of one or more cargos to a mammal as described herein can be used to alter (e.g., increase or decrease) the gene expression of a mammalian cell. Examples of cargos that can be used for altering the gene expression of a mammalian cell include, without limitation, nucleic acid molecules, lipids, and polypeptides. In some embodiments, administration of exosomes to a mammal can decrease branched-chain amino acid (BCAA) expression in a mammal cell. For example, the expression of BCAT1, BCAT2, and/or genes encoding enzymes involved in purine metabolism can be altered by the exosome-mediated delivery of one or more cargos to a mammalian cell.

In some embodiments, extracellular vesicle-mediated delivery of one or more cargos to a mammal as described herein can be used to increase the muscle strength of a mammalian cell. Examples of cargos that can be used for increasing the muscle strength of a mammal include, without limitation, nucleic acid molecules, lipids, and polypeptides.

In some embodiments, extracellular vesicle-mediated delivery of one or more cargos to a mammal as described herein can be used to enhance neurological processes or treat cognitive impairment of a mammal. Examples of cargos that can be used for enhancing neurological processes or treating cognitive impairment of a mammal include, without limitation, nucleic acid molecules, lipids, and polypeptides. For example, administration of exosomes to a mammal can increase sensorimotor gating and/or cognitive performance (e.g., spatial learning and memory) in a mammal.

In some embodiments, extracellular vesicle-mediated delivery of one or more cargos to a mammal as described herein can be used to treat a mammal having a disease. Examples of cargos that can be used for treating a mammal having a disease include, without limitation, nucleic acid molecules, lipids, and polypeptides. For example, administration of exosomes to a mammal can be used to treat a mammal having sarcopenia, muscle loss after injury, atherosclerosis, cancer, immune diseases, impaired fecundity, and/or cognitive impairment (e.g., memory loss).

In some embodiments, the present disclosure provides a method of altering the uptake of a milk exosome into a mammalian cell or tissue, said exosome having a biological membrane comprising one or more glycoprotein(s), comprising modifying the biological membrane of the exosome. In some embodiments, the uptake of the milk exosome into a mammalian cell or tissue is increased. In some embodiments, the uptake of the milk exosome into a mammalian cell or tissue is decreased. In some embodiments, the uptake of the milk exosome into a mammalian cell or tissue is selectively increased in a targeted mammalian cell or tissue. In some embodiments, the uptake of the milk exosome into a mammalian cell or tissue is selectively decreased in a targeted mammalian cell or tissue. In some embodiments, the present disclosure provides a method of targeting a milk exosome to a selected mammalian cell or tissue, said exosome having a biological membrane comprising one or more glycoprotein(s), comprising modifying the biological membrane of the exosome. Any of these methods can be effected by using any of the UVs or exosomes described herein.

In other embodiments, a method of correcting dysbiosis or improving the gut microbiome or gut health of a subject is provided, comprising administering to said subject an effective amount of any of the exosomes provided herein. In other embodiments, a method of treating inflammatory bowel disease in a subject is provided, comprising administering to a subject in need thereof an effective amount of any of the exosomes described herein. In other embodiments, a method of treating obesity in a subject, is provided comprising administering to a subject in need thereof an effective amount of any of the exosomes described herein. In other embodiments, a method of treating non-alcoholic fatty liver in a subject is provided, comprising administering to a subject in need thereof an effective amount of any of the exosomes provided herein. In other embodiments, a method of increasing muscle strength, enhancing sensorimotor gating or cognitive performance, or increasing fertility or fecundity in a subject is provided, comprising administering to said subject an effective amount of any of the exosome provided herein or a nutritional supplement provided herein. In other embodiments, a method of treating sarcopenia, muscle loss after injury, atherosclerosis, cancer, an immune disease, impaired fecundity, or cognitive impairment is provided, comprising administering to a subject in need thereof any of the exosomes provided herein or a nutritional supplement provided herein.

Humans and microbes have established a symbiotic association over time, and perturbations in this association have been linked to several immune-mediated inflammatory diseases (IMID) including inflammatory bowel disease, rheumatoid arthritis, and multiple sclerosis. IMID is a term used to describe a group of chronic, highly disabling diseases that affect different organ systems. Though a cornerstone commonality between IMID is the idiopathic nature of disease, a considerable portion of their pathobiology overlaps including epidemiological co-occurrence, genetic susceptibility loci and environmental risk factors. At present, it is clear that persons with an IMID are at an increased risk for developing comorbidities, including additional IMID. Advancements in sequencing technologies and a parallel explosion of 16S rDNA and metagenomics community profiling studies have allowed for the characterization of microbiomes throughout the human body including the gut, in a myriad of human diseases and in health. See, e.g., Forbes, J. D. et al., *Front Microbiol.* 2016, 7, 1081.

Most IMID are highly prevalent in well-developed industrialized countries; in Western populations the prevalence of IMID is approximately 5-8% and encompasses over 100 different clinical diseases including inflammatory bowel disease (IBD), multiple sclerosis (MS), rheumatoid arthritis (RA), ankylosing spondylitis (AS), systemic lupus erythematosus (SLE), and psoriasis/psoriatic arthritis. The healthy human gut is dominated by the presence of four bacterial phyla: Bacteroidetes, Firmicutes, Actinobacteria, and Proteobacteria with Bacteroidetes and Firmicutes accounting for a large majority of endemic bacteria in the gut. Within the healthy human gut, the phylum Firmicutes are divided into two major classes of Gram-positive bacteria: Bacilli and Clostridia (primarily *Clostridium* cluster IV and *Clostridium* XIVa). The Bacteroidetes are Gram-negative bacteria, of which the *Bacteroides* represents one of the most abundant genera in the gut. Altered community composition has been established in a number of gastrointestinal diseases: IBD, celiac disease, irritable bowel syndrome, functional dyspepsia, antibiotic-associated diarrhea, tropical enteropathy, and others. Accumulating evidence proposes that dysbiosis of the intestinal microbiota is not limited to gastrointestinal diseases thereby suggesting that gut bacteria can affect the systemic immunological response. A number of studies have investigated gut dysbiosis in relation to obesity, diabetes, chronic periodontitis, vaginosis, atopic diseases, non-alcoholic steatohepatitis (NASH), Alzheimer's disease, and others. Forbes, J. D. et al., *Front Microbiol.* 2016, 7, 1081.

For example, in IBD, studies frequently document an overall reduction of diversity, the total number of species in a community. In fact, data from the MetaHIT consortium suggest that persons with IBD harbor on average 25% fewer microbial genes than healthy persons. Diversity is reduced in the fecal and mucosal microbiomes of IBD and has also been documented among monozygotic twins discordant for Crohn's Disease (CD). Decreased diversity has been attributed to shifts in the abundance of the Firmicutes, and more specifically the *Clostridium leptum* and *C. coccoides* group (Manichanh et al., *Gut.* 2006 February; 55(2):205-11). Likewise, utilizing a custom phylogenetic microarray Kang et al. (2010) reported some bacteria belonging to the Firmicutes phylum including *Eubacterium* rectale of the Lachnospiraceae and *Ruminococcus albus, R. callidus, R. bromii*, and *F. prausnitzii* of the Ruminococcaceae were 5- to more abundant in healthy persons compared to CD. Kang et al., *Inflamm Bowel Dis.* 2010 December; 16(12):2034-42.

*Bacteroides* is the most dominant genus in Western microbiotas and can both positively and negatively affect the host. Generally, while the overall abundance of the order Bacteroidales is increased in IBD, in certain circumstances particular species may be reduced; *Parabacteroides distasonis* is significantly decreased in inflamed IBD mucosa (Zitomersky et al., PLoS One. 2013; 8(6):e63686). Pathogenic bacteria including *E. coli*, and *Shigella*, and others such as *Rhodococcus* and *Stenotrophomonas maltophilia* are increasingly observed in IBD. Other pathobionts with potential roles in the disease course include Prevotellaceae, *C. difficile, Klebsiella pneumoniae, Proteus mirabilis*, and *Helicobacter hepaticus*.

The relative abundance of the Enterobacteriaceae in persons with IBD (Kolho et al., *Am J Gastroenterol.* 2015 June; 110(6):921-30) and mouse models of IBD (Nagao-Kitamoto et al., CMGH Cell. Mol. Gastroenterol. Hepatol. 2 468-481) is increased. Much research has focused on the role of *E. coli*, specifically AIEC, in IBD etiology; AIEC strains have been isolated from ileal-involving CD tissue and the genera *Escherichia* and *Shigella* (indistinguishable by 16S analysis) are highly enriched in patients with IBD and this enrichment was more pronounced in mucosal samples versus stool samples.

Pharmaceutical Compositions and Formulations; Routes of Delivery

Cargos may be in the form of pharmaceutically acceptable salts. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some embodiments, an extracellular vesicle (e.g., an exosome) encapsulating one or more cargos described herein can be formulated as a pharmaceutical composition and/or a nutritional supplement (e.g., a "nutraceutical"). For example, an extracellular vesicle preparation can be formulated to contain a pharmaceutically and/or nutritionally acceptable carrier for administration to a mammal. Examples of such carriers include, without limitation, sterile aqueous or non-aqueous solutions, solvents, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other carriers used for oral administration. In some embodiments, a nutritional supplement containing exosomes as described herein can be used in infant formulas.

The term "pharmaceutically acceptable carrier, adjuvant, or vehicle" refers to a non-toxic carrier, adjuvant, or vehicle that does not destroy the pharmacological activity of the compound (or microvesicle, as the case may be) with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The cargo can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the cargo may be admixed with at least one inert diluent such as sucrose, lactose or starch. Such dosage forms may also comprise, as is normal practice, additional substances other than inert diluents, e.g., tabletting lubricants and other tabletting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the subject treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

A pharmaceutical composition and/or a nutritional supplement can be formulated for administration in solid or liquid form including, without limitation, sterile solutions, suspensions, sustained-release formulations, tablets, capsules, pills, powders, and granules.

Methods of administration include, for example, subcutaneous, intraperitoneal, intravenous, and oral administration.

The invention will be further described in the following examples, which do not limit the scope of the invention described in the claims.

EXAMPLES

Example 1. Methods Used in Milk Exosome Studies

A. Isolation of Exosomes from Bovine Milk

Cow's milk (1% fat or skim milk) was obtained from a local grocery store. Exosomes were isolated from cow's milk using ultracentrifugation. The milk was centrifuged at either 12,000×g at 4° C. for 30 min or 13,200×g at 4° C. for 30 min to remove somatic cells and debris. The supernatant was mixed 1:1 (by vol) with 250 mM EDTA (pH 7.0) on ice for 15 min to precipitate milk casein and exosomes coated with casein. The suspension was ultra-centrifuged at either 80,000×g or 100,000×g at 4° C. for 60 min ($F_{37}L$-8 3 100 rotor; Thermo Scientific) to remove precipitated protein, milk fat globules, and microvesicles larger than the exosomes. The supernatant was ultracentrifuged at 120,000×g for 90 min at 4° C. to collect exosomes. The exosome pellet was resuspended in a small volume of sterile PBS containing 0.01% sodium azide, filtered twice through a 0.22-mm membrane filter (Milex), and stored at 4° C. if used the same day or −20° C. for up to 5 days. Zempleni et al., *The Intestinal Transport of Bovine Milk Exosomes Is Mediated by Endocytosis in Human Colon Carcinoma Caco-2 Cells and Rat Small Intestinal IEC-6 Cells*, J Nut 2015; 145:2201-6.

B. Confirmation of Exosome Identity and Purity

The identity, purity, and integrity of the isolated exosomes were confirmed using nanoparticle tracker, western blot, and transmission electron microscopy. Absence of aggregation and exosome purity were assessed as recommended by the International Society for Extracellular Vesicles. Lotvall J, et al. Minimal experimental requirements for definition of extracellular vesicles and their functions: a position statement from the International Society for Extracellular Vesicles. J Extracell Vesicles 2014; 3:26913. Briefly, absence of exosome aggregation was confirmed using transmission electron microscopy (Hitachi H7500; Hitachi) in the Microscopy Core Facility at the University of Nebraska-Lincoln. ImageJ was used to analyze the exosome size distribution, which averaged 69±20 nm in diameter.

Figure 1:
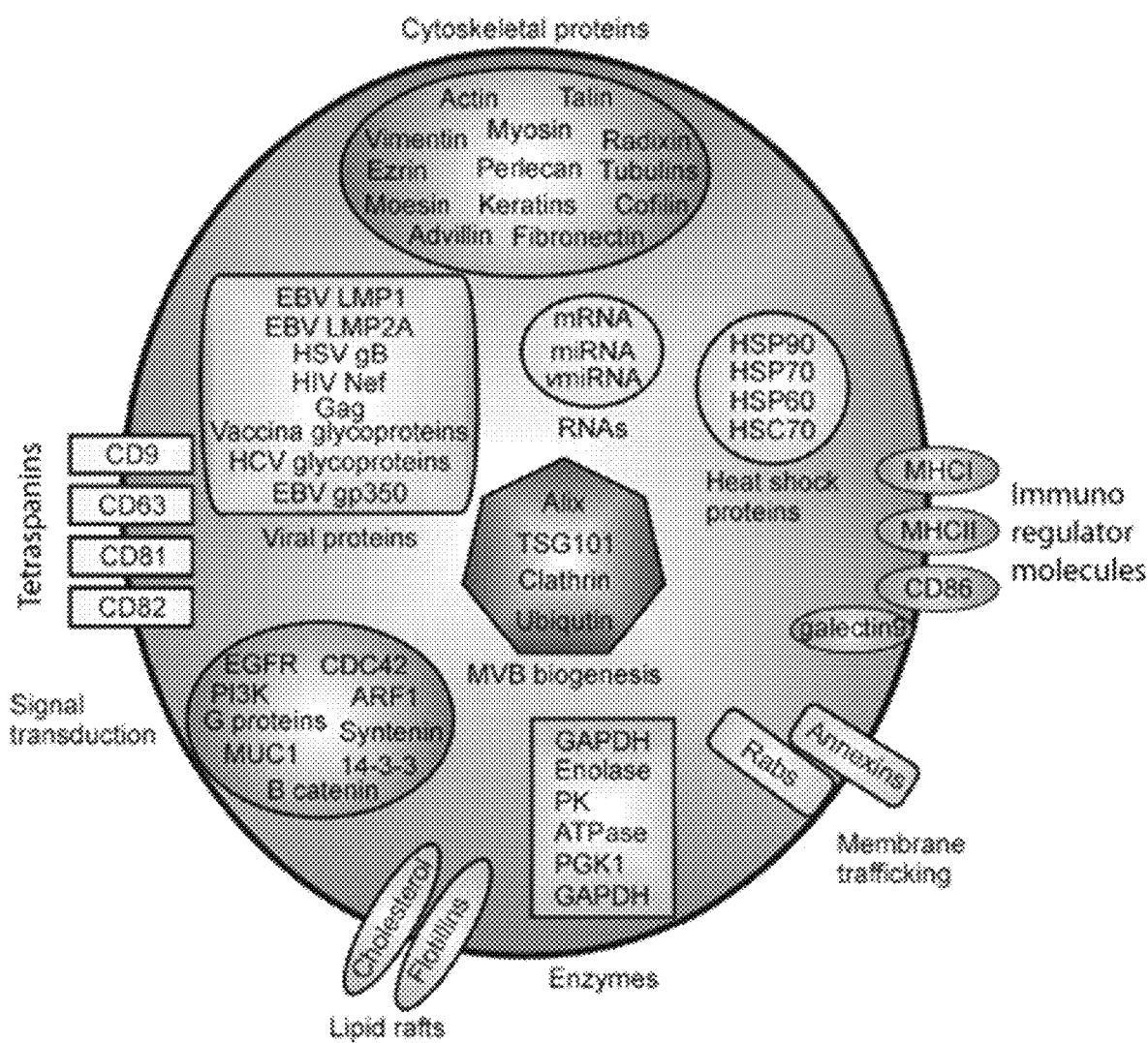
Figure 2A:
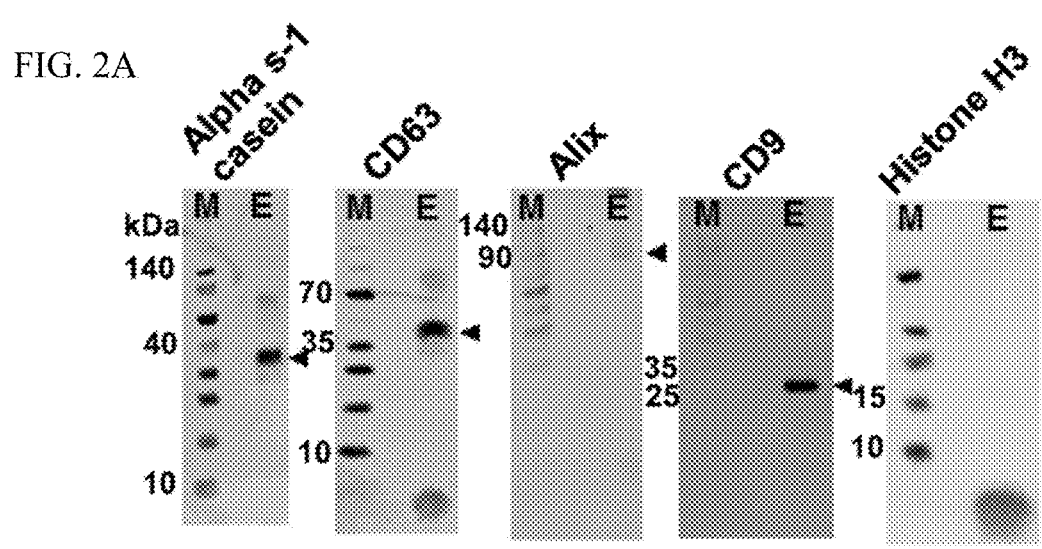
Figure 2B:
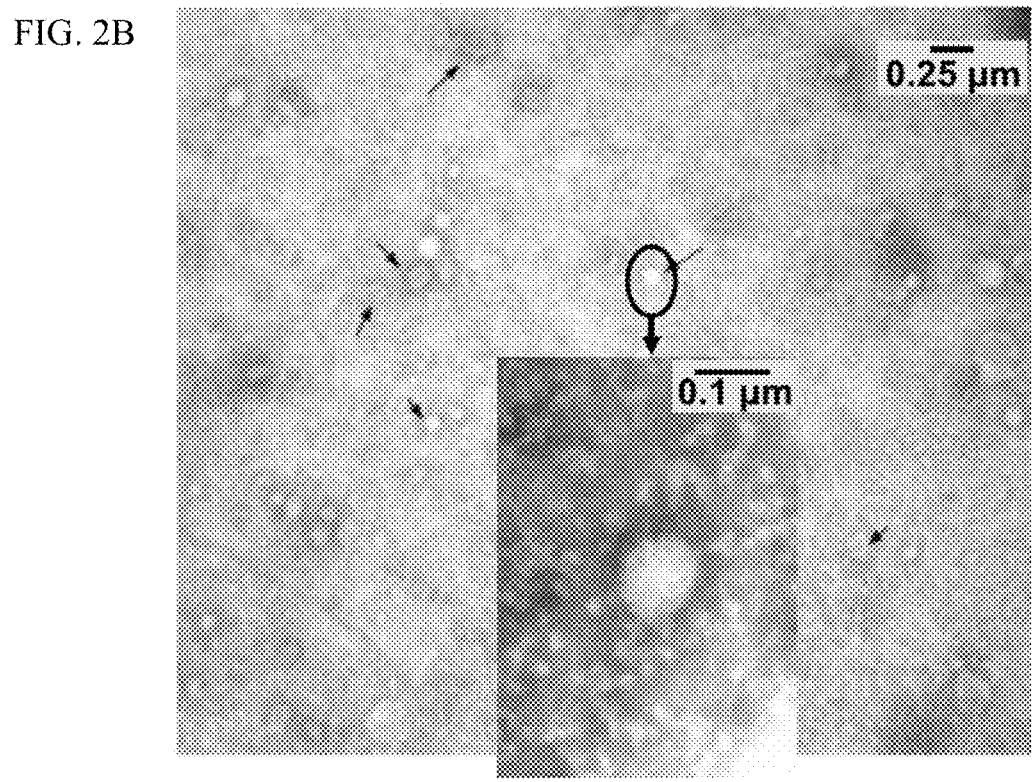
Figure 3A:
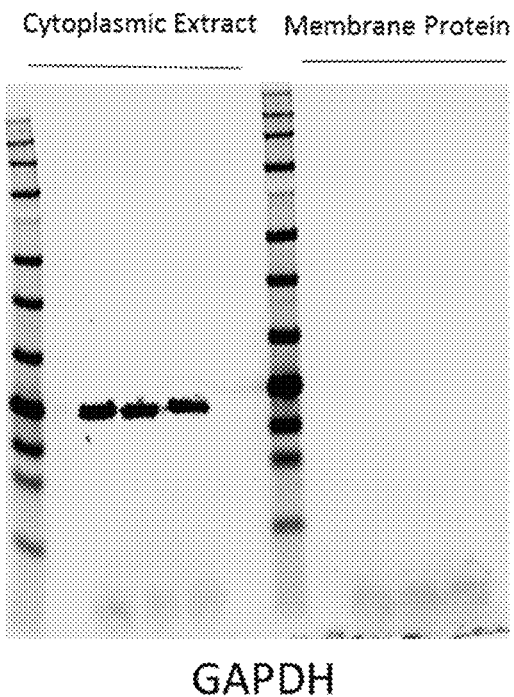
Figure 3B:
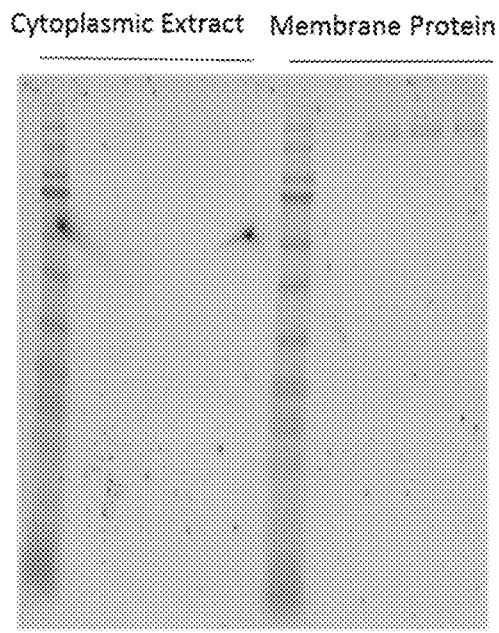
Figure 3C:
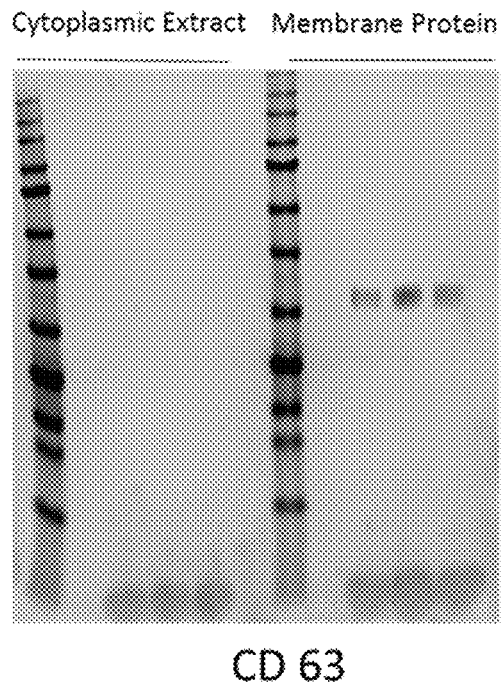
Figure 3D:
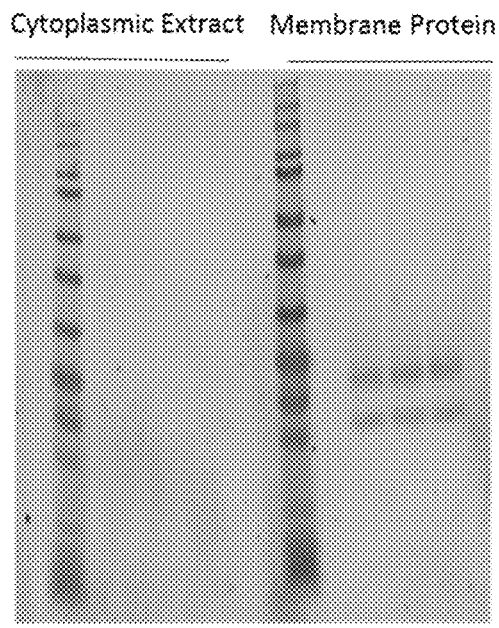

Exosome purity and identity were confirmed using whole protein extracts from exosomes resolved by gel electrophoresis (10 μg protein/lane) as described in: An K, et al. *Exosomes neutralize synaptic-plasticity-disrupting activity of Abeta assemblies in vivo*. Mol Brain 2013; 6:47. Membranes were probed using mouse anti-bovine CD63 (catalog no. MCA2042GA; AbD Serotec), mouse anti-CD9 (catalog no. ab61873; Abcam), goat anti-bovine Alix (catalog no. sc-49268; Santa Cruz Biotechnology) as markers for exosomes, rabbit antiserum to bovine α-s1-casein as a marker for the animal species of exosome origin, and goat anti-bovine histone H3 (catalog no. sc-8654; Santa Cruz Biotechnology) as a negative control (all at 1,000-fold dilutions). Protein extracts were run on the same gel, membranes were cut for probing with the cited antibodies, and images were reassembled after probing. Bands were visualized using an Odyssey infrared imaging system (Licor) and IRDye 800CW-labeled secondary antibodies (50,000-fold dilution; catalog nos. 926-32210, 926-32214, and 926-32211; Licor). FIG. 2A shows milk exosome preparations from cow's milk. Exosome extracts were probed using anti-CD63, anti-CD9, anti-Alix, anti-α-s1 casein, and anti-histone H3. Protein extracts were run on the same gel, membranes were cut for probing with the cited antibodies, and images were reassembled after probing. FIG. 2B shows transmission electron microscope images of exosome preparations. The large field image was obtained with a 15,000-fold magnification; the insert depicts a single particle selected from the same image. FIGS. 3A-2D shows proteins expressed in exosome cytoplasmic extract and membrane protein extract of milk exosome. Exosome extracts were probed using GAPDH, ALIX, anti-CD63, and anti-CD9 (ALIX, CD63, and CD9 are markers for exosomes). Glyceraldehyde 3-phosphate dehydrogenase (GAPDH) is a glycolytic enzyme and is a marker for cytoplasmic proteins. Protein extracts were run on the same gel, membranes were cut for probing with the cited antibodies, and images were reassembled after probing.

Figure 4:
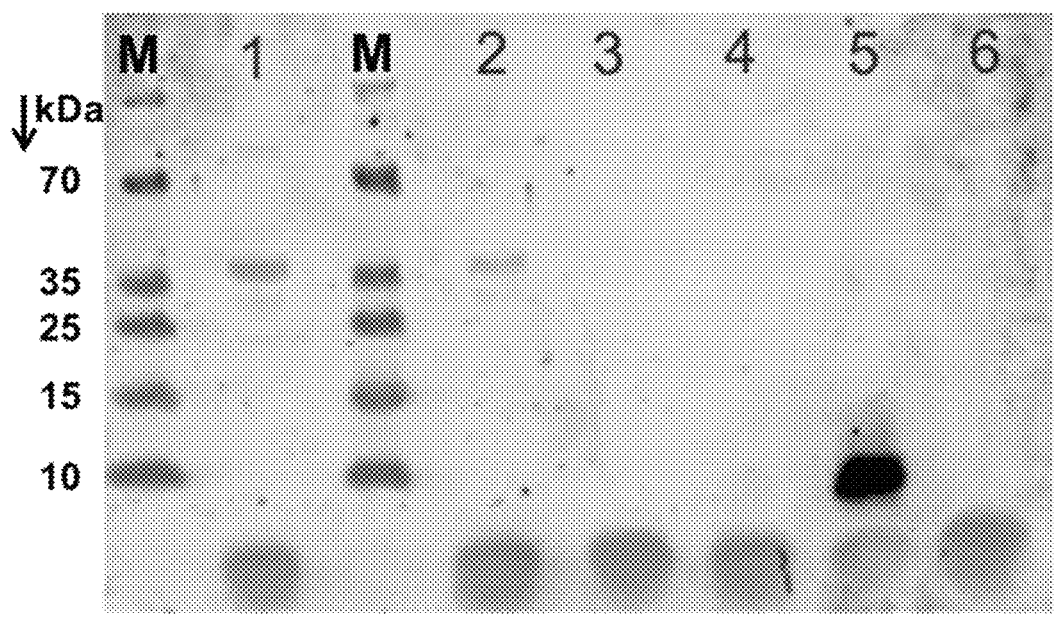

Anti-bovine α-s1-casein was raised in rabbits (Cocalico) using an acetylated casein-based sequence and coupled to keyhole limpet hemocyanin through a C-terminal cysteine. FIG. 4 shows gel electrophoresis and membrane blot results in which the anti-serum produced bands of the expected size with cow's milk exosomes (lane 1), cow's milk (lane 2), and α-s1 casein peptide (lane 5), but not with negative controls such as human breast milk (lane 4), an unrelated synthetic peptide (platelet glycoprotein 1) (lane 4), and exosomes from chicken egg yolk (lane 6). Ten micrograms of milk and exosome protein were loaded per lane, whereas only 1 μg of synthetic peptides were loaded. M, molecular weight markers.

C. Other Methods

For studies in cell cultures, exosomes were labeled with FM-464 (Molecular Probes) as known in the field. Unbound fluorophore was removed by pelleting the exosomes at 120,000 g and 4° C. for 90 min, followed by three wash and ultracentrifugation cycles with sterile phosphate-buffered saline. For studies in mice, exosomes were labeled with a cyanine-based fluorophore, 1,1'-dioctadecyltetramethyl indotricarbocyanine iodide (DiR) as described elsewhere herein. Exosome integrity and absence of aggregation was confirmed by transmission electron microscopy. The concentration of exosome protein was measured using a Nanodrop-1000 spectrophotometer (NanoDrop Technologies), and exosomes were diluted with F-12K media to produce the desired protein concentration.

Example 2. Non-Sonicated Versus Sonicated Microvesicles

Sonication of microvesicles, e.g., exosomes, has an effect on exosome size, physical properties, and functional properties of the microvesicle. The effects of sonication on the physical/structural properties as well as the functional properties have been studied and are reported here. Sonication of exosomes is known in the art, see, e.g., *J Nutr.* 2014, October; 144(10): 1495-500.

Figure 5:
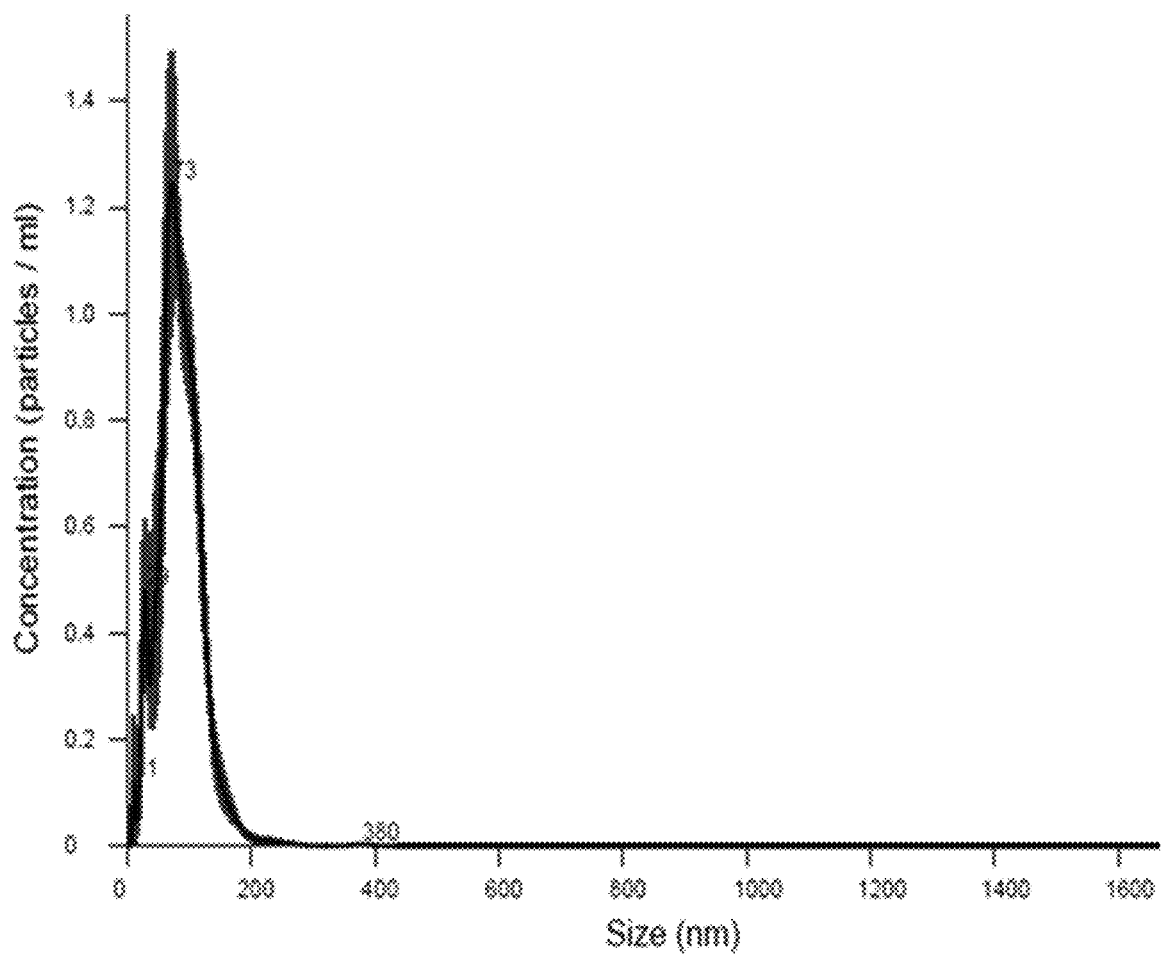
FIG. 5 shows nano tracking analyzer size analysis of milk exosomes.
Figure 6:
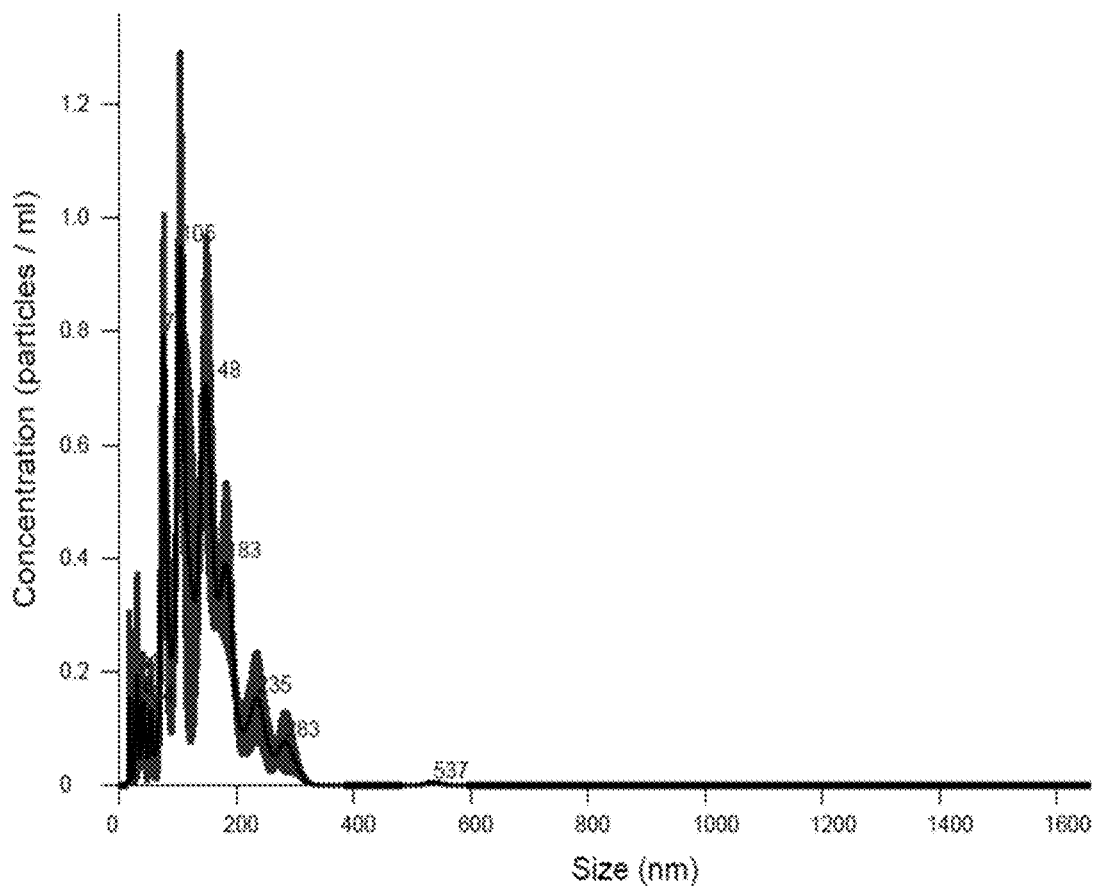
FIG. 6 shows nano tracking analyzer size analysis of sonicated milk exosomes.

Sonication of microvesicles, e.g., exosomes, affects the physical (e.g., structural) properties of the microvesicles. For example, FIGS. 5-8 show that the average diameter of microvesicles, e.g. milk exosomes, are modulated by sonication. Specifically, sonication affects the structure of the exosomes such that the structures are more variable, resulting in a greater average diameter in sonicated exosomes as compared with non-sonicated exosomes. FIG. 5 shows nano tracking analyzer size analysis of milk exosomes indicating an exosome size range under 200 nm. FIG. 6 shows nano tracking analyzer size analysis of sonicated milk exosomes indicating an exosome size range of up to 300 nm. Further structural studies showed that natural (non-sonicated) exosomes have smooth, well-formed surfaces whereas sonicated exosomes have rough, more irregular surfaces and some clustering or aggregation (FIGS. 7A and 8A showing the atomic force microscopy results of non-sonicated and sonicated exosomes, respectively). FIG. 7B shows that natural (non-sonicated) exosomes have a diameter range of 120-200 nm. FIG. 8B shows that sonicated exosomes have a diameter range of 120-250 nm. In addition, sonication can affect the membrane properties of the exosome, including, for example, altering the types and amount of glycoproteins found in/on the membrane or surface of exosomes and/or the types, extent, and/or amount of glycosylation of the surface glycoproteins.

Sonication also affects the functional properties of the microvesicle, e.g., exosomes, for example, by altering its delivery and transport properties, altering its cellular targeting, altering its cellular uptake, altering its stability against degradation, altering its delivery of endogenous cargo, altering its delivery of exogenous cargo, as well as other functional biological properties. In some instances, sonication modifies the microvesicle surface glycoprotein, which may in turn modify the cellular uptake of the microvesicle. In some instances, sonication reduces the number of surface glycoproteins and/or surface glycans presented on the outer surface of the microvesicle. In some instances, sonication increases microvesicle stability against degradation, such as by macrophages. In some instances, sonication decreases the rate of cellular uptake of the microvesicle. For example, FIGS. 9A, 9B, and FIG. 10 show that sonication of milk exosomes decreases the uptake of exosomes into mammalian cells, e.g., Caco-2 cells (FIG. 9A), FH cells (FIG. 9B), and U937 cells (FIG. 10). In some instances, sonication affects the rate of delivery of the microvesicle cargo, e.g., endogenous and/or exosome cargo.

Sonication may also be used to empty endogenous microvesicle contents. Sonication may also be used to load an exogenous cargo. See, e.g., Luan, X. et al., "Engineering exosomes as refined biological nanoplatforms for drug delivery," *Acta Pharmacologica Sinica* 2017, 38: 754-763, hereby incorporated by reference.

Example 3. Distribution of Bovine Milk Exosomes in Mammalian Tissues

Until recently, miRNAs have been considered endogenous regulators of genes, i.e., miRNAs synthesized in a given organism regulate the expression of genes in that host. However, studies we have performed refute this paradigm and provide strong evidence that 1) humans absorb biologically meaningful amounts of miRNAs from nutritionally relevant doses of cow's milk, 2) milk miRNAs are delivered to peripheral human tissues, 3) physiological concentrations of milk miRNAs affect human gene expression in vivo and in cell cultures, and 4) endogenous synthesis of miRNAs does not compensate for dietary miRNAs deficiency in mice. These discoveries were corroborated in a recent report by investigators from the National Institutes of Health (NIH)-supported Genboree database, who detected numerous dietary miRNAs in 6.8 billion sequencing reads from 528 human samples. Our studies further detected bovine-specific miRNAs in human plasma following milk consumption using next generation sequencing ("Computational Characterization of Exogenous MicroRNAs that Can Be Transferred into Human Circulation," Shu J, Chiang K, Zempleni J, Cui J. PLoS One. 2015 Nov. 3; 10(11): e0140587). Other studies suggest that human and rat intestinal cells transport cow's milk exosomes by endocytosis and that milk exosomes may cross the intestinal mucosa without repackaging in mice and enter the peripheral circulation in intact form. On the basis of these previous observations it is reasonable to propose that a fraction of dietary exosomes from foods of animal origin enters the peripheral circulation, and that mechanisms exist for the transfer of these exosomes across vascular endothelia. Further tests were performed to demonstrate that human vascular endothelial cells transport cow's milk exosomes by a carrier mediated process similar to the mechanism reported for the uptake of exosomes in intestinal cells, i.e., endocytosis.

A. Human Vascular Endothelial Cells Transport Foreign Exosomes from Cow's Milk by Endocytosis The transport of milk exosomes was studied to determine the mechanism by which dietary exosomes and their cargo are delivered to peripheral tissues. Using human umbilical vein endothelial cells and fluorophore labeled exosomes isolated from cow's milk studies were performed to demonstrate that human vascular endothelial cells transport milk exosomes via endocytosis. Exosome uptake followed Michaelis-Menten kinetics ($V_{max}$=0.057±0.004 ng exosome protein×40,000 cells/h; $K_m$=17.97±3.84 µg exosomal protein/200 µl media) and decreased by 80% when the incubation temperature was lowered from 37° C. to 4° C. When exosome surface proteins were removed by treatment with proteinase K, or transport was measured in the presence of the carbohydrate competitor D-galactose or measured in the presence of excess unlabeled exosomes, transport rates decreased by 45% to 80% compared with controls. Treatment with an inhibitor of endocytosis, cytochalasin D, caused a 50% decrease in transport. When fluorophore-labeled exosomes were administered retro-orbitally, exosomes accumulated in liver, spleen, and lungs in mice. These studies are described in greater detail below and demonstrate that human vascular endothelial cells transport bovine exosomes by endocytosis which is an important step in the delivery of dietary exosomes and their cargo to peripheral tissues. Further, exosome surface proteins and their carbohydrate content play a significant role in milk exosome transport.

(i) Cell Culture

Exosomes were isolated as described in Example 1. Human umbilical vein endothelial cells (HUVEC, passages 38-45) were purchased from American Type Culture Collection (CRL-1730) and cultured in F-12K medium, supplemented with 0.04 mg/ml endothelial cell growth supplement, 0.1 mg/ml heparin, 100,000 U/l penicillin and 100 mg/l streptomycin (all from Sigma), and 10% exosome-free fetal bovine serum in a humidified atmosphere at 5% $CO_2$ and 37° C. Exosome-free fetal bovine serum was prepared by sonicating the serum in a water bath for 1 h to disrupt membranes, which granted milk RNases access to exosome RNAs and caused the degradation of 60%, 65%, and 86% of miR-15b, miR-21, and miR-200c, respectively. miRNAs were quantified in exosome extracts by using quantitative real-time PCR, U6 snRNA for normalization, and miSPIKE as internal standard (IDT Technologies), and miRNA-specific PCR primers as described previously. Media were replaced with fresh media every 48 h.

(ii) Protocols

In a typical experiment, 15×10$^3$ HUVECs were seeded per well in a 96-well plate and allowed to adhere overnight. Fluorophore-labeled exosomes were added to the wells to produce the desired concentration of exosome protein. Cells were incubated for various lengths of time. Media were removed and cells were washed three times with sterile PBS to remove extracellular exosomes. Controls were prepared by washing the cells immediately after addition of exosomes. Cell fluorescence (excitation 560 nm, emission 645 nm) was measured in a microplate fluorescence detector (BioTek). Cells were harvested using trypsin and counted using a hemocytometer. Units of fluorescence were converted into mass of exosome bound by labeling a known mass of exosomes (protein) with fluorophore, and quantifying the fluorescence after removing unbound fluorophore. In select experiments, exosome binding was determined under the following conditions: 1) cells were treated with 5 or 10 µg/ml of the endocytosis inhibitor cytochalasin D (GIBCO) for 30 min before adding exosomes; 2) cells were treated with 150 mM carbohydrate competitors D-glucose or D-galactose for 30 min before adding exosomes; and 3) milk exosomes were treated with 100 µg/ml of proteinase K at 37° C. for 30 min to remove surface proteins. All assays were performed in three independent experiments, each in triplicate analyses. Binding kinetics were modeled using the Michaelis-Menten equation and nonlinear regression (GraphPad Prism 6.0; GraphPad Software, La Jolla, CA).

(iii) Confirmation that Exosomes Enter the Intracellular Space
(a) Methods

The possibility that adherence to cells, rather than uptake into cells, accounted for cell fluorescence was dismissed based on the following cell death-based and enhanced green fluorescent protein (eGFP) protocols. Milk exosomes were suspended in BTXpress electroporation buffer (BTX, Holliston, MA; final concentration 100 µg/µ0.1 protein), containing zero (negative control), 56 µM, or 223 µM puromycin in a 4-mm electroporation cuvette. Exosomes were loaded with puromycin or with a mammalian eGFP expression plasmid by electroporation in a Gene Pulser Xcell electroporator (Bio-Rad) using 250 V, 950 µF, and infinite resistance. Extra-exosomal puromycin was removed by ultracentrifugation and washing, and exosomes were resuspended in 300 µl of exosome-depleted cell culture media. In cell death assays, 100 µl of the suspension were added per well in a 96-well cell culture plate (containing ~200 µl of media) and cells were cultured for 24 h, when viability was assessed using the MTT assay. Positive controls were created by adding puromycin directly to the media without encapsulation in exosomes, thereby producing a concentration of 1,837 µM puromycin. In eGFP assays, cells were cultured in media in which eGFP-loaded milk exosomes were substituted for exosomes in fetal bovine serum. Expression of eGFP was assessed by using confocal microscopy 3 days after initiation of cultures.

(b) Results

Treatment of cells with puromycin-loaded exosomes provided compelling evidence that exosomes truly entered the intracellular space, as opposed to exosomes adhering to the cell surface. When cells were treated with puromycin-loaded exosomes, viability decreased 75% to 84% of controls (FIG. 11A). Not surprisingly, when 1,837 µM puromycin was added directly to media, viability decreased to 37% of puromycin-free controls (positive control). Cell death was caused by exosome-mediated delivery of puromycin as opposed to release of puromycin from exosomes, based on the following observation. When cells were cultured in media containing exosomes loaded with a plasmid coding for eGFP, they expressed eGFP protein (FIG. 11B).

(iv) The Uptake of Milk Exosomes into HUVECs is a Carrier Mediated Process.

It was established that exosome uptake was linear with time for up to 2 h if 20 µg exosome protein was added to 200 µl media, i.e., concentrations below transporter saturation (see below). Temporal patterns were similar when 70 µg exosome protein/200 µl media were used (data not shown). Subsequent transport studies were carried out using an incubation time of 1 h. Exosome uptake followed Michaelis-Menten kinetics: $V_{max}=0.057\pm0.004$ ng exosome protein× 40,000 cells/h and $K_m=18.0\pm3.8$ µg exosome protein/200 µl media. Exosome uptake depended on the incubation temperature. When 100 µg of unlabeled exosomes was added to the cell cultures (equaling 5 times $K_m$), the uptake of fluorophore-conjugated exosomes decreased to 16.8±7.2% of controls (P<0.05, n=3 biological replicates each measured in triplicate). When cells were treated with 5 µg/ml or 10 µg/ml cytochalasin D, exosome uptake decreased to 63.5±21.3% and 40.8±22.0%, respectively, of controls, consistent with endocytosis (P<0.05, n=3).

B. Transport and Distribution of MilkExosome into Mammalian Tissues (In Vivo Studies)
(i) Protocol To determine whether intravenously administered, DiR-labeled milk exosomes cross vascular endothelia cells and accumulate in tissues, $1\times10^{11}$ DiR-labeled exosomes/g body wt were injected retro-orbitally (intravenously) in female C57BL/6 mice. The mice were 11 wk of age (~25 g body wt) and were fed Teklad Global 16% Protein Rodent Diet (catalog no. Teklad 2016, Envigo). Controls were injected with free DiR or unlabeled exosomes. Eighteen hours after injection, the distribution of exosomes was assessed using an iBox small animal imaging system in live mice and excised tissues. Dissected issues were flushed with cold saline to remove circulating exosomes prior to imaging. The experiments in mice were approved by the Institutional Animal Care Program at the University of Nebraska-Lincoln (protocol no. 963). Statistical analysis. Homogeneity of variances was confirmed using Bartlett's test. Statistical significance of differences among treatment groups was assessed using one-way ANOVA and Tukey-Kramer's or Dunnett's post hoc test. Analyses were performed using GraphPad Prism. Differences were considered significant if P<0.05. Means±SD are reported.

Exosome purification protocol yielded preparations of nonaggregated extracellular vesicles that were primarily composed of exosomes. When protein extracts were probed with anti-CD63, anti-Alix, anti-CD9, or anti-bovine α-s1-casein, strong bands were observed in western blots; in contrast, when protein extracts were probed with anti-histone H3 (negative control), no band was visible. The particle suspension was largely free of aggregates, and the shape and contour of exosomes suggested vesicle integrity. The average particle size was 69±19.5 nm in diameter, as expected for exosomes. A few particles were detected that had a diameter less than that of exosomes; these particles probably represent small fat globules.

(ii) Results

Figure 12C:
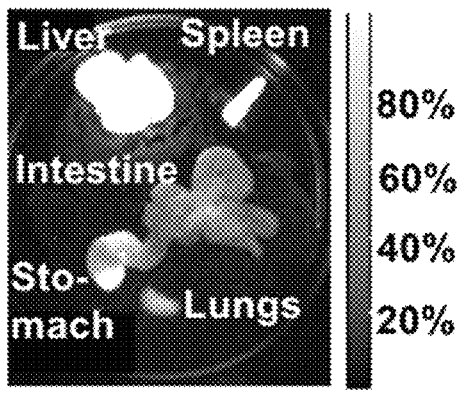

Imaging studies in mice demonstrated that milk exosomes can cross vascular endothelial cells for delivery to tissues. Eighteen hours after intra-orbital injection of DiR-labeled milk exosomes, the majority of exosomes was cleared from circulation and accumulated in a region near the liver; no signal was detected in mice injected with free DiR or unlabeled exosomes. In excised tissues, strong signals were detectable in liver and spleen when the exposure time was 20 s, whereas traces were detectable in intestine, stomach, and lungs only when the exposure time was increased from 20 s to 30 s under the experimental conditions. The signal in liver and spleen was fully saturated at 20 s, i.e., the extension of the exposure time caused an artificial bias towards a stronger signal in intestine, stomach, and lungs. FIGS. 12A-C show the distribution of milk exosomes in C57BL/6 mice who received retro-orbital injections of 1,1'-dioctadecyltetramethyl indotricarbocyanine iodide (DiR)-labeled exosomes, free DiR, or unlabeled exosomes. FIG. 12A: whole mice, 18 h after injection. FIG. 12B: excised tissues, 20 s exposure time. FIG. 12C: same sample as shown in (B) but exposure time increased to 30 s. Scale bars depict fluorescence intensity in units of percent saturation.

Further studies using super resolution microscopy shows that exosomes are present in the cytosol of cells following uptake by cells. In these studies, the nuclei of the cell was stained with Hoechst-blue, cytosol (f-Actin) with CF-594-red, and milk exosomes with PKH-67-green. FIG. 13A shows split image for only cells, only exosomes (top left and right panels, respectively) and only nucleus and both exosomes and cells (bottom left and right panels, respectively). FIG. 13B shows an orthogonal cross sectional image showing the presence of exosome in the cytosol after its uptake by the cells.

Example 4: Bovine Milk Exosomes and Their Corresponding Cargo are Present in Mammalian Tissues A. Introduction Until recently, miRNAs have been considered endogenous regulators of genes, i.e., miRNAs synthesized in a given organism regulate the expression of genes in that host. However, studies we have performed refute this paradigm and provide strong evidence that 1) humans absorb biologically meaningful amounts of miRNAs from nutritionally relevant doses of cow's milk, 2) milk miRNAs are delivered to peripheral human tissues, 3) physiological concentrations of milk miRNAs affect human gene expression in vivo and in cell cultures, and 4) endogenous synthesis of miRNAs does not compensate for dietary miRNAs deficiency in mice. These discoveries were corroborated in a recent report by investigators from the National Institutes of Health (NIH)-supported Genboree database, who detected numerous dietary miRNAs in 6.8 billion sequencing reads from 528 human samples. Our studies further detected bovine-specific miRNAs in human plasma following milk consumption using next generation sequencing. Other studies suggest that human and rat intestinal cells transport cow's milk exosomes by endocytosis and that milk exosomes may cross the intestinal mucosa without repackaging in mice and enter the peripheral circulation in intact form. On the basis of these observations it is reasonable to propose that a fraction of dietary exosomes from foods of animal origin enters the peripheral circulation, and that mechanisms exist for the transfer of these exosomes across vascular endothelia.

The studies in Example 3 showed that human vascular endothelial cells transport cow's milk exosomes by a carrier mediated process similar to the mechanism reported for the uptake of exosomes in intestinal cells, i.e., endocytosis. Specifically, the described studies showed that the transport of cow's milk exosomes across vascular endothelial cells is mediated by endocytosis and that proteins on the surface of milk exosomes are compatible with proteins on the surface of human vascular endothelial cells. The studies and results shown in FIG. 21 further confirmed that exosomes are transported into mammalian tissue following cellular uptake.

This further corroborates the notion that dietary miRNAs have biological activity in humans which has far-reaching implications for human nutrition and health. The National Cancer Institute defines bioactive compounds as "a type of chemical found in small amounts in plants and certain foods [ . . . ]. Bioactive compounds have actions in the body that may promote good health. They are being studied in the prevention of [ . . . ] diseases". Milk miRNAs meet that definition, based on our previous studies which suggest that cow's milk microRNAs regulate genes in circulating cells and peripheral human tissues. The studies described herein indicate that dietary exosomes are cleared primarily by uptake into liver and spleen.

B. The Bioavailability and Distribution of Bovine Milk Exosomes is Distinct from that of Their RNA Cargos in Mice (i) Methods Exosomes were isolated from bovine milk using ultracentrifugation. Exosome membranes were labeled using the fluorophore, DiR, as described elsewhere herein. RNA cargos were labeled using EXO-Glow Red in separate experiments. Identity, integrity, fine dispersion, and count of exosomes were assessed using transmission electron microscopy, western blots, and nanoparticle tracker (not shown). Exosomes were administered orally by gavage ($1 \times 10^{12}$ exosomes/g) in BALB/c mice. Absorption and distribution of exosomes and their cargos was monitored at timed intervals for up to 24 h using an iBox® Small Animal Imaging system and LiCor Odyssey CLx. At timed intervals, mice were euthanized and various tissues were excised and collected for densitometry analysis using VisionWorks® LS and Image Studio software.

Figure 16B:
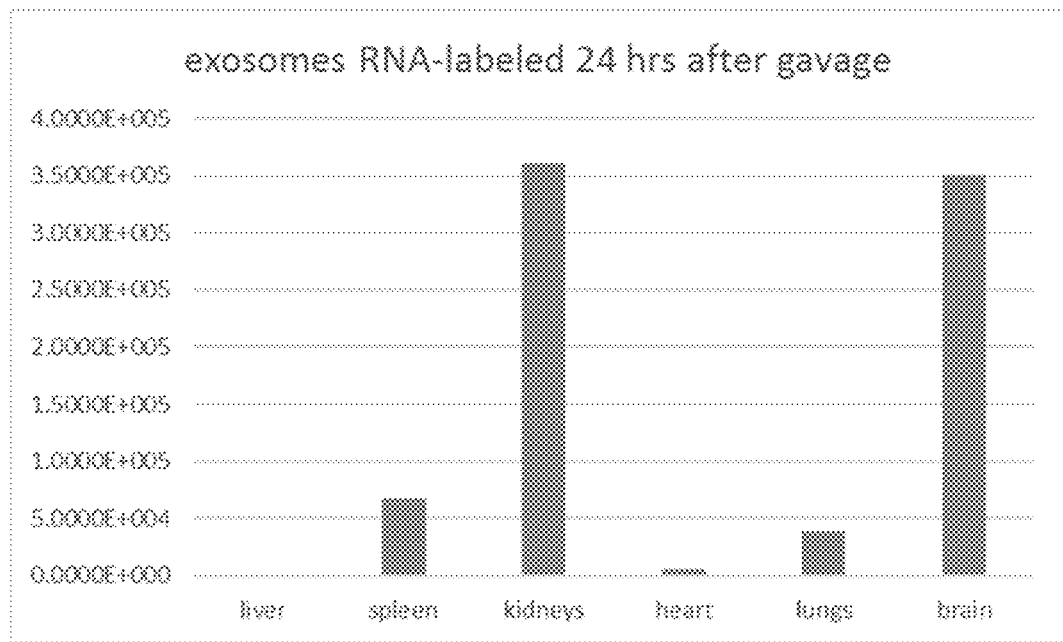

(ii) Results Show Differential Distribution of Exosomes and RNA Cargo in Mammalian Tissue When DiR-labeled cow's milk exosomes were administered orally to Balb/c mice, the majority of exosomes localized in mucosa cells in the upper small intestine, but exosomes were also detectable in liver and spleen. Bioavailability and distribution largely depended on glycoproteins on the surface of exosomes and intestinal cells, and on uptake by macrophages. At t=12 h after administration of DiR-labeled exosomes by gavage, only a faint DiR signal was detected in peripheral tissues (FIG. 14A). In contrast, labeled RNA was detected in all peripheral tissues with a preference for kidneys, brain, lungs and liver (FIG. 14B: 12 hours; FIG. 14C: 24 hours). FIG. 15 depicts the densitometry analysis of labeled RNA, corrected by the signal produced by unconjugated Exo– glow. At t=24 h, the majority of absorbed exosomes accumulated in liver (FIG. 16A), whereas the RNA cargo accumulated preferably in brain and kidneys (FIG. 16B).

When milk exosomes, at a concentration of 5 times the $K_m$, were added to the upper chamber in transwell plates, Caco-2 cells accumulated miR-29b and miR-200c in the lower chamber, and reverse transport was minor. In transwell studies Caco-2 cells were seeded at a density of 9000 cells/well with 75 mL of media in 96-well polycarbonate plates with a pore size of 0.4 mm (EMD Millipore). The cells were allowed to grow a differentiated monolayer for 21-24 d (33). Caco-2 cell monolayer integrity was formally confirmed using the Lucifer yellow (LY) rejection assay according to the manufacturer's instructions (33). LY fluorescence was measured in the transwell apical and basolateral chambers after 1 h of incubation at 37° C. In parallel experiments, Caco-2 cells were cultured in exosome-depleted media to which milk exosomes were added back to produce a concentration of 275 mg/100 mL exosomal protein in either the upper, apical chamber or the lower, basolateral chamber. Controls were cultured in exosome-depleted media. Aliquots of media were collected from the upper chamber and bottom chamber after 2 h of incubation for analysis of microRNAs. Twenty-five attomoles of internal standard (miSPIKE Synthetic RNA; IDT Technologies) was added to samples before microRNA extraction and subsequent analysis of miR-29b and miR-200c in transwell chambers by quantitative real-time PCR and microRNA-specific primers; miSpike was also used for PCR calibration. Values were corrected for the internal standard to normalize for extraction efficiency.

The studies described herein show that endothelial transfer of dietary miRNAs occurs, based on the following observations: 1) Human colon carcinoma Caco-2 cells form tight monolayers. Our studies of intestinal transport of milk exosomes using Caco-2 cells and transwell plates (Lucifer Yellow rejection rate 99.8%) suggest that miRNAs are transferred.

These studies showed that exosome transport exhibited saturation kinetics at 37° C. (Michaelis constant ($K_m$)=55.5 to 48.6 mg exosomal protein/200 mL of media) and was consistent with carrier-mediated transport in Caco-2 cells. Exosome uptake was decreased by 61-85% under the following conditions compared with controls in Caco-2 cells: removal of exosome and cell surface proteins by proteinase K, inhibition of endocytosis and vesicle trafficking by synthetic inhibitors, and inhibition of glycoprotein binding by carbohydrate competitors. Transport characteristics were similar in IEC-6 cells and Caco-2 cells, except that substrate affinity and transporter capacity were lower in IEC-6 cells. across intestinal epithelia. 2) Previous studies used miRNA reporter genes and quantified the abundance of miRNA in human kidney cell cultures, circulating primary human cells, and mouse livers to demonstrate that dietary miRNAs are delivered to cells. 3) When vesicles are administered subcutaneously, intraperitoneally, or intravenously they accumulate in liver and peripheral tissues. 4) When fluorophore-labeled milk exosomes are administered orally (gavage) or intravenously, the majority of exosomes accumulates in liver and spleen. 5) Studies using puromycin-loaded and eGFP plasmid-loaded exosomes suggest that milk exosomes enter cells, as opposed to merely adsorbing to the cell surface.

(iii) Summary

Bovine milk exosomes and their RNA cargos are bioavailable and accumulate in distinct tissues in mice. The data suggest that bovine milk exosomes are disassembled in the intestinal mucosa, and RNA cargos are repackaged in endogenous exosomes for transfer to tissues, preferably brain and kidneys. The data further suggest that milk exosomes are absorbed, and that a fraction of these exosomes escapes re-packaging in the intestinal mucosa and reaches tissues in intact form; the majority of exosomes accumulates in macrophages. The following paper demonstrated that macrophages play an important role in clearing foreign exosomes (the paper studied exosomes secreted by mouse cancer cells and injected into mice): J Extracell Vesicles. 2015 Feb. 9; 4:26238.

Example 5: mRNAs in Bovine Milk Exosomes are Translated into Protein

Exosomes were isolated from bovine milk as previously described herein. mRNAs were extracted, sequenced using an Illumina HiSeq 2500 platform (RNAseq) and annotated using the bovine reference genome. Rabbit Reticulocyte Lysates (RRL) was used to translate mRNAs using BODIPY-labeled lysine; products were assessed using 2-D gel electrophoresis and mass spectrometry. About 3600 bovine mRNAs were identified by RNAseq. As expected, most mRNAs were truncated with a bias toward enrichment at the 3' end. However, 107 mRNAs contained an ATG start codon, making them putative candidates for translation. Thirteen of the 107 mRNAs encode amino acid sequences not present in their human orthologs, making them candidates for eliciting an immune response. Seventy-two bovine proteins were identified by RRL and mass spectrometry. This shows that mRNAs in bovine milk exosomes are translatable into protein which indicates that endogenous mRNA present in a disclosed bovine milk exosome is translated into protein by a mammalian subject, affording the opportunity for treatment of disease or affecting a physiologic condition in the mammalian subject, such as any of the conditions discussed herein.

Example 6: Bovine Milk Exosomes and Their Corresponding Cargo have Various Physiological Functions A. Depletion of Dietary microRNAs from Cow's Milk Causes an Increase of Purine Metabolites in Human Body Fluids and Mouse Livers Previous studies described herein demonstrate that exosomes and their cargo are transported into cells via endocytosis and delivered to peripheral issues. The studies described below show that exosomes and their cargo have physiological effect. For instance, dietary depletion of milk miRNAs causes aberrant (an increase in) purine metabolites in mouse tissues and human body fluids. A reversed-phased HPLC method was developed to quantify eight purine metabolites in a comprehensive analysis of purine metabolism.

(i) Exo− and Exo+ Diet

C57BL/6 mice were obtained from Jackson Labs Mice were fed AIN-93G-based diets, defined by their content of bovine milk exosomes and their RNA cargos: exosome RNA-depleted (Exo−) versus exosome RNA-sufficient (Exo+). The composition of the two diets is identical, including vesicle count, except that the milk exosomes in the Exo− diet were depleted of RNAs by sonication and incubation. Mice were housed in groups of four mice per cage, separated by sex. Both males and females were studied. True randomization of group assignment was achieved by labeling mice with numbers and randomly assigning numbers to groups. At timed intervals mice were sampled from different cages to avoid cage effects, and euthanized for sample collection.

(ii) Purine Metabolite Study

In a first screen, C57BL/6 mice were fed a diet depleted of miRNAs (encapsulated in exosomes) from age 3 to 7 weeks [denoted Exosome (E) Minus, Exo−], whereas controls were fed a miRNA-sufficient diet (Exo+). Mouse liver metabolites were analyzed using non-targeted LC/MS-MS, and targeted enzymatic assays for purine metabolites. Subsequently, purine metabolites in urine and plasma from human dairy avoiders and dairy consumers was assessed. The statistical significance of differences was assessed by t-test.

Principal Components Analysis (PCA), a dendrogram performed with hierarchical clustering, Variable Important in Projection (VIP) scores, and a heat map analysis consistently indicated that concentrations of purine metabolites were higher in livers of Exo− fed mice than in E+ fed mice, and that purine metabolites were affected by milk miRNA intake to a greater extent than any of the other metabolites that were identified ($p<0.01$; $n=5$). As for effect size, the concentrations of xanthine were 16.6±3.3 µM and 10.1±1.0 µM in the livers of Exo− and Exo+ mice, respectively ($p<0.05$). Likewise, the concentrations of plasma xanthine and urinary uric acid were 81.6% and 19.3% higher in human dairy avoiders compared with dairy consumers ($n=6$).

B. Depletion of Dietary microRNAs from Cow's Milk Causes an Decrease in Fertility and Fecundity in Mice Exosome feeding studies suggest that dietary depletion elicits a substantial decrease in fertility, intrauterine growth and postnatal survival. The studies and corresponding results are described below.

(i) Fertility Study

Mice were fed an exosome-depleted diet versus an exosome-sufficient diet as described above. Mice fed an exosome-depleted (Exo−) diet demonstrated lower fertility than mice fed an exosome-sufficient (Exo+) mice, particularly when both males and females were fed the Exo+ diet. As shown in FIGS. 17, 62% to 75% of mating did not result in pregnancy if at least one parent was fed the Exo− diet, compared with only one (12.5%) failed mating in controls. As shown in FIG. 18, the average litter size produced by Exo+/Exo+ fed breeders was twice the size in other groups:

7.6±1.9 pups for Exo+ fed males/Exo+ fed females, 3.6±3.2 for Exo+ fed males/Exo− fed females, 3.5±3.0 for Exo− fed males/Exo+ fed females, and 4.1±3.4 for Exo− fed males/Exo− fed females; P<0.05, n=8). The average birth weight of pups born to dams fed the Exo− diet (Exo+ males) was 1.13±0.11 g compared to 1.30±0.09 g in Exo+ fed/Exo+ fed breeders (P<0.05). MicroRNA depletion also impaired survival of litters to weaning (3 weeks) if dams were continued on the previous diets. As shown in FIG. 19, there was 100% survival of litters in Exo+/Exo+ fed breeders, zero survival in Exo+/Exo− breeders and Exo−/Exo+ breeders, and one surviving litter in Exo−/Exo− breeders.

Gene expression analysis and purine feeding studies are used to identify the step(s) in purine metabolism targeted by milk miRNAs. The hepatic concentrations of purine metabolites were 65% higher in Exo− fed females compared to Exo+ fed females (16.6±3.3 vs. 10.1±1.0 μmon xanthine; P<0.05, n=5), indicating that loss of the positive effects from endogenous miRNAs leads to lowered fecundity. Dietary depletion of milk miRNAs causes an increase in purine metabolites in mouse tissues and decreases in fecundity and fertility.

C. Dietary Depletion of microRNAs from Bovine Milk Exosomes Elicits Changes in Amino Acid Metabolism in Mice (i) The Diet and Study C57BL/6 mice, age 3 weeks, were fed an exosome-depleted (Exo−) AIN93G-based diet for four weeks; controls were fed an exosome-sufficient (Exo+) diet as described above. Livers were harvested and the hepatic metabolome was assessed by non-targeted LC/MS-MS and by peak intensity analysis; the hepatic transcriptome was assessed by RNAseq using an Illumina HiSeq2500 platform. A second cohort of mice was fed Exo− or Exo+ diets for 4-6 weeks for subsequent analysis of grip strength, respiratory exchange ratio (RER) and feeding and activity patterns; skeletal muscle samples are currently analyzed by RNAseq. Statistical significance was assessed using unpaired, two-tailed t-test.

(ii) Altered Amino Acid Metabolism

Bovine milk exosomes alter amino acid metabolism in C57BL/6 mice. Hepatic concentrations of amino acids were up to 1800% higher in mice fed the Exo− diet than in mice fed the Exo+ diet (control) N=8, *p<0.05 vs. Exo+. (FIGS. 20A-E). FIG. 20A shows the abundance of leucine in mice fed the Exo− versus Exo+ diet. FIG. 20B shows the abundance of phenylalanine in mice fed the Exo− versus Exo+ diet. FIG. 20C shows the abundance of alanine in mice fed the Exo− versus Exo+ diet. FIG. 20D shows the abundance of leucine-lysine dipeptide metabolite in mice fed the Exo− versus Exo+ diet. FIG. 20E shows the abundance of glutamyl-isoleucine dipeptide metabolite in mice fed the Exo− versus Exo+ diet.

FIGS. 21A and 21B show the mRNA expression of branched chain amino acid (BCAA) transporters 1 (cytoplasm) (BCAT1) and 2 (mitochondria) (BCAT2) in livers of C57BL/6 mice fed an Exo− or Exo+ (control) diet for 4 weeks. N=8, *p<0.05 vs. Exo+. The mRNA expression of branched chain amino acid (BCAA) transporters 1 (cytoplasm; BCAT1; FIG. 20A) and 2 (mitochondria, BCAT2; FIG. 20B) was greater in mice fed the Exo− diet compared to mice fed the Exo+ diet (n.s. for BCAT2). The respiratory exchange ratio (RER) was not affected by feeding, whereas grip strength was a moderate 5% higher in Exo+ vs. Exo− fed females after only 4 weeks of feeding (n.s.; not shown). The trend toward a greater grip strength was not caused by differences in food and water consumption or physical activity, which were not significantly different between treatment groups in males and females.

D. Depletion of Dietary microRNAs in Bovine Milk Exosomes Impairs Sensorimotor Gating and Spatial Learning in Mice C57BL/6 mice were fed AIN-93G based, bovine milk exosome-defined diets for up to 20 weeks. Exosome-depleted diets are denoted Exo− or E−; exosome-sufficient controls are denoted Exo+ or E+. Spatial learning and memory were assessed using the Barnes maze and Morris water maze. Sensorimotor gating was assessed using an acoustic startle response (ASR) system. The statistical significance of differences was assessed by unpaired, two-tailed t-test.

The time needed to locate the escape hole in the Barnes maze increased by up to 130% in mice fed the Exo− diet compared to mice fed the Exo+ diets (controls) (FIG. 22). Likewise, the time needed to locate and reach the submerged escape platform in the Morris water maze was significantly greater in female mice fed the Exo− diet than female controls fed the Exo+ diet (FIG. 23). Prepulse inhibition (PPI) of the ASR is a measure of sensorimotor gating and was significantly lower in female mice fed the Exo− diet than in female controls fed the Exo+ diet (FIG. 24). Diet did not affect PPI in male mice (p>0.05). These studies show that bovine milk exosomes improve sensorimotor gating and cognitive performance in mice.

Example 7. Bovine Milk Exosomes and Their Corresponding Cargo have an Effect on the Mammalian Microbiome A. A Diet Defined by its Content of Bovine Milk Exosomes Alters the Composition of the Intestinal Microbiome in C57BL/6 Mice Exosomes play important roles in cell-to-cell communication, facilitated by the transfer of exosome cargos such as RNAs, proteins and lipids from donor cells to recipient cells. Bacteria communicate with their environment through exosome-like vesicles. Although dietary exosomes in bovine milk are bioavailable, a fraction of milk exosomes reaches the large intestine in mice.

The results described here suggest that exosomes in bovine milk change the composition of the gut microbiome, which is associated with changes in the hepatic transcriptome in mice. Several different studies were performed that demonstrate that bovine milk exosomes alter certain microbial taxa in the gut microbiome in mice.

The alteration in microbial communities in non-bovine species indicate that exosomes and their cargos participate in the crosstalk between bacterial and animal kingdoms. First, prokaryotic and eukaryotic microbes communicate with their environment through exosome-like vesicles. This observation includes gram-positive bacteria, which use vesicles for communication despite the cell wall posing a barrier for vesicle transport. Viruses may participate in exosome signaling through hijacking and modifying exosomes. Second, up to 20% and 40% of RNA sequence reads in plasma from healthy adults map to bacterial and fungal genomes, respectively. Third, evidence suggests that orally administered, fluorophore-labeled exosomes from bovine milk are delivered to peripheral tissues. These findings are largely consistent with the studies suggesting that endogenously and exogenously labeled milk exosomes accumulate in liver and spleen, but that a considerable fraction of orally administered exosomes escapes absorption and reaches the large intestine.

(i) Exosome-Depleted (E) AIN93G-based Diet Versus Exosome-Sufficient (E+) Diet (3-42 weeks)

In one study, C57BL/6 mice, age 3 weeks, were fed an exosome-depleted (Exo−) AIN93G-based diet for up to 42 weeks; controls were fed an exosome-sufficient (Exo+) diet. At timed intervals (age 7, 15, 45 weeks), cohorts of mice were euthanized and colon content was flash frozen in liquid nitrogen for subsequent analysis of gut microbiota by 16S rRNA gene sequencing of the V4 region using Illumina's MiSeq platform. Microbial sequences were clustered into Operational Taxonomic Units (OTUs). High-throughput bacterial 16S rRNA gene sequencing followed by clustering of short sequences into operational taxonomic units (MIN) is widely used for microbiome profiling. Non-parametric test was used for statistical analysis.

Depending on sex and age, a total of 51 OTUs were differentially abundant between treatment groups; See FIGS. 25-26 for a heat map of the top 18 OTUs (P<0.05 for age 15 and 45 weeks). For example, the relative abundance of Firmicute classes Clostridia (Ruminococcaceae) and Verrucomicrobia classes Verrucomicrobiae (Muciniphila) were greater in mice fed E− diet compared with E+ diet at age 15 weeks, whereas the relative abundance of Firmicute classes Clostridia (Clostridiales) was less in mice fed E− diet compared with E+ diet at age 45 weeks.

(ii) Exosome/RNA-Depleted (ERD) Diet Versus Exosome/RNA-Sufficient (ERS) Diet (3-47 Weeks)

Dietary bovine milk exosomes and their RNA cargos elicited changes in the composition of the intestinal microbiome and the hepatic transcriptome in C57BL/6 Mice. C57BL/6 mice were fed AIN-93G diets, defined by their content of bovine milk exosomes and RNA cargos: exosome/RNA-depleted (ERD) versus exosome/RNA-sufficient (ERS) diets. Feeding was initiated at age three weeks and continued through age 47 weeks, and cecum content and liver samples were collected at ages 7, 15 and 47 weeks. 16S rRNA gene sequencing and whole transcriptome sequencing were used to profile microbial communities in the cecum and transcripts in the liver, respectively, using multivariate protocols.

The dietary intake of exosomes and age, and to a lesser extent sex, had significant effects on the microbial communities in the cecum. At the phyla level, the abundance of Verrucomicrobia was greater in mice fed the ERD diet compared to the ERS diet, and the abundance of both Firmicutes and Tenericutes was less in mice fed the ERD compared to the ERS at age 47 weeks. At the family level, the abundance of Ruminococcaceae and Lachnospiraceae was greater in males and an unnamed family from the order of Clostridiales was smaller in females fed the ERS diet compared to the ERD diet at age 7 weeks. Exosome feeding altered the abundance of 543 operational taxonomic units; diet effects were particularly strong in the Lachnospiraceae, Ruminococcaceae and the Verrucomicrobiaceae families.

(a) Mouse Feeding Studies

C57BL/6 mice were obtained from Jackson Labs. (stock number 000664) at age three weeks when dietary treatment was initiated. Mice were fed AIN-93G-based diets, defined by their content of bovine milk exosomes and their RNA cargos, exosome RNA-depleted (ERD) versus exosome RNA-sufficient (ERS). The composition of the two diets is identical, including vesicle count, except that the milk exosomes in the ERD diet were depleted of RNAs by sonication and incubation. Mice were housed in groups of four mice per cage, separated by sex. Both males and females were studied. True randomization of group assignment was achieved by labeling mice with numbers and randomly assigning numbers to groups. At timed intervals (ages 7, 15 and 47 weeks), mice were sampled from different cages to avoid cage effects, and euthanized for sample collection (N=8 for each sex and age). Cecum content was collected, flash frozen in liquid nitrogen and stored at −80° C.; livers were collected and flash frozen in liquid nitrogen and stored at −80° C. The study was approved by the Institutional Animal Care and Use Committee at the University of Nebraska-Lincoln (protocol 1229).

(b) Analysis of Microbial Communities

Cecum content was extracted and DNA was purified using the PowerSoil DNA Isolation Kit (Mo Bio Laboratories Inc., Carlsbad, CA, USA) following the manufacturer's instructions. DNA purity and integrity were confirmed by using the 260-to-280 nm ratio (Nanodrop ND-1000, Nanodrop Technologies, Wilmington, DE, USA) and agarose gel (0.8%) electrophoresis. The V4 region in the 16S rRNA gene was amplified and sequenced as described previously. The sequencing reads were quality filtered and analyzed as described previously. Briefly, contigs were generated from paired-end reads and were screened using MOTHUR v.1.38.1 to exclude low quality sequences and reads containing ambiguous bases or homopolymers longer than 8 bp. Additionally, the resulting reads were trimmed to only retain reads between 245 base pairs (bp) and 275 bp. The UPARSE pipeline (USEARCH v7.0.1090) was then used to cluster quality-filtered sequences into operational taxonomic units (OTUs) at 97% identity, after removal of chimeras using UCHIME. ChimeraSlayer gold.fa was used as the reference database for chimera detection. Sequence alignment was performed using the SILVA v123 reference and was used to build a phylogenetic tree using Clearcut. Taxonomy assignment (Greengenes database: gg_13_8_otus) was performed using QIIME v.1.9.1. Eighty-two samples with an average read count of 40,468 reads and a range of 4,112-144,788 reads were used for downstream analysis. Alpha diversity metrics were used to evaluate richness (Chao1), diversity (Shannon-Weiner index), and coverage (Good's coverage). Rarefaction curves were constructed using Chao1 values. A core measurable microbiome was identified based on factors diet, sex, and age. The core measurable microbiome was defined as the group of OTUs that are present in at least 80% of the samples within each factor. Differences in bacterial communities were assessed using permutational multivariate analysis of variance (PERMANOVA) utilizing the weighted UniFrac distance matrix. Additionally, the weighted UniFrac distance matrix was used for principal coordinate analysis (PCoA). The Linear Discriminant Analysis of Effect Size (LefSe) algorithm with default parameters was used to identify OTUs that were differentially abundant in the ERS and ERD feeding groups at different ages. Sequence data were deposited in the NCBI-BioProject database under accession no. PRJNA413623. Kruskal-Wallis sum-rank test was used to identify the significant differences in abundance between groups at P<0.05. The Wilcoxon rank-sum test was used for pairwise comparisons at adjusted P<0.05, with the Benjamini and Hochberg correction. Differences were considered statistically significant if P<0.05.

Alpha diversity (Table 2; FIG. 27) and Beta diversity (Table 3; FIG. 27) suggested that effects of age on microbial communities were statistically significant (P<0.05), effects of diet on communities trended toward statistical significance (P=0.075) and sex had no significant effect on microbial communities (P=0.215).

TABLE 2

Comparison of the Alpha diversity in pools defined by age, diet and sex.

| Group 1 | Group 2 | Group 1 mean ± SD | Group 2 mean ± SD | T value | P value |
|---|---|---|---|---|---|
| Age 47 weeks | Age 15 weeks | 184 ± 13.9 | 158 ± 24.8 | 4.795 | 0.003 |
| Age 15 weeks | Age 7 weeks | 158 ± 24.8 | 142 ± 19.1 | 2.475 | 0.016 |
| Age 47 weeks | Age 7 weeks | 184 ± 13.9 | 142 ± 19.1 | 9.341 | 0.0015 |
| ERS | ERD | 165 ± 27.4 | 157 ± 23.8 | 1.386 | 0.170 |
| Male | Female | 159 ± 25.0 | 164 ± 27.2 | −0.838 | 0.399 |

SD, Standard deviation.

TABLE 3

Effect of age, diet and sex on microbial communities in the cecum of mice

| | Df | SumsOfSqs | MeanSqs | F. Model | $R^2$ | Pr(>F) |
|---|---|---|---|---|---|---|
| Sex | 1 | 0.001 | 0.001 | 1.341 | 0.008 | 0.215 |
| Diet | 1 | 0.002 | 0.002 | 2.342 | 0.014 | 0.075 |
| Age | 2 | 0.065 | 0.032 | 40.297 | 0.484 | 0.001 |
| Sex:Diet | 1 | 0.001 | 0.001 | 1.047 | 0.006 | 0.326 |
| Sex:Age | 2 | 0.002 | 0.001 | 1.345 | 0.016 | 0.215 |
| Diet:Age | 2 | 0.003 | 0.002 | 1.950 | 0.023 | 0.064 |
| Sex:Diet:Age | 2 | 0.004 | 0.002 | 2.376 | 0.029 | 0.039 |
| Residuals | 70 | 0.056 | 0.001 | | 0.420 | |
| Total | 81 | 0.134 | | | 1.000 | |

Df, degree of freedom; SumsOfSqs, sum of squares; MeanSqs = SumsOfSqs/df, mean squares; F. Model, F-tests.

Combinatorial effects of independent variables on microbial communities were statistically significant for the sex×diet×age interaction and trended toward significance for the diet×age interaction (Table 3). The following key observations were made at the phyla level regarding age effect (FIG. 28). Among the three most abundant phyla, Bacteroidetes increased over time and was the second most abundant phylum at age 47 weeks (P<0.001). The abundance of Firmicutes remained constant between ages 7 and 15 weeks, but decreased by about 50% at age 47 weeks. Verrucomicrobia were significantly more abundant in mice fed the ERD diet than in mice fed the ERS diet (P=0.030). The abundance of Actinobacteria decreased considerably over time and this phylum almost disappeared in mice aged 47 weeks (P<0.001).

Some of the changes at the phylum level involved age×diet interactions. For example, Firmicutes and Tenericutes were not significantly different in mice fed ERS and ERD diets at age 7 and 15 weeks (P>0.05), but were significantly less abundant in mice fed the ERD diet compared with ERS at age 47 weeks (P=0.046 for Firmicutes and P=0.028 for Tenericutes). Some age× diet interactions were detected at younger ages. For example, the abundance of Actinobacteria was greater (P=0.041) in mice fed the ERS diet compared with ERD at age 15 weeks. No significant changes at the phylum level were detected when sex was used as an individual independent variable (P>0.05). A total of 19 families were identified by 16S rRNA sequencing. Lachnospiraceae, Ruminococcaceae and a family from the order Clostridiales were the three most abundant families affected by age, diet or sex (FIG. 29). Exosome-defined diets altered the microbial communities at the family level, and some of these effects depended on diet×age, diet×sex or diet×age×sex interactions. For example, at age 7 weeks, Ruminococcaceae, Lachnospiraceae, Coriobacteriaceae, Lactobacillaceae and Mogibacteriaceae families were significantly more abundant in male mice fed the ERS diet compared with males fed the ERD diet (all five P<0.05). In contrast, the abundance of a family from the order Clostridiales was significantly less abundant in female mice fed the ERS diet compared with ERD at age 7 weeks (P=0.010). No significant differences were detected at the family level in females and males at age 15 weeks. At age 47 weeks, females fed the ERD diet harbored significantly more Bifidobacteriaceae (P=0.005) and less Lactobacillaceae (P=0.018) than ERS females age 47 weeks. Males fed the ERD diet harbored significantly more Mogibacteriaceae compared with ERS males age 47 weeks (P=0.033).

At the level of OTUs, the consumption of milk exosome-defined diets had a strong effect on microbial communities in the mouse cecum (FIG. 30). Two OTUs from the family of Lachnospiraceae were significantly more abundant in mice fed the ERS diet compared with ERD-fed mice at age 7 weeks (P=0.009 and P=0.044, respectively). At age 15 weeks, OTUs from the families Verrucomicrobiaceae and S24-7 increased significantly in abundance and became the predominant OTUs in mice fed the ERD diet compared to ERS diet (P=0.016 and P=0.021, respectively). The diversity of microbial OTUs continued to increase and peaked at age 47 weeks and these OTUs are from the same families shown in FIG. 28 in both diet groups.

B. Bovine Milk Exosomes Alter Microbial Communities in the Murine Cecum Which Changes Contribute to Changes in the Murine Hepatic Transcriptome Exosome-dependent changes in microbial communities correlated with changes in the hepatic transcriptome, e.g., in pathways implicated in non-alcoholic fatty liver disease and oxidative phosphorylation.

(i) Analysis of the Hepatic Transcriptome

Livers from six female mice, age 15 weeks, were used for RNA sequencing studies (N=3 from each feeding group). Briefly, RNA was extracted using the mRNA Seq Sample Prep Kit (Illumina) and shipped on dry ice to the genomics center of University of Minneapolis, MN for sequencing analysis. RNA quality was assessed using an Agilent Bioanalyzer and absorbance at 260 and 280 nm. The RNA Integrity Number and the 260-to-280 nm ratio was greater than 7 and 1.8, respectively, for all samples. Libraries were generated using TruSeq Stranded Total RNA Library Prep Kit and sequenced using the Illumina HiSeq 2500 platform and a paired ends protocol generating reads with a length of 125 bp. Data quality control was performed using FastQC. After removing adaptors and reads containing ambiguous bases or having average quality score less than 30, sequencing reads were aligned to the mouse reference genome [GRCm38, mm10] using Tophat. Cufflinks was applied to identify the transcripts and quantify their expression in units of reads per kilobase of exon model per million (RPKM). Cuffdiff was applied to identify the differentially expressed transcripts between two feeding groups and only those with equal or more than 2-fold change were considered for the downstream analysis. KEGG pathways were identified by using clusterProfiler. Raw sequencing data were deposited in the NCBI-BioProject database under accession ID PRJNA400248.

(ii) Correlation Analysis of Microbial Communities and Hepatic Transcriptome.

Correlations between the significantly differentially abundant OTUs and the top 69 significantly differentially expressed genes were calculated using the Pearson productmoment correlation and bootstrapping with 1000 permutations to calculate the p-values of the correlation scores (QIIME v.1.9.1). To visualize the microbial features that correlated with gene expression, a heatmap was generated using R software package 3.3.3 (The R Foundation). Bray-Curtis dissimilarity was used to calculate the distance for rows and columns, and average linkage hierarchical clustering was used to generate dendrograms.

Sixty-nine genes were differentially expressed by at least 2-fold in the livers of female mice fed the ERS diet compared to ERD females at age 15 weeks (P<0.01). Changes in the hepatic transcriptome correlated with changes in microbial communities in the cecum. The strong correlation between OTUs from the family of Lachnospiraceae (phylum Firmicutes) with hepatic transcripts is particularly noteworthy (FIG. 31). For example, Lachnospiraceae OTUs 22, 7 and 40 correlated strongly with the expression of the differentially expressed genes in the liver of female mice fed milk exosome-defined diets. Strong correlations were also observed for Ruminococcaceae OTUs 19 and 34, Erysipelotrichaceae OTU 3 and five OTUs that could not be assigned to a family (OTUs 10, 18, 30, 33 and an unnamed OTU). A full record of correlation and Gene IDs for the genes are shown in the tables below.

TABLE 4

Genes and Corresponding Gene IDs from FIG. 31

| Gene | Gene ID |
|---|---|
| Marco | 8685 (human) |
| | 17167 (mouse) |
| Cxcl13 | 10563 (human) |
| | 55985 (mouse) |
| Dnajc12 | 56521 (human) |
| | 30045 (mouse) |
| Saa3 | 6290 (human) |
| | 20210 (mouse) |
| A2m | 2 (human) |
| | 232345 (mouse) |
| Rpph1 | 85495 (human) |
| | 85029 (mouse) |
| Mup9 | 100038948 (mouse) |
| Pfdn6 | 10471 (human) |
| | 14976 (mouse) |
| Ndufs6 | 4726 (human) |
| | 407785 (mouse) |
| Ssna1 | 8636 (human) |
| | 68475 (mouse) |
| Zfp524 | 66056 (mouse) |
| Gfer | 2671 (human) |
| | 11692 (mouse) |
| Ccdc124 | 115098 (human) |
| | 234388 (mouse) |
| Ndufb2 | 4708 (human) |
| | 68198 (mouse) |
| Isoc2b | 67441 (mouse) |
| Use1 | 55850 (human) |
| | 67023 (mouse) |
| Rpp21 | 79897 (human) |
| | 67676 (mouse) |
| Rnaseh2c | 84153 (human) |
| | 67209 (mouse) |
| Cblc | 23624 (human) |
| | 80794 (mouse) |
| Nat9 | 26151 (human) |
| | 66176 (mouse) |
| Brms1 | 25855 (human) |
| | 107392 (mouse) |
| Crip1 | 1396 (human) |
| | 12925 (mouse) |
| Tpgs1 | 91978 (human) |
| | 110012 (mouse) |
| Rnaseh2a | 10535 (human) |
| | 69724 (mouse) |

TABLE 4-continued

Genes and Corresponding Gene IDs from FIG. 31

| Gene | Gene ID |
|---|---|
| Pet100 | 100131801 (human) |
| | 100503890 (mouse) |
| Bcl7c | 9274 (human) |
| | 12055 (mouse) |
| Trappc6a | 79090 (human) |
| | 67091 (mouse) |
| Ddx49 | 54555 (human) |
| | 234374 (mouse) |
| Trappc5 | 126003 (human) |
| | 66682 (mouse) |
| Sssca1 | 10534 (human) |
| | 56390 (mouse) |
| Zfp771 | 244216 (human) |
| Timm50 | 92609 (human) |
| | 66525 (mouse) |
| Scnm1 | 79005 (human) |
| | 69269 (mouse) |
| Fars2 | 10667 (human) |
| | 69955 (mouse) |
| Acbd5 | 91452 (human) |
| | 74159 (mouse) |
| Stx4a | 6810 (human) |
| | 20909 (mouse) |
| Smagp | 57228 (human) |
| | 207818 (mouse) |
| Mrps16 | 51021 (human) |
| | 66242 (mouse) |
| Hspbp1 | 23640 (human) |
| | 66245 (mouse) |
| Zap70 | 7535 (human) |
| | 22637 (mouse) |
| Cenpm | 79019 (human) |
| | 66570 (mouse) |
| Slc16a11 | 162515 (human) |
| | 21687 (mouse) |
| Ndufa5 | 4698 (human) |
| | 68202 (mouse) |
| Epb4.1/4aos | 269587 (human) |
| Tmem223 | 79064 (human) |
| | 66836 (mouse) |
| Lgals1 | 3956 (human) |
| | 16852 (mouse) |
| Rps19bp1 | 91582 (human) |
| | 66538 (mouse) |
| Mrps21 | 54460 (human) |
| | 66292 (mouse) |
| Uqcc3 | 790955 (human) |
| | 107197 (mouse) |
| Mrpl23 | 6150 (human) |
| | 19935 (mouse) |
| Cox7a1 | 1346 (human) |
| | 12865 (mouse) |
| BC029214 | Replaced by Paxx |
| | 227622 (mouse) |
| Pmf1 | 11243 (human) |
| | 67037 (mouse) |
| Ccdc23 | Listed as SVPB |
| | 374969 (human) |
| | 69216 (mouse) |
| Smim22 | 440335 (human) |
| | 432995 (mouse) |
| Haus7 | 55559 (human) |
| | 73738 (mouse) |
| Cda | 978 (human) |
| | 72269 (mouse) |
| Tmem238 | 388564 (human) |
| | 664968 (mouse) |
| Bola2 | 552900 (human) |
| | 66162 (mouse) |
| Mup1 | 17840 (mouse) |
| Mup12 | 100039054 (mouse) |
| Gpihbp1 | 338328 (human) |
| | 68453 (mouse) |
| Nr0b2 | 8431 (human) |
| | 23957 (mouse) |

TABLE 4-continued

Genes and Corresponding Gene IDs from FIG. 31

| Gene | Gene ID |
|---|---|
| Mrps18a | 55168 (human) |
|  | 68565 (mouse) |
| Atoh8 | 84913 (human) |
|  | 71093 (mouse) |
| Nudt1 | 4521 (human) |
|  | 17766 (mouse) |
| Gsta4 | 2941 (human) |
|  | 14860 (mouse) |
| Mup21 | 381531 (mouse) |

TABLE 5

Microbiome and Transcriptome Correlation Results.

| gene | Lactobacillaceae | No Assigned Family | Erysipelotrichaceae_1 | Lachnospiraceae_7 | No Assigned Family_4 | No Assigned Family_7 | No Assigned Family_10 |
|---|---|---|---|---|---|---|---|
| A2m | 0.01 | 0.62 | 0.77 | 0.95 | 0.32 | 0.60 | 0.97 |
| Acbd6 | 0.99 | 0.06 | 1.00 | 0.17 | 0.65 | 0.67 | 0.12 |
| Atoh8 | 0.95 | 0.05 | 0.81 | 0.20 | 0.43 | 0.54 | 0.12 |
| BC029214 | 0.93 | 0.13 | 1.00 | 0.21 | 0.65 | 0.72 | 0.14 |
| Bcl7c | 0.98 | 0.11 | 0.98 | 0.25 | 0.74 | 0.68 | 0.12 |
| Bola2 | 0.91 | 0.13 | 0.94 | 0.18 | 0.76 | 0.76 | 0.15 |
| Brms1 | 0.94 | 0.06 | 1.00 | 0.20 | 0.68 | 0.75 | 0.22 |
| Cblc | 0.99 | 0.10 | 1.00 | 0.23 | 0.69 | 0.74 | 0.16 |
| Ccdc124 | 0.88 | 0.07 | 1.00 | 0.15 | 0.76 | 0.80 | 0.14 |
| Ccdc23 | 0.84 | 0.14 | 0.98 | 0.23 | 0.58 | 0.74 | 0.21 |
| Cda | 0.98 | 0.09 | 0.97 | 0.03 | 0.57 | 0.64 | 0.07 |
| Cenpm | 0.95 | 0.03 | 1.00 | 0.25 | 0.62 | 0.61 | 0.10 |
| Cox7a1 | 0.98 | 0.08 | 1.00 | 0.19 | 0.65 | 0.69 | 0.12 |
| Crip1 | 0.99 | 0.08 | 0.99 | 0.30 | 0.71 | 0.72 | 0.15 |
| Cxcl13 | 0.16 | 0.43 | 0.67 | 0.41 | 0.04 | 0.40 | 0.64 |
| Ddx49 | 0.91 | 0.13 | 0.97 | 0.00 | 0.65 | 0.68 | 0.14 |
| Dnajc12 | 0.16 | 0.29 | 0.38 | 0.27 | 0.05 | 0.54 | 0.33 |
| Epb4.1l4aos | 0.92 | 0.10 | 0.98 | 0.23 | 0.67 | 0.63 | 0.15 |
| Fars2 | 0.97 | 0.06 | 1.00 | 0.14 | 0.69 | 0.71 | 0.06 |
| Gfer | 0.95 | 0.08 | 0.95 | 0.13 | 0.62 | 0.74 | 0.15 |
| Gpihbp1 | 0.81 | 0.02 | 0.99 | 0.06 | 0.57 | 0.76 | 0.06 |
| Gsta4 | 0.78 | 0.09 | 0.98 | 0.13 | 0.54 | 0.60 | 0.14 |
| Haus7 | 0.88 | 0.13 | 1.00 | 0.13 | 0.60 | 0.68 | 0.17 |
| Hspbp1 | 0.98 | 0.08 | 0.98 | 0.13 | 0.60 | 0.70 | 0.08 |
| Isoc2b | 0.99 | 0.07 | 0.94 | 0.14 | 0.68 | 0.70 | 0.17 |
| Lgals1 | 1.00 | 0.11 | 0.98 | 0.24 | 0.72 | 0.77 | 0.08 |
| Marco | 0.14 | 0.44 | 0.71 | 0.49 | 0.01 | 0.38 | 0.44 |
| Mrpl23 | 1.00 | 0.07 | 0.99 | 0.16 | 0.64 | 0.71 | 0.14 |
| Mrps16 | 0.96 | 0.06 | 1.00 | 0.20 | 0.53 | 0.74 | 0.12 |
| Mrps18a | 0.98 | 0.08 | 0.83 | 0.08 | 0.42 | 0.57 | 0.21 |
| Mrps21 | 0.96 | 0.06 | 0.99 | 0.23 | 0.69 | 0.70 | 0.18 |
| Mup12 | 0.97 | 0.07 | 0.98 | 0.23 | 0.72 | 0.88 | 0.19 |
| Mup1 | 0.98 | 0.03 | 1.00 | 0.16 | 0.68 | 0.75 | 0.17 |
| Mup21 | 0.96 | 0.19 | 0.08 | 0.91 | 0.07 | 0.00 | 0.57 |
| Mup9 | 1.00 | 0.04 | 0.51 | 0.19 | 0.63 | 0.91 | 0.11 |
| Nat9 | 0.96 | 0.11 | 1.00 | 0.24 | 0.70 | 0.72 | 0.17 |
| Ndufa5 | 0.97 | 0.09 | 0.97 | 0.30 | 0.52 | 0.71 | 0.15 |
| Ndufb2 | 0.97 | 0.13 | 0.99 | 0.09 | 0.71 | 0.69 | 0.12 |
| Ndufs6 | 0.97 | 0.12 | 1.00 | 0.14 | 0.62 | 0.72 | 0.18 |
| Nr0b2 | 0.97 | 0.09 | 0.79 | 0.02 | 0.44 | 0.52 | 0.18 |
| Nudt1 | 0.95 | 0.14 | 0.97 | 0.21 | 0.48 | 0.52 | 0.09 |
| Pet100 | 0.92 | 0.13 | 0.98 | 0.21 | 0.72 | 0.70 | 0.13 |
| Pfdn6 | 1.00 | 0.12 | 0.98 | 0.15 | 0.66 | 0.76 | 0.18 |
| Pmf1 | 0.95 | 0.09 | 0.99 | 0.22 | 0.55 | 0.71 | 0.14 |
| Rnaseh2a | 0.86 | 0.13 | 1.00 | 0.18 | 0.71 | 0.66 | 0.12 |
| Rnaseh2c | 0.97 | 0.08 | 1.00 | 0.17 | 0.57 | 0.66 | 0.13 |
| Rpp21 | 0.96 | 0.05 | 1.00 | 0.24 | 0.57 | 0.78 | 0.14 |
| Rpph1 | 0.79 | 0.17 | 0.80 | 0.18 | 0.74 | 0.93 | 0.20 |
| Rps19bp1 | 0.98 | 0.11 | 0.99 | 0.26 | 0.64 | 0.71 | 0.11 |
| Saa3 | 0.05 | 0.52 | 0.74 | 0.99 | 0.23 | 0.49 | 0.89 |
| Scnm1 | 0.97 | 0.16 | 1.00 | 0.18 | 0.65 | 0.69 | 0.14 |
| Slc16a11 | 0.97 | 0.07 | 1.00 | 0.21 | 0.48 | 0.65 | 0.13 |
| Smagp | 0.99 | 0.11 | 1.00 | 0.24 | 0.54 | 0.61 | 0.14 |
| Smim22 | 0.95 | 0.14 | 1.00 | 0.19 | 0.75 | 0.70 | 0.13 |
| Ssna1 | 0.92 | 0.11 | 1.00 | 0.19 | 0.64 | 0.69 | 0.15 |
| Sssca1 | 0.87 | 0.11 | 0.96 | 0.15 | 0.65 | 0.73 | 0.13 |
| Stx4a | 1.00 | 0.13 | 1.00 | 0.21 | 0.59 | 0.63 | 0.15 |
| Timm50 | 0.99 | 0.09 | 1.00 | 0.12 | 0.67 | 0.76 | 0.17 |
| Tmem223 | 0.96 | 0.09 | 1.00 | 0.17 | 0.77 | 0.71 | 0.07 |

TABLE 5-continued

Microbiome and Transcriptome Correlation Results.

| | | | | | | | |
|---|---|---|---|---|---|---|---|
| Tmem238 | 0.92 | 0.10 | 0.97 | 0.19 | 0.74 | 0.67 | 0.17 |
| Tpgs1 | 0.91 | 0.15 | 1.00 | 0.16 | 0.63 | 0.65 | 0.19 |
| Trappc5 | 0.90 | 0.11 | 1.00 | 0.11 | 0.75 | 0.69 | 0.16 |
| Trappc6a | 0.90 | 0.13 | 0.97 | 0.03 | 0.64 | 0.68 | 0.15 |
| Uqcc3 | 1.00 | 0.09 | 1.00 | 0.26 | 0.67 | 0.77 | 0.18 |
| Use1 | 0.93 | 0.17 | 0.98 | 0.14 | 0.57 | 0.75 | 0.13 |
| Zap70 | 0.99 | 0.03 | 0.99 | 0.21 | 0.61 | 0.69 | 0.09 |
| Zfp524 | 0.95 | 0.08 | 1.00 | 0.16 | 0.70 | 0.76 | 0.17 |
| Zfp771 | 0.88 | 0.10 | 1.00 | 0.25 | 0.73 | 0.62 | 0.10 |

| gene | Lachnospiraceae_22 | No Assigned Family_17 | No Assigned Family_18 | Erysipelotrichaceae_3 | Lachnospiraceae_28 | No Assigned Family_21 | No Assigned Family_22 |
|---|---|---|---|---|---|---|---|
| A2m | 0.74 | 0.00 | 0.63 | 0.77 | 0.89 | 0.41 | 0.27 |
| Acbd6 | 0.72 | 0.83 | 0.06 | 0.15 | 0.94 | 0.99 | 0.97 |
| Atoh8 | 0.65 | 0.92 | 0.03 | 0.13 | 0.81 | 0.96 | 0.86 |
| BC029214 | 0.64 | 0.88 | 0.08 | 0.11 | 0.68 | 0.98 | 0.92 |
| Bcl7c | 0.59 | 0.77 | 0.01 | 0.16 | 0.85 | 0.97 | 1.00 |
| Bola2 | 0.58 | 0.67 | 0.05 | 0.13 | 0.58 | 0.91 | 0.86 |
| Brms1 | 0.18 | 0.72 | 0.02 | 0.11 | 0.82 | 0.98 | 1.00 |
| Cblc | 0.13 | 0.76 | 0.03 | 0.17 | 0.71 | 1.00 | 0.99 |
| Ccdc124 | 0.10 | 0.64 | 0.05 | 0.15 | 0.83 | 0.99 | 1.00 |
| Ccdc23 | 0.08 | 0.75 | 0.05 | 0.15 | 1.00 | 0.96 | 1.00 |
| Cda | 0.08 | 0.73 | 0.02 | 0.07 | 0.88 | 1.00 | 0.95 |
| Cenpm | 0.08 | 0.70 | 0.03 | 0.07 | 0.86 | 1.00 | 0.99 |
| Cox7a1 | 0.08 | 0.88 | 0.02 | 0.07 | 0.71 | 0.98 | 0.99 |
| Crip1 | 0.08 | 0.73 | 0.06 | 0.11 | 0.61 | 0.96 | 0.97 |
| Cxcl13 | 0.07 | 0.22 | 0.46 | 0.25 | 0.81 | 0.32 | 0.27 |
| Ddx49 | 0.07 | 0.73 | 0.05 | 0.17 | 0.77 | 0.94 | 0.98 |
| Dnajc12 | 0.07 | 0.19 | 0.22 | 0.30 | 0.88 | 0.35 | 0.26 |
| Epb4.1l4aos | 0.07 | 0.89 | 0.07 | 0.17 | 0.79 | 0.99 | 0.95 |
| Fars2 | 0.07 | 0.77 | 0.02 | 0.06 | 0.95 | 1.00 | 0.92 |
| Gfer | 0.07 | 0.68 | 0.11 | 0.18 | 0.82 | 0.98 | 1.00 |
| Gpihbp1 | 0.07 | 0.65 | 0.03 | 0.06 | 0.71 | 0.97 | 0.96 |
| Gsta4 | 0.07 | 0.99 | 0.04 | 0.16 | 0.97 | 0.99 | 0.78 |
| Haus7 | 0.07 | 0.91 | 0.05 | 0.07 | 0.72 | 0.90 | 0.94 |
| Hspbp1 | 0.06 | 0.79 | 0.09 | 0.05 | 0.88 | 0.99 | 0.97 |
| Isoc2b | 0.06 | 0.65 | 0.02 | 0.19 | 0.81 | 1.00 | 1.00 |
| Lgals1 | 0.06 | 0.79 | 0.02 | 0.14 | 0.74 | 0.98 | 1.00 |
| Marco | 0.06 | 0.14 | 0.45 | 0.44 | 0.70 | 0.33 | 0.16 |
| Mrpl23 | 0.06 | 0.78 | 0.05 | 0.11 | 0.73 | 0.95 | 0.99 |
| Mrps16 | 0.06 | 0.75 | 0.07 | 0.14 | 0.94 | 1.00 | 0.95 |
| Mrps18a | 0.06 | 0.79 | 0.07 | 0.08 | 0.87 | 0.98 | 0.96 |
| Mrps21 | 0.06 | 0.75 | 0.04 | 0.11 | 0.89 | 0.98 | 0.99 |
| Mup12 | 0.06 | 0.78 | 0.01 | 0.11 | 0.62 | 0.96 | 0.98 |
| Mup1 | 0.05 | 0.74 | 0.04 | 0.08 | 0.56 | 0.99 | 0.98 |
| Mup21 | 0.05 | 0.82 | 0.37 | 0.82 | 0.05 | 0.02 | 0.07 |
| Mup9 | 0.05 | 0.77 | 0.05 | 0.13 | 0.55 | 0.96 | 0.99 |
| Nat9 | 0.05 | 0.65 | 0.06 | 0.17 | 0.70 | 1.00 | 0.97 |
| Ndufa5 | 0.05 | 0.85 | 0.01 | 0.13 | 0.83 | 0.97 | 0.99 |
| Ndufb2 | 0.05 | 0.78 | 0.04 | 0.13 | 0.82 | 0.99 | 1.00 |
| Ndufs6 | 0.05 | 0.75 | 0.03 | 0.12 | 0.85 | 0.99 | 1.00 |
| Nr0b2 | 0.05 | 0.82 | 0.03 | 0.15 | 0.75 | 0.98 | 0.98 |
| Nudt1 | 0.04 | 0.83 | 0.01 | 0.11 | 0.99 | 0.98 | 0.94 |
| Pet100 | 0.04 | 0.72 | 0.03 | 0.16 | 0.82 | 0.91 | 0.97 |
| Pfdn6 | 0.04 | 0.72 | 0.06 | 0.10 | 0.82 | 1.00 | 1.00 |
| Pmf1 | 0.04 | 0.93 | 0.06 | 0.09 | 0.79 | 0.99 | 0.94 |
| Rnaseh2a | 0.04 | 0.67 | 0.04 | 0.13 | 0.81 | 0.98 | 0.95 |
| Rnaseh2c | 0.04 | 0.79 | 0.02 | 0.17 | 0.69 | 0.99 | 0.98 |
| Rpp21 | 0.04 | 0.76 | 0.03 | 0.14 | 0.87 | 0.98 | 1.00 |
| Rpph1 | 0.04 | 0.64 | 0.05 | 0.22 | 0.53 | 0.88 | 0.85 |
| Rps19bp1 | 0.04 | 0.79 | 0.05 | 0.14 | 0.91 | 0.98 | 1.00 |
| Saa3 | 0.04 | 0.00 | 0.55 | 0.76 | 0.94 | 0.38 | 0.19 |
| Scnm1 | 0.03 | 0.70 | 0.03 | 0.10 | 0.95 | 0.99 | 0.96 |
| Slc16a11 | 0.03 | 0.88 | 0.02 | 0.16 | 0.81 | 1.00 | 0.92 |
| Smagp | 0.03 | 0.70 | 0.03 | 0.14 | 0.93 | 0.98 | 0.95 |
| Smim22 | 0.03 | 0.67 | 0.04 | 0.09 | 0.61 | 0.97 | 0.97 |
| Ssna1 | 0.02 | 0.69 | 0.02 | 0.09 | 0.79 | 0.99 | 1.00 |
| Ssscal | 0.02 | 0.76 | 0.07 | 0.15 | 0.70 | 0.95 | 0.95 |
| Stx4a | 0.02 | 0.74 | 0.05 | 0.05 | 1.00 | 0.97 | 0.98 |
| Timm50 | 0.02 | 0.79 | 0.00 | 0.15 | 0.90 | 0.96 | 0.99 |
| Tmem223 | 0.02 | 0.80 | 0.04 | 0.14 | 0.80 | 0.99 | 1.00 |
| Tmem238 | 0.02 | 0.66 | 0.02 | 0.17 | 0.65 | 0.96 | 0.92 |
| Tpgs1 | 0.02 | 0.73 | 0.02 | 0.26 | 0.81 | 0.97 | 0.96 |
| Trappc5 | 0.02 | 0.66 | 0.05 | 0.20 | 0.70 | 0.95 | 0.95 |
| Trappc6a | 0.02 | 0.66 | 0.02 | 0.13 | 0.86 | 0.97 | 1.00 |
| Uqcc3 | 0.01 | 0.84 | 0.00 | 0.13 | 0.82 | 0.99 | 1.00 |

TABLE 5-continued

Microbiome and Transcriptome Correlation Results.

| | | | | | | | |
|---|---|---|---|---|---|---|---|
| Use1 | 0.01 | 0.72 | 0.01 | 0.11 | 0.74 | 0.97 | 0.98 |
| Zap70 | 0.01 | 0.77 | 0.01 | 0.08 | 0.96 | 1.00 | 0.92 |
| Zfp524 | 0.01 | 0.72 | 0.00 | 0.10 | 0.75 | 1.00 | 0.91 |
| Zfp771 | 0.00 | 0.63 | 0.02 | 0.13 | 0.76 | 0.96 | 0.97 |

| gene | Ruminococcaceae_19 | Clostridiaceae_2 | Lachnospiraceae_40 | No Assigned Family_30 | Lachnospiraceae_43 | Lachnospiraceae_44 |
|---|---|---|---|---|---|---|
| A2m | 0.78 | 0.17 | 0.96 | 0.80 | 0.12 | 0.04 |
| Acbd6 | 0.11 | 0.23 | 0.18 | 0.17 | 0.41 | 0.65 |
| Atoh8 | 0.19 | 0.24 | 0.18 | 0.07 | 0.35 | 0.54 |
| BC029214 | 0.14 | 0.24 | 0.24 | 0.32 | 0.48 | 0.72 |
| Bcl7c | 0.13 | 0.24 | 0.21 | 0.17 | 0.55 | 0.86 |
| Bola2 | 0.19 | 0.52 | 0.23 | 0.23 | 0.73 | 0.91 |
| Brms1 | 0.27 | 0.28 | 0.23 | 0.17 | 0.70 | 0.81 |
| Cblc | 0.09 | 0.26 | 0.20 | 0.20 | 0.50 | 0.78 |
| Ccdc124 | 0.16 | 0.29 | 0.20 | 0.09 | 0.64 | 0.84 |
| Ccdc23 | 0.23 | 0.39 | 0.22 | 0.08 | 0.48 | 0.80 |
| Cda | 0.04 | 0.28 | 0.02 | 0.09 | 0.56 | 0.83 |
| Cenpm | 0.10 | 0.27 | 0.20 | 0.05 | 0.59 | 0.75 |
| Cox7a1 | 0.16 | 0.22 | 0.33 | 0.22 | 0.49 | 0.75 |
| Crip1 | 0.05 | 0.14 | 0.15 | 0.10 | 0.60 | 0.73 |
| Cxcl13 | 0.16 | 0.15 | 0.36 | 0.53 | 0.06 | 0.17 |
| Ddx49 | 0.19 | 0.31 | 0.02 | 0.11 | 0.66 | 0.86 |
| Dnajc12 | 0.37 | 0.09 | 0.19 | 0.56 | 0.13 | 0.23 |
| Epb4.1l4aos | 0.17 | 0.27 | 0.22 | 0.14 | 0.35 | 0.64 |
| Fars2 | 0.21 | 0.28 | 0.20 | 0.11 | 0.45 | 0.64 |
| Gfer | 0.18 | 0.33 | 0.18 | 0.09 | 0.63 | 0.79 |
| Gpihbp1 | 0.16 | 0.49 | 0.03 | 0.22 | 0.94 | 0.92 |
| Gsta4 | 0.15 | 0.28 | 0.10 | 0.25 | 0.35 | 0.35 |
| Haus7 | 0.15 | 0.28 | 0.07 | 0.14 | 0.39 | 0.66 |
| Hspbp1 | 0.15 | 0.29 | 0.20 | 0.12 | 0.59 | 0.74 |
| Isoc2b | 0.15 | 0.18 | 0.13 | 0.13 | 0.66 | 0.75 |
| Lgals1 | 0.10 | 0.19 | 0.16 | 0.18 | 0.52 | 0.71 |
| Marco | 0.41 | 0.14 | 0.65 | 0.67 | 0.11 | 0.21 |
| Mrpl23 | 0.14 | 0.17 | 0.18 | 0.20 | 0.54 | 0.75 |
| Mrps16 | 0.14 | 0.20 | 0.23 | 0.15 | 0.56 | 0.74 |
| Mrps18a | 0.09 | 0.29 | 0.05 | 0.08 | 0.31 | 0.60 |
| Mrps21 | 0.12 | 0.30 | 0.18 | 0.07 | 0.50 | 0.77 |
| Mup12 | 0.13 | 0.33 | 0.19 | 0.35 | 0.81 | 0.83 |
| Mup1 | 0.17 | 0.26 | 0.12 | 0.25 | 0.74 | 0.79 |
| Mup21 | 0.66 | 0.41 | 0.87 | 0.18 | 0.72 | 0.39 |
| Mup9 | 0.01 | 0.40 | 0.21 | 0.41 | 0.80 | 0.86 |
| Nat9 | 0.14 | 0.15 | 0.20 | 0.12 | 0.72 | 0.83 |
| Ndufa5 | 0.19 | 0.29 | 0.17 | 0.16 | 0.46 | 0.72 |
| Ndufb2 | 0.13 | 0.20 | 0.02 | 0.21 | 0.66 | 0.68 |
| Ndufs6 | 0.11 | 0.23 | 0.19 | 0.08 | 0.60 | 0.67 |
| Nr0b2 | 0.14 | 0.29 | 0.01 | 0.11 | 0.27 | 0.69 |
| Nudt1 | 0.14 | 0.17 | 0.21 | 0.13 | 0.35 | 0.65 |
| Pet100 | 0.21 | 0.34 | 0.13 | 0.14 | 0.56 | 0.81 |
| Pfdn6 | 0.14 | 0.26 | 0.15 | 0.13 | 0.53 | 0.73 |
| Pmf1 | 0.13 | 0.29 | 0.26 | 0.22 | 0.48 | 0.65 |
| Rnaseh2a | 0.23 | 0.54 | 0.18 | 0.13 | 0.66 | 0.82 |
| Rnaseh2c | 0.08 | 0.23 | 0.20 | 0.14 | 0.61 | 0.81 |
| Rpp21 | 0.12 | 0.19 | 0.15 | 0.16 | 0.59 | 0.83 |
| Rpph1 | 0.18 | 0.69 | 0.12 | 0.32 | 0.94 | 0.97 |
| Rps19bp1 | 0.10 | 0.24 | 0.21 | 0.15 | 0.49 | 0.77 |
| Saa3 | 0.65 | 0.23 | 0.99 | 0.77 | 0.13 | 0.06 |
| Scnm1 | 0.17 | 0.25 | 0.12 | 0.12 | 0.40 | 0.61 |
| Slc16a11 | 0.11 | 0.27 | 0.14 | 0.18 | 0.46 | 0.74 |
| Smagp | 0.16 | 0.26 | 0.26 | 0.10 | 0.42 | 0.64 |
| Smim22 | 0.18 | 0.32 | 0.17 | 0.16 | 0.38 | 0.70 |
| Ssna1 | 0.06 | 0.29 | 0.19 | 0.09 | 0.57 | 0.69 |
| Sssca1 | 0.27 | 0.37 | 0.11 | 0.15 | 0.65 | 0.79 |
| Stx4a | 0.15 | 0.23 | 0.23 | 0.10 | 0.39 | 0.65 |
| Timm50 | 0.17 | 0.25 | 0.18 | 0.08 | 0.37 | 0.64 |
| Tmem223 | 0.25 | 0.23 | 0.15 | 0.14 | 0.38 | 0.72 |
| Tmem238 | 0.09 | 0.26 | 0.22 | 0.29 | 0.87 | 0.87 |
| Tpgs1 | 0.22 | 0.32 | 0.23 | 0.07 | 0.61 | 0.83 |
| Trappc5 | 0.26 | 0.38 | 0.13 | 0.12 | 0.60 | 0.77 |
| Trappc6a | 0.19 | 0.33 | 0.07 | 0.10 | 0.57 | 0.86 |
| Uqcc3 | 0.12 | 0.15 | 0.22 | 0.12 | 0.53 | 0.77 |
| Use1 | 0.09 | 0.17 | 0.16 | 0.19 | 0.60 | 0.80 |
| Zap70 | 0.07 | 0.31 | 0.18 | 0.09 | 0.61 | 0.73 |
| Zfp524 | 0.18 | 0.25 | 0.22 | 0.12 | 0.59 | 0.68 |
| Zfp771 | 0.13 | 0.30 | 0.24 | 0.19 | 0.64 | 0.69 |

TABLE 5-continued

Microbiome and Transcriptome Correlation Results.

| gene | Ruminococcaceae_34 | No Assigned Family_33 | Lachnospiraceae_46 | Lachnospiraceae_47 |
|---|---|---|---|---|
| A2m | 0.89 | 0.66 | 0.65 | 0.66 |
| Acbd6 | 0.01 | 0.16 | 0.74 | 0.93 |
| Atoh8 | 0.09 | 0.04 | 1.00 | 1.00 |
| BC029214 | 0.11 | 0.23 | 0.72 | 0.94 |
| Bcl7c | 0.01 | 0.20 | 0.79 | 1.00 |
| Bola2 | 0.03 | 0.37 | 0.72 | 0.91 |
| Brms1 | 0.07 | 0.32 | 0.68 | 1.00 |
| Cblc | 0.10 | 0.22 | 0.63 | 1.00 |
| Ccdc124 | 0.04 | 0.15 | 0.63 | 0.86 |
| Ccdc23 | 0.10 | 0.22 | 0.80 | 0.97 |
| Cda | 0.07 | 0.08 | 0.81 | 0.90 |
| Cenpm | 0.03 | 0.13 | 0.75 | 1.00 |
| Cox7a1 | 0.08 | 0.20 | 0.74 | 0.98 |
| Crip1 | 0.07 | 0.32 | 0.68 | 1.00 |
| Cxcl13 | 0.60 | 0.30 | 0.55 | 0.80 |
| Ddx49 | 0.09 | 0.21 | 0.70 | 1.00 |
| Dnajc12 | 0.44 | 0.18 | 0.63 | 0.45 |
| Epb4.1l4aos | 0.11 | 0.15 | 0.83 | 1.00 |
| Fars2 | 0.06 | 0.11 | 0.77 | 0.98 |
| Gfer | 0.07 | 0.10 | 0.72 | 0.87 |
| Gpihbp1 | 0.10 | 0.20 | 0.79 | 1.00 |
| Gsta4 | 0.09 | 0.10 | 0.97 | 0.87 |
| Haus7 | 0.08 | 0.20 | 0.72 | 1.00 |
| Hspbp1 | 0.11 | 0.10 | 0.74 | 1.00 |
| Isoc2b | 0.07 | 0.08 | 0.84 | 1.00 |
| Lgals1 | 0.08 | 0.12 | 0.74 | 0.93 |
| Marco | 0.70 | 0.34 | 0.51 | 0.80 |
| Mrpl23 | 0.11 | 0.21 | 0.71 | 0.96 |
| Mrps16 | 0.09 | 0.09 | 0.73 | 1.00 |
| Mrps18a | 0.08 | 0.10 | 1.00 | 1.00 |
| Mrps21 | 0.09 | 0.18 | 0.75 | 0.96 |
| Mup12 | 0.06 | 0.27 | 0.64 | 0.91 |
| Mup1 | 0.13 | 0.29 | 0.81 | 0.96 |
| Mup21 | 0.27 | 0.04 | 0.02 | 0.08 |
| Mup9 | 0.24 | 0.31 | 0.51 | 0.47 |
| Nat9 | 0.11 | 0.21 | 0.66 | 0.93 |
| Ndufa5 | 0.01 | 0.24 | 0.83 | 0.98 |
| Ndufb2 | 0.10 | 0.14 | 0.80 | 0.98 |
| Ndufs6 | 0.05 | 0.10 | 0.75 | 0.75 |
| Nr0b2 | 0.05 | 0.04 | 0.96 | 0.91 |
| Nudt1 | 0.05 | 0.09 | 0.84 | 0.91 |
| Pet100 | 0.06 | 0.16 | 0.74 | 1.00 |
| Pfdn6 | 0.08 | 0.09 | 0.79 | 0.86 |
| Pmf1 | 0.08 | 0.19 | 0.74 | 0.89 |
| Rnaseh2a | 0.06 | 0.25 | 0.76 | 1.00 |
| Rnaseh2c | 0.07 | 0.27 | 0.73 | 1.00 |
| Rpp21 | 0.01 | 0.18 | 0.68 | 0.94 |
| Rpph1 | 0.17 | 0.49 | 0.53 | 0.76 |
| Rps19bp1 | 0.15 | 0.07 | 0.82 | 0.99 |
| Saa3 | 1.00 | 0.83 | 0.63 | 0.76 |
| Scnm1 | 0.11 | 0.06 | 0.75 | 0.97 |
| Slc16a11 | 0.09 | 0.14 | 0.77 | 1.00 |
| Smagp | 0.12 | 0.07 | 0.76 | 1.00 |
| Smim22 | 0.08 | 0.24 | 0.65 | 0.92 |
| Ssna1 | 0.16 | 0.13 | 0.76 | 0.86 |
| Sssca1 | 0.10 | 0.26 | 0.74 | 0.95 |
| Stx4a | 0.08 | 0.18 | 0.81 | 1.00 |
| Timm50 | 0.12 | 0.10 | 0.76 | 0.97 |
| Tmem223 | 0.11 | 0.16 | 0.80 | 0.97 |
| Tmem238 | 0.09 | 0.41 | 0.65 | 0.98 |
| Tpgs1 | 0.10 | 0.14 | 0.77 | 1.00 |
| Trappc5 | 0.10 | 0.31 | 0.64 | 1.00 |
| Trappc6a | 0.08 | 0.14 | 0.75 | 0.91 |
| Uqcc3 | 0.05 | 0.19 | 0.83 | 0.98 |
| Use1 | 0.11 | 0.24 | 0.70 | 0.94 |
| Zap70 | 0.18 | 0.08 | 0.81 | 1.00 |
| Zfp524 | 0.05 | 0.27 | 0.81 | 0.86 |
| Zfp771 | 0.14 | 0.23 | 0.75 | 1.00 |

These 69 differentially expressed genes are implicated in many diseases, such as Huntington's disease, Alzheimer's disease, Non-alcoholic fatty liver disease (NAFLD) and Parkinson's disease (FIG. 32) as determined by KEGG pathway analysis for metabolic functions that are enriched in the hepatic transcriptome in female mice, age 15 weeks fed exosome RNA-sufficient (ERS) or exosome RNA-depleted (ERD).

This study provides strong evidence that dietary exosomes and their RNA cargos, at least those in milk, are responsible for some of the effects of diet on the gut microbiome. This study indicates that dietary RNAs elicit changes in gene expression across kingdoms, in this case animals and bacteria. This concept is based on a report suggesting that MIR-168a in rice is bioavailable and binds to the mRNA coding for low-density lipoprotein receptor adaptor protein 1, thereby lowering mRNA expression in the liver of mice. This study suggests that gut microorganisms might act as transmitters or amplifiers of dietary exosome signals. Previous reports have suggested that microRNA cargos in dietary exosomes achieve tissue concentrations that are too low to elicit biological effects and that the bioavailability of milk exosomes might be low. Here evidence is provided that exosome-defined diets alter microbial communities in the murine cecum, and effects are particularly strong if studied at the OTU level. Importantly, milk exosomes that escape absorption by mucosal cells may still elicit major biological effects, facilitated by the gut microbiome.

C. The Microbial Communities Altered By Milk Exosome-Defined Diets are Related to Pathological and Physiological Conditions It is now widely accepted that prokaryotic and eukaryotic microbes communicate with their environment through exosome-like vesicles. Changes in microbial communities are paralleled by changes in the production of microbial metabolites, which may transmit and amplify milk exosome signals. These studies provide evidence that milk exosome-dependent changes in microbial communities can explain changes observed in the hepatic transcriptome in mice.

The microbial communities altered by milk exosome-defined diets are related to pathological and physiological conditions, as evidenced by the following examples. A loss of Lachnospiraceae and Ruminococcaceae and a gain in Enterobacteriaceae in the ileal mucosa have been implicated in inflammatory bowel disease. The ratio of Firmicutes and Bacteroidetes is greater in obese compared with lean subjects. See, e.g., Daulatzai M. A., *Mol. Genet. Med. S*1:005 10.4172/1747-0862.S1-005.

Dysbiosis in the gut microbiome may cause liver disease due to microbial metabolites altering the metabolism in hepatic cells via innate immune receptors, e.g., a decreased abundance of Ruminococcaceae and *Escherichia* has been linked with non-alcoholic fatty liver disease. See, e.g., Adams, L. A. et al., *Curr. Hepatol. Rep.* 15 96-102. 10.1007/s11901-016-0299-5. Inflammatory bowel disease, obesity and non-alcoholic fatty liver disease are major health concerns in the United States.

Gut microbiota are likely not the only amplifiers of exosome and RNA cargo signals. It has been proposed that microRNAs elicit biological effects through binding to Toll-like receptors or by surface antigen-mediated delivery of exosomes to immune cells to create an exosome-rich microenvironment; mere exosome-cell surface interactions might also alter cell signaling pathways.

This study provides strong evidence that milk exosomes and their RNA cargos elicit biological effects across species boundaries and even kingdoms. Of significant importance is the observation that exosomes that escape intestinal absorption have biological activity, caused by exosome-microbiota interactions.

Example 8: Glycoproteins on the Surface of Milk Exosomes Mediate the Uptake of Exosomes into Human and Other Mammalian Cells Extracellular vesicles (EVs), such as exosomes, carry cargo that includes various species of RNA, proteins, and lipids. Encapsulation of such cargos in EVs confers protection against degradation and a pathway for cellular uptake by endocytosis. EVs are secreted by donor cells for delivery to recipient cells, and EV cargo has emerged as an important mediator in intercellular communication. There are 3 major classes of EVs, i.e., exosomes, microvesicles, and apoptotic bodies. Exosomes are of particular interest because they are loaded with microRNAs in a targeted, nonstochastic process that involves sorting mechanisms.

The intestinal transport of bovine milk exosomes (and microRNAs) can be assessed using fluorophore-labeled bovine milk exosomes in mammalian cell cultures, such as human epithelial colon adenocarcinoma Caco-2 cells, normal rat small intestinal IEC-6 cells, human small intestinal cells (FH), and human umbilical vein endothelial cells (HUVEC). Transport kinetics and mechanisms can be characterized using such assays as: dose-response studies, inhibitors of vesicle transport, carbohydrate competitors, proteolysis of surface proteins on cells and exosomes, and transepithelial transport in transwell plates.

The studies described herein demonstrate that: (1) milk exosomes are transported into human and mammalian cells in a dose-dependent manner (until saturation); (2) transport occurs via endocytosis; (3) cell surface glycoproteins play a significant role in the transport of exosomes; and (4) glycans on surface glycoproteins play a significant role in the transport of exosomes. Modification of the exosome surface glycoproteins and/or glycans can be used not only to regulate the rate and amount of exosome transport (and cargo delivery), but can also be used to direct exosomes to a particular cellular target.

A. Transport of Milk Exosomes into Human and other Mammalian Cells

Exosomes were isolated from cow's milk using ultracentrifugation as described in Example 1. The identity, purity, and integrity of the isolated exosomes were confirmed using nanoparticle tracker, western blot, and transmission electron microscopy as described in Example 1.

(i) Temporal Studies

Caco-2 cells and IEC-6 cells were seeded at a density of 20,000 and 7000 cells/well, respectively, in 96-well plates, and allowed to adhere for 48 h, when cells were 75% confluent. The exosomes were labeled with the fluorophore, FM 4-64 (Molecular Probes). One microliter of a stock solution of FM 4-64 (5.9 mmol/L) was added to 1 mL of exosome suspension and incubated for 15 min at 37° C., and excess FM 4-64 was removed by ultracentrifugation at 120,000 3 g at 4° C. for 90 min. Transport studies were conducted using FM4-64-labeled exosomes using 3-110 mg of exosomal protein/well (Caco-2 cells) or 27-652 mg of exosomal protein/well (IEC-6 cells) and incubating cells for various periods of time to assess saturation kinetics; blanks were created using solvent. Assays were calibrated by quantifying the fluorescence of a known mass of exosomes labeled with FM 4-64. Exosome uptake was analyzed by measuring the cell fluorescence at 515 (excitation) and 640 nm (emission) using a Biotek FLx800 plate reader (BioTek Instruments). Fluorescence readings were corrected for cell autofluorescence by subtracting signals measured in cells incubated with exosome-depleted media. Transport kinetics was modeled using the Michaelis-Menten equation and nonlinear regression; modeling was conducted using GraphPad Prism 6.0 (GraphPad Software). In Caco-2 cells, exosome uptake was linear for up to 120 min if transport was measured using nonsaturating substrate concentrations (FIG. 33A): y=0.0012x+0.014 ($r2$=0.97; P<0.05). In IEC-6 cells exosome uptake was linear for only up to 60 min if transport was measured using nonsaturating substrate concentrations (FIG. 33B): y=0.0033x+0.033 ($r2$=0.75; P<0.05). Subsequent transport studies were conducted using incubation times of 8 hours for Caco-2 cells (FIG. 34B). Transport of milk exosome uptake was also studied in human umbilical vein endothelial cells (HUVECs) human small intestinal cells (FHs cells). FIG. 34A shows separate experiments in which transport of milk exosomes in HUVECs was measured over 120 minutes (2 hours) (insert for FIG. 34A) and 480 minutes (4 hours) using 20 μg exosome protein/200 μl of media (FIG. 34A). FIG. 34C shows an exosome uptake study in human small intestinal cells (FHs cells) over the course of 8 hours.

(ii) Substrate Studies

In both mammalian cells, the uptake of bovine milk exosomes was mediated by saturable transport mechanisms. Transport kinetics was modeled using the Michaelis-Menten equation. Exosome uptake was analyzed by measuring the cell fluorescence at 515 (excitation) and 640 nm (emission) using a Biotek FLx800 plate reader (BioTek Instruments) as previously described above. In Caco-2 cells, Michaelis constant (Km) and maximal transport rate were 55.5+48.6 μg exosomal protein/200 μL medium and 0.08+0.06 ng of exosomal protein/81,750 cells$^{-1}$/h$^{-1}$, respectively ($r2$=0.75; FIG. 35A). In IEC-6 cells Km and maximal transport rate were 152+39.5 μg/200 μL and 0.14+0.01 ng of exosomal protein/36,375 cells 30$^{-1}$/min$^{-1}$, respectively ($r2$=0.56; FIG. 35B). When the incubation temperature was decreased from 37° C. to 4° C., the transport rate decreased from 100%+56% to 54%+13% using a substrate concentration of 55.5 μg exosomal protein/200 μL in Caco-2 cells (P<0.05; n=3). Likewise, when the incubation temperature was decreased from 37° C. to 4° C., the transport rate decreased from 100%+11% to 44%+25% using a substrate concentration of 153 μg exosomal protein/200 μL in IEC-6 cells (P<0.05; n=3). Subsequent transport studies were conducted using substrate concentrations of 55 μg/200 mL and 153 μg/200 mL in Caco-2 cells and IEC-6 cells, respectively. FIG. 36A shows saturation kinetics of milk exosome uptake in CaCo2 as a function of substrate concentration at 37° C. (N=3; p<0.05). FIG. 36B shows exosome uptake into human umbilical vein endothelial cells as a function of substrate concentration at 37° C. FIGS. 37A and 37B show saturation kinetics of milk exosome uptake in human small intestinal cells (FHs cells).

B. Removal of Surface Glycoproteins Alters (Decreases) Transport of Milk Exosomes into Human and Other Mammalian Cells (i) Removal of Surface Glycoproteins Studies showed that the uptake of bovine milk exosomes into human and rat intestinal cells depended on surface proteins in both exosomes and cells. FIG. 38 shows a scheme for exosome processing to remove glycoproteins on the surface of milk exosomes. To remove surface protein from milk exosomes, the exosomes were subjected to various proteases, including trypsin, proteinase K, AspN, GluC, ArgC. As shown in FIG. 39, trypsin cleaves at lysine or arginine residues; chymotrypsin cleaves at aromatic amino acids (cleaves on the C-terminal phenylalanine, tryptophan, and tyrosine) on peptide chains; lys-C cleaves at the C-terminal side of lysine residues; Arg-C cleaves at arginine and lysine residues; Glu-C cleaves at glutamic acid and aspartic acid residues; and Asp-N cleaves at aspartic acid residues. Table A below shows the specificities of various proteases. Following protease treatment, the exosomes were subject to ultracentrifugation. The supernatant containing the enzyme cleaved surface peptides were identified using LC-MS/MS using LC/MS-MS and Mascot, and glycoproteins were identified using SwissProt. One way Anova and Bonferroni's Multiple comparison was used to test for statistical significance. The pellet containing the exosomes with its surface proteins removed was resuspended in 1×PBS and used for the transport studies shown in FIGS. 40-43.

TABLE A

Proteases and Their Specificities

| Protease Name | Family | Cleavage Site | Terminal Cleavage | pH |
|---|---|---|---|---|
| Trypsin | Serine Protease | Lysine or Arginine (except when either is followed by proline) | C | 8 |
| Asp N | Metalloprotease | Aspartic Acid | N | 8 |
| Glu C | Serine Protease | Glutamic acid and Aspartic Acid | C | 8 |
| Arg C | Cysteine Protease | Arginine when followed by proline and also Lysine | C | 8 |
| Chymotrypsin | Serine Protease | Aromatic amino acids (phenylalanine, tryptophan, and tyrosine) | C | 8 |
| Lys-C | Serine Protease | Lysine residues | C | 8 |

(ii) Transport Studies Show Decreased Transport Using Exosomes and Cells with Surface Proteins Removed The uptake of bovine milk exosomes into human and rat intestinal cells depended on surface proteins in both exosomes and cells. Exosomes were treated with proteases as described above and depicted in FIG. 39. Where applicable, exosomes were treated with the proteases Glu-C (targeting glu), trypsin (targeting arg and lys), Glc C (targeting glutamic acid and aspartic acid), AspN (targeting aspartic acid), ArgG (targeting arginine and lysine), or proteinase K (nonspecific); controls were not treated with proteases. Exosome uptake was analyzed by measuring the cell fluorescence at 515 (excitation) and 640 nm (emission) using a Biotek FLx800 plate reader as previously described above.

When surface proteins were removed from exosomes or Cacos-2 cells via treatment with proteinase K (100 mg/mL), exosome uptake decreased to 32%±25% (exosome treatment) and 18%±16% (CaCo2 cell treatment) of controls (P<0.05; n=3) (data not shown). FIG. 40B shows the effect on exosome uptake in CaCo2 cells after treatment of milk exosomes with trypsin or Glu-C (FIG. 40B) or Arg-C or Asp-N FIG. 40C), demonstrating a significant decrease in exosome transport into CaCo-2 cells when surface proteins were removed from the exosome. Studies using rat intestinal IEC-6 cells showed that milk exosomes treated with 0.105 mMol/L trypsin for 30 mins demonstrated a decrease in transport into IEC-6 cells. Exosome uptake decreased to 82%±8% of controls (P, 0.05; n=3). (Data not shown). FIG. 40A shows that surface proteins played an important role in facilitating exosome uptake into HUVECs. When exosomal surface proteins were removed by treatment with proteinase K, exosome uptake decreased to ~50% of controls (FIG. 40A).

FIGS. 41A and 41B show exosome uptake by Caco-2 cells after treatment of the exosomes (FIG. 41A) or treatment of the CaCo-2 cells (FIG. 41B) with protease(s) trypsin, Glc C, Arg C, Asp N, or a mixture thereof (n=3; p<0.05). As shown, treatment of exosomes with protease decreases the uptake of cow's milk exosomes in CaCo-2 cells by greater than 50%. Likewise, treatment of Caco-2 cells with protease decreases the uptake of cow's milk exosomes in CaCo2 cells by greater than 50%. *P<0.05 vs. control. (N=3, means±S.D.).

FIGS. 42A and 42B show the effects on exosome transport in human small intestinal FH cells after treatment with a protease (n=3; p<0.05). Protease treatment of exosomes (FIG. 42A) results in a decrease in the uptake of cow's milk exosomes in FH cells. Protease treatment of FH cells (FIG. 42B) with protease decreases the uptake of cow's milk exosomes in FH cells. *P<0.05 vs. control. (N=3, means±S.D.).

FIGS. 43A and 43B show the effects on exosome transport in human macrophage U937 cells after treatment with a protease (n=3; p<0.05). Protease treatment of exosomes (FIG. 43A) results in a decrease in the uptake of cow's milk exosomes in U937 cells. Protease treatment of U937 cells (FIG. 43B) with protease decreases the uptake of cow's milk exosomes in U937 cells. *P<0.05 vs. control. (N=3, means±S.D.).

C. Altered Transport of Milk Exosomes into Human and other Mammalian Cells by Removal of Glycans from Surface Glycoproteins (i) Removal of Glycans From Surface Glycoproteins FIG. 48 shows a scheme for exosome processing to remove glycans from glycoproteins on the surface of milk exosomes. To remove glycans from the surface protein of milk exosomes, the exosomes were subjected to various glycosidases, including neuraminidase, O-glycosidase, β-galactosidase, β-N-acetylglucosaminidase, and PNGaseF. As shown in Table B, neuraminidase cleaves all branched and unbranched chain sialic acids, cleaves serine and threonine linked unsubstituted Gal-β (1→3)-GalNAc, (3 (1→4)-galactosidase cleaves β (1→4)-linked nonreducing terminal galactose, β-N-acetylglucosaminidase cleaves non-reducing terminal β-linked Nacetylglucosamine residues, and PNGaseF which cleaves asparagine-linked complex, hybrid, or high mannose oligosaccharides (except when fucosylated). Following glycosidase treatment, the oligosaccharide fraction is removed for testing using LC/MS-MS.

The exosomes with one or more types of glycans removed from its surface proteins were subject to ultracentrifugation. The pellet containing the exosomes with its one or more types of glycans removed was resuspended in 1×PBS and used for the transport studies shown in FIGS. 46-48, 50, and 51.

TABLE B

| Enzyme Name | Cleavage Site | Time (hours) | Temperature (° C.) |
| --- | --- | --- | --- |
| A-(2→3,6,8,9)-Neuraminidase | All branched and unbranched sialic acids | 12 | 37 |
| O-Glycosidase | Serine or Threonine linked unsubstituted Gal-β(1→3)-GalNAc | 12 | 37 |
| N-Glycosidase | N-linked glycans, including glycans with α(1,3)-linked core fucose | 12 | 37 |
| β(1→4)-Galactosidase | β(1→4)-linked nonreducing terminal galactose | 12 | 37 |
| β-N-Acetylglucosaminidase (exoglycosidase) | Nonreducing terminal β-linked N-acetylglucosamine | 12 | 37 |
| PNGase F (glycoamidase) | Asparagine linked complex, hybrid, or high mannose oligosaccharides (except when fucosylated) bond between GlcNAc and Asn | 12 | 37 |

(ii) Predicted Glycan Binding Sites on Identified Exosome Membrane Proteins

FIG. 2 shows several membrane proteins identified in the membrane fraction of milk exosomes, e.g., ALIX, CD9, and CD63. FIG. 44 shows a table of exemplary enzyme treatments, the expected number of Transmembrane Helices (TMHs), and the predicted number of glycan binding sites on identified exosome surface proteins in the presence of specific protease treatment versus total deglycosylation (T.D). FIG. 45 shows a Venn diagram comparison for identified membrane proteins after specific protease treatment versus specific protease treatment and total glycan removed. LC/MS-MS studies identified 4 N-, 2 O-, and 2 C-glycosylated proteins on the milk exosome surface. The presence of greater numbers of TMHs after treatments that remove glycans suggests that the glycans were indeed presented on the surface of the exosomes.

(iii) Transport Studies Show Decreased Transport Using Exosomes and Cells with Glycans Removed from Surface Proteins The uptake of bovine milk exosomes into human and rat intestinal cells depended on glycan content in membrane proteins found on the surface of both exosomes and cells. Exosomes were treated with glycosidases as described above and depicted in Table 3. For example, exosomes and cells were treated with the glycosidases A-(2→3,6,8,9)-Neuraminidase which cleaves branched and unbranched sialic acids, O-Glycosidase which cleaves serine or threonine linked unsubstituted Gal-β(1→3)-GalNAc, N-Glycosidase which cleaves N-linked glycans, β(1→4)-Galactosidase which cleaves β(1→4)-linked nonreducing terminal galactose, β-N-Acetylglucosaminidase which cleaves nonreducing terminal β-linked N-acetylglucosamine, and PNGase F which cleaves asparagine linked complex, hybrid, or high mannose oligosaccharides (except when fucosylated). Exosome uptake was analyzed by measuring the cell fluorescence at 515 (excitation) and 640 nm (emission) using a Biotek FLx800 plate reader (BioTek Instru-ments) as previously described above. The following studies demonstrated that exosome uptake is decreased following glycan removal from surface proteins of exosomes or mammalian cells (via treatment with a glycosidase). FIG. 46 shows exosome uptake in Caco2 cells following enzymatic removal of glycan from exosome surface proteins using PNGase, β-galactosidase, O-glycosidase, N-acetyl-glucosamidase, or a mixture thereof. Removal of glycan results in a decrease in exosome uptake in Caco-2 cells. FIGS. 47A and 47B show exosome uptake in Caco2 cells following enzymatic removal of glycan from surface proteins in exosomes and CaCo-2 cells, respectively using β-N-acetylglucosamidase, PNGase F, β-galactosidase, O-glycosidase, neuraminadase, or a mixture thereof. Removal of glycan from either exosomes or CaCo-2 cells results in a decrease in exosome uptake in Caco-2 cells. (both studies *P<0.05 vs. control; N=3, means±S.D.) FIGS. 48A and 48B show exosome uptake in human small intestinal FH cells following enzymatic removal of glycan from surface proteins in exosomes and FH cells, respectively using β-N-acetyl-glucosamidase, PNGase F, β-galactosidase, O-glycosidase, neuraminadase, or a mixture thereof. Removal of glycan from either exosomes or FH cells results in a decrease in exosome uptake in FH cells. (both studies *P<0.05 vs. control; N=3, means±S.D.) FIGS. 49A and 49B show exosome uptake in U937 cells following enzymatic removal of glycan from surface proteins in exosomes and U937 cells, respectively using β-N-acetyl-glucosamidase, PNGase F, β-galactosidase, O-glycosidase, neuraminadase, or a mixture thereof. Removal of glycan from exosomes results in a decrease in exosome uptake in U937 cells. Removal of glycan from U937 cells results in a decrease in exosome uptake in U937 cells following treatment with β-N-acetyl-glucosamidase, neuraminidase, and a mixture of glycosidases. (both studies *P<0.05 vs. control; N=3, means±S.D.)

(iv) Use of Lectins to Identify Glycans on the Surface of Milk Exosomes

Figure 50A:
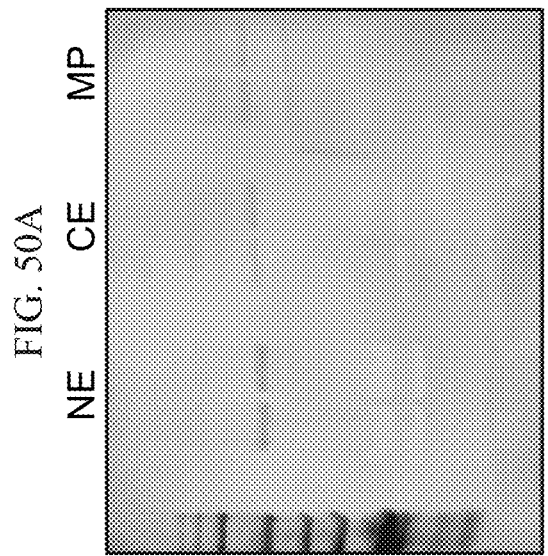

FIGS. 50A-D show Eastern/Lectin Blots that identify glycans present on the membranes of milk exosomes. NE-Normal Exosome; CE-Cytoplasmic Extract; MP-Membrane Protein. FIG. 50A shows a lectin blot using Con A, which is specific for alpha linked mannose, as a probe. FIG. 50B shows a lectin blot using PNA, which is specific for Gal 1-3 GalNAc 1 Ser/Thr, as a probe. FIG. 50C shows a lectin blot using SBA, which is specific for GalNAc, as a probe. FIG. 50D shows a lectin blot using SNA, which is specific for sialic acid, as a probe. These results demonstrate the presence of alpha linked mannose, Gal β 1-3 GalNAc 1 Ser/Thr, GalNAc, and sialic acid glycans in the membranes of exosomes.

TABLE C

| Lectin Symbol | Lectin | Source | Ligand Motif |
|---|---|---|---|
| Mannose-Binding Lectins | | | |
| ConA | Concanavalin A | *Canavalia ensiformis* | α-D-mannosyl and α-D-glucosyl residues branched α-mannosidic structures (high α-mannose type, or hybrid type and biantennary complex type N-Glycans) |
| LCH | Lentil lectin | *Lens culinaris* | Fucosylated core region of bi- and triantennary complex type N-Glycans |
| GNA | Snowdrop lectin | *Galanthus nivalis* | α 1-3 and α 1-6 linked high mannose structures |
| Galactose/N-acetylgalactosamine binding lectins | | | |
| RCA | Ricin, *Ricinus communis* Agglutinin, RCA120 | *Ricinus communis* | Galβ1-4GalNAcβ1-R |
| PNA | Peanut agglutinin | *Arachis hypogaea* | Galβ1-3GalNAcα1-Ser/Thr (T-Antigen) |
| AIL | Jacalin | *Artocarpus integrifolia* | (Sia)Galβ1-3GalNAcα1-Ser/Thr (T-Antigen) |
| VVL | Hairy vetch lectin | *Vicia villosa* | GalNAcα-Ser/Thr (Tn-Antigen) |
| DBA | *Dolichos biflorus* agglutinin | | α-linked N-acetylgalactosamine |
| SBA | Soybean agglutinin | soybean | terminal - and -N-acetylgalactosamine and galactopyranosyl residues |
| N-acetylglucosamine binding lectins | | | |
| WGA | Wheat Germ Agglutinin, WGA | *Triticum vulgaris* | GlcNAcβ1-4GlcNAcβ1-4GlcNAc, Neu5Ac (sialic acid) |
| PHA-E | *Phaseolus vulgaris* agglutinin | Red kidney bean | terminal galactose, N-acetylglucosamine and mannose residues of complex glycans |
| N-acetylneuraminic acid binding lectins | | | |
| SNA | Elderberry lectin | *Sambucus nigra* | Neu5Acα2-6Gal(NAc)-R |
| MAL | *Maackia amurensis* leukoagglutinin | *Maackia amurensis* | Neu5Ac/Gcα2,3Galβ1,4Glc(NAc) |
| MAH | *Maackia amurensis* hemoagglutinin | *Maackia amurensis* | Neu5Ac/Gcα2,3Galβ1,3(Neu5Acα2,6)GalNac |
| Fucose binding lectins | | | |
| UEA | *Ulex europaeus* agglutinin | *Ulex europaeus* | Fucα1-2Gal-R |
| AAL | *Aleuria aurantia* lectin | *Aleuria aurantia* | Fucα1-2Galβ1-4(Fucα1-3/4)Galβ1-4GlcNAc, R2-GlcNAcβ1-4(Fucα1-6)GlcNAc-R1 |

(v) Lectin Blockage of Glycans on the Surface Membrane of Exosomes Results in Decreased Transport in FH Cells The uptake of bovine milk exosomes into human small intestinal FH cells depended on glycan function in membrane proteins found on the surface of both exosomes and cells. In this transporter assay study, various lectins were used to bind to and block certain glycans. Exosome uptake was analyzed by measuring the cell fluorescence at 515 (excitation) and 640 nm (emission) using a Biotek FLx800 plate reader (BioTek Instru-ments) as previously described above. FIGS. 51A and 51B show the results of a lectin blocking study in which exosomes or FH cells were treated with various lectins, including ConA (binds to α-D-mannosyl and α-D-glucosyl residues), PHA-E (binds to terminal galactose, N-acetylglucosamine and mannose residues of complex glycans), SNA (binds to Neu5Acα2-6Gal(NAc)-R), PNA (binds to Galβ1-3GalNAcα1-Ser/Thr), WGA (binds to GlcNAcβ1-4GlcNAcβ1-4GlcNAc,Neu5Ac), RCA (binds to Galβ1-4GalNAcβ1-R), DBA (binds to α-linked N-acetylgalactosamine), SBA (binds to terminal- and -N-acetylgalactosamine and galactopyranosyl residues), MAL (binds to Neu5Ac/Gcα2,3Galβ1,4Glc(NAc)) and UEA (binds to Fucα1-2Gal-R). The blocking of glycans present on exosomes or on FH cells (FIG. 51A and FIG. 51B, respectively) with lectin decreases the uptake of cow's milk exosomes in FH cells. (*P<0.05 vs. control; N=3, means±S.D.).

D. Inhibition of Endocytosis, Vesicle Trafficking, and Carbohydrate Blocking Results in Decreased Exosome Transport into Cells Exosome transport was measured in HUVEC cells (expressed as ng exosomal protein/81,750 cells/h) pretreated for 30 min with 10 mg/mL Cyt D, 20 mg/mL BFA or 150 mmol/L carbohydrate competitors (glucose, galactose), using an exosome concentration of 55 mg/200 mL (n=5). Treatment with Cyt D, BFA, and carbohydrate competitors (glucose, galactose) was continued for the duration of the transport studies. Exosome uptake was analyzed by measuring the cell fluorescence at 515 (excitation) and 640 nm (emission) using a Biotek FLx800 plate reader (BioTek Instruments) as previously described above. FIG. 52 shows the results of an exosome transport study in which inhibitors of endocytosis (cytochalasin D=Cyt D), vesicle trafficking (brefeldin A=BFA), and carbohydrate blockage (glucose, galactose) were shown to cause a decrease in exosome uptake in HUVEC cells. *Different from control, P, 0.05. Values are means 6 SDs. Specifically, exosome transport into HUVEC cells decreased to <50% of controls (FIG. 52), indicating that exosomes are trafficked to HUVEC and transported into cells via endocytosis. Also, the carbohydrate competitor galactose, but not glucose, caused a significant decrease in exosome uptake indicating that galactose can compete with surface glycans on milk exosomes that mediate transport.

Results 417 exosomal surface proteins were identified, including N-glycans (4), O-glycans (2), and C-glycans (2). When exosomes were treated with Glu-C or trypsin, transport rates (Vmax) decreased compared with controls (arbitrary units): 88±1 for control, 40±0.6 for trypsin, 19±0.3 for Glu-C (P<0.05 vs. control). For comparison, 504 proteins were identified in breast milk exosomes (6-N-glycans, 4 O-glycans, and 3 C-glycans). The identities of surface glycoproteins were distinct in bovine and human milk exosomes.

Conclusion

Eight glycoproteins identified on the surface of cow's milk exosomes appear to be essential for intestinal transport. Glycan features, as opposed to protein features, are important for exosome recognition by intestinal cells.

Example 9: Animal Studies Showing that Modification of Glycans Found on Milk Exosomes Alter the Uptake of Exosomes into Mammalian Tissues A. In Vivo Transport of Exosomes Having Altered Glycan in Surface Proteins Milk exosomes having altered glycan in their surface proteins demonstrate altered uptake in various tissues in vivo. Milk exosomes were isolated as described in Example 1. A. The milk exosomes were treated with a glycosidase, for example, A-(2→3,6,8,9)-Neuraminidase, O-Glycosidase, N, -Glycosidase, β(1→4)-Galactosidase, β-N-Acetylglucosaminidase, PNGase F, as described above in Example 1. E (i) and as shown in FIG. 55A. For example, in some embodiments, all branched and unbranched sialic acids are removed. In some embodiments, serine or threonine linked unsubstituted Gal-β(1→3)-GalNAc glycans are removed. In some embodiments, N-linked glycans are removed. In some embodiments, glycans with α(1,3)-linked core fucose are removed. In some embodiments, glycans with β(1→4)-linked nonreducing terminal galactose are removed. In some embodiments, glycans with nonreducing terminal β-linked N-acetylglucosamine are removed. In some embodiments, asparagine linked complex, hybrid, or high mannose oligosaccharides are removed.

In one specific example, PnGase F was used to remove asparagine-linked complex, hybrid, or high mannose oligosaccharides from the surface proteins of milk exosomes. FIG. 55A shows a scheme for exosome processing to remove certain glycans from membrane proteins on the surface of exosomes, e.g., asparagine-linked complex, hybrid, or high mannose oligosaccharides (via the use of PnGase F). Milk exosomes with their native surface proteins (control) and milk exosomes having altered glycan in their surface proteins were separately ultracentrifuged to pellet the exosomes and the pelleted exosomes were then labeled with DiR. 1,1'dioctadecyl-3, 3, 3', 3'-tetramethylindotricarbocyanineiodide, DiR, is a lipophilic tracer that can be used to label lipoproteins in living or fixed tissues which does not affect cell viability, development, or basic physiological properties (Invitrogen). The DiR-labelled control exosomes and DiR-labelled exosomes with altered glycan were separately administered via oral gavage to wild-type mice (n=3 for each exosome group). After 12 hours, the mice were sacrificed and various tissues were examined using fluorescence. FIG. 25B shows the results of a fluorescence study in which fluorescent-labelled exosomes having native glycosylation (control) versus altered glycosylation (removal of asparagine-linked complex, hybrid, or high mannose oligosaccharides via the use of PnGase F) were compared. As shown in FIG. 55B, control exosomes exhibited significant uptake in various tissues as determined by the bright fluorescence observed in heart, lung, spleen, and liver with little accumulation in stomach and small intestine. In contrast, the glycan-altered exosomes showed significantly decreased uptake in heart, lung, spleen, and liver and significantly increased accumulation of non-absorbed exosomes in the small intestine, as determined by fluorescence intensity. This indicates that the presence of asparagine-linked complex, hybrid, or high mannose oligosaccharides on milk exosomes facilitates the uptake of milk exosomes from the gastrointestinal tract for delivery to heart, lung, spleen and liver and. In contrast, the removal of asparagine-linked complex, hybrid, or high mannose oligosaccharides on milk exosomes results in a loss of transport from the gastrointestinal tract to tissues compared with milk exosomes having native glycosylation.

B. Production of Transgenic Knock-Out Mice Having Deletion of Different Glycan Transferase Genes Bmi1$^{tm1(cre/ERT)Mrc}$/J mice mice to generate transgenic conditional (tamoxifen-inducible) knockout mice homozygous for deletion of a glycan transferase gene (FIG. 53A). FIG. 54B shows the Cre-LoxP mediated gene deletion method used to knock-out the glycan transferase gene. Cre-LoxP recombination is a well-known technique in which recombination between LoxP sites is catalysed by Cre recombinase. Floxing a gene of interest (sandwiching the gene between two LoxP sites) allows the gene to be deleted (knocked out), translocated or inverted via Cre-Lox recombination. Nagy A at al., (2000). "Cre recombinase: the universal reagent for genome tailoring." Genesis. 26 (2): 99-109. FIG. 54B depicts the Cre-LoxP mediated gene deletion method used to knock-out the glycan transferase gene.

Floxed genes can also be used to produce tissue-specific knockout mice by using the Cre recombinase with a tissue-specific promoter which causes the foxed gene to be inactivated (knocked out) only in the specific targeted tissue. Cre-Lox knockouts can also be inducible, for example, using tamoxifen to induce Cre recombinase. In this case, Cre recombinase is fused to a portion of the mouse estrogen receptor, which is naturally localized to the cytoplasm via its interactions with chaperone proteins such as heat shock protein 70 and Tamoxifen binds to the estrogen receptor and disrupts its interactions with the chaperones which allows the Cre-estrogen receptor fusion protein to enter the nucleus and perform recombination on the foxed gene. Hayashi, Shigemi; McMahon, Andrew P. (2002). "Efficient Recombination in Diverse Tissues by a Tamoxifen-Inducible Form of Cre: A Tool for Temporally Regulated Gene Activation/Inactivation in the Mouse". Developmental Biology. 244 (2): 305-318. Using this process, several tamoxifen-inducible conditional glycan transferase knockout mice were made (FIGS. 53 and 54). Tamoxifen-inducible conditional glycan transferase knockout mice having a glycan transferase gene deleted or otherwise knocked out (see Table D below) are made. For example, transgenic knockout mice having a conditionally deleted glucosaminyl (N-acetyl) transferase 3, mucin type (GCNT3); O-linked 13-N-acetyl-glucosamine transferase (OGT); Protein-O-fucosyl transferase (PoFUT1); or Mannoside acetyl glucosaminyltransferase (MGAT1) gene deleted were made. FIG. 54B shows the genotyping results for transgenic mice having a deleted MGAT1 or PoFUT1 gene, showing the knockout of these respective genes. The transgenic mice are used to study or monitor the effect of specific glycosylation on exosome transport to various tissues.

TABLE D

| Knockout | Strain | Glycan/Enzyme/Loss |
| --- | --- | --- |
| B6.129-Gcnt3$^{tm1Jxm}$/J | JL | Glucosaminyl (N-Acetyl) Transferase 3, mucin type (beta-6-N-acetylglucosamine-transferase) catalyzes the formation of core 2 and core 4 O-glycans on mucin-type glycoproteins loss of core 2 and 4 O-glycans |
| OGT$^{tm}$ | JH | UDP-N-acetylglucosamine—peptide N-acetylglucosaminyltransferase (EC 2.4.1.255) (O-linked β-N-acetylglucosamine transferase; O-GlcNAc-transferase) catalyzes the addition of a single N-acetylglucosamine in O-glycosidic linkage to serine or threonine residues loss of O-glycans; loss of O-GlcNAcylation |
| Pofut1 | PS | Protein-O-fucosyl transferase adds O-fucose through an O-glycosidic linkage to conserved serine or threonine residues loss of O-fucose glycans |
| B6.129S2-Mgat1$^{tm}$ | PS | Alpha-1,3-mannosyl-glycoprotein 2-beta-N-acetylglucosaminyltransferase (Mannoside acetyl glucosaminyltransferase) synthesis of hybrid and complex N-glycans loss of N-glycans |

C. Exosome Transport Using Transgenic Knock-Out Mice having Deletion of Different Glycan Transferase Genes Tamoxifen-inducible conditional glycan transferase knockout mice (homozygous) are made as described above. FIGS. 54A and 54B show various gene knockouts which result in alteration of glycosylation and corresponding genotyping results. Differences in milk exosome uptake in these knockout mice as compared with wild type mice can be used to further identify or characterize the glycosylation of surface proteins involved in exosome uptake, as well as the glycan transferase enzymes involved in exosome uptake. Such characterization is useful for the design of modified exosomes with improved stability, improved uptake, altered uptake, targeted uptake and/or improved delivery of cargo.

Exosomes are isolated as described in Example 1. A. Fluorescence-labelled (DiR) is added to the exosome pellet. The DiR-labelled exosomes are administered via oral gavage to wild-type mice (n=3) and tamoxifen-inducible conditional glycan transferase knockout mice (n=3) having a conditional deletion in a glycan transferase gene (or other gene involved in glycosylation), for example, GCNT3 gene, OGT gene, PoFUT1 gene, or MGAT1 gene. After 12 hours, the wild-type mice and transgenic mice are sacrificed and various organs (e.g., heart, lungs, liver, spleen, kidney, intestine, stomach, etc) are examined via fluorescence. Fluorescent-labelled exosomes having native glycosylation (control wild-type mice) versus fluorescent-labelled exosomes having altered glycosylation (e.g., lacking core 2 and 4 O-glycans, lacking O-GlcNAcylation or O-glycans, lacking O-fucose glycans, or lacking N-glycans) as found in the transgenic mice are compared to determine the effect of altered glycosylation on the uptake of exosomes, e.g., milk exosomes, in vivo. These methods provide other means for determining or monitoring exosome uptake of milk exosomes having altered glycan in its surface proteins. Such characterization is useful for the design of modified exosomes with improved stability, improved uptake, altered uptake (increased or decreased), targeted uptake and/or improved delivery of cargo. The transgenic mice can also be used as a means of producing milk exosomes having various altered glycosylation of its surface proteins.

Example 10: Method of Loading Exosomes with an Exogenous Cargo

Microvesicles of the present disclosure, including milk exosomes, can be loaded with cargos using various methods known in the art such as electroporation or transfection with cationic lipid reagents. Other methods include loading by ultracentrifugation. For example, procedures for loading cargos are provided in U.S. Pat. No. 9,085,778, US 2016/0000710, and WO 2015/161184, each of which is hereby incorporated by reference. Additional literature on loading methods for exosomes includes Luan, X. et al., Acta Pharmacol Sin. 2017 June; 38(6): 754-763 and Munagala R, et al., Cancer Lett. 2016 Feb. 1; 371(1):48-61, each of which is hereby incorporated by reference.

Those procedures include i) suspending therapeutic agents in PEG-400, mixing with milk-derived exosomes, followed by low-speed centrifugation; ii) dissolving therapeutic agents in ethanol, mixing with milk- or colostrum-derived exosomes, low-speed centrifugation (10,000×g) to remove unbound therapeutic agent, and finally high-speed centrifugation; and iii) mixing therapeutic agents in ethanol with 100,000 whey (obtained after the 100,000×g centrifugation), low-speed centrifugation and finally 120,000×g centrifugation. In one procedure, incubation of exosomes in PBS with test agents in the presence of 10% ethanol or 10% ethanol:acetonitrile (1:1) will load therapeutic agents into the exosomes. Sucrose density gradient ultracentrifugation can be used to confirm the presence of drugs embedded in the exosomes. Testing for in vitro release may be performed using dialysis tubes against buffer containing the surfactant Tween-80 at 37° C.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A milk exosome comprising:
a biological membrane surrounding a lumen, wherein the biological membrane comprises one or more glycoprotein(s) comprising galactose,
wherein the biological membrane is modified such that it has an increased number of the one or more glycoprotein(s) comprising galactose as compared with the natural biological membrane of the milk exosome.

2. The milk exosome of claim 1, wherein the biological membrane is further modified such that it includes one or more glycoprotein(s) that is not naturally present in the natural biological membrane.

3. The milk exosome of claim 1, wherein the biological membrane is further modified such that one or more of its native glycoprotein(s) is altered.

4. The milk exosome of claim 1, wherein the one or more glycoprotein(s) comprising galactose are native glycoprotein(s).

5. The milk exosome of claim 3, wherein the one or more native glycoprotein(s) is altered such that the number of glycan residues present on the one or more glycoprotein(s) is decreased.

6. The milk exosome of claim 3, wherein the one or more native glycoprotein(s) is altered such that it comprises a modified glycan.

7. The milk exosomes of claim 6, wherein the modified glycan comprises at least one carbohydrate moiety that differs from that of the glycan in the native glycoprotein(s).

8. The exosome of claim 6, wherein the modified glycan comprises one or more D- or L-glucose, erythrose, fucose, mannose, lyxose, gulose, xylose, arabinose, ribose, 2'-deoxyribose, glucosamine, lactosamine, polylactosamine, glucuronic acid, sialic acid, sialyl-Lewis X (SLex), N-acetylglucosamine, N-acetyl-galactosamine, neuraminic acid, N-glycolylneuraminic acid (Neu5Gc), N-acetylneuraminic acid (Neu5Ac), an N-glycan chain, an O-glycan chain, a Core 1, Core 2, Core 3, or Core 4 structure, or a phosphate- or acetate-modified analog thereof or a combination thereof.

9. The exosome of claim 1, wherein uptake of the milk exosome into a mammalian cell is altered as compared with the uptake of a corresponding milk exosome having its natural biological membrane.

10. The milk exosome of claim 9, wherein uptake of the milk exosome into a mammalian cell is increased.

11. The exosome of claim 9, wherein the mammalian cell is selected from an intestinal cell, venous endothelial cell or other endothelial cell, immune cell, macrophage, intestinal mucosa, peripheral cell of the liver, spleen, lung, brain, kidneys, or pancreas, cancer cell, or fetal cell.

12. The exosome of claim 1, wherein the stability of the milk exosome in the gastrointestinal tract, systemic circulation, lymphatic circulation, intracellular conditions, or other tissues or organs of a subject is increased as compared with an exosome having its natural biological membrane.

13. The exosome of claim 1, wherein the stability of the milk exosome under physiological conditions in a subject is increased as compared with a milk exosome having its natural biological membrane.

14. The milk exosome of claim 1, further comprising an exogenous cargo encapsulated in said lumen.

15. The milk exosome of claim 1, wherein the milk exosome further comprises an miRNA or mRNA that is biologically active in a mammal.

16. The milk exosome of claim 1, wherein the milk exosome is isolated from sheep, goat, camel, horse, donkey, reindeer, yak, buffalo, or bovine Ecew) milk or colostrum.

17. The milk exosome of claim 14, wherein the exogenous cargo is selected from one or more nucleic acid molecules, polypeptides, lipids, vitamins, minerals, small molecules, pharmaceuticals, hormones, or enzymes.

18. The milk exosome of claim 14, wherein the exogenous cargo comprises a therapeutic agent.

19. The milk exosome of claim 18, wherein the therapeutic agent is selected from mRNAs, polypeptides, miRNAs, miRNA antagonists, nutrients, antibiotics, cancer drugs, activators of Toll-like receptors, or molecules capable of delivery to macrophages.

20. The milk exosome of claim 18, wherein the therapeutic agent is a cancer drug selected from a chemotherapeutic, an immunotherapeutic, a hormone therapeutic, or a targeted therapeutic.

21. A method of altering the uptake of a milk exosome into a mammalian cell or tissue, the milk exosome having a biological membrane comprising one or more glycoprotein(s) comprising galactose, comprising modifying the biological membrane of the exosome such that is has an increased number of the one or more glycoprotein(s) comprising galactose as compared with the natural biological membrane of the milk exosome.

22. The method of claim 21, wherein the uptake of the milk exosome into a mammalian cell or tissue is increased.

23. The method of claim 21, wherein the uptake of the milk exosome into a mammalian cell or tissue is selectively increased in a targeted mammalian cell or tissue.

24. The method of claim 21, wherein the biological membrane is further modified such that it includes one or more glycoprotein(s) that is not naturally present in the natural biological membrane.

25. The method of claim 21, wherein the biological membrane is further modified such that one or more of its native glycoprotein(s) is altered.

26. The method of claim 25, wherein the one or more native glycoprotein(s) is altered such that the number of glycan residues present on the glycoprotein(s) is increased.

27. The method of claim 25, wherein the one or more native glycoprotein(s) is altered such that the number of glycan residues present on the glycoprotein(s) is decreased.

28. The method of claim 21, wherein the mammalian cell is selected from an intestinal cell, venous endothelial cell or other endothelial cell, immune cell, macrophage, intestinal mucosa, peripheral cell of the liver, spleen, lung, brain, kidneys, or pancreas, cancer cell, or fetal cell.

29. A method of targeting a milk exosome to a selected mammalian cell or tissue, the milk exosome having a biological membrane comprising one or more glycoprotein(s) comprising galactose, comprising modifying the biological membrane of the milk exosome such that it has an increased number of the one or more glycoprotein(s) comprising galactose as compared with the natural biological membrane of the milk exosome.

\* \* \* \* \*